United States Patent
Aicher et al.

(10) Patent No.: US 8,022,222 B2
(45) Date of Patent: Sep. 20, 2011

(54) GLUCOKINASE ACTIVATORS

(75) Inventors: Thomas D. Aicher, Superior, CO (US); Steven Armen Boyd, Longmont, CO (US); Mark Joseph Chicarelli, Longmont, CO (US); Kevin Ronald Condroski, Lafayette, CO (US); Rustam Ferdinand Garrey, Loveland, CO (US); Ronald Jay Hinklin, Longmont, CO (US); Ajay Singh, Aurora, CO (US); Timothy M. Turner, Longmont, CO (US)

(73) Assignee: Array Biopharma, Inc., Boulder, CO (US)

( * ) Notice: Subject to any disclaimer, the term of this patent is extended or adjusted under 35 U.S.C. 154(b) by 213 days.

(21) Appl. No.: 12/161,366

(22) PCT Filed: Jan. 24, 2007

(86) PCT No.: PCT/US2007/001956
§ 371 (c)(1),
(2), (4) Date: Jul. 18, 2008

(87) PCT Pub. No.: WO2007/089512
PCT Pub. Date: Aug. 9, 2007

(65) Prior Publication Data
US 2009/0247526 A1 Oct. 1, 2009

Related U.S. Application Data

(60) Provisional application No. 60/763,173, filed on Jan. 27, 2006.

(51) Int. Cl.
*C07D 417/00* (2006.01)
*A61K 31/44* (2006.01)
(52) U.S. Cl. .................... 546/270.7; 514/342
(58) Field of Classification Search ............... 546/270.7; 514/342
See application file for complete search history.

(56) References Cited

U.S. PATENT DOCUMENTS

| | | |
|---|---|---|
| 6,586,424 B2 | 7/2003 | Bilodeau et al. |
| 6,875,767 B2 | 4/2005 | Bilodeau et al. |
| 7,214,681 B2 | 5/2007 | Fyfe et al. |
| 2004/0023978 A1 | 2/2004 | Ren et al. |
| 2004/0023981 A1 | 2/2004 | Ren et al. |
| 2005/0282851 A1 | 12/2005 | Bebernitz |
| 2006/0199846 A1 | 9/2006 | Mitchell et al. |
| 2008/0081811 A1 | 4/2008 | Iwasawa et al. |

FOREIGN PATENT DOCUMENTS

| | | |
|---|---|---|
| WO | 2003078423 A1 | 9/2003 |
| WO | 2004041164 A2 | 5/2004 |
| WO | 2005056530 A1 | 6/2005 |
| WO | 2006081172 A2 | 8/2006 |
| WO | 2006135604 A2 | 12/2006 |

OTHER PUBLICATIONS

Hcaplus 2004:1082034, "P-38 inhibitors", Dong et. al., Dec. 2004.*
Bilodeau et. a. "Potent N-(1,3-Thiazol-2-yl)pyridin-2-amine Vascular Endothelial Growth Factor Receptor Tyrosine Kinase Inhibitors with Excellent Pharmacokinetics and Low Affinity for the hERG Ion Channel", 2004, 47, pp. 6363-6372.*
Patani et. al., "Bioisosterism: A Rational Approach in Drug Design", Chem. Rev. 1996, 96, pp. 3147-3176.*
Mark T. Bilodeau et al., "Potent N-(1,3-Thiazol-2-yl)pyridin-2-amine Vascular Endothelial Growth Factor Receptor Tyrosine Kinase Inhibitors with Excellent Pharmacokinetics and Low Affinity for the hERG Ion Channel", XP-002437591, J. Med Chem, 2004, 47, pp. 6363-6372.
Jagabandhu Das et al., "Discovery of 2-Amino-heteroaryl-benzothiazole-6-anilides as Potent p56lck Inhibitors", XP-002329103, Bioorganic & Medicinal Chemistry Letters 13, 2003, pp. 2587-2590.
Bilodeau, Mark T., et al., "The discovery of N-(1,3-thiazol-2-yl) pyridin-2-amines as potent inhibitors of KDR kinase," Bioorganic & Medicinal Chemistry Letters 14 (2004) 2941-2945.

* cited by examiner

*Primary Examiner* — Andrew D. Kosar
(74) *Attorney, Agent, or Firm* — Banner & Witcoff, Ltd.

(57) ABSTRACT

Provided are compounds of formula I

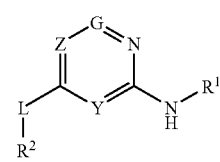

wherein $R^2$, L, Z, Y, G and $R^1$ are as defined herein, that are useful in the treatment and/or prevention of diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed herein.

16 Claims, No Drawings

GLUCOKINASE ACTIVATORS

PRIORITY OF INVENTION

This application claims priority to U.S. Provisional Application No. 60/763,173 that was filed on 27 Jan. 2006, which is hereby incorporated herein by reference in its entirety.

FIELD OF THE INVENTION

Provided are compounds that are useful in the treatment and/or prevention of diseases mediated by deficient levels of glucokinase activity, such as diabetes mellitus, and methods of preparing such compounds. Also provided are methods of treating diseases and disorders characterized by underactivation of glucokinase activity or which can be treated by activating glucokinase, comprising administering an effective amount of a compound of this invention.

BACKGROUND OF THE INVENTION

Diabetes mellitus comprises a group of syndromes characterized by an inability of the body to produce adequate insulin or to properly use insulin. Most diabetes patients can be classified clinically as having either insulin-dependent diabetes mellitus (IDDM) or non-insulin-dependent diabetes mellitus (NIDDM). Nearly all forms of diabetes mellitus result from either a decrease in the secretion and blood concentration of insulin or a decrease in the response of tissues to insulin (insulin resistance), often associated with an elevated level of hormones (e.g., glucagon) that act contrary to insulin. Such abnormalities give rise to changes in carbohydrate, lipid and protein metabolism. The syndrome's hallmark is hyperglycemia; other complications can include cardiovascular disease, retinopathy, neuropathy, nephropathy, skin disorders and gastroparesis.

Diabetes mellitus affects millions of persons worldwide, including over 18 million in the United States. It is estimated that IDDM (Type I diabetes), which results from the body's failure to produce insulin, accounts for 5-10% of the cases of diabetes diagnosed in the United States. The majority of diabetes patients in the United States are diagnosed with NIDDM (Type II diabetes), which results from insulin resistance combined with the inability of the pancreas to secrete sufficient insulin to overcome such resistance. Type II diabetes occurs in at least 5% of the United States population, and in 1996 alone NIDDM affected 16 million people (Roman, S. H.; Harris, M. I., *Endocrinology and Metabolism Clinics of North America*, 1997, 26.3, 443-474). Impaired glucose tolerance (IGT), a syndrome characterized by impaired glucose processing that presents symptoms similar to a mild form of Type II diabetes, is even more prevalent, affecting 35 to 40 million adults in the United States.

Diabetes is most frequently diagnosed either by the presentation of a fasting plasma glucose of greater than or equal to 126 mg/dL on two occasions, or by an oral glucose tolerance test (OGTT) with a 2 hour post load value of greater than 200 mg/dL plus classic symptoms such as polydipsia, polyphagia and/or polyuria (The Expert Committee on the Diagnosis and Classification of Diabetes Mellitus, *Diabetes Care*, 1998, 21, S5-19). In the case of IGT, a fasting plasma glucose of less than 126 mg/dL but a 2-hour post-oral glucose challenge lever greater than 140 mg/dL is observed.

A primary goal in the treatment of each of these conditions is the reduction and control of blood glucose levels. The reduction of hyperglycemia in insulin-dependent diabetes (IDDM) can attenuate the development of many of the attendant complications of IDDM (Diabetes Control and Complications Trial Research Group, *New England J. Med.*, 1993, 329, 977-986). For example, tight control of blood glucose levels through intensive insulin therapy can reduce the development of retinopathy, nephropathy and neuropathy by >50% each in IDDM patients. These findings, together with the similarity of the pathologies seen in IDDM and NIDDM, suggest that control of blood glucose levels would produce similar benefits in NIDDM patients (American Diabetes Association, *Diabetes Care*, 1998, 21, S88-90), as has been reported (Ohkubo, Y., et al., *Diabetes Res. Clin. Pract.* 1995, 28, 103-117).

Several methods to treat hyperglycemia have been attempted. Patients with Type I diabetes receive insulin. In patients with Type II diabetes, the pancreas secretes insulin, but in insufficient amounts to overcome the intrinsic insulin resistance of the disease. The administration of agents such as metformin (De Froinzo, R. A.; Goodman, A. M. *N. Engl. J. Med.*, 1995, 333, 541-549; Bailey, C. J. Biguanides and NIDDM, *Diabetes Care* 1992, 15, 773-784) and glitazone (PPAR agonist class of drugs; Willson, T. M., et al., *J. Med. Chem.* 1996, 39, 665-668) can at least partially ameliorate insulin resistance, but these agents do not promote insulin secretion. Treatment with certain sulfonylureas has been shown to promote insulin secretion by affecting an ion channel; however, the increase in insulin caused by this class of drugs is not glucose dependent or even glucose sensitive, and such treatment can actually raise the risk of overt hypoglycemia. DPP-IV inhibitors, such as GLP or a GLP mimetic (such as Exedin), promote CANT secretion at the β-cell through an incretin mechanism, and administration of these agents promotes insulin release in a glucose dependent manner (Vahl, T. P., D'Alessio, D. A., *Expert Opinion on Invest. Drugs* 2004, 13, 177-188). However, even with these potential treatments, it is difficult to achieve tight control of blood glucose levels in NIDMM patients in accordance with the guidelines recommended by the American Diabetes Association. Accordingly, there is significant demand for novel therapeutic approaches that allow sufficient glycemic control.

Possible approaches to glycemic control include enhancing clearance of glucose from the blood and increasing the rate of glucose storage or utilization. Glucose enters most cells by a specific transport protein, where it is phosphorylated to form glucose-6-phosphate in a reaction catalyzed by a hexokinase. Inside the cell, glucose-6-phosphate has one of several fates: it can be broken down via the glycolytic pathway, converted into glycogen or it can be oxidized via the pentose phosphate pathway.

Glucokinase (GK) (ATP:D-hexose 6-phosphotransferase), one of the four types of mammalian hexokinases (hexokinase IV), plays an essential role in blood glucose homeostasis. Expression of glucokinase is largely localized in the liver and pancreatic β-cells, where several types of glucokinase are expressed: these types differ in the sequence of the 15 N-terminal amino acids due to differences in splicing, but their enzymatic properties are virtually identical. Glucokinase is also expressed in a population of neurons in the hypothalamus.

Unlike the enzymatic activities of the other three hexokinases (I, II, III), each of which becomes saturated at a glucose concentration of below 1 mM, glucokinase has a $K_m$ for glucose of 8 mM, which is close to the physiological glucose level (5 mM). Thus, at lower glucose levels, glucose is more rapidly utilized in brain, muscle and other peripheral tissues—through conversion by a hexokinase other than glucokinase—than in the liver. At elevated glucose levels, such as after a meal or overnutrition (the postprandial glucose level can exceed 10-15 mM), glucokinase-mediated glucose metabolism in the liver and pancreas is accelerated. Moreover, hexokinases I, II and III are inhibited by high concentrations of glucose-6-phosphate, lowering glucose utilization, whereas glucokinase continues to catalyze utilization of glucose even at high levels of glucose-6-phosphate.

In tissues where glucokinase is expressed, it plays an important role in glucose uptake and utilization: in the β-cell, the glucose-6-phosphate produced is a necessary signal for insulin release; in the hypothalamus glucose-6-phosphate acts as a satiety signal and might contribute to the secretion of enteroincretins; and in the liver, where glucose-6-phosphate production by the action of glucokinase acts as a mechanism for disposal of excessive glucose through storage as glycogen (Printz, R. L., et al., *Annu. Rev. Nutr.*, 1993, 13, 463-496). Glucokinase-catalyzed glucose phosphorylation is the rate-limiting reaction for glycolysis in hepatocytes and pancreatic O-cells. In the liver, glucokinase determines the rates of both glucose uptake and glycogen synthesis, and it is also thought to be essential for the regulation of various glucose-responsive genes (Girard, J., et al., *Annu. Rev. Nutr.*, 1997, 17, 325-352). In both liver and pancreatic β-cells, glucokinase is rate limiting for glucose utilization, and consequently is a major component of the regulation of insulin secretion from the β-cell and glycogen storage in the liver. The control of insulin secretion and the control of glycogen storage are deficient in diabetes (DeFronzo, R. A., *Diabetes*, 1988, 37, 667-687).

The theoretical importance of glucokinase in diabetes is supported by studies of genetic populations and genetic manipulation of animal models of NIDDM. Mutation of glucokinase to a less active form of the kinase is the cause of the Maturity Onset of Diabetes in the Young (NODY-2) (Froguel, P., et al., *New England J. Med.*, 1993, 328, 697-702; Bell, G. I., et al., *Annual Rev. of Physiol.*, 1996, 58, 171-186). Conversely, humans with a glucokinase activation mutation are less prone to hyperglycemia and have increased insulin secretion in response to a glucose challenge (Christesen, H. B., et al., *Diabetes*, 2002, 51, 1240-1246; Gloyn, A. L, et al., *Diabetes*, 2003, 52, 2433-2440; Glaser, B., et al., *New England J. Med.*, 1998, 338, 226-230). Also, NIDDM patients have been reported to have inappropriately low glucokinase activity. Furthermore, over expression of glucokinase in dietary or genetic animal models of diabetes either prevents, ameliorates, or reverses the progress of pathological symptoms in the disease (Caro, J. F., et al., *Hormone & Metabolic Res.*, 1995, 27, 19-22). For these reasons, compounds that activate glucokinase have been sought by the pharmaceutical industry.

Substituted benzyl carbamoyl, substituted heterobenzyl carbamoyl, substituted phenyl carbamoyl; and substituted heteroaryl carbamoyl compounds have been disclosed as glucokinase activators. See, for example, WO 03/000267, WO 03/015774, WO 04/045614, WO 04/046139, WO 05/04480, WO 05/054200, WO 05/054233, WO 05/044801, WO 05/056530, WO 03/080585, WO 04/076420, WO 04/081001, WO 04/063194, WO 04/050645, WO 03/055482, WO 04/002481, WO 05/066145, WO 04/072031, WO 04/072066, U.S. Pat. No. 6,610,846, WO 00/058293, WO 03/095438, WO 01/44216, WO 01/083465, WO 01/083478, WO 01/085706, WO 01/085707, WO 02/008209, WO 02/014312, WO 02/046173, WO 02/048106, WO 03/095438, WO 04/031179, and WO 04/052869. These compounds either lower the $K_m$ for glucose and/or increase the $V_{max}$ of glucokinase. A class of glucokinase activators that can lower the $K_m$ of glucose moderately to 2-5 mM at low activator concentrations is desirable.

SUMMARY OF THE INVENTION

The present invention relates to compounds that are activators of glucokinase which are useful in the treatment of diseases and disorders that would benefit from activation of glucokinase.

More specifically, one aspect of this invention provides compounds of Formula I

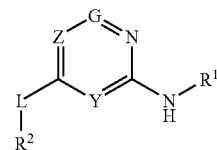

and solvates, metabolites and pharmaceutically acceptable salts and prodrugs thereof, wherein L, Y, Z, G, $R^1$ and $R^2$ are as defined herein.

The invention also provides pharmaceutical compositions comprising a therapeutically effective amount of a compound of Formula I, or a solvate, metabolite, or pharmaceutically acceptable salt or prodrug thereof, and a pharmaceutically acceptable carrier.

The inventive compounds may be used advantageously in combination with other known therapeutic agents. Accordingly, this invention also provides pharmaceutical compositions comprising a therapeutically effective amount of a compound of Formula I or a solvate, metabolite, or pharmaceutically acceptable salt or prodrug thereof, in combination with a second therapeutic agent.

This invention also provides methods of preventing or treating a disease or disorder characterized by underactivation of glucokinase or which can be treated by activating glucokinase in a mammal, comprising administrating to said mammal one or more compounds of Formula I, or a metabolite, solvate, or pharmaceutically acceptable salt or prodrug thereof, in an amount effective to treat said disease or disorder. The compounds of the present invention can be used, for example, as prophylactics or therapeutic agents for treating diseases or disorders mediated by deficient levels of glucokinase activity, including, but not limited to, diabetes mellitus (type I and type II), impaired glucose tolerance, IFG (impaired fasting glucose) and IFG (impaired fasting glycemia), as well as other diseases and disorders characterized by underactivation of glucokinase or which can be treated by activation of glucokinase, such as those discussed below.

This invention also provides compounds of Formula I for use as medicaments in the treatment of diseases or disorders characterized by underactivation of glucokinase or which can be treated by activating glucokinase.

An additional aspect of the invention is the use of a compound of Formula I for the preparation of a medicament for the treatment or prevention of a disease or disorder characterized by underactivation of glucokinase or which can be treated by activating glucokinase in a mammal suffering from such disorder.

This invention further provides kits for the treatment or prevention of a disease or disorder characterized by underactivation of glucokinase, said kit comprising a compound of Formula I, or a solvate, metabolite, or pharmaceutically acceptable salt or prodrug thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms, wherein the allyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2C_1H_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

In certain embodiments, the term "alkyl" refers to a saturated linear or branched-chain monovalent hydrocarbon radical of one to six carbon atoms, wherein the alkyl radical may be optionally substituted independently with one or more substituents described below.

The term "alkylene" as used herein refers to a linear or branched saturated divalent hydrocarbon radical of one to twelve carbon atoms, wherein the alkylene radical may be optionally substituted independently with one or more substituents described herein. Examples include, but are not limited to, methylene, ethylene, propylene, 2-methylpropylene, pentylene, and the like.

In certain embodiments, the term "alkylene" refers to a linear or branched saturated divalent hydrocarbon radical of one to four carbon atoms, wherein the alkylene radical may be optionally substituted independently with one or more substituents described herein.

The term "alkenyl" as used herein refers to a linear or branched-chain monovalent hydrocarbon radical of two to twelve carbon atoms with at least one site of unsaturation, i.e., a carbon-carbon sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), 1-buten-1-yl, 1-buten-2-yl, and the like.

In certain embodiments, the term "alkenyl" as used herein refers to a linear or branched-chain monovalent hydrocarbon radical of two to six-carbon atoms with at least one site of unsaturation, wherein the alkenyl radical may be optionally substituted independently with one or more substituents described herein, and includes radicals having "cis" and "trans" orientations.

The term "alkenylene" as used herein refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkenylene" includes linear or branched divalent hydrocarbon radical of two to four carbons containing at least one double bond, wherein the alkenylene radical may be optionally substituted independently with one or more substituents described herein.

The term "alkynyl" as used herein refers to a linear or branched monovalent hydrocarbon radical of two to twelve carbon atoms with at least one site of unsaturation, i.e., a carbon-carbon sp triple bond, wherein the alkynyl radical may be optionally substituted independently with one or more substituents described herein. Examples include, but are not limited to, ethynyl (—$C\equiv CH$), propynyl (propargyl, —$CH_2C\equiv CH$) and the like.

In certain embodiments, the term "alkynyl" refers to a linear or branched monovalent hydrocarbon radical of two to six carbon atoms with at least one carbon-carbon sp triple bond.

The term "alkynylene" as used herein refers to a linear or branched divalent hydrocarbon radical of two to twelve carbons containing at least one triple bond, wherein the alkynylene radical may be optionally substituted independently with one or more substituents described herein. Examples include, but are not limited to, ethynylene, propynylene, and the like.

In certain embodiments, the term "alkynylene" refers to a linear or branched divalent hydrocarbon radical of two to four carbons containing at least one triple bond.

The term "heteroalkyl" as used herein refers to saturated linear or branched-chain monovalent hydrocarbon radical of one to twelve carbon atoms, wherein at least one of the carbon atoms is replaced with a heteroatom independently selected from N, O, or S, and wherein the radical may be a carbon radical or heteroatom radical. The heteroalkyl radical may be optionally substituted independently with one or more substituents described herein. The term "heteroalkyl" encompasses alkoxy and heteroalkoxy radicals.

The terms "cycloalkyl," "carbocycle," "carbocyclyl" and "carbocyclic ring" are used interchangeably and refer to a saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated, partially unsaturated or aromatic cycloalkyl or heterocyclic ring. Examples of cycloalkyl groups include, but are not limited to, cyclopropyl, cyclobutyl, cyclopentyl, cyclopentenyl, cyclohexyl, cyclohexenyl, cycloheptyl, cycloheptenyl, and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently with one or more substituents described herein.

"Aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "heterocyclyl" and "heterocyclic ring" as used herein are used interchangeably and refer to a saturated or partially unsaturated carbocyclic radical of 3 to 12 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (═O) moieties are isoindoline-1,3-dionyl and 1,1-dioxo-thiomorpholinyl. The heterocycle groups herein are unsubstituted or, as specified, substituted in one or more substitutable positions with various groups described herein.

The term "heteroaryl" as used herein refers to a monovalent aromatic radical of a 5-, 6-, or 7-membered ring, and includes fused ring systems (at least one of which is aromatic) of 5-12 atoms, containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently at one or more substitutable positions with one or more substituents described herein.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or 3-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" as used herein means fluoro, chloro, bromo or iodo.

The term "a" as used herein means one or more.

As used herein, the terms "compound of this invention," "compounds of the present invention" and "compounds of Formula I" include compounds of Formula I and tautomers, resolved enantiomers, resolved diastereomers, racemic mixtures, solvates, metabolites, and pharmaceutically acceptable salts and prodrugs thereof.

In general, the various moieties or functional groups of the compounds of this invention may be optionally substituted by one or more substituents. Examples of substituents suitable for purposes of this invention include, but are not limited to, oxo, halogen, CN, nitro, trifluoromethyl, difluoromethyl, fluoromethyl, fluoromethoxy, difluoromethoxy, trifluoromethoxy, azido, $V_n$—NR"SO$_2$R', $V_n$—SO$_2$NR'R", $V_n$—C(=O)R', $V_n$—C(=O)OR', $V_n$—OC(=O)R', $V_n$—NR"C(=O)OR', $V_n$—NR"C(=O)R', $V_n$—C(=O)NR'R", $V_n$—NR'R", $V_n$—NR'''C(=O)N'R", $V_n$—OR', $V_n$—SR', $V_n$—S(O)$_2$R', $V_n$—S(O)$_2$R', alkyl, alkenyl, alkynyl, $V_n$-heteroalkyl, $V_n$-cycloalkyl, $V_n$-heterocyclyl, $V_n$-aryl, and $V_n$-heteroaryl, where R', R" and R''' are independently H, alkyl, alkenyl, alkynyl, heteroalkyl, cycloalkyl, heterocyclyl, aryl, or heteroaryl.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

Glucokinase Activators

The present invention provides compounds, and pharmaceutical formulations thereof, that are useful in the treatment of diseases, conditions and/or disorders characterized by underactivation of glucokinase or which can be treated by activation of glucokinase.

One aspect of the invention provides compounds of Formula I

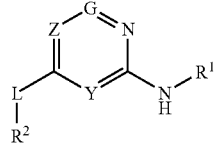

I and tautomers, resolved enantiomers, resolved diastereomers, racemic mixtures, solvates, metabolites and pharmaceutically acceptable salts and prodrugs thereof, wherein:

L is O, S, S(=O), S(=O)$_2$, NR$^{14}$CR$^{14}$R$^{15}$, or C(=O);
Y is N or CR$^4$;
G is N or CR$^{11}$;
Z is N or CR$^3$, wherein at least one of G or Z is not N;
R$^1$ is a heteroaryl ring represented by the formula

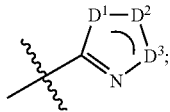

D$^1$ is S, O or N;
D$^2$ is N or CR$^{12}$;
D$^3$ is S, O or CR$^{13}$;
R$^2$ is aryl, heteroaryl, saturated or partially unsaturated cycloalkyl, or saturated or partially unsaturated heterocyclyl optionally substituted with oxo, wherein said aryl, heteroaryl, cycloalkyl and heterocyclyl are monocyclic or bicyclic and are further optionally substituted with one or more groups independently selected from alkyl, alkenyl, alkynyl, heteroalkyl, saturated and partially unsaturated cycloalkyl, saturated and partially unsaturated heterocyclyl, aryl, heteroaryl, F, Cl, Br, I, CF$_3$, CN, OR$^6$, C(=O)R$^6$, C(=O)OR$^6$, OC(=O)R$^6$, O(CH$_2$)$_n$C(=O)OR$^6$, O(CH$_2$)$_n$C(=O)NR$^6$R$^7$, C(=O)NR$^6$R$^7$, NR$^6$R$^7$, NR$^6$C(=O)R$^7$, SR$^6$, S(O)R$^6$, S(O)$_2$R$^6$, NO$_2$, and wherein said alkyl, alkenyl, alkynyl, heteroalkyl, cycloalkyl, heterocyclyl, aryl, and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-aryl, $V_n$-heterocyclyl, $V_n$-aryl, $V_n$-heteroaryl, $V_n$—F, $V_n$—Cl, $V_n$—Br, $V_n$—I, $V_n$—CF$_3$, $V_n$—CN, $V_n$—OR$^8$, $V_n$—C(=O)R$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, $V_n$—SR$^8$, $V_n$—S(O)R$^8$, and $V_n$—S(O)$_2$R$^8$;

R$^3$ is H, alkyl, alkenyl, alkynyl, heteroalkyl, saturated or partially unsaturated cycloalkyl, saturated or partially unsaturated heterocyclyl, aryl, heteroaryl, F, Cl, Br, I, CN, OR$^6$, C(=O)R$^6$, C(=O)OR$^6$, OC(=O)R$^6$, C(=O)NR$^6$R$^7$, OC(=O)NR$^6$R$^7$, OC(=S)NR$^6$R$^7$, NR$^6$R$^7$, NR$^6$C(=O)R$^7$, SR$^6$, S(O)R$^6$, S(O)$_2$R$^6$ or S(O)$_2$NR$^6$R$^7$, wherein said alkyl, alkenyl, alkynyl, heteroalkyl, cycloalkyl, heterocyclyl, aryl and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—Cl, $V_n$—Br, $V_n$—I, $V_n$—CF$_3$, $V_n$—CN, $V_n$—OR$^8$, $V_n$—C(=O)R$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, $V_n$—SR$^8$, $V_n$—S(O)R$^8$, $V_n$—S(O)$_2$R$^8$ and $V_n$—S(O)$_2$NR$^8$R$^9$;

R$^4$ is H, methyl, ethyl, F, Cl, Br, I, CF$_3$, CHF$_2$ or CH$_2$F;

R$^6$ and R$^7$ are independently H, alkyl, alkenyl, alkynyl, saturated or partially unsaturated cycloalkyl, saturated or partially unsaturated heterocyclyl, aryl, heteroaryl, OR$^8$, NR$^8$R$^9$, C(=O)NR$^8$R$^9$, C(=O)R$^8$, or C(=O)OR$^8$, wherein said alkyl, alkenyl, alkynyl, cycloalkyl, heterocyclyl, aryl and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl optionally substituted with C(O)O(C$_1$-C$_6$ alkyl), $V_n$-aryl, $V_n$-heteroaryl, $V_n$—F, $V_n$—Cl, $V_n$—Br, $V_n$—I, $V_n$—CF$_3$, $V_n$—CN, $V_n$—OR$^8$, $V_n$—C(=O)R$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, $V_n$—SR$^8$, $V_n$—S(O)R$^8$, $V_n$—S(O)$_2$R$^8$, and $V_n$—S(O)$_2$NR$^8$R$^9$, or R$^6$ and R$^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $V_n$—F, $V_n$—Cl, $V_n$—Br, $V_n$—I, $V_n$—OR$^8$, V —C(=O)OR$^8$, $V_n$—C(=O)NR$^8$R$^9$, $V_n$—NR$^8$R$^9$, $V_n$—NR$^8$C(=O)R$^9$, $V_n$—NR$^8$C(=O)NR$^9$R$^{10}$, alkyl, alkenyl, and alkynyl;

R$^8$, R$^9$ and R$^{10}$ are independently H, alkyl, alkenyl, alkynyl, saturated or partially unsaturated cycloalkyl, saturated or partially unsaturated heterocyclyl, aryl or heteroaryl, wherein said alkyl, alkenyl, alkynyl, cycloalkyl, heterocyclyl, aryl and heteroaryl are optionally substituted with one or more groups independently selected from oxo, alkyl, alkenyl, alkynyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—Cl, $V_n$—Br, $V_n$—I, $V_n$—OR$^a$, $V_n$—NR$^a$R$^b$, $V_n$—C(=O)OR$^a$, $V_n$—C(=O)NR$^a$R$^b$, and $V_n$—NR$^a$C(=O)R$^b$, or R$^8$ and R$^9$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, $V_n$—F, $V_n$—Cl, $V_n$—Br, $V_n$—I, $V_n$OR$^3$, and $V_n$—CN, or R$^9$ and R$^{10}$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, $V_n$—F, $V_n$—Cl, $V_n$—Br, $V_n$—I, $V_n$—OR$^a$, and $V_n$—CN;

R$^{11}$ is H, methyl, ethyl, F, Cl, Br, I, CF$_3$, CHF$_2$, CH$_2$F, OH, O—(C$_1$-C$_4$ alkyl), or NH$_2$;

R$^{12}$ and R$^{13}$ are independently H, alkyl, alkenyl, alkynyl, heteroalkyl, saturated or partially unsaturated cycloalkyl, saturated or partially unsaturated heterocyclyl, aryl, heteroaryl, F, Cl, Br, I, CF$_3$, CN, OR$^6$, C(=O)R$^6$, C(=O)OR$^6$, OC(O)R$^6$, C(=O)NR$^6$R$^7$, NR$^6$R$^7$, NR$^6$C(=O)R$^7$, SR$^6$, S(O)R$^6$ or S(O)$_2$R$^6$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN; $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, alkyl, alkenyl, alkynyl, saturated and partially unsaturated $V_n$-cycloalkyl, saturated and partially unsaturated $V_n$-heterocyclyl, $V_n$-aryl, and $V_n$-heteroaryl, wherein said heterocyclyl is optionally substituted with one or more oxo, or R$^{12}$ and R$^{13}$ together with the atoms to which they are attached form a saturated, partially unsaturated or aromatic carbocyclic or heterocyclic ring, wherein said carbocyclic and heterocyclic rings are optionally substituted with one or more groups independently selected from alkyl, alkenyl, alkynyl, heteroalkyl, saturated or partially unsaturated cycloalkyl, saturated or partially unsaturated heterocyclyl, aryl, heteroaryl, oxo, F, Cl, Br, I, CF$_3$, CN, OR$^6$, C(=O)R$^6$, C(=O)OR$^6$, OC(=O)R$^6$, C(=O)NR$^6$R$^7$, NR$^6$R$^7$, NR$^6$C(=O)R$^7$, SR$^6$, S(O)R$^6$, S(O)$_2$R$^6$ and SO$_2$NR$^6$R$^7$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN, $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, alkyl, alkenyl, alkynyl, saturated and partially unsaturated $V_n$-heterocyclyl, $V_n$-aryl, and $V_n$-heteroaryl;

R$^{14}$ and R$^{15}$ are independently H, methyl, ethyl, F, Cl, Br, I, CF$_3$, CHF$_2$, CH$_2$F, OH, O—(C$_1$-C$_4$ alkyl), or NH$_2$;

R$^a$ and R$^b$ are independently H, alkyl, alkenyl, alkynyl, saturated or partially unsaturated $V_n$-cycloalkyl, saturated or partially unsaturated $V_n$-heterocyclyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocyclyl, $V_n$-aryl, and $V_n$-heteroaryl are optionally substituted with one or more OH;

V is alkylene having from 1 to 12 carbons, or alkenylene or alkynylene each having from 2 to 12 carbons, wherein said alkylene, alkenylene, or alkynylene are optionally substituted with one or more groups independently selected from alkyl, alkenyl, alkynyl, heteroalkyl, saturated and partially unsaturated cycloalkyl, saturated and partially unsaturated heterocyclyl, aryl, heteroaryl, F, Cl, Br, I, CF$_3$, cyano, OR$^8$, C(=O)OR$^8$, OC(=O)R$^8$, C(=O)NR$^8$R$^9$, NR$^8$R$^9$, and NR$^8$C(=O)R$^9$; and n is 0 or 1.

In certain embodiments of Formula I wherein R$^1$ and R$^2$ are each 5 membered single-ring heteroaryl groups, R$^1$ does not have a substituent represented by C(=O)OR$^d$ or C(=O) NR$^e$R$^f$, wherein R$^d$ is H, alkyl, alkenyl, alkynyl, cycloalkyl, cycloalkyl-alkyl, cycloalkenyl-alkyl, arylalkyl or aryl, and R$^e$ and R$^f$ are independently H, alkyl, alkenyl, alkynyl, cycloalkyl, cycloalkyl-alkyl, cycloalkenyl-alkyl, arylalkyl, aryl heterocyclyl, or acyl, or R$^e$ and R$^f$ together with the N atom form a heterocyclic ring. The compounds according to this definition were disclosed in the provisional application from which the present invention claims priority, and are provided as an embodiment of the invention.

In certain embodiments, provided are compounds of Formula I wherein:

R$^2$ is aryl, heteroaryl, saturated or partially unsaturated cycloalkyl, or saturated or partially unsaturated heterocyclyl, wherein said aryl, heteroaryl, cycloalkyl and heterocyclyl are monocyclic or bicyclic and are further optionally substituted with one or more groups independently selected from alkyl, alkenyl, alkynyl, heteroalkyl, saturated and partially unsaturated cycloalkyl, saturated and partially unsaturated heterocyclyl, aryl, heteroaryl, F, Cl, Br, I, CF$_3$, CN, OR$^6$, C(=O)R$^6$, C(=O)OR$^6$, OC(=O)R$^6$, O(CH$_2$)$_n$C(=O)OR$^6$, O(CH$_2$)$_n$C(=O)NR$^6$R$^7$, C(=O)NR$^6$R$^7$, NR$^6$R$^7$, NR$^6$C(=O)R$^7$, SR$^6$, S(O)R$^6$, and S(O)$_2$R$^6$, and wherein said alkyl, alkenyl, alkynyl, heteroalkyl, cycloalkyl, heterocyclyl, aryl, and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—Cl, $V_n$—Br, $V_n$—I, $V_n$—CF$_3$, $V_n$—CN, $V_n$—OR$^8$, $V_n$—C(=O)R$^8$, $V_n$—C(=O)OR$^8$, $V_n$—OC(=O)R$^3$, $V_n$—C(=O)NR$^8$R$^9$, $V_n$—NR$^8$R$^9$, $V_n$—NR$^8$C(=O)R$^9$, $V_n$—SR$^8$, $V_n$—S(O)R$^8$, and $V_n$—S(O)$_2$R$^8$; and R$^6$ and R$^7$ are independently H, alkyl, alkenyl, alkynyl, saturated or partially unsaturated cycloalkyl, saturated or partially unsaturated heterocyclyl, aryl, heteroaryl, OR$^8$, NR$^8$R$^9$, C(=O)NR$^8$R$^9$, C(=O)R$^8$, or C(=O)OR$^8$, wherein said alkyl, alkenyl, alkynyl, cycloalkyl, heterocyclyl, aryl and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—Cl, $V_n$—Br, $V_n$—I, $V_n$—CF$_3$, $V_n$—CN, $V_n$—OR$^8$$V_n$—C(=O)R$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, $V_n$—SR$^8$, $V_n$—S(O)R$^8$, $V_n$—S(O)$_2$R$^8$, and $V_n$—S(O)$_2$NR$^8$R$^9$, or R$^6$ and R$^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $V_n$—F, $V_n$—Cl, $V_n$—Br, $V_n$—I, $V_n$—OR$^8$, $V_n$—C(=O)OR$^8$, $V_n$—C(=O)NR$^8$R$^9$, $V_n$—NR$^8$R$^9$, $V_n$—NR$^8$C(=O)R$^9$, $V_n$—NR$^8$C(=O) NR$^9$R$^{10}$, alkyl, alkenyl, and alkynyl.

In certain embodiments, provided are compounds of Formula I wherein G is CH or CCl, Y is CH, and Z is CR$^3$.

In certain embodiments, L is O.
In certain embodiments, L is S.
In certain embodiments, L is SO.
In certain embodiments, L is SO$_2$.
In certain embodiments, L is NR$^{14}$. In particular embodiments, L is NH.
In certain embodiments, L is CR$^{14}$R$^{15}$. In particular embodiments, L is CH$_2$.

In certain embodiments, L is C(=O).

The compounds of Formula I include compounds having the Formula Ia

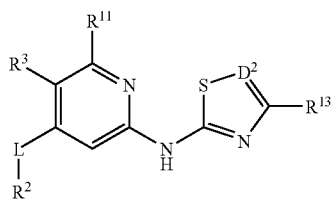

Ia wherein:

L is O, S, SO, SO$_2$, CHOH, C(O), or CH$_2$;

D$^2$ is CR$^{12}$ or N;

R$^2$ is aryl, heteroaryl, saturated or partially unsaturated cycloalkyl, or saturated or partially unsaturated heterocyclyl optionally substituted with oxo, wherein said aryl, heteroaryl, cycloalkyl and heterocyclyl are monocyclic or bicyclic and are further optionally substituted with one or more groups independently selected from C$_1$-C$_6$ alkyl, F, Cl, Br, I, CF$_3$, CN, OR$^6$, C(=O)R$^6$, C(=O)OR$^6$, O(CH$_2$)$_n$C(=O)OR$^6$, C(=O)NR$^6$R$^7$ and NO$_2$;

R$^3$ is H, Br, OR$^6$, SR$^6$, C(O)OR$^6$, C(O)NR$^6$R$^7$, C(O)R$^6$, heteroaryl, or C$_1$-C$_6$ alkyl substituted with one or more groups independently selected from V$_n$-aryl, V$_n$—OR$^8$, V$_n$—C(=O)OR$^8$ and V$_n$—NR$^8$R$^9$;

R$^6$ and R$^7$ are independently H, C$_1$-C$_6$ alkyl, saturated or partially unsaturated cycloalkyl, aryl, or heteroaryl, wherein said alkyl is optionally substituted with one or more groups independently selected from V$_n$-heterocyclyl [optionally substituted with C(O)O(C$_1$-C$_6$ alkyl)], V$_n$-heteroaryl, V$_n$—C(=O)OR$^8$, or R$^6$ and R$^7$ together with the atoms to which they are attached form a saturated or partially unsaturated heterocyclic ring, wherein said heterocyclic ring optionally comprises one or more additional ring nitrogen heteroatoms, wherein said heterocyclic ring is optionally substituted with one or more groups independently selected from C$_1$-C$_6$ alkyl;

R$^8$, R$^9$ and R$^{10}$ are independently H or alkyl;

R$^{11}$ is H or Cl;

R$^{12}$ and R$^{13}$ are independently H, C$_1$-C$_6$ alkyl (optionally substituted with one or more groups independently selected from V$_n$—OR$^8$, or V$_n$—C(=O)OR$^8$)$_3$ saturated or partially unsaturated cycloalkyl, saturated or partially unsaturated heterocyclyl, aryl, or heteroaryl (optionally substituted with C$_1$-C$_6$ alkyl), or R$^{12}$ and R$^{13}$ together with the atoms to which they are attached form a saturated, partially unsaturated or aromatic heterocyclic ring;

each V is independently alkylene having from 1 to 4 carbons or alkenylene having from 2 to 4 carbons; and each n is independently 0 or 1.

In certain embodiments of compounds of Formula I, R$^{11}$ is hydrogen.

In certain embodiments of compounds of Formula I, R$^4$ is hydrogen.

In certain embodiments of compounds of Formula I, R$^1$ is a heteroaryl ring selected from

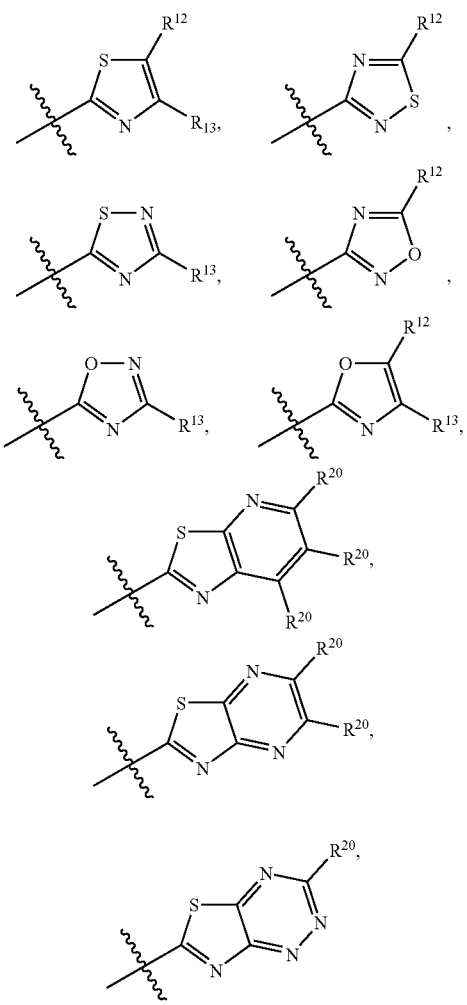

wherein R$^{20}$ is H, alkyl, alkenyl, alkynyl, heteroalkyl, saturated or partially unsaturated cycloalkyl, saturated or partially unsaturated heterocyclyl, aryl, heteroaryl, F, Cl, Br, I, CF$_3$, CN, OR$^6$, C(=O)R$^6$, C(=O)OR$^6$, OC(=O)R$^6$, C(=O)NR$^6$R$^7$, NR$^6$R$^7$, NR$^6$C(=O)R$^7$, SR$^6$, S(O)R$^6$, S(O)$_2$R$^6$ or SO$_2$NR$^6$R$^7$, wherein said alkyl, alkenyl, alkynyl, cycloalkyl, heterocyclyl, aryl and heteroaryl are optionally substituted with one or more groups independently selected from oxo, V$_n$—F, V$_n$—Cl, V$_n$—Br, V$_n$—I, V$_n$—CF$_3$, V$_n$—CN, V$_n$—OR$^8$, V$_n$—C(=O)OR$^8$, V$_n$—OC(=O)R$^3$, V$_n$—C(=O)NR$^8$R$^9$, V$_n$—NR$^8$R$^9$, V$_n$—NR$^8$C(=O)R$^9$, alkyl, alkenyl, alkynyl, saturated and partially unsaturated V$_n$-cycloalkyl, saturated and partially unsaturated V$_n$-heterocyclyl, V$_n$-aryl, and V$_n$-heteroaryl, and wherein each R$^{20}$ is independent of the other.

In particular embodiments of Formula I, R$^1$ is selected from the structures:

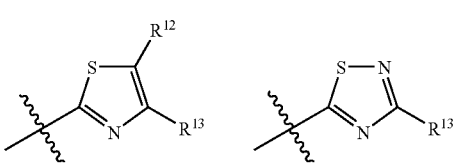

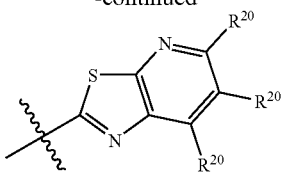

wherein $R^{12}$ and $R^{13}$ are as defined herein.

In particular embodiments, $R^{20}$ is H.

In certain embodiments, $R^{12}$ and $R^{13}$ are independently selected from H, alkyl, alkenyl, alkynyl, $OR^6$, $C(=O)OR^6$, $C(=O)NR^6R^7$, $NR^6R^7$, $NR^6C(=O)R^7$ and heterocyclyl, wherein said alkyl, alkenyl, alkynyl, and heterocyclyl are optionally substituted with one or more groups independently selected from $V_n$—$OR^6$, $V_n$—$C(=O)OR^6$, $V_n$—$C(=O)NR^6R^7$, $V_n$—$NR^6R^7$, $V_n$—$NR^6C(=O)R^7$ and $V_n$-heterocyclyl. For example, in certain embodiments $R^{12}$ and $R^{13}$ are independently selected from H, $CH_3$, $CH_2CH_2OH$, $CH_2COOH$ and $CH_2CH_2COOH$. In certain embodiments, $R^{12}$ is H and $R^{13}$ is methyl.

In other embodiments of Formula I, $R^{12}$ and $R^{13}$ are independently selected from H, $CF_3$, $C_1$-$C_6$ alkyl [optionally substituted with $V_n$—$OR^8$, $V_n$—$C(=O)OR^8$ or $V_n$-aryl], $C_3$-$C_6$ cycloalkyl, a 5-6 membered heterocyclyl having an oxygen atom, heteroaryl, and $CO_2R^6$. In certain embodiments, V is $C_1$-$C_4$ alkylene and n is 0 or 1.

In other embodiments of Formula I, $R^{13}$ is an N-(1-6C alkanoyl)-piperidin-4-yl group. As used herein, the term "alkanoyl" as used herein, refers to the group —$C(=O)$-(1-6C alkyl), wherein the alkyl portion is of the straight or branched configuration. Exemplary alkanoyl groups include, but are not limited to, acetyl (ethanoyl), n-propanoyl, n-butanoyl, 2-methylpropanoyl and n-pentanoyl.

Examples of $R^{12}$ and $R^{13}$ when represented by a $C_1$-$C_6$ alkyl group substituted by $V_n$—$OR^8$ include groups where V is $C_1$-$C_4$ alkylene, n is 1, and $R^6$ is $C_1$-$C_6$ alkyl or H. A particular value includes —($C_1$-$C_6$ alkyl)OH.

Examples of $R^{12}$ and $R^{13}$ when represented by a $C_1$-$C_6$ alkyl group substituted by $V_n$—$CO_2R^6$ include groups where V is $C_1$-$C_4$ alkylene, n is 1, and $R^1$ is $C_1$-$C_6$ alkyl or H. Particular values include —($C_1$-$C_6$ alkyl)$CO_2H$ and —($C_1$-$C_6$ alkyl)$CO_2$($C_1$-$C_6$ alkyl).

Examples of $R^{12}$ and $R^{13}$ when represented by a $C_1$-$C_6$ alkyl group substituted by $V_n$-aryl include groups where V is $C_1$-$C_4$ alkylene, n is 1, for example and aryl is phenyl. A particular value is a benzyl group.

A particular value for $R^{12}$ and $R^{13}$ when represented by a 5-6 membered heterocycle having an oxygen atom is a tetrahydrofuranyl ring.

Examples of $R^{12}$ and $R^{13}$ when represented by a heteroaryl ring include 5-6 membered heteroaryl rings having one to three heteroatoms independently selected from N and S. Particular values include pyridyl and thienyl rings.

Examples of $R^{12}$ and $R^{13}$ when represented by a $CO_2R^6$ group include groups where $R^6$ is H or $C_1$-$C_6$ alkyl.

In particular embodiments of Formula I, $R^{12}$ and $R^{13}$ are independently H, methyl, ethyl, isopropyl, butyl, isobutyl, t-butyl, $CF_3$, cyclopropyl, cyclohexyl, —$CH_2CH_2OH$, $(CH_2)_2CO_2H$, —$(CH_2)_2CO_2Me$, —$(CH_2)CO_2Et$, $CH_2CH_2Ph$, phenyl, 2-pyridyl, 3-pyridyl, 4-pyridyl, 3-thienyl, 2-tetrahydrofuranyl or $CO_2Et$.

In particular embodiments, $R^{12}$ is H.

In certain embodiments of Formula I, $R^2$ is an aryl or cycloalkyl ring selected from phenyl, 1-naphthyl, 2-naphthyl, 1-tetrahydronaphthalenyl, 2-tetrahydronaphthalenyl, 3-tetrahydronaphthalenyl, 4-tetrahydronaphthalenyl, 5-tetrahydronaphthalenyl, 6-tetrahydronaphthalenyl, 7-tetrahydronaphthalenyl, 8-tetrahydronaphthalenyl, cyclohexyl, and substituted forms thereof.

In certain embodiments, $R^2$ is selected from

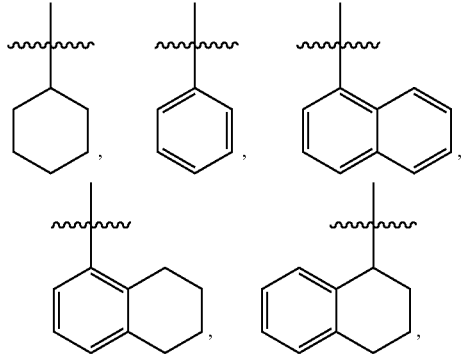

and substituted forms thereof.

For example, in certain embodiments, $R^2$ is phenyl optionally substituted with one or more groups independently selected from F, Cl, Br, I, CN, alkyl, $CF_3$, $OR^6$, $C(=O)OR^6$, $O(CH_2)_nC(=O)OR^6$, $C(=O)NR^6R^7$ and $NR^6C(=O)R^7$, wherein said alkyl is optionally substituted with one or more groups independently selected from $V_n$—$OR^6$, $V_n$—$C(=O)OR^6$, $V_n$—$O(CH_2)_nC(=O)OR^6$, $V_n$—$C(=O)NR^6R^7$ and $V_n$—$NR^6C(=O)R^7$.

In other embodiments, $R^2$ is phenyl optionally substituted with one or more groups independently selected from F, Cl, CN, $CF_3$, —$OR^6$, —$CO_2R^6$, —$O(CH_2)_nC(=O)OR^6$, —$C(=O)NR^6R^7$ and $C_1$-$C_6$ alkyl (optionally substituted with OH).

Examples of phenyl substituents having the formula —$OR^6$ include groups wherein $R^6$ is H or $C_1$-$C_6$ alkyl.

Examples of phenyl substituents having the formula —$C(=O)OR^6$ include groups wherein $R^6$ is H or a $C_1$-$C_6$ alkyl group optionally substituted with OH.

Examples of phenyl substituents having the formula —$O(CH_2)C(O)OR^6$ include groups wherein $R^6$ is H or $C_1$-$C_6$ alkyl.

Examples of phenyl substituents having the formula —$C(=O)NR^6R^7$ include groups wherein $R^6$ and $R^7$ are independently H or $C_1$-$C_6$ alkyl. In certain embodiments the alkyl group is substituted with —$NR^8R^9$ (wherein $R^8$ and $R^9$ are independently H or $C_1$-$C_6$ alkyl), a 5-membered heteroaryl having 1-2 ring nitrogen atoms, or a 5-6 membered heterocycle having 1-2 ring heteroatoms independently selected from N and O.

Further examples of phenyl substituents having the formula —$C(=O)NR^6R^7$ include groups wherein —$NR^6R^7$ forms a 5-6 membered heterocyclic ring optionally having a ring nitrogen and optionally having a second ring N atom. Exemplary values of the heterocyclic ring include pyrrolidinyl, piperidinyl, and piperazinyl. In particular examples, $NR^6R^7$ form a piperidinyl ring. In certain embodiments the heterocyclic ring is substituted with $C_1$-$C_6$ alkyl, such as methyl or ethyl.

Examples of phenyl substituents represented by a $C_1$-$C_6$ alkyl group substituted by $V_n$—$OR^6$ include groups wherein V is $C_1$-$C_4$ alkylene, n is 0 or 1, and $R^6$ is H or $C_1$-$C_6$ alkyl. A particular-value is $CH_2CH_2OH$.

In particular embodiments of Formula I, $R^2$ is phenyl optionally substituted with one or more groups independently selected from Cl, F, CN, Me, iPr, CF₃, —OCH₃, —OH, —OCH₂CH₂OH, —CH₂OH, —OCH₂CO₂H, —OCH₂CO₂(t-Bu), —CO₂Me, —CO₂Et, —CO₂H, —C(O)NHCH₂CH₂NMe₂, C(O)NHCH₂CH₂CH₂N(CH₃)₂, —C(O)N(Me)CH₂CH₂N(CH₃)₂, C(O)NHCH₂CH₂NHCH(CH₃)₂, —C(O)NH(CH₂)₃(N-morpholinyl), —C(O)(N-pyrrolidinyl), —C(O)NHCH₂CH₂(imidazolyl), —OCH₂C(O)OC(CH₃)₂, —OCH₂C(O)OH,
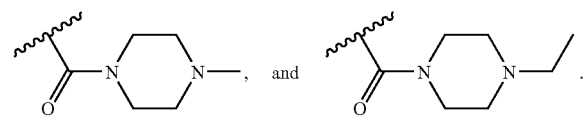
Further exemplary embodiments of R² include, but are not limited to, the structures:
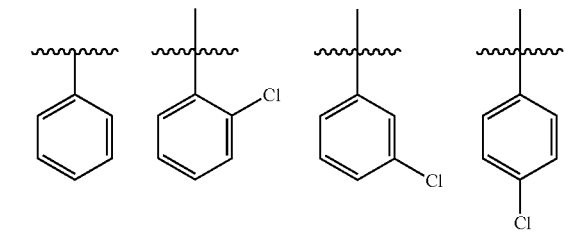
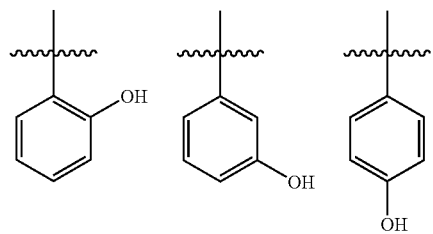
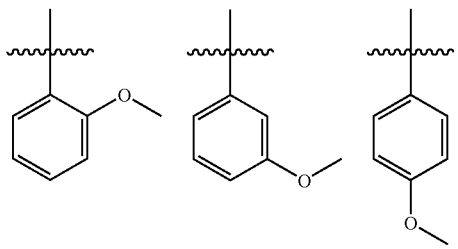
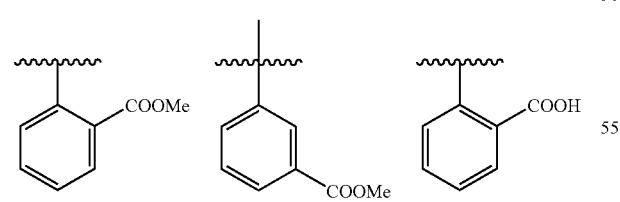
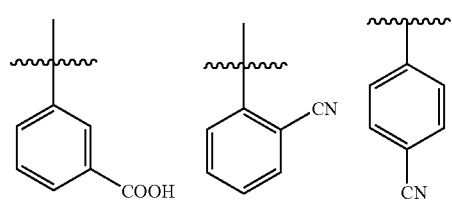
-continued
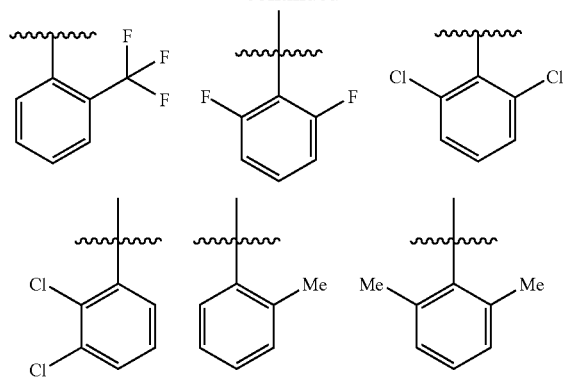
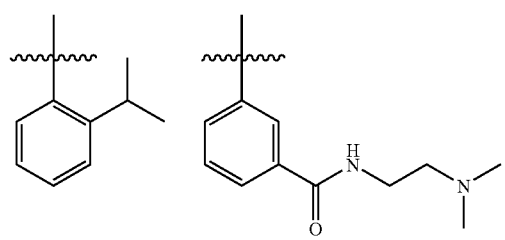
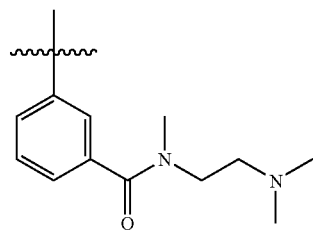
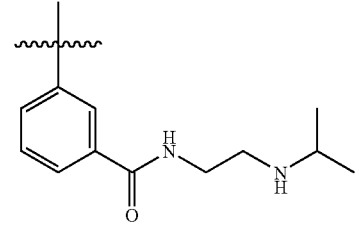
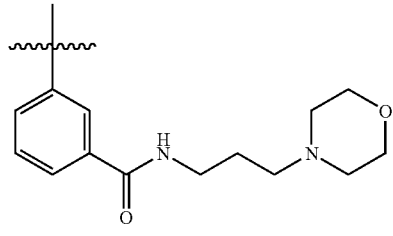
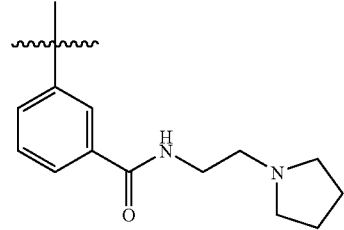

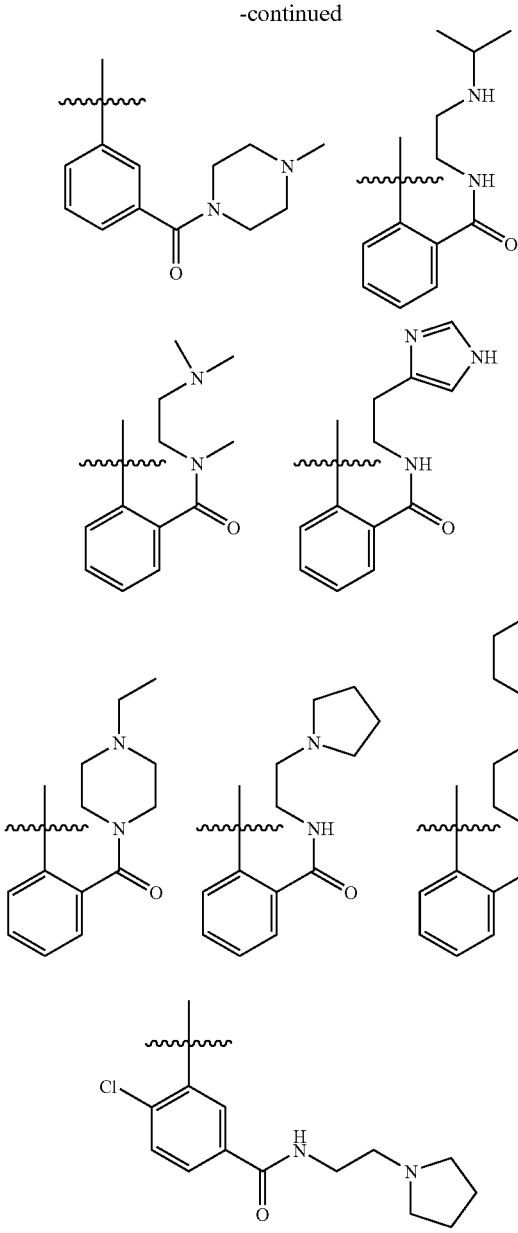
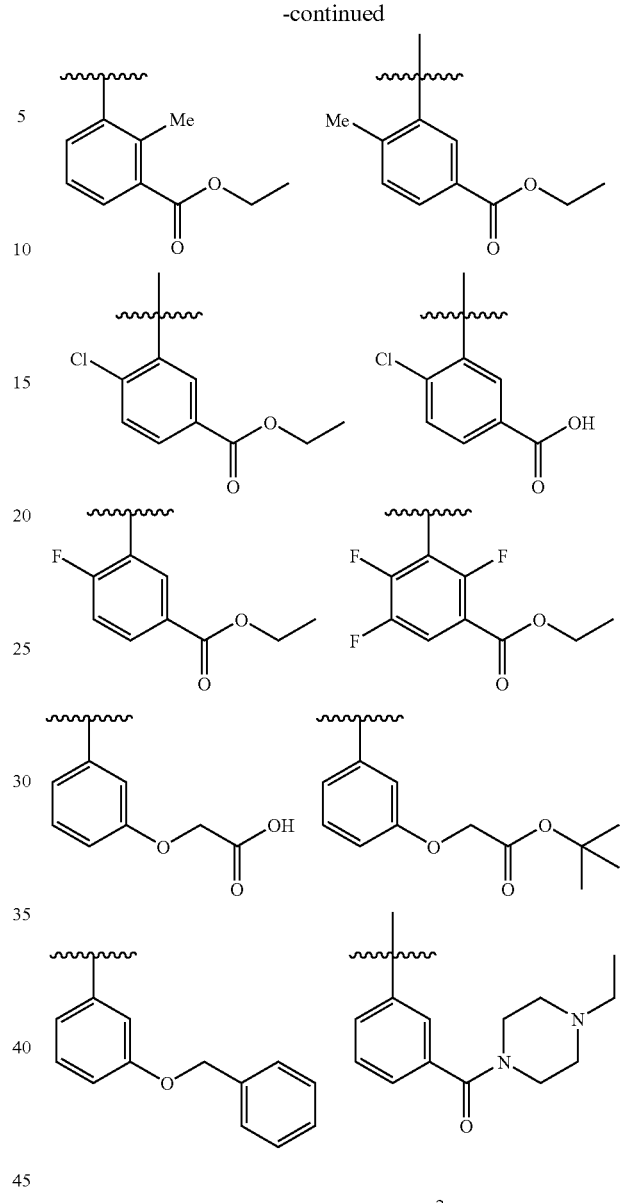
Further exemplary embodiments of R² include the structures:
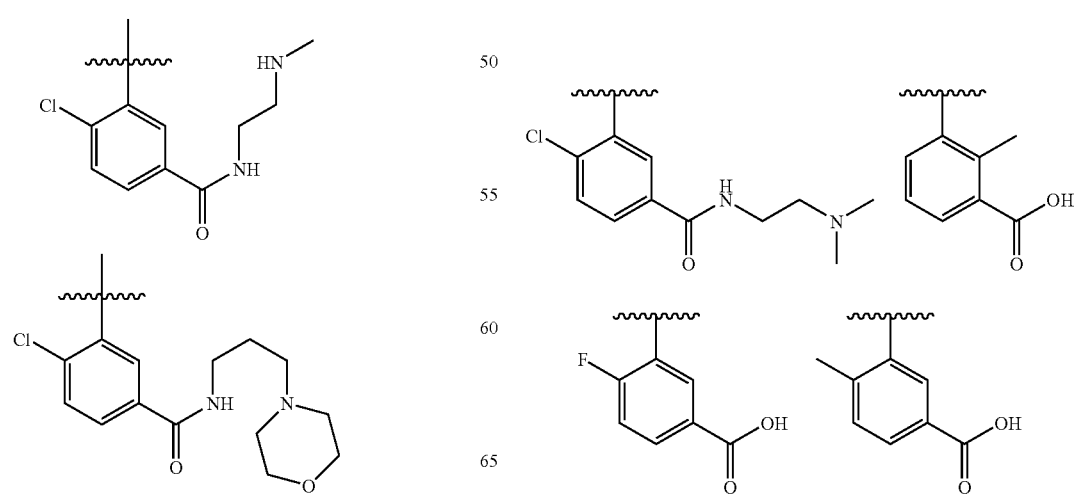

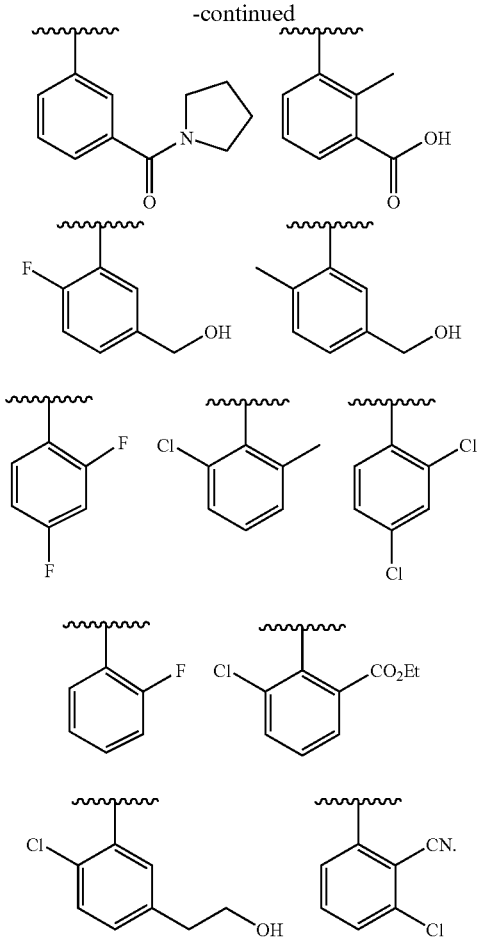

Exemplary embodiments of R² further include, but are not limited to, heteroaryl and heterocyclic rings selected from 2-pyridyl, 3-pyridyl, 4-pyridyl, 2-quinolinyl, 3-quinolinyl, 4-quinolinyl, 5-quinolinyl, 6-quinolinyl, 7-quinolinyl, 8-quinolinyl, 2-quinoxalinyl, 3-quinoxalinyl, 5-quinoxalinyl, 6-quinoxalinyl, 7-quinoxalinyl, 8-quinoxalinyl, benzo[d]thiazol-2-yl, 4-benzo[d]thiazolyl, 5-benzo[d]thiazolyl, 6-benzo[d]thiazolyl, 7-benzo[d]thiazolyl, 2-1H-benzo[d]imidazolyl, 1H-benzo[d]imidazole-4-yl, 1H-benzo[d]imidazole-5-yl, 1H-benzo[d]imidazole-6-yl, 1H-benzo[d]imidazole-7-yl, 2-thiophenyl, 3-thiophenyl, 5-tetrahydroquinolinyl, 6-tetrahydroquinolinyl, 7-tetrahydroquinolinyl, 8-tetrahydroquinolinyl, 5-tetrahydroisoquinolinyl, 6-tetrahydroisoquinolinyl, 7-tetrahydroisoquinolinyl, 8-tetrahydroisoquinolinyl, 1-pyrazolyl, 2-pyrazolyl, 3-pyrazolyl, 4-pyrazolyl, 5-pyrazolyl, 1-piperidinyl, 2-piperidinyl, 3-piperidinyl, 4-piperidinyl, and substituted forms thereof.

In other embodiments, R² is a 5-6 membered heteroaryl ring having 1-3 heteroatoms independently selected from N and O (provided the ring does not contain a O—O bond). Examples of heteroaryl rings include 2-pyridyl, 3-pyridyl, 4-pyridyl, 2-imidazolyl, 3-furyl, 1,2,4-oxadiazol-5-yl, 1,3,4-oxadiazol-2-yl, and 2-oxazolyl.

In particular embodiments, R² is a heteroaryl ring optionally substituted with one or two groups independently selected from NO₂, Cl, Br, CN, CF₃, and C₁-C₆ alkyl.

Exemplary embodiments of R² includes the structures:

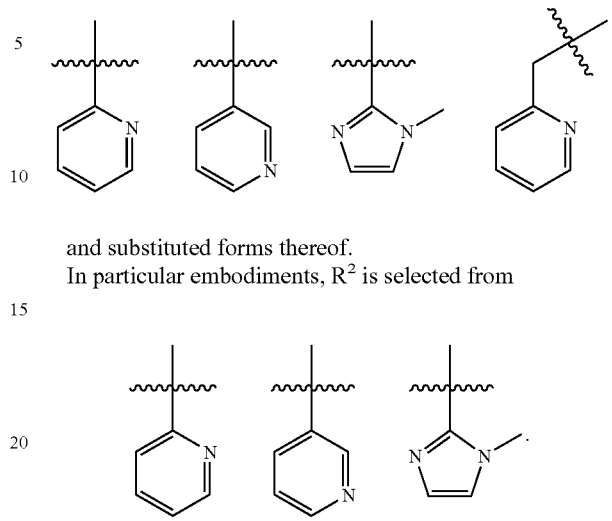

and substituted forms thereof.
In particular embodiments, R² is selected from

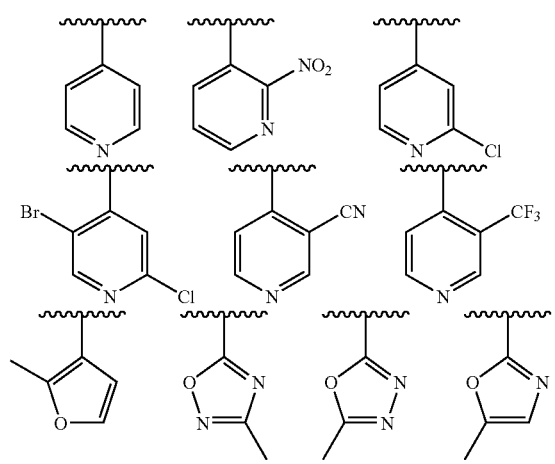

Further exemplary embodiments of R² when represented by a heteroaryl ring include the structures:

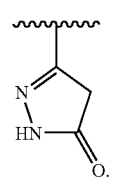

In another embodiment, R² is a saturated or partially unsaturated 5 membered heterocyclic ring. In certain embodiments, there heterocyclic ring has one or two ring heteroatoms, for example, a 4,5-dihydro-1H-pyrazolyl ring. In certain embodiments, the heterocyclic ring is substituted with oxo. A particular example of R² is the structure:

In other embodiments, R² is a 9-10 membered heteroaryl ring having a nitrogen atom and optionally having 1 to 2 additional ring heteroatoms independently selected from N, O and S (provided the ring does not contain a O—O or S—S bond). In certain embodiments, the bicyclic heterocyclic ring is quinolyl, isoxazolo[5,4-b]pyridyl, thienopyridyl, pyrazolopyrimidyl, or 5,6,7,8-tetrahydropyrido[4,3-d]pyrimidyl.

In certain embodiments, the bicyclic heterocyclic ring is substituted with $C_1$-$C_6$ alkyl (for example, methyl).

Further exemplary embodiments when $R^2$ is represented by a 9-10 membered heteroaryl ring include the structures:

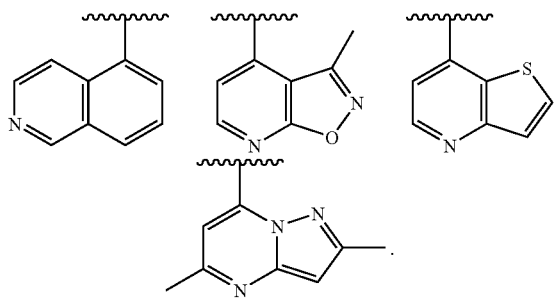

In certain embodiments, $R^2$ is a partially unsaturated 10 membered bicyclic heterocyclic ring having 1-3 nitrogen atoms. In certain embodiments, the bicyclic heterocyclic ring is substituted with C(O)O-tBu. Exemplary embodiments include the structures:

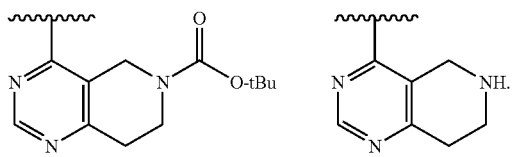

In certain embodiments, $R^2$ is a 5-6 membered cycloalkyl ring optionally substituted with $C_1$-$C_6$ alkyl. In particular embodiments, $R^2$ is cyclopentyl, cyclohexyl or 2-methylcyclohexyl.

In certain embodiments of Formula I, Z is N.

In other embodiments of Formula I, Z is $CR^3$.

In certain embodiments of Formula I, $R^3$ is selected from F, Cl, Br, I, CN, $V_n$—$OR^6$, $V_n$—$SR^6$, $V_n$—$S(O)R^6$, $V_n$—$S(O)_2R^6$, $V_n$—$NR^6R^7$, $V_n$—$C(\!=\!O)NR^6R^7$, $V_n$—$C(\!=\!O)OR^6$, $V_n$—$C(\!=\!O)R^6$, $V_n$-aryl, $V_n$-heteroaryl, alkyl, alkenyl and alkynyl, wherein said aryl, heteroaryl, alkyl, alkenyl and alkynyl are substituted or unsubstituted.

In other embodiments of Formula I, $R^3$ is H, Br, $OR^6$, $SR^6$, $C(O)OR^6$, $C(O)NR^6R^7$, $C(O)R^6$, a 5-6 membered heteroaryl group having at least one ring nitrogen atom, or a $C_1$-$C_6$ alkyl group optionally substituted with $V_n$—$CO_2R^6$, $V_n$—$OR^6$, $V_n$—$NR^6R^7$ or $V_n$—Ar. In certain embodiments, V is $C_1$-$C_4$ alkylene or $C_2$-$C_4$ alkenylene. In certain embodiments, n is 0 or 1.

In certain embodiments, $R^3$ is alkyl, alkenyl or alkynyl substituted with $V_n$—$SR^6$ wherein $R^6$ is alkyl, alkenyl, alkynyl, cycloalkyl, heterocycle, aryl or heteroaryl, wherein said alkyl, alkenyl, alkynyl, cycloalkyl, heterocycle, aryl and heteroaryl are optionally substituted with one or more groups independently selected from alkyl, alkenyl, alkynyl, $V_n$-cycloalkyl, $V_n$-heterocycle, $V_n$-aryl and $V_n$-heteroaryl. For example, in certain embodiments $R^3$ is S-cyclohexyl, S-phenyl, S-(4-pyridyl), $SCH_2CH_2C(\!=\!O)OMe$, $SCH_2CH_2NMe_2$, $SCH_2CH_2Me_2$, $SCH_2$-phenyl, $SCH_2$-(2-pyridyl), or $SCH_2$-(4-piperidinyl).

In other embodiments of Formula I, $R^3$ is a group having the formula $SR^6$ wherein $R^6$ is cycloalkyl, aryl, heteroaryl, a $C_1$-$C_6$ alkyl group substituted with $V_n$—$C(O)OR^8$, $V_n$-heteroaryl, or $V_n$-heterocyclyl [wherein the heterocyclyl group is optionally substituted with $C(O)O(C_1$-$C_6$ alkyl)]. In certain embodiments, V is $C_1$-$C_4$ alkylene. In certain embodiments, n is 0 or 1.

A particular example of $SR^6$ when represented by S-cycloalkyl includes S—($C_3$-$C_6$ cycloalkyl). A particular value includes S-cyclohexyl.

A particular example of $SR^1$ when represented by S-aryl includes S-phenyl.

Particular examples of $SR^6$ when represented by S-heteroaryl include groups wherein the heteroaryl moiety is a 5-6 membered ring having a nitrogen atom and optionally having an additional atom selected from N and S, for example, pyridyl, pyrazinyl and thienyl rings. Particular examples include the structures:

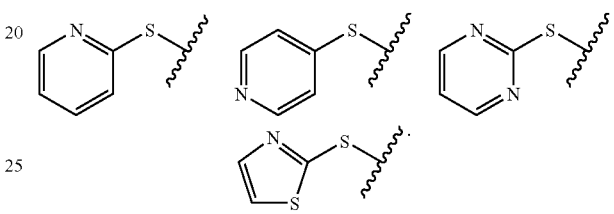

Examples of $SR^6$ when $R^6$ represents a $C_1$-$C_6$ alkyl group substituted with $V_n$—$C(O)OR^8$ include groups wherein V is $C_1$-$C_4$ alkylene, n is 1 and $R^8$ is $C_1$-$C_6$ alkyl. A particular value is S—$CH_2CH_2C(O)OCH_3$.

Examples of $SR^6$ when $R^6$ represents a $C_1$-$C_6$ alkyl group substituted with $V_n$-heteroaryl include groups wherein the heteroaryl moiety is a 6 membered heteroaryl, such as a pyridyl or pyrimidyl group. A particular value includes S—$CH_2$-(2-pyridyl).

Examples of $SR^6$ when $R^6$ represents ($C_1$-$C_6$ alkyl)-heterocyclyl include groups wherein the heterocycle is a 5-6 membered azacycle, such as a piperidyl ring. In certain embodiments the azacycle is substituted with $CO_2$-tBu. Particular values include:

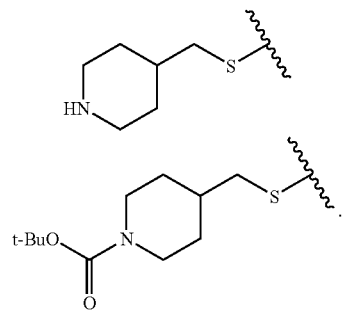

In other embodiments, $R^3$ is alkyl, alkenyl or alkynyl substituted with $V_n$—$OR^6$ wherein $R^6$ is H, alkyl, alkenyl, alkynyl, aryl, heteroaryl, or $C(\!=\!O)OR^8$, wherein said alkyl, alkenyl, alkynyl, aryl and heteroaryl are optionally substituted with one or more groups independently selected from alkyl, alkenyl, alkynyl, $V_n$-aryl, $V_n$-heteroaryl, or $V_n C(\!=\!O)OR^8$. For example, in certain embodiments $R^3$ is $CH_2OH$, OH, OMe $OCH_2$-phenyl, $OCH_2$-(3-pyridyl), or $OCH_2C(\!=\!O)OMe$.

In a particular embodiment, $R^3$ is $CH_2OH$.

In other embodiments of Formula I, $R^3$ is a group having the formula $OR^6$. In certain embodiments, $R^6$ is H or $C_1$-$C_6$ alkyl. In particular embodiments, $R^3$ is OH or $OCH_3$.

In other embodiments, $R^3$ is alkyl, alkenyl or alkynyl, wherein said alkyl, alkenyl and alkynyl are optionally substituted with one or more groups independently selected from alkyl, alkenyl, alkynyl, $V_n$-cycloalkyl, $V_n$-heterocyclyl, $V_n$-aryl and $V_n$-heteroaryl. For example, in certain embodiments $R^3$ is $CH_2CH(CH_3)_2$, $CH_2$-(1-piperidinyl), $CH_2CH_2$(4-piperidinyl), or $CH_2CH_2$(2-pyridyl).

In other embodiments of Formula I, $R^3$ is a $C_1$-$C_6$ alkyl group substituted with Ar. In certain embodiments, Ar is phenyl. A particular value of $R^3$ includes a benzyl group.

In other embodiments, $R^3$ is alkyl, alkenyl or alkynyl substituted with $V_n$—$NR^6R^7$. For example, in certain embodiments $R^3$ is $CH_2NMe_2$, $CH_2NH$-cyclohexyl, or $CH_2NHCH_2CH_2NMe_2$.

In other embodiments of Formula I, $R^3$ is a $C_1$-$C_6$ alkyl group or a $C_2$-$C_6$ alkene group substituted with $V_n$—$NR^6R^7$. In certain embodiments, V is $C_2$-$C_4$ alkenylene, and n is 0 or 1. In certain embodiments, $R^6$ and $R^7$ are independently H, (3-6C)cycloalkyl, $C_1$-$C_6$ alkyl or $(C_1$-$C_6$ alkyl)N$(C_1$-$C_6$ alkyl)$_2$]. Particular values of $R^3$ include CH=CHCH$_2$N(CH)$_3$, $CH_2NMe_2$, $CH_2NH$-cyclohexyl, and $CH_2NHCH_2CH_2NMe_2$. In other embodiments, $R^3$ is a $C_1$-$C_6$ alkyl group substituted with $V_n$—$NR^6R^7$ wherein $NR^6R^7$ forms a 5-6 membered azacyclic ring, for example a piperidyl ring. A particular value for $R^3$ includes $CH_2$-(1-piperidinyl).

In other embodiments, $R^3$ is optionally substituted aryl or heteroaryl. For example, in certain embodiments $R^3$ is selected from phenyl, 3-pyridyl, 4-pyridyl and substituted forms thereof.

A particular value for $R^3$ is 2-pyridyl.

In other embodiments, $R^3$ is alkyl, alkenyl or alkynyl substituted with one or more groups independently selected from $V_n$—C(=O)$NR^6R^7$ or $V_n$—C(=O)$OR^6$. In certain embodiments, V is $C_1$-$C_4$ alkylene or $C_2$-$C_4$ alkenylene, and n is 0 or 1. For example, in certain embodiments $R^3$ is $CH_2CH_2CO_2Me$, or CH=CHC(O)$OCH_3$.

In certain embodiments of Formula I, $R^3$ is a group having the formula $CO_2R^6$. In certain embodiments, $R^6$ is H or $C_1$-$C_6$ alkyl. Particular values of $R^3$ include $CO_2H$ and $CO_2Et$.

In certain embodiments of Formula I, $R^3$ is a group having the formula $COR^6$. A particular value of $R^3$ is C(O)H.

In certain embodiments of Formula I, $R^3$ is a group having the formula C(O)$NR^6R^7$. In certain embodiments, $R^6$ and $R^7$ are independently H or $C_1$-$C_6$ alkyl optionally substituted with N$(C_1$-$C_6$ alkyl)$_2$. In other embodiments, $NR^6R^7$ forms a 5-6 membered azacyclic ring optionally substituted with $C_1$-$C_6$ alkyl, for example an optionally substituted piperidyl ring. Particular values of $R^3$ include C(O)NHCH$_2$CH$_2$N(CH$_3$)$_2$ and C(O)(N-ethylpiperazin-4-yl).

In certain embodiments of Formula I, $R^3$ is Br.

In certain embodiments of Formula I, $R^3$ is H.

The compounds of Formula I include compounds having the Formula Ib

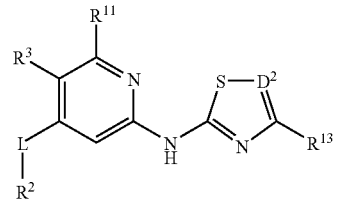

wherein $R^{13}$ is N-(1-6C alkanoyl)-piperidin-4-yl and $R^2$, $R^3$, $R^{11}$, and $D^2$ are as defined for Formula Ia.

In one embodiment of Formula Ib, L is O, S, SO, $SO_2$, CHOH, C(O), or $CH_2$;

In one embodiment of Formula Ib, $D^2$ is $CR^{12}$ or N.

In one embodiment of Formula Ib, $R^2$ is aryl, 3-pyridyl or 8-quinolinyl, wherein said aryl, pyridyl and quinolinyl are optionally substituted with one or more groups independently selected from 1-6C alkyl, Cl, CN, and C(=O)$NR^6R^7$.

In one embodiment of Formula Ib, $R^3$ is H, Br, S-aryl, O-aryl, $CH_2$-aryl, S-heteroaryl, O-heteroaryl or $CH_2$-heteroaryl, wherein said aryl and heteroaryl portions are optionally substituted with one or more groups independently selected from (1-3C) alkyl, F, Cl, Br, CN, $CF_3$, and O-(1-3C alkyl).

In one embodiment of Formula Ib, $R^6$ and $R^7$ are independently H, 1-6C alkyl, -(1-6C alkyl)$NH_2$, -(1-6C alkyl)NH(1-6C alkyl), -(1-6C alkyl)N(1-6C alkyl)$_2$, -(1-6C alkyl)-heteroaryl and -(1-6C alkyl)-heterocycle.

In one embodiment of Formula Ib, $R^8$ and $R^9$ are independently H or 1-6C alkyl;

In one embodiment of Formula Ib, $R^{11}$ is H or Cl.

In one embodiment of Formula Ib, $R^{12}$ is H or 1-6C alkyl.

In certain embodiments of Formula Ib, $D^2$ is $CR^{12}$.

In certain embodiments of Formula Ib, $D^2$ is N.

In certain embodiments of Formula Ib, L is O.

In certain embodiments of Formula Ib, L is S.

In certain embodiments of Formula Ib, L is SO.

In certain embodiments of Formula Ib, L is $SO_2$.

In certain embodiments of Formula Ib, L is CHOH.

In certain embodiments of Formula Ib, L is C(O).

In certain embodiments of Formula Ib, L is $CH_2$.

In certain embodiments of Formula Ib, $R^{11}$ is H.

In certain embodiments of Formula Ib $R^{12}$ is H, methyl, ethyl, propyl, isopropyl, butyl, isobutyl, or t-butyl.

In particular embodiments of Formula Ib, $R^{12}$ is H.

In certain embodiments of Formula Ib, $R^2$ is aryl optionally substituted with one or more groups independently selected from Cl, 1-6C alkyl, and C(=O)$NR^6R^7$.

Examples of aryl substituents for Formula Ib having the formula —C(=O)$NR^6R^7$ include groups wherein $R^6$ and $R^7$ are independently H, 1-6C alkyl, -(1-6C alkyl)$NH_2$, -(1-6C alkyl)NH(1-6C alkyl), -(1-6C alkyl)N(1-6C alkyl)$_2$, -(1-6C alkyl)-heteroaryl and -(1-6C alkyl)-heterocycle.

Examples of $R^6$ and $R^7$ for Formula Ib when represented by -(1-6C alkyl)-heterocycle include groups wherein the heterocycle is a 5-6 membered ring having 1-2 atoms independently selected from N and O. A particular example of the heterocyclic ring is a morpholinyl group.

Examples, of $R^6$ and $R^7$ for Formula Ib when represented by -(1-6C alkyl)-heteroaryl include groups wherein the heteroaryl is a 5-membered ring having 1-2 nitrogen atoms. A particular value for the heteroaryl is an imidazolyl group.

In certain embodiments of Formula Ib, $R^2$ is a phenyl group optionally substituted with one or more groups independently selected from Cl, Me, —C(O)NHCH$_2$CH$_2$NMe$_2$, —C(O)

NHCH$_2$CH$_2$CH$_2$N(CH$_3$)$_2$, —C(O)NMe)CH$_2$CH$_2$N(CH$_3$)$_2$, —C(O)N—HCH$_2$CH$_2$NHCH(CH$_3$)$_2$, —C(O)NH(CH$_2$)$_3$(N-morpholinyl), —C(O)(N-pyrrolidinyl) and —C(O)NHCH$_2$CH$_2$(imidazolyl).

In particular embodiments of Formula Ib, R$^2$ is phenyl optionally substituted with one or two groups independently selected from Cl, Me and —C(O)NHCH$_2$CH$_2$NMe$_2$.

Particular values of R$^2$ for Formula Ib include the structures:

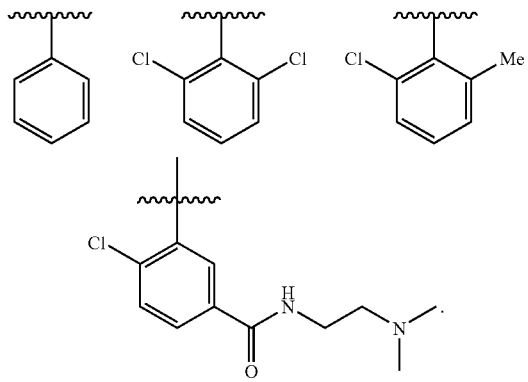

In other embodiments of Formula Ib, R$^2$ is 3-pyridyl optionally substituted with one or more groups independently selected from (1-6C alkyl), CN, and C(=O)NR$^6$R$^7$, wherein the C(=O)NR$^6$R$^7$ group is as defined above.

Exemplary embodiments of R$^2$ for Formula Ib include 3-pyridyl optionally substituted with one or more groups independently selected from methyl, CN, —C(O)NHCH$_2$CH$_2$NMe$_2$, —C(O)NHCH$_2$CH$_2$CH$_2$N(CH$_3$)$_2$, —C(O)N(Me)CH$_2$CH$_2$N(CH$_3$)$_2$, —C(O)NHCH$_2$CH$_2$NHCH(CH$_3$)$_2$, —C(O)NH(CH$_2$)$_3$(N-morpholinyl), —C(O)(N-pyrrolidinyl) and —C(O)NHCH$_2$CH$_2$(imidazolyl).

In particular embodiments of Formula Ib, R$^2$ is 3-pyridyl optionally substituted with one or two groups independently selected from methyl, CN and —C(O)NHCH$_2$CH$_2$NMe$_2$.

Particular values for R$^2$ of Formula Ib include the structures:

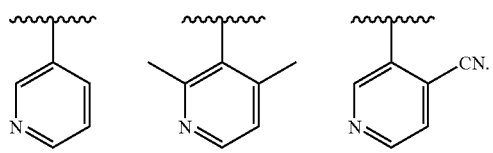

In certain embodiments of Formula Ib, R$^2$ is 8-quinolinyl.

In certain embodiments of Formula Ib, R$^3$ is S-aryl optionally substituted with one or more groups independently selected from (1-3C) alkyl, F, Cl, Br, CN, CF$_3$, and O-(1-3C alkyl).

A particular value for R$^3$ of Formula Ib is S-phenyl.

In certain embodiments of Formula Ib, R$^3$ is S-heteroaryl optionally substituted with one or more groups independently selected from (1-3C) alkyl, F, Cl, Br, CN, CF$_3$, and O-(1-3C alkyl). Exemplary embodiments of R$^3$ of Formula Ib when represented by S-heteroaryl include groups wherein the heteroaryl moiety is a 5-6 membered ring having a nitrogen atom and optionally having an additional atom selected from N and S, for example, pyridyl, pyrimidyl and thiazolyl rings.

Particular values of R$^3$ for Formula Ib include the structures:

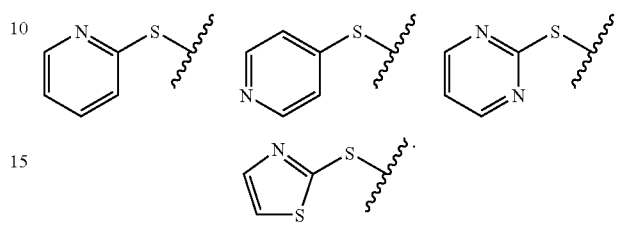

In other embodiments of Formula Ib, R$^3$ is O-aryl optionally substituted with one or more groups independently selected from (1-3C) alkyl, F, Cl, Br, CN, CF$_3$, and O-(1-3C alkyl). A particular value is O-phenyl.

In certain embodiments of Formula Ib, R$^3$ is O-heteroaryl optionally substituted with one or more groups independently selected from (1-3C) alkyl, F, Cl, Br, CN, CF$_3$, and O-(1-3C alkyl) A particular value of the heteroaryl is a 2-pyridyl, 3-pyridyl or 4-pyridyl group;

In certain embodiments of Formula Ib, R$^3$ is CH$_2$-aryl optionally substituted with one or more groups independently selected from (1-3C) alkyl, F, Cl, Br, CN, CF$_3$, and O-(1-3C alkyl). A particular value is CH$_2$-phenyl.

In certain embodiments of Formula Ib, R$^3$ is CH$_2$-heteroaryl optionally substituted with one or more groups independently selected from (1-3C) alkyl, F, Cl, Br, CN, CF$_3$, and O-(1-3C alkyl). A particular value of the heteroaryl is a 2-pyridyl, 3-pyridyl or 4-pyridyl group.

Exemplary embodiments of compounds of Formula I include, but are not limited to, compounds of the general formulas

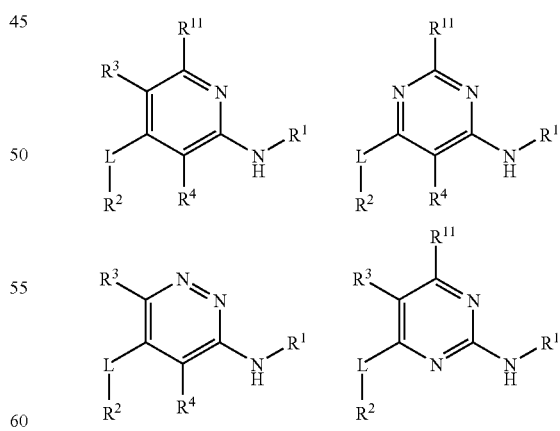

and substituted forms thereof, wherein L, R$^1$, R$^2$, R$^3$, R$^4$ and R$^{11}$ are as defined above.

Additional exemplary embodiment of compounds of Formula I include, but are not limited to, compounds of the general formulas

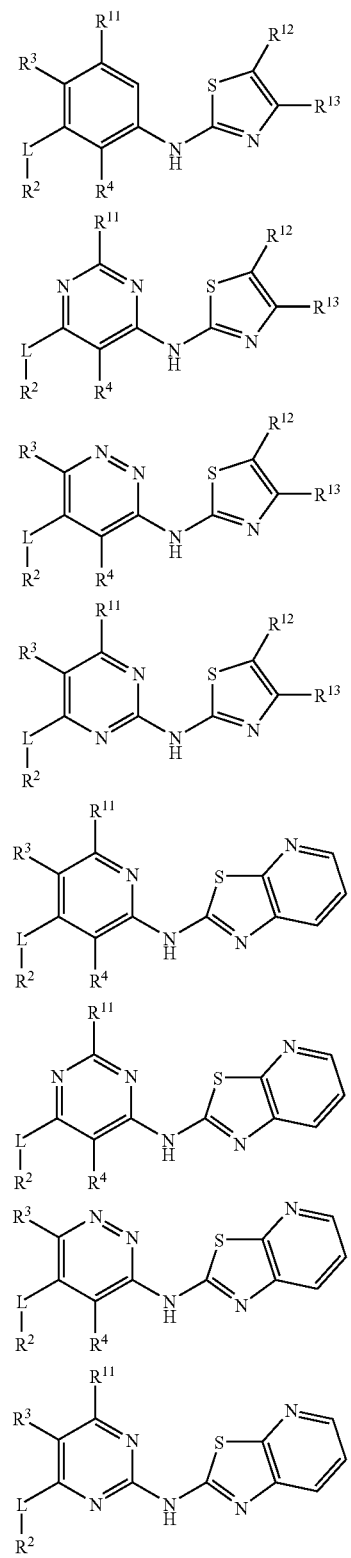

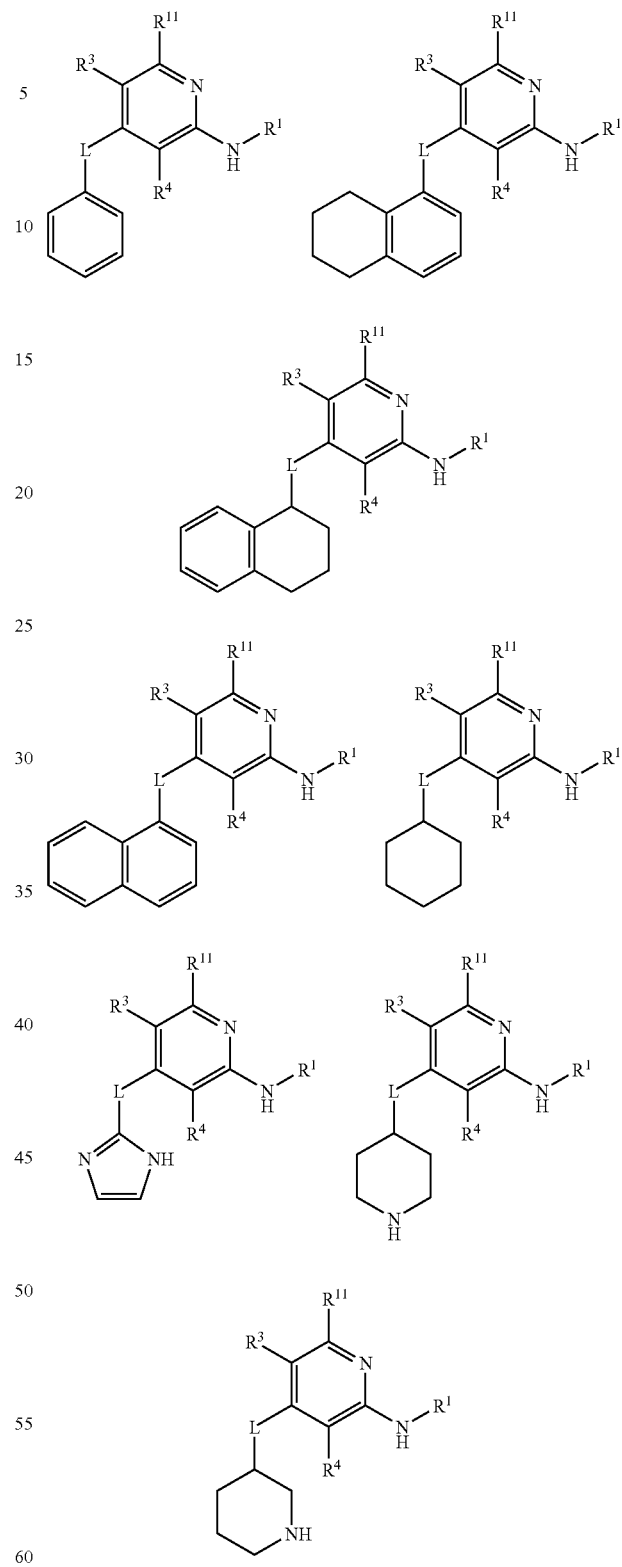

and substituted forms thereof, wherein L, $R^2$, $R^3$, $R^4$, $R^{11}$, $R^{12}$ and $R^{13}$ are as defined above.

Additional exemplary embodiment of compounds of Formula I include, but are not limited to, compounds of the general formulas and substituted forms thereof, wherein L, $R^1$, $R^3$, $R^4$, and $R^{11}$ are as defined above.

Additional exemplary embodiment of compounds of Formula I include, but are not limited to, compounds of the general formulas

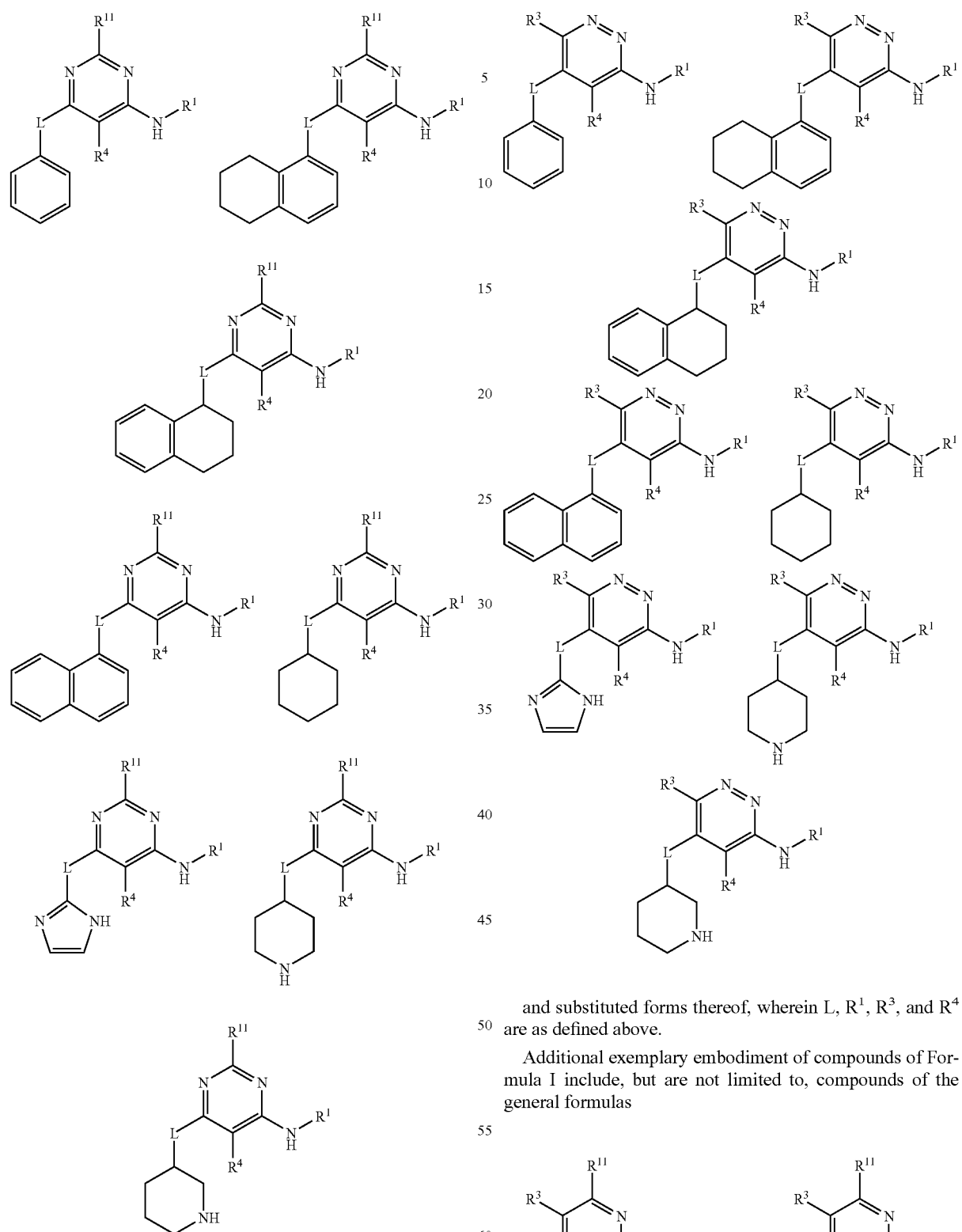

and substituted forms thereof, wherein L, $R^1$, $R^4$, and $R^{11}$ are as defined above.

Additional exemplary embodiment of compounds of Formula I include, but are not limited to, compounds of the general formulas and substituted forms thereof, wherein L, $R^1$, $R^3$, and $R^4$ are as defined above.

Additional exemplary embodiment of compounds of Formula I include, but are not limited to, compounds of the general formulas

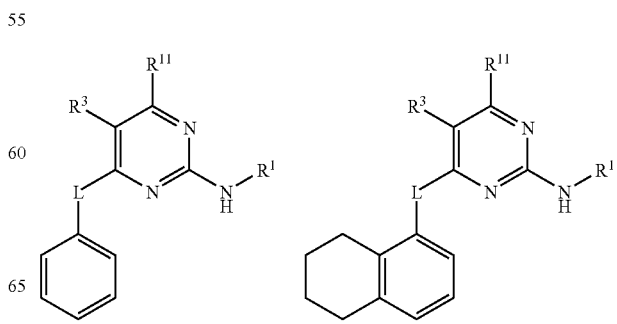

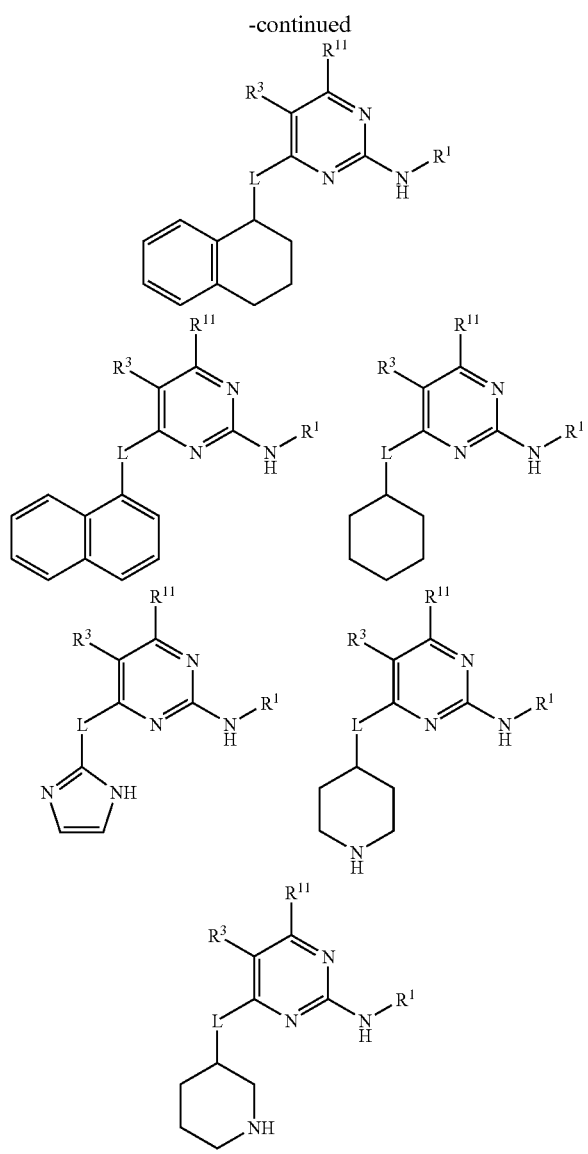

and substituted forms thereof, wherein L, $R^1$, $R^3$, and $R^{11}$ are as defined above.

In certain embodiments, the phrase "or $R^6$ and $R^7$ together with the atoms to which they are attached form a saturated or partially unsaturated heterocyclic ring" refers to a ring formed from an $R^6$ and $R^7$ radical attached to the same nitrogen atom, such as in a group having the formula $V_n$—C(=O)NR$^6$R$^7$, $V_-$—NR$^6$R$^7$, or $V_n$—S(O)$_2$NR$^6$R$^7$.

In certain embodiments, the phrase "or $R^6$ and $R^7$ together with the atoms to which they are attached form a saturated or partially unsaturated heterocyclic ring" refers to a ring formed through an $R^6$ and $R^7$ radical attached to different atoms within the same group, such as in a group having the formula $V_n$—NR$^6$C(=O)R$^7$.

In certain embodiments, the phrase "or $R^8$ and $R^9$ together with the atoms to which they are attached form a saturated or partially unsaturated heterocyclic ring" refers to a ring formed through an $R^8$ and $R^9$ radical attached to the same nitrogen atom, such as in a group having the formula $V_n$—C(=O)NR$^8$R$^9$ or $V_n$—NR$^8$R$^9$.

In certain embodiments, the phrase "or $R^8$ and $R^9$ together with the atoms to which they are attached form a saturated or partially unsaturated heterocyclic ring" refers to an $R^8$ and $R^9$ radical attached to different atoms within the same group, such as in a group having the formula $V_n$—NR$^6$C(=O)R$^7$ or $V_n$—NR$^8$C(=O)NR$^9$R$^{10}$.

In certain embodiments, the phrase "or $R^9$ and $R^{10}$ together with the atoms to which they are attached form a saturated or partially unsaturated heterocyclic ring" refers to a ring formed through an $R^9$ and $R^{10}$ radical attached to the same nitrogen atom, such as in a group having the formula $V_n$—NR$^8$C(=O)NR$^9$R$^{10}$.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In addition to compounds of Formula I, the invention also includes solvates, pharmaceutically acceptable prodrugs, and pharmaceutically acceptable salts of such compounds.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified is contemplated within the scope of the compounds of the invention, and their uses.

Also falling within the scope of this invention are the in vivo metabolic products of compounds of Formula I described herein.

Synthesis of Gluocokinase Activators

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie,* 4, Aufl. ed. Springer-Verlag, Berlin, including supplements).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, or pharmaceutically acceptable salts thereof.

For illustrative purposes, Schemes A-W show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme A shows a method of preparing compound (3A) of Formula I wherein $R^1$ is thiazolyl. To prepare compound (3A), a 2-aminoheterocycle (1) is reacted with benzoylisothiocyanate to afford a benzoylthiourea intermediate, which is hydrolyzed to the thiourea (2) with a base such as; but not limited to, potassium carbonate in a suitable solvent such as, but not limited to, ethanol. Alternatively, the aminoheterocycle (1) can be treated with an inorganic or ammonium isothiocyanate, e.g., Meckler's procedure, in the presence of an acid to afford the thiourea (2) in one step. Treatment of the thiourea (2) with an α-haloketone $R^{13}COCHR^{12}X$, wherein X=OTs, Cl, Br, I, or $NR^3$ (wherein $R=C_1-C_6$ alkyl), in a suitable base such as triethylamine, Hunig's base, DBU, alkali carbonate, sodium hydroxide, etc. and a suitable solvent such as ethanol affords the thiazole (3A). If the desired α-halo ketone $R^{13}COCHR^{12}X$ is not commercially available, it can be prepared by various methods known to those skilled in the art. Examples include, but are not limited to, bromination of commercially or readily synthesized methyl ketones (*Tetrahedron* (1970) 5611-5615; *Organic Synthesis* (1946) 13-15; *Tetrahedron* (1990) 2943-2964), diazomethane treatment of carbonyl chlorides, oxidation of 1-chloro-2-alkanols, bromination of silyl enol ethers, or halogenation of O-keto esters followed by decarboxylation.

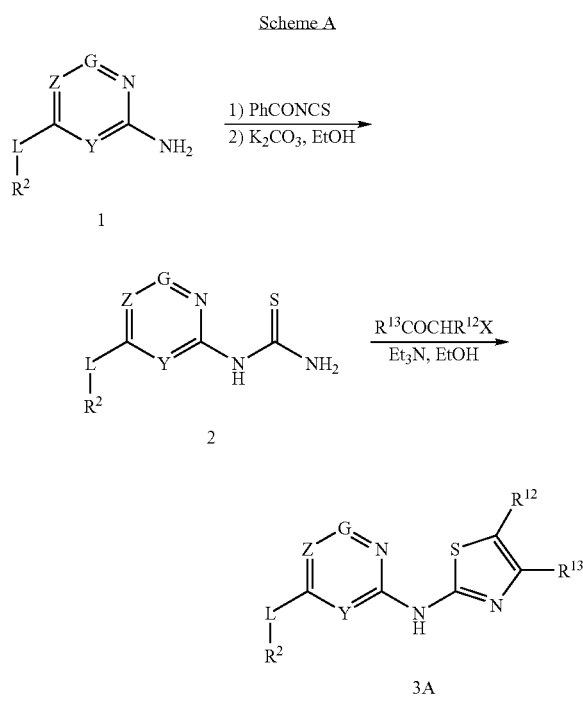

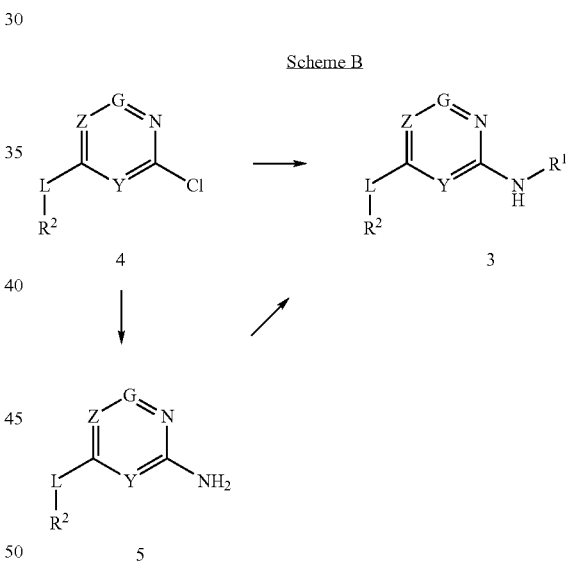

Scheme B shows an alternative method of preparing a compound of Formula I. According to Scheme B, compound (4) can be converted directly to a compound (3) of Formula: I upon treatment with $R^1NH_2$ via base catalysis or via copper or palladium catalysis; i.e., the Buchwald reaction. Alternatively, 2-haloheterocycle (4) can be converted to compound (5) by the method of Hartwig et al. (for an example of this transformation via analogy see: *Organic Letters* (2001) 2729-2732), or by treatment with a Pd catalyst and benzophenone imine, or by heating in the presence of ammonia (or $NH_2PG$ where PG is a protecting group). Compound (5) can be converted to compound (3) of Formula I upon reaction with an aryl or heteroaryl halide $R^1X$ in the presence of a base catalyst or metal (e.g., copper or palladium) catalyst.

Scheme C

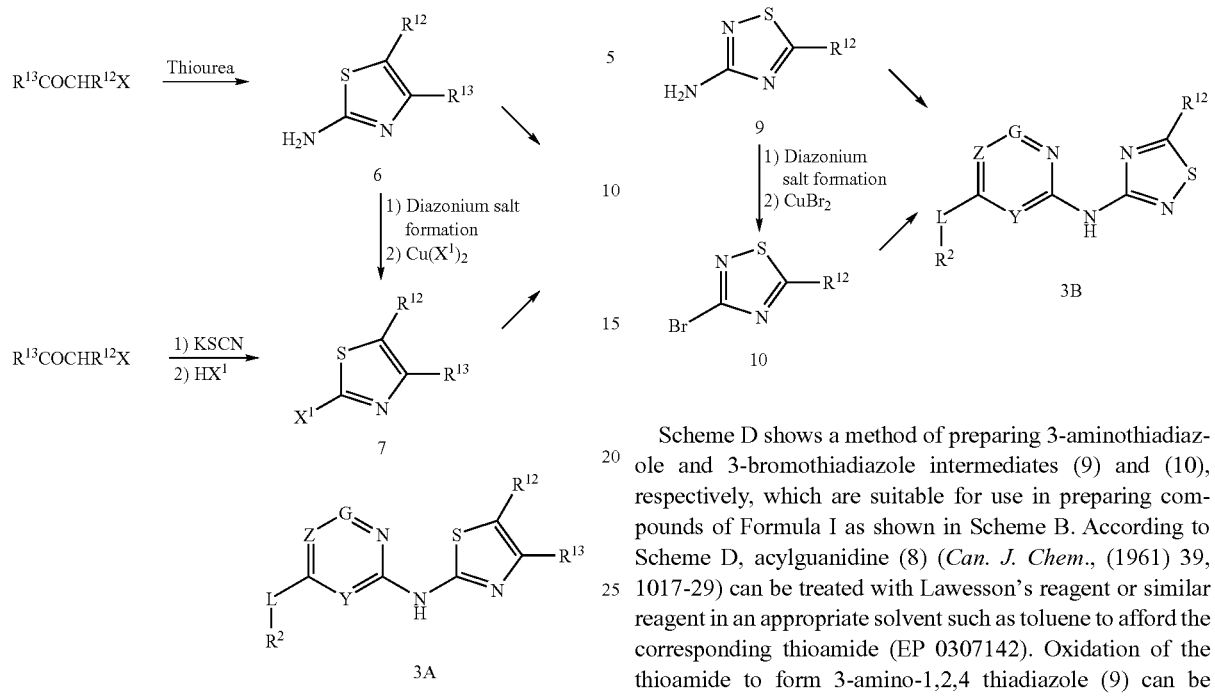

Scheme C shows a method of preparing 2-aminothiazole and 2-bromothiazole intermediates (6) and (7), respectively, which are suitable for use in preparing compounds of Formula I as shown in Scheme B. According to Scheme C, α-haloketone $R^{13}COCHR^{12}X$ can be treated with thiourea in the presence of a suitable base such as potassium carbonate or triethylamine in an appropriate solvent such as DMF or ethanol to afford aminothiazole (6). The aminothiazole (6) can be converted to a diazonium salt intermediate by numerous methods including, but not limited to, treatment with sodium nitrite in acid or isobutylnitrite. Treatment of the in situ diazonium salt with $Cu(X^1)_2$ ($X^1$=Cl or Br) or HBr affords the corresponding 2-halothiazole (7). Alternatively, using the Hantzsch synthetic method, the α-haloketone $R^{13}COCHR^{12}X$ can be treated first with KSCN, then with HX wherein X is Cl or Br, to provide the 2-halothiazole (7). The 2-halothiazole compounds (6) and (7) can be converted into compound (3A) by the methods shown in Scheme B.

Scheme D shows a method of preparing 3-aminothiadiazole and 3-bromothiadiazole intermediates (9) and (10), respectively, which are suitable for use in preparing compounds of Formula I as shown in Scheme B. According to Scheme D, acylguanidine (8) (*Can. J. Chem.*, (1961) 39, 1017-29) can be treated with Lawesson's reagent or similar reagent in an appropriate solvent such as toluene to afford the corresponding thioamide (EP 0307142). Oxidation of the thioamide to form 3-amino-1,2,4 thiadiazole (9) can be accomplished with bromine, iodine, hydrogen peroxide or nitric acid. Cyclization of compound (8) may also be achieved by treatment with hydroxylamine-O-sulphonic acid in an alcohol solvent such as methanol or ethanol in the presence of pyridine (EP 0307142). Formation of the diazonium salt of compound (9), followed by treatment of the in situ diazonium salt with $CuBr_2$, affords the corresponding 3-bromo-1,2,4-thiadiazole (10) (EP 0307142). The chloro derivative of compound (10) could also be synthesized through the use of $CuCl_2$. Alternatively, palladium-mediated coupling of the commercially available 3-bromo-5-chloro-1,2,4-thiadiazole (11) with a zinc reagent affords 3-bromo-1,2,4-thiadiazole (10) (WO 2003/037894). Intermediate thiadiazoles (9) and (10) can be converted into compound (3B) of Formula I by the methods shown in Scheme B.

Scheme D

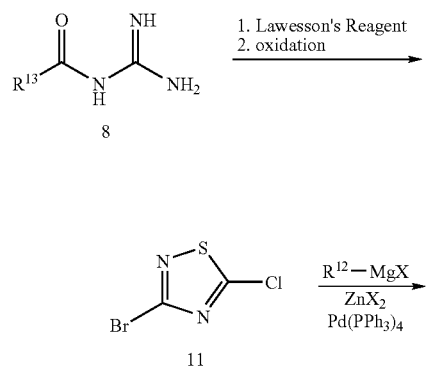

Scheme E

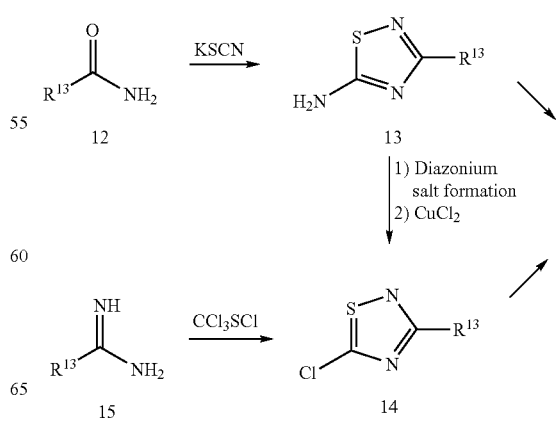

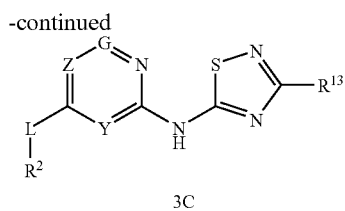

3C

Scheme E shows a method of preparing 5-amino-1,2,4-thiadiazole and 5-chloro-1,2,4-thiadiazole intermediates (13) and (14), respectively, which are suitable for use in preparing compounds of Formula I as shown in Scheme B. According to Scheme E, primary amide (12) can be converted into 5-amino-1,2,4 thiadiazole (13) by heating with KSCN in an appropriate solvent such as methanol or ethanol (*Adv. Heterocycl. Chem.*, (1982) 32, 285). Formation of the diazonium salt of compound (13), followed by treatment of the in situ diazonium salt with $CuCl_2$ affords the corresponding 5-chloro-1,2,4-thiadiazole (14). The corresponding bromo derivative can also be synthesized through the use of $CuBr_2$. Alternatively, reaction of amidine (15) with perchloromethyl mercaptan affords 5-chloro-1,2,4-thiadiazole (13) (*Bioorg. Med. Chem.*, (2003) 11, 5529-5537). Intermediates (13) and (14) can be converted into compound (3C) of Formula I by the methods shown in Scheme B.

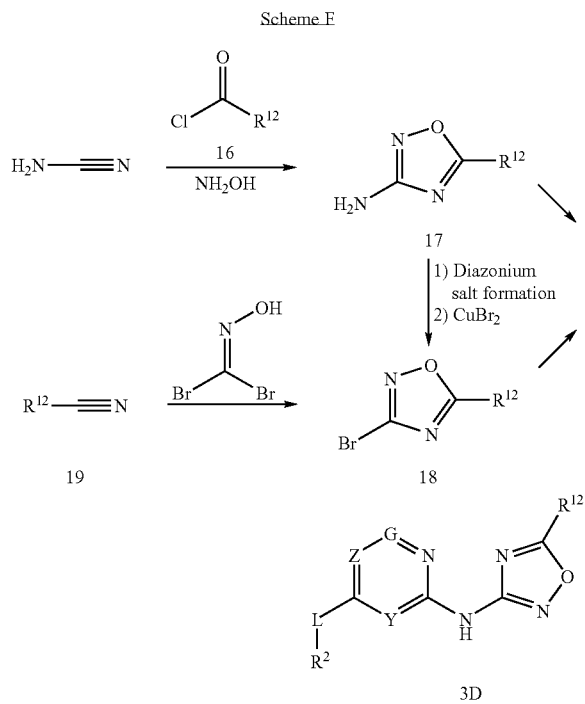

Scheme F shows a method of preparing 3-amino-1,2,4-oxadiazole and 3-bromo-1,2,4-oxadiazole intermediates (17) and (18), respectively, which are suitable for use in preparing compounds of Formula I as shown in Scheme B. According to Scheme F, cyanamide can be reacted with an appropriate acylchloride (16) or the corresponding anhydride, and subsequently reacted with hydroxylamine to afford 3-amino-1,2,4-oxadiazole (17) (*Heterocycles*, (2002) 57, 811-823). Formation of the diazonium salt of (17), followed by treatment of the in situ diazonium salt with $CuBr_2$ affords the corresponding 3-bromo-1,2,4-oxadiazole (18). The chloro derivative can also be synthesized through the use of $CuCl_2$. Alternatively, alkyl nitrile (19) can be reacted with dibromoformaldoxime (neat) in the presence of an appropriate base such as sodium bicarbonate to afford 3-bromo-1,2,4-oxadiazole (18) (*J. Heterocyclic Chem.*, (1989) 26, 23-24). The oxadiazole intermediates (17) and (18) can be converted into compound (3D) of Formula I by the methods shown in Scheme B.

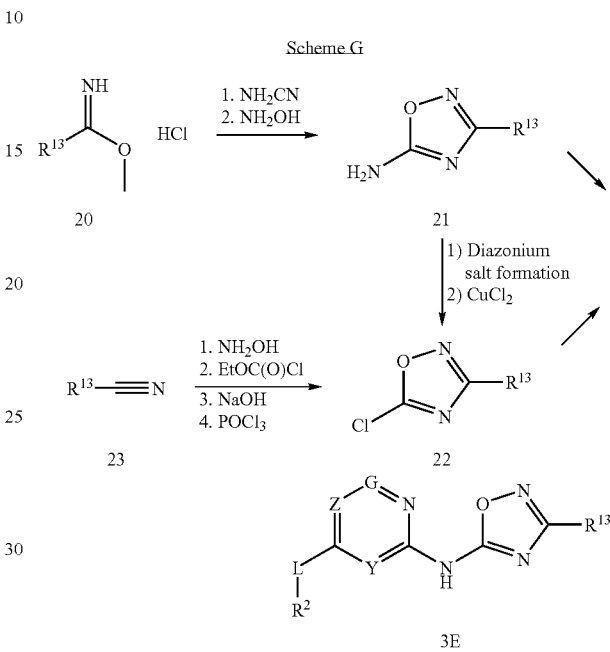

Scheme G shows a method of preparing 5-amino-1,2,4-oxadiazole and 5-chloro-1,2,4-oxadiazole intermediates (21) and (22), respectively, which are suitable for use in preparing compounds of Formula I as shown in Scheme B. According to Scheme G, imidate hydrochloride salt (20) (made via the Pinner reaction) can be reacted with cyanamide in a suitable solvent such as methanol or ethanol to afford an intermediate N-cyanoimidate. Cyclization can be achieved by reacting the N-cyanoimidate with hydroxylamine hydrochloride in an appropriate solvent such as methanol or ethanol in the presence of an appropriate base such as triethylamine, Hunig's base, pyridine or sodium acetate to afford 5-amino-1,2,4-oxadiazole (21) (*J. Org. Chem.*, (1963) 28, 1861-21). Formation of the diazonium salt of compound (21), followed by treatment of the in situ diazonium salt with $CuCl_2$ affords the corresponding 5-chloro-1,2,4-oxadiazole (22). The bromo derivative can also be synthesized through the use of $CuBr_2$. Alternatively, alkyl nitrile (21) can be converted into 5-chloro-1,2,4-oxadiazole (22) (WO 95/005368) by reaction with hydroxylamine hydrochloride in an appropriate solvent such as methanol or ethanol, in the presence of an appropriate base such as triethylamine, Hunig's base, pyridine or sodium acetate, followed by cyclization to a 1,2,4-oxadiazolone with a bisacylating agent such as ethyl chloroformate, carbonyldiimidazole or phosgene. In certain embodiments, the cyclization requires the use of a base such as NaOH, NaH or triethylamine to allow for the formation of the 1,2,4-oxadiazolone. Reaction of the 1,2,4-oxadiazolone with a dehydrating agent such as $POCl_3$, $POBr_3$ or $PCl_5$ affords the 5-halo-1,2,4-oxadiazole (22). The oxadiazole intermediates (21) and (22) can be converted into a compound (3E) of Formula I by the methods shown in Scheme B.

Scheme H

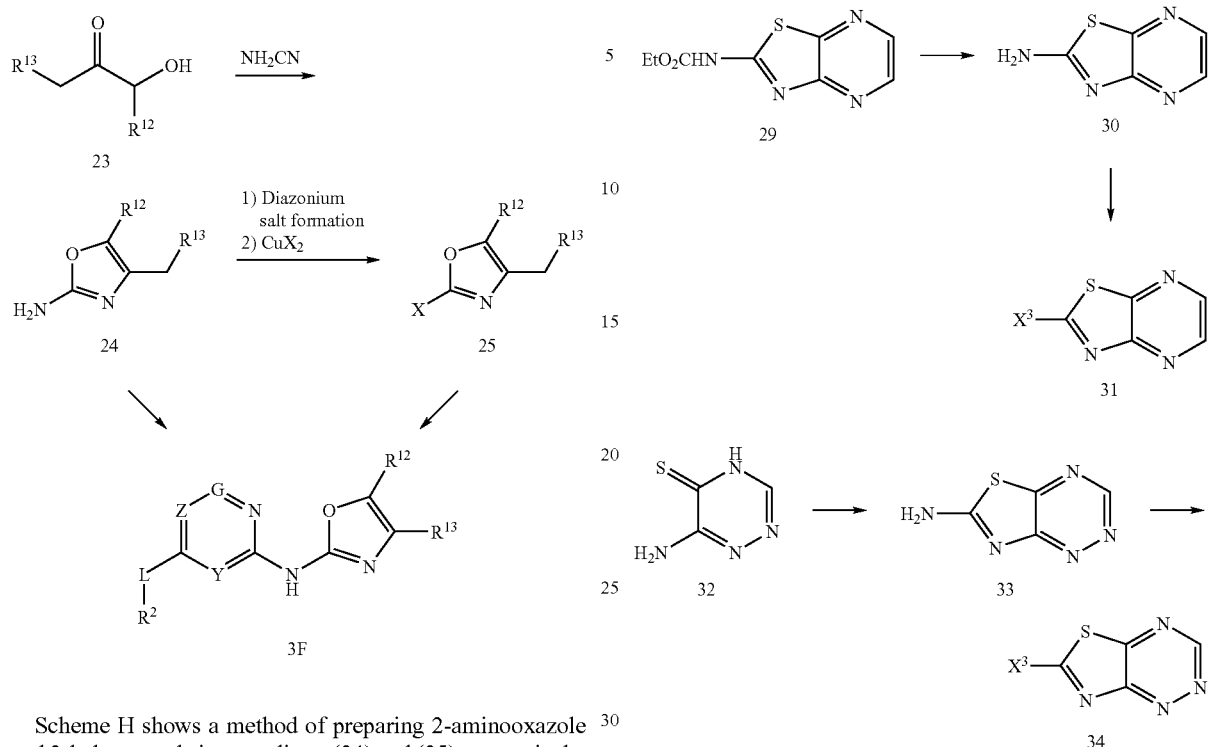

Scheme H shows a method of preparing 2-aminooxazole and 2-halo-oxazole intermediates (24) and (25), respectively, which are suitable for use in preparing compounds of Formula I as shown in Scheme B. According to Scheme H, α-hydroxyketone (23) is reacted with cyanamide to afford 2-aminooxazole (24) (*Aust. J. Chem.* (1985), 38, 447-458). Formation of the diazonium salt of compound (24), followed by treatment of the in situ diazonium salt with $CuX_2$ (where X=Cl or Br) affords the corresponding 5-halo-1,2,4-thiadiazole (25). Intermediates (24) and (25) can be converted into compound (3F) of Formula I by the method of Scheme B.

Scheme I

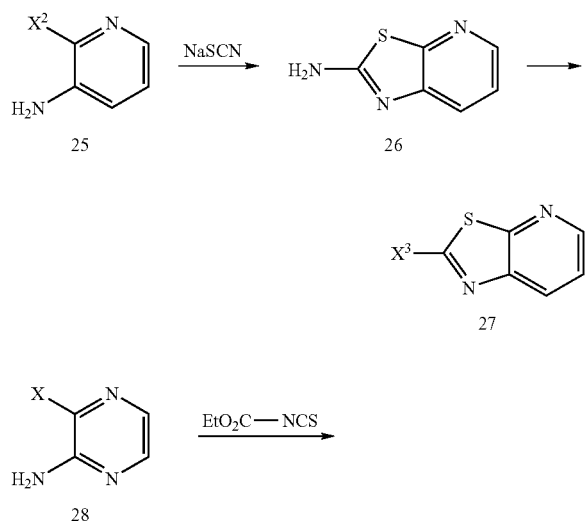

Scheme I describes the preparation of intermediates (27), (31) and (34) and substituted forms thereof suitable for use in preparing compounds of Formula (3A) wherein $R^{12}$ and $R^{13}$ form a fused heterocyclic ring. Thiazolopyridine (26) is prepared from 2-halo-3-aminopyridine (25) by reaction with a thiocyanate (for example, sodium or potassium thiocyanate) in acidic media (for example, acetic acid). The aminoheterocyclic compound (26) can be converted to the corresponding 2-halo compound (27) by standard methods (for example, by diazotization of the amine with $NaNO_2$ and $HX^3$, followed by reaction with $Cu(CX^3)_2$).

In another example, the 2-amino-3-halopyridazine (28) can be reacted with a protected isothiocyanate to provide protected 2-aminothiazolopyridazines (29), which may be deprotected under standard hydrolytic conditions to provide 2-aminothiazolopyridazines (30) (Koren, B., et al., *Heterocycles* 1987, 26(3), 689-697). The aminoheterocyclic compound (30) can be converted to the corresponding 2-halo compound (31), for example, as described above.

In another example, the 2-aminothiazolotriazine (33) can be prepared from compound (32) (Jacobsen, N. W., et al., *Aust. J. Chem.* 1987, 40(3), 491-499) by treatment sequentially with MeI, $CS_2$ and ammonia. The aminoheterocyclic compound (33) can be converted to the corresponding 2-halo compound (34), for example, as described above.

It will be appreciated that the aminoheterocycles (27), (31) and (34) can be further functionalized if desired, for example by halogenation of the 6-membered ring (for example with NBS or bromrine). Such halogenated derivatives may be further modified using well known methods

Scheme J

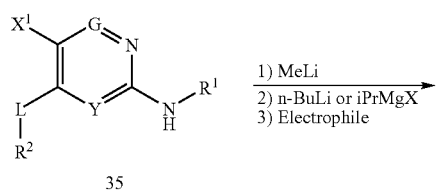

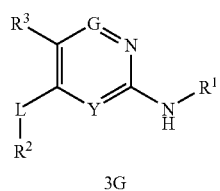

Scheme J shows a method of preparing compound (3G) of Formula I wherein Z is CR³. According to Scheme J, the halo-substituted heterocycle (35) (prepared by the method of Scheme A or B) wherein $X^1$=Cl, Br or I, is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with an electrophile to provide compound (3G). Suitable electrophiles include, but are not limited to: 1) aldehydes, 2) nitriles, 3) N-methoxy-N-methylamides (Weinreb amides), 4) dialkyldisulphides, 5) hexachloroethane, 6) trialkyl boronates, 7) sulphonyl chlorides, 8) sulfamyl chlorides, 9) isocyanates, 10) carbon dioxide, (11) alkyl halides, (12) trifluoroiodomethane, (13) Mander's reagent, and (14) chloroformates. Exemplary compounds of the present invention which can be prepared according to the method: of Scheme J include compounds wherein R³ is alkyl, phenylalkyl, cycloalkyl, hydroxylalkyl (from $R^3Si(CH_2)_nI$), Cl, SH, SR, SORW, $SO_2R'$, $OR^8$, I, $SCH_2R'$, $OCH_2R'$, $CO_2H$, CH(OH)—R, and C(=O)R, wherein $R^1$ is alkyl, alkenyl, alkynyl, cycloalkyl, or aryl.

Alternatively, the halo-substituted heterocycle (35) can be converted to compound (3G) wherein R³ is alkyl, aryl, heteroaryl, alkenyl or alkynyl, via a metal (e.g., Cu or Pd) mediated coupling reaction such as, but not limited to, the Negishi reaction, the Suzuki reaction, the Sonogashira reaction, or the Stille reaction Scheme K shows a method of preparing compounds (3H) of Formula I, wherein Z=C—SR³ or C—OR³, from a halo substituted heterocycle (35). According to Scheme K, the halo-substituted heterocycle (35), prepared by the method of Scheme A or B, can be converted to a thiol or alcohol (36) via one of several procedures. According to one method, the halo-substituted heterocycle (35) is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with either elemental sulfur or bis(trimethylsilyl) peroxide to form the corresponding mercapto- or hydroxyl-substituted compound (36). Alternatively, the anion can be quenched with trimethyl borate and oxidized with either hydrogen peroxide (*J. Med. Chem.* (2004) 3089-3104) or N-methyl morpholine oxide (*Syn. Lett.* (1995) 931-932) to afford the phenol (36). As a third synthetic route, the halide (35) can be converted under Pd-mediated conditions to thiol or phenol (36) utilizing potassium triisopropylsilanethiolate (*Tetrahedron Letters* (1994) 3225-3226) or sodium tert-butyldimethylsiloxide (*J. Org. Chem.*, (2002) 5553-5566). The thiol or phenol (36) can be alkylated with a variety of electrophiles using standard reaction conditions to provide the corresponding ether (3H) of Formula I. Suitable electrophiles include, but are not limited to, alkyl halides, benzylic halides, aryl halides and heteroaryl halides, heteraroyl-$CH_2X$, cycloalkyl halides, Michael acceptors, and activated heteroaryl halides such as, but not limited to, 2-fluorocyanobenzene, 4-fluorocyanobenzene, 2-fluoronitrobenzene, 4-fluoronitrobenzene, 2-chloro-4-nitropyridine, 2-halopyridine, 2-halopyrimidine and 4-halopyrimidine.

Alternatively, halide (35) can be converted to an alkylsulfide using Pd-mediated conditions with appropriately functionalized sulfides. Examples of such sulfides include, but are not limited to, esters of 3-mercaptopropanoic acid, 3-mercaptopropanenitrile or 2-(trimethylsilyl)ethanethiol. Sulfides of this type can be deprotected to the thiol and alkylated with a variety of electrophiles under standard conditions (*Chemical & Pharmaceutical Bulletin* (1990), 38(10), 2667-75).

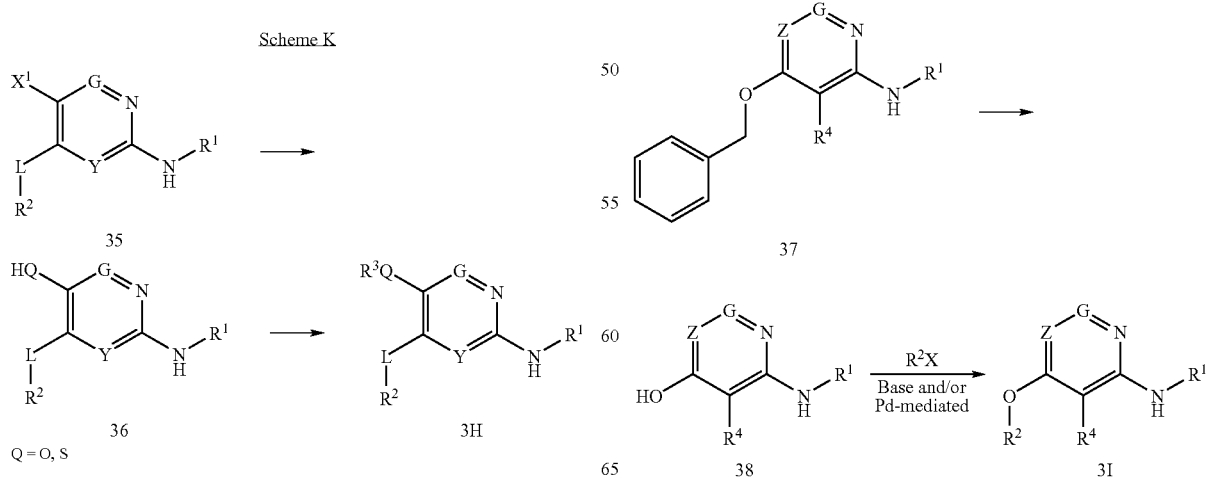

Scheme L shows an alternate method of adding the linker OR² to a core heterocycle to provide a compound (3I) of Formula I. According to Scheme L, a benzyl ether (37), prepared by the method of Scheme A or B, can be converted to the hydroxyl substituted heterocycle (38), for example by hydrolysis with a strong acid (e.g., 6N HCl) or by hydrogenation (e.g., H₂ or ammonium formate in the presence of a metal catalyst). Reaction of the hydroxylated heterocycle (38) with R²X, wherein X=F, Cl, Br, I, or NO₂, in the presence of a base such as, but not limited to, cesium carbonate, in a suitable solvent such as, but not limited to, DMF, affords compound (3I) of Formula I.

The method shown in Scheme L can also be used to prepare compounds of Formula I wherein L is S utilizing a paramethoxybenzyl thioether derivative of compound (37).

Scheme M shows a method of preparing compounds of Formula I wherein G=CR¹¹ or N, Z=CR³ wherein R³ is OC(=O)NR⁶R⁷ or OR⁶, and Y=CR⁴. According to Scheme M, the carbamate (39) is ortholithiated with n-BuLi/TMEDA and reacted with a suitable electrophile such as (1) diaryl disulphides, heteroaryl disulphides or dialkyl disulphides (2) benzylic halides or heteroaryl-CHRX, (3) aryl aldehydes, heteroaryl aldehydes, cycloalkyl aldehydes, or heterocyclic aldehydes, or (4) boronic acids (which can be converted to the phenol with oxidants, and then alkylated or arylated to afford compounds wherein L=O) to provide compound (40). The resulting carbamate (40) can then be converted to compounds (41) or (41A) of Formula I by the methods of Schemes A and B. Compounds (41) and (41A) can be converted to the phenol (45), which can be converted to aryl ethers, other carbamates, and acyl derivatives (46) by routine synthetic methods.

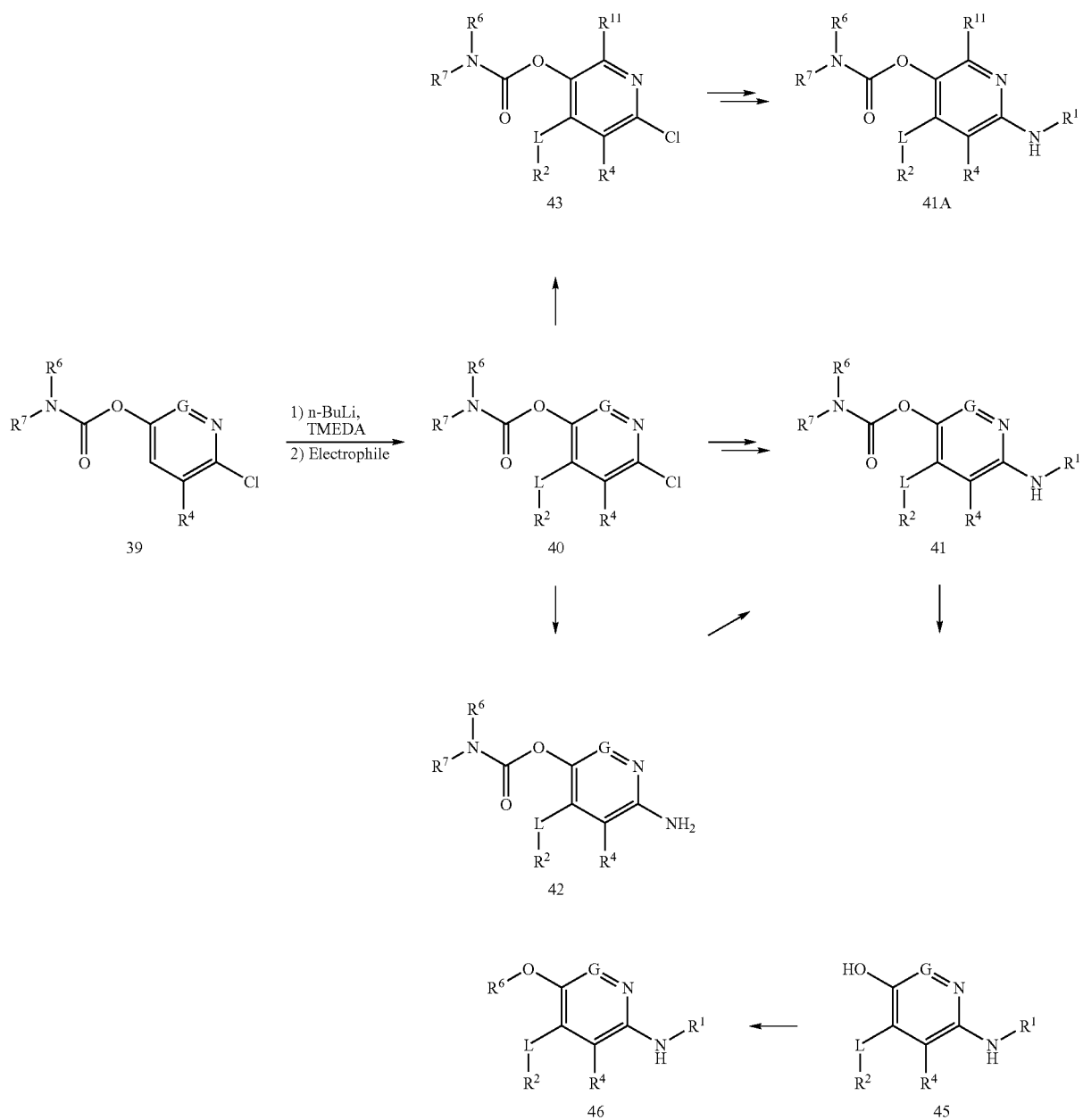

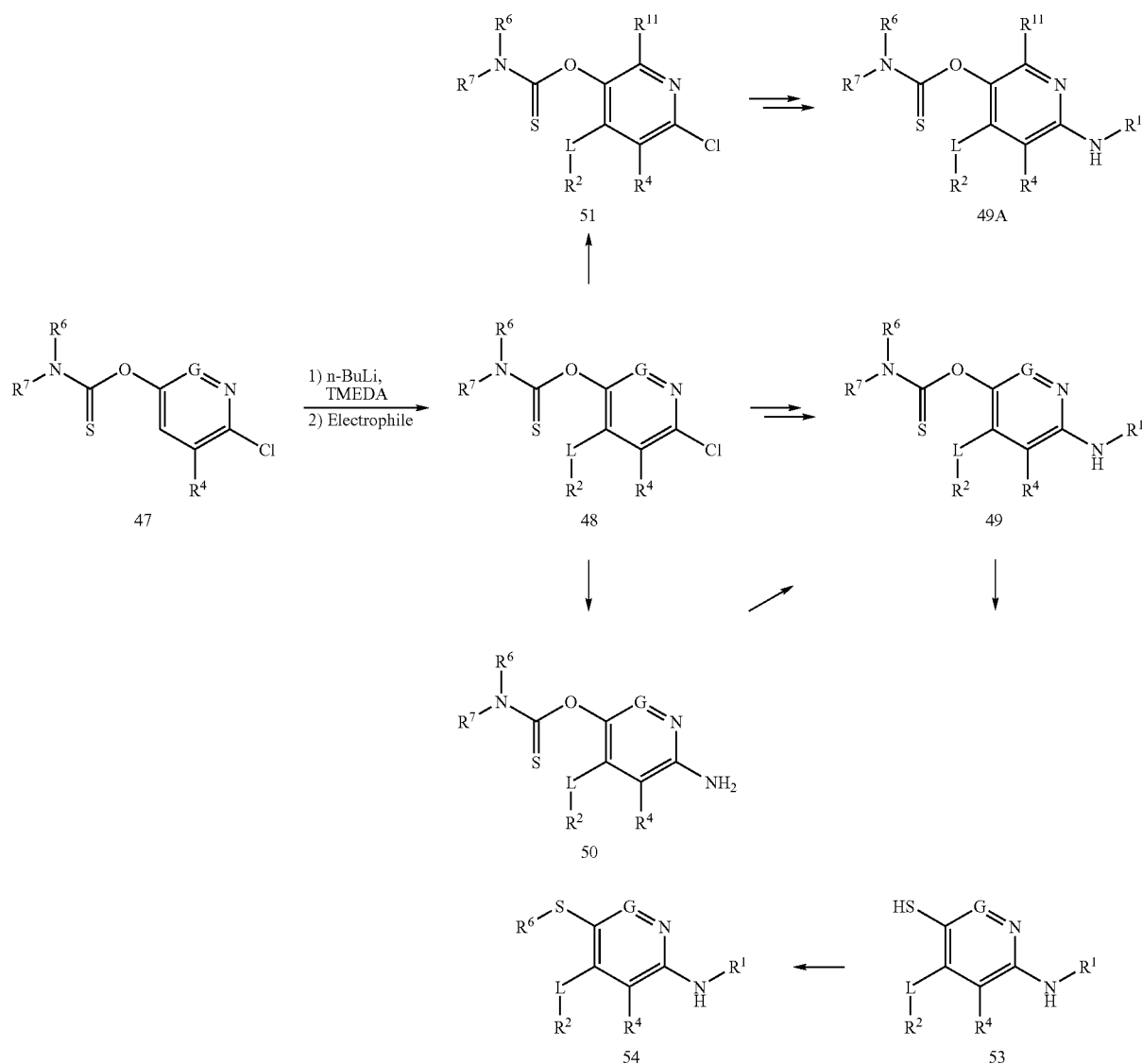

Scheme N shows a method of preparing a compound Formula I wherein G=CR$^{11}$ or N, Z=CR$^3$ wherein R$^3$ is SR$^6$ or OC(=S)NR$^6$R$^7$, and Y=CR$^4$. According to Scheme N, the thiocarbamate (47) is ortholithiated with n-BuLi/TMEDA and reacted with a suitable electrophile such as (1) diaryl disulphides, heteroaryl disulphides or dialkyl disulphides (2) benzylic halides or heteroaryl-CHRX, (3) aryl aldehydes, heteroaryl aldehydes, cycloalkyl aldehydes, or heterocyclic aldehydes, or (4) boronic acids (which can be converted to the phenol with oxidants, and then alkylated or arylated to afford compounds wherein L=O). The resulting thiocarbamates are then converted to compounds (49) or (49A) of Formula I by the methods of Scheme A or B. The thiocarbamates (49) and (49A) can be converted to the thiophenol (53) via the Newman rearrangement (J. Org. Chem. (1966) 31, 3980-3984) which can be converted to the aryl thioether (54) by treatment with a suitable electrophile.

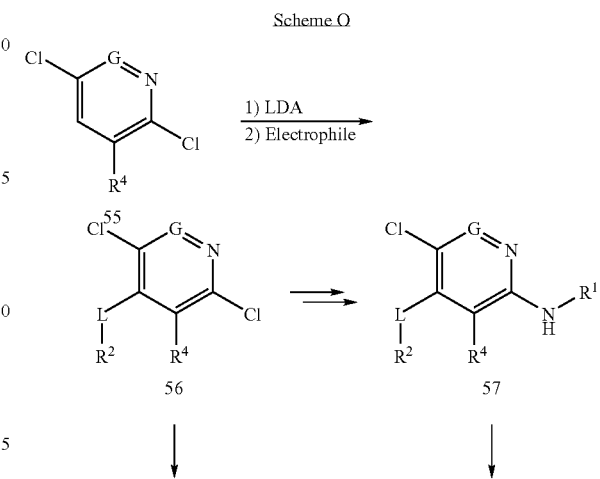

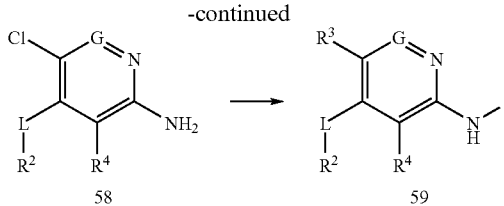

Scheme O shows a method of preparing compound (59) of Formula I wherein G=CR[11] or N, Z=CR[3], and Y=CR[4].

According to Scheme O, the dichloroheterocycle (55) is selectively ortholithiated with LDA and reacted with a suitable electrophile such as (1) diaryl disulphides, heteroaryl disulphides or dialkyl disulphides (2) benzylic halides or heteroaryl-CHRX, (3) aryl aldehydes, heteroaryl aldehydes, cycloalkyl aldehydes, or heterocyclic aldehydes, or (4) boronic acids (which can be converted to the phenol with oxidants, and then alkylated or arylated to afford compounds wherein L=O) to provide the dichloride (56). The dichloride (56) is then converted to compounds of structures (57) or (58) via selective Pd-mediated chemistry in Schemes A and B.

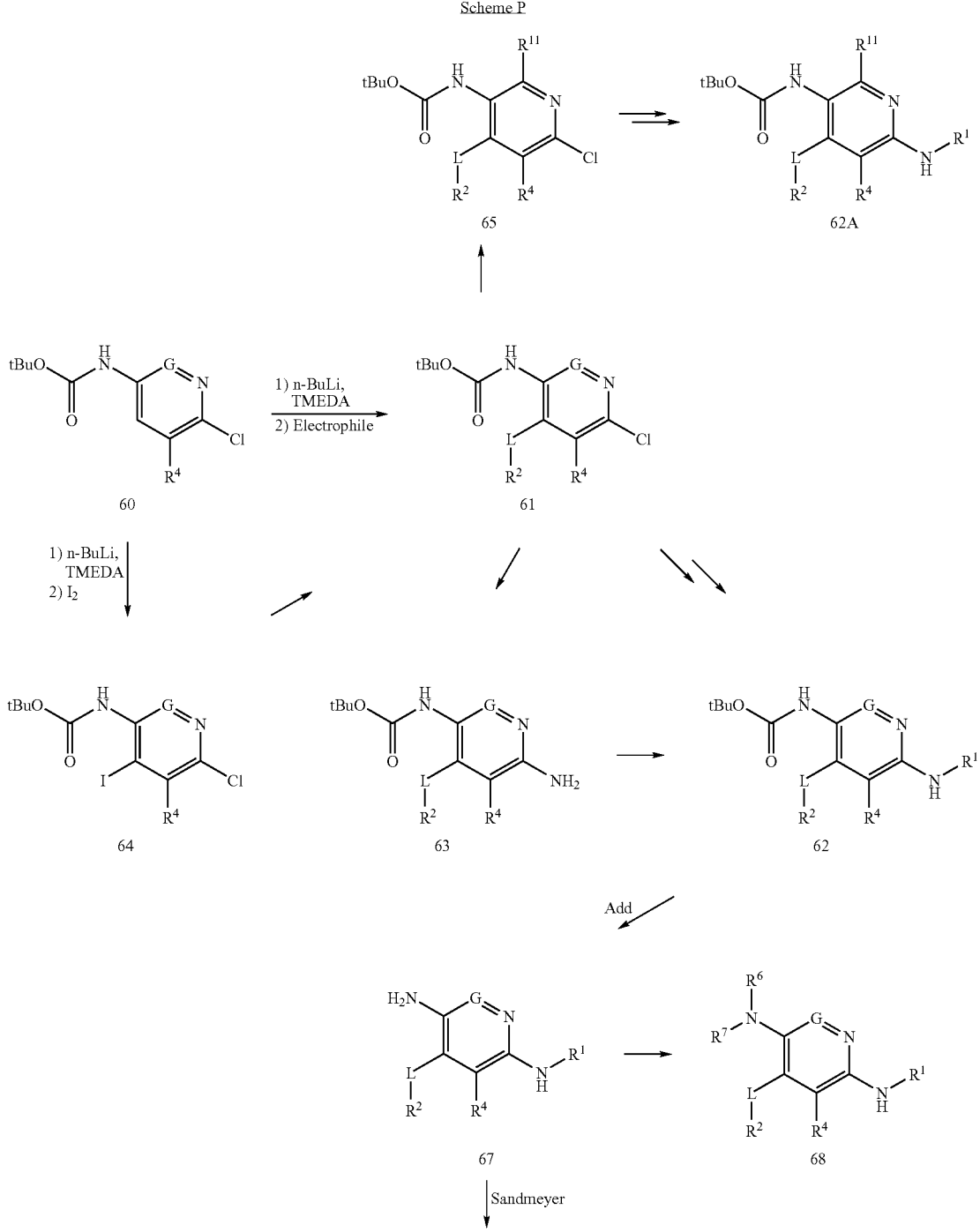

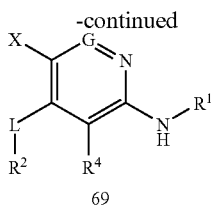

69

Scheme P shows a method of preparing compounds of Formula I wherein G=CR$^{11}$ or N, Z=CR$^3$ wherein R$^3$ is NR$^6$R$^7$, NH(C=O)alkyl or halogen, and Y=CR$^4$. According to Scheme P, the Boc-protected aniline (60) is ortholithiated with n-BuLi/TMEDA and reacted with a suitable electrophile such as (1) diaryl disulphides, heteroaryl disulphides or dialkyl disulphides (2) benzylic halides or heteroaryl-CHRX, (3) aryl aldehydes, heteroaryl aldehydes, cycloalkyl aldehydes, or heterocyclic aldehydes, (4) boronic acids (which can be converted to the phenol with oxidants, and then alkylated or arylated to afford compounds wherein L=O), or (5) iodine (to provide compound (64) which can be converted easily with Pd-mediated catalyzed reactions such as the Suzuki or Negishi reactions) to provide compounds (61). The resulting Boc-protected anilines (61) are then converted to compounds (61) or (61A) of Formula I by the methods of Scheme A or B. The Boc-protected aniline (61) or (61A) can then be converted to the aniline (67) via treatment with acid such as TFA or hydrochloric acid. Aniline (67) can be acylated, sulfonylated or converted to ureas or thioureas (68), or converted to a halide (69) via the Sandmeyer reaction. This halide is useful for further elaboration via the methods contained in Schemes J or K.

Scheme Q

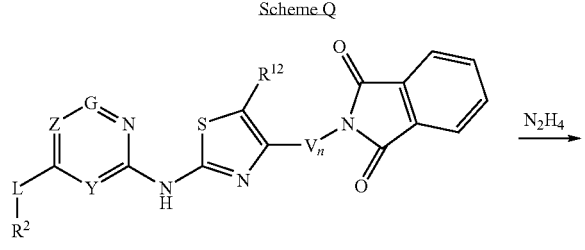

70

-continued

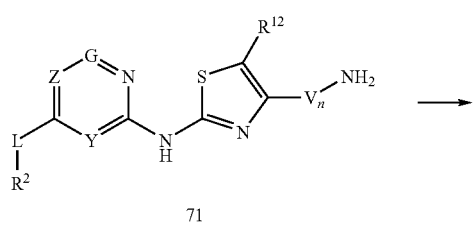

71

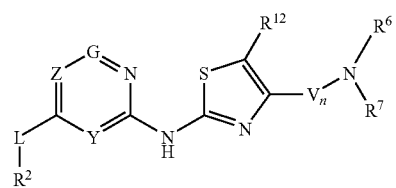

72

Scheme Q shows a method of preparing compounds of Formula I wherein R$^1$ is a substituted thiazolyl. According to Scheme Q, phthalimide-containing compound (70) wherein V$_n$ is alkylene optionally substituted by one or more alkyl groups and n is 1, which can be prepared by the method of Scheme A or B, can be converted to amine (71) via treatment with hydrazine. Amine (71) can be elaborated to the amide, carbamate, urea, thiourea, monoalkylamine, dialkylamine, amidine, or guanidine (72) by routine methods in the literature.

Scheme R

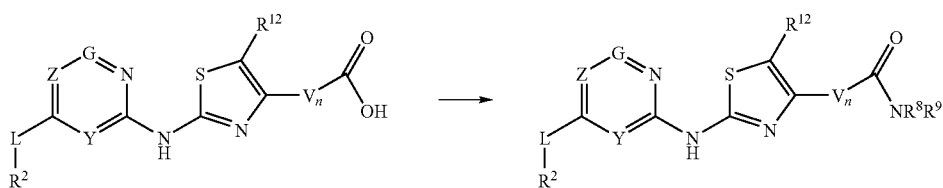

74 75

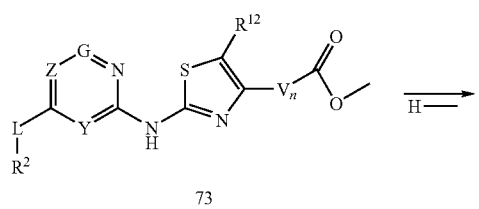
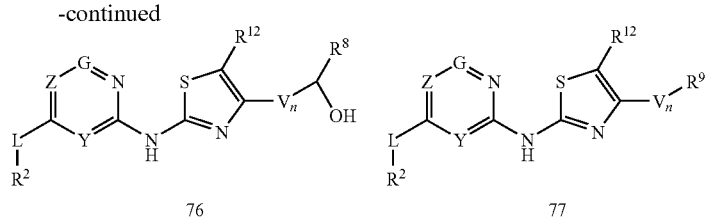

73 76 77

Scheme R shows an alternative method of preparing compounds of Formula I wherein $R^1$ is a substituted thiazolyl. According to Scheme R, the ester-containing compound (73) wherein $V_n$ is alkylene optionally substituted by one or more alkyl groups and n is 1, which can be prepared by the method of Scheme A or B, can be converted to alcohol (76) or carboxylic acid (74) by reduction or hydrolysis with a hydride or hydroxide, respectively. The carboxylic acid (74) can be converted to a primary, secondary or tertiary amide (75) using a variety of amide coupling methods known to those skilled in the art. Compound (74) can also be converted to compound (77), wherein $R^9$ is a heterocyclyl group such as, but not limited to, tetrazolyl, imidazolyl, triazolyl, or thiazoyl, by coupling methods known to those skilled in the art.

can be prepared from compounds (80), (82) or (84), which can be made by a variety of methods, including those shown in Scheme S.

According to one method, substituted 2-halo-4-nitropyridine (80) (if not commercially available) can be prepared by the following sequence: Oxidation of the commercially available (or readily available from 3-bromopyridine via known methods) 3-substituted pyridine (78) by treatment with MCPBA, hydrogen peroxide or another suitable oxidant, affords the N-oxide derivative, which upon treatment with $POCl_3$, affords the pyridyl chloride (79). Oxidation of the pyridyl chloride (79), followed by treatment with nitration conditions such as nitric acid in acetic acid, followed by treatment with $PBr_3$ regioselectively affords the 2-halo-4-

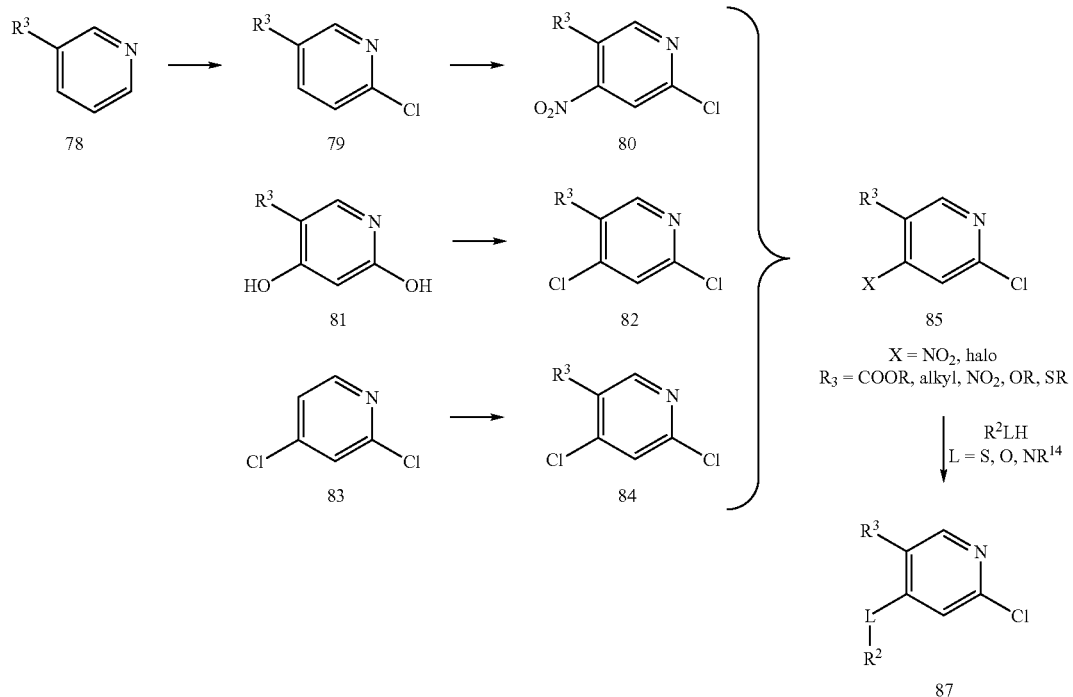

Scheme S shows several methods for preparing compound (87), wherein G and Y are CH, which is suitable for preparing compounds of Formula I. In Scheme S, halo- or dihalosubstituted heterocycles (85) (X=NO₂ or halo) are reacted with a nucleophile (86) in the presence of base and a suitable solvent (e.g., NaH in DMF) to afford the halo-substituted heterocycle (87) (for similar regioselective displacement of 4-nitro-2-substituted pyridines, see *Eur J. Med. Chem.* (2004) 433-447; for similar regioselective displacement reactions of 2,4-dihalopyridines, see WO 2005/028452). Compound (85)

nitrosubstituted pyridine (80) (see *Eur. J. Org. Chem.* (2004) 3477-3488). The intermediate 3-substituted pyridine N-oxides can also be regioselectively nitrated at the 4-position with nitric acid in acetic or sulfuric acid (see *J. Org. Chem.* (1954) 1633-1640). Treatment of the pyridine N-oxide with $POCl_3$ forms the 2-halo-4-nitrosubstituted pyridine (80).

According to another method, substituted 2,4-dihalopyridine (82) can be made from 2,4-dihydroxylated pyridine (81), which is formed via a condensation reaction (e.g., for R=COOMe, see *J. Het. Chem.* (1983) 1363) by treatment with POCl₃ (see ester see WO 2005/028452). Alternatively, 2,4-dihalopyridine (83) can be regioselectively lithiated at low temperature and treated with an electrophile (see: *J. Org. Chem.* (2005) 2494-2502) to provide compound (84). For example, when using bromine or iodine as the electrophile, 2,4-dichloro-5-bromopyridine or 2,4-5-iodopyridine can be prepared via this method (see *J. Org. Chem.* (2005) 2494-2502 and *Eur. J. Org. Chem.* (2001) 1371-1376). The 4-Cl group of compound (84) is preferentially displaced by a nucleophiles R²LH (e.g., upon treatment with NaH in DMF). Alternatively, the 5-iodide derivative can be preferentially lithiated to form the lithium anion and be quenched with electrophiles (a two step procedure to the same compounds).

Compound (87) can be converted to a compound of Formula I by the procedure shown in Scheme A or Scheme B.

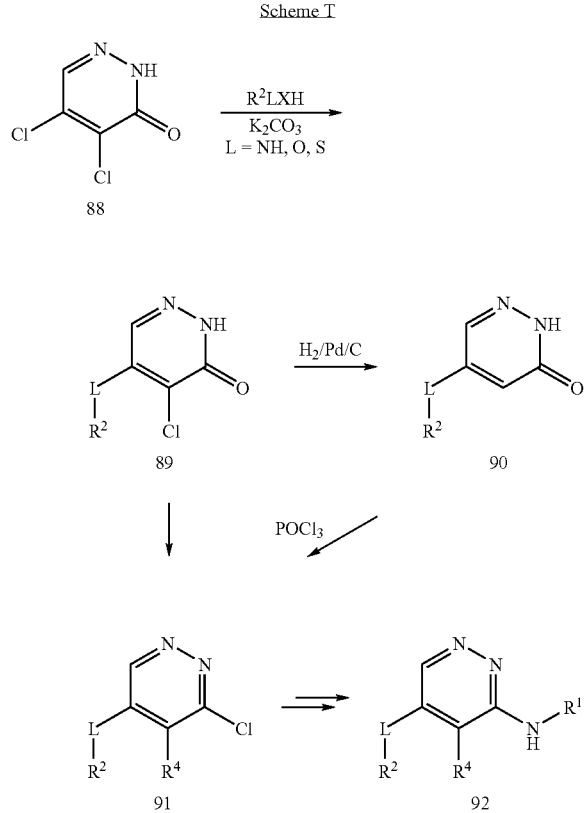

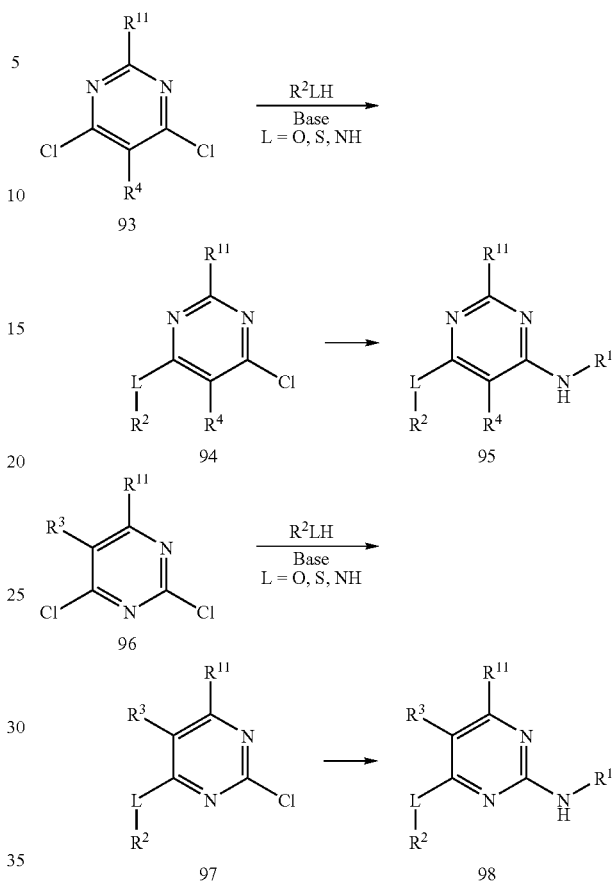

Scheme T shows a method of preparing a compound of Formula I wherein G is N, Y is CR⁴ and Z is CH. According to Scheme T, the 5-chloro substituent of compound (88) is selectively displaced by the nucleophile R²LXH to afford compound (89) (for a similar procedure using 88, see *J. Med. Chem.* (2004) 4716-4719). Compound (89) can be converted directly to compound (91) upon treatment with POCl₃, or alternatively compound (89) can be hydrogenated with Pd/C with hydrogen to afford compound (90) which is treated POCl₃ to afford compound (91) (where R⁴=H). Compound (91) can be converted to compound (92) of Formula I.

Scheme U shows tow general methods of preparing compounds of Formula I, i.e., compound (95) wherein G is CR¹¹, Z is N and Y is CR⁴, and compound (98) wherein G is CR¹¹, Z is CR³ and Y is N.

According to the first method of Scheme U, nucleophile R²LH is added to 4,6-dichloropyrimidine (95) in the presence of a suitable base such as potassium or cesium carbonate, or an alkali hydride in a suitable solvent such as DMF, ethanol or DMSO. The reaction proceeds to afford the monoaddition adduct in good yields. The compounds 94 can be easily converted to compounds of Formula I (95) by the conditions found in Scheme B. If compound (95) is not commercially available, it can be prepared by the addition of guanidine (where R¹¹=NHR; see *Chem. Ber.* (1963) 96, 2786), or amidine (where R¹¹=H, or alkyl, see *J. Med. Chem.* (2002) 45, 3639-3648) to a diester of malonic acid, or a diester of a monoalkylated (R³) malonic acid. Treatment of the dihydroxyl intermediate with POCl₃ affords compound (93) or (95).

In the second general method, treatment of the dihalopyrimidine (96) with a nucleophile R²LH in the presence of a suitable base (potassium or cesium carbonate, alkali hydrides, etc.) in a suitable solvent such as DMSO, DMF, or ethanol, affords the mono adduct (97) regioselectively (e.g., see *Aust. J. Chem.* (1985) 38, 825-833). Compound (97) can be converted easily to compound (98) of Formula I by the method described in Scheme B. If the 4,6-dihalopyrimidine (96) is not commercially available, it can be prepared via general literature procedures; e.g., condensation of β-keto esters (R¹¹COCR³COOR) with urea to afford a dihydroxylated pyrimidine, which is then reacted with POCl₃ to afford the dihalopyrimidine (96).

Scheme V

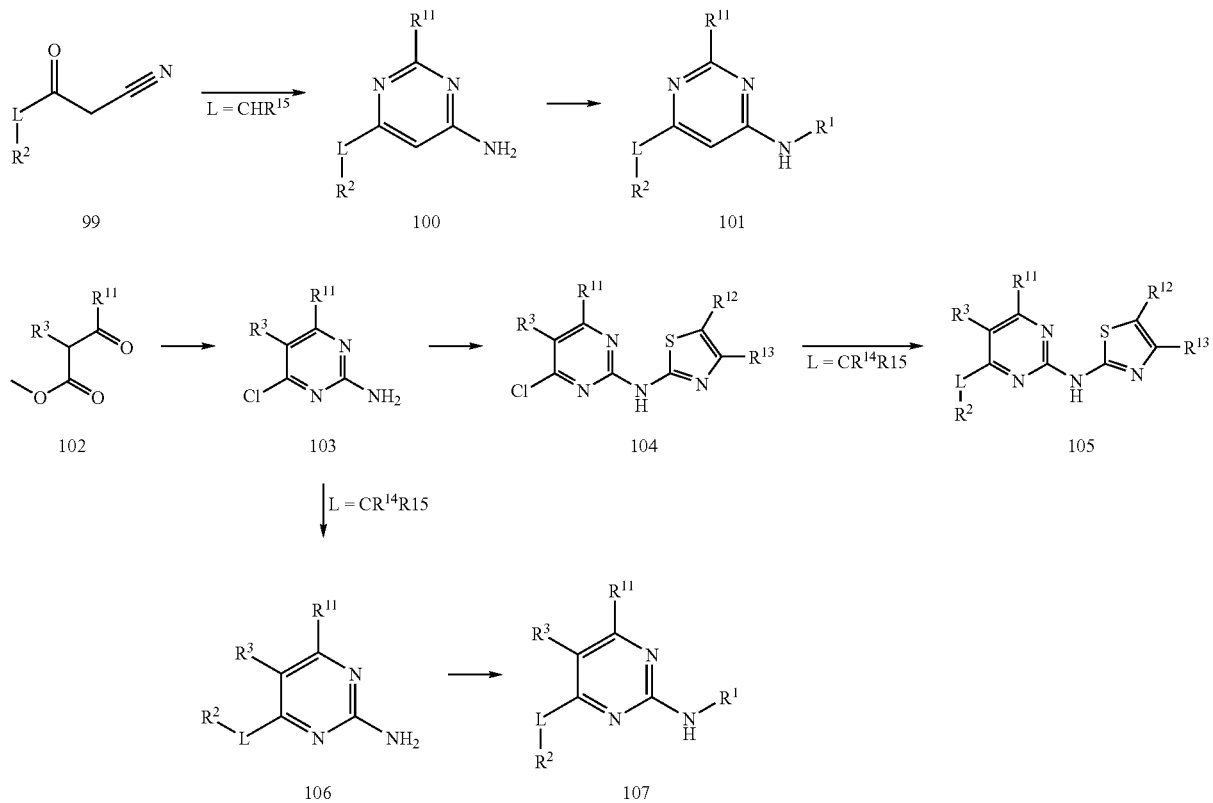

Scheme V shows two general methods for preparing compounds (101) and (107) of Formula I wherein L is CHR$^{15}$ and CR$^{14}$R$^{15}$, respectively.

In the first general method, useful for preparation of compounds of Formula I where L=CHR$^5$, the β-ketonitrile (99) is condensed with formamide or amidine to afford compound (100). Compound (100) can be readily converted to compounds (101) of Formula I by the methods described in Schemes A or B.

In the second general method, useful for pyrimidines of Formula I where L=CR$^{14}$R$^{15}$, the β-diketoesters (102) are treated with guanidine and then with POCl$_3$ to afford compound (103). Compound (103) can be converted to compound (104) by procedures found in Schemes A or B. Compound (104) can then be converted to other compounds (105) of Formula I by the methods found in Schemes J, K and U. Alternatively, compound (103) can be transformed to compound (106) by the methods found in Schemes J, K and U. The resulting compound (106) can be converted to compound (107) of Formula I by the methods described in Scheme A or B.

Scheme W

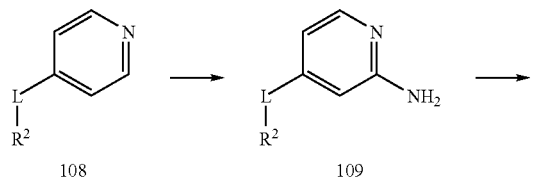

-continued

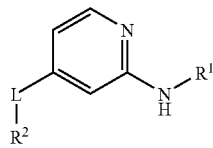

Scheme W shows a method of preparing a compound of Formula I wherein L=O, S, or CHR$^{15}$. Compound (108), wherein R$^2$ is an aryl, heteroaryl, cycloalkyl, or heterocyclyl moiety, can be made from 4-pyridine carboxaldehyde via an addition of R$^2$MgX, followed by a reduction with a palladium catalyst with hydrogen. For compounds wherein L=CHR$^{15}$, the intermediate carbinol is oxidized to the ketone, followed by addition of RMgX, followed by catalytic hydrogenation. Subsequently, compound (108) is subjected to a Chichibabin reaction to afford the 2-aminopyridyl derivative (109) (for similar compounds made via this procedure, see *J. Het. Chem.* (1996) 1195-1200). Compound (109) can be converted to compound (110) of Formula I by the methods described in Schemes A or B.

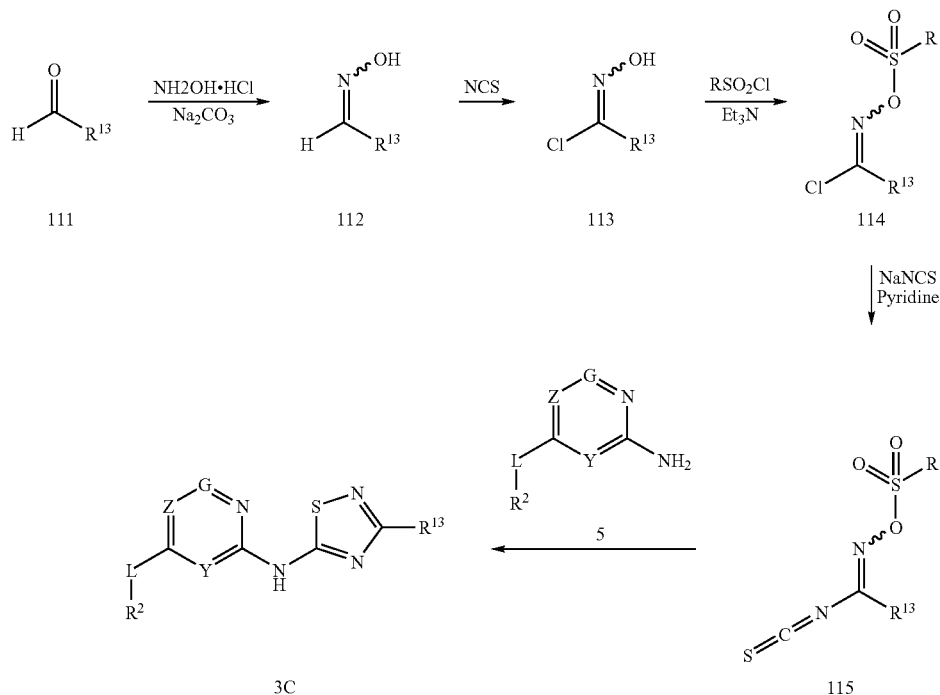

Scheme X shows an alternative method for producing compounds of the formula 3C. Formation of oxime (112) from aldehyde (111) allows for the chlorination with N-chlorosuccinimide in a suitable solvent, such as DMF, to produce (113). This product can then be sulfonylated with a sulfonyl chloride in the presence of a base, such as but not limited to triethylamine, to afford (114) (see U.S. Pat. No. 3,983,246). Reaction of (114) in a suitable solvent such as acetonitrile, with a thiocyanate salt such as NaNCS, in the presence of a base such as but not limited to pyridine, affords the activated intermediate (115) (see Takeuchi, K., JP 2001081084). This intermediate can be reacted in situ with an appropriate amino heterocycle (5) to afford compounds of the structure (3C) of Formula I.

Accordingly, another embodiment of the invention provides a method for preparing a compound of Formula I or a salt thereof, comprising:

(a) reacting a compound of the formula

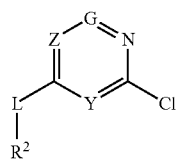

with a compound of the formula $R^1NH_2$ in the presence of a base catalyst or metal catalyst; or (b) reacting a compound of the formula

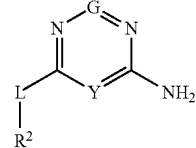

with a compound of the formula $R^1$—X, wherein X is Cl or Br, in the presence of a base catalyst or metal catalyst; or
reacting a compound of the formula

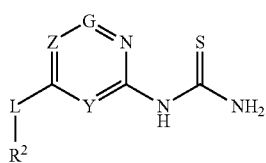

with a compound of the formula $R^{13}COCHR^{12}X^1$, wherein $X^1$ is a leaving group, in the presence of a base. Examples of suitable leaving groups include OTs, Cl, Br, I, and $N(C_1\text{-}C_6 \text{ alkyl})_3$.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for Methods of Treatment with Compounds of Formula I The compounds of the present invention can be used as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below. Furthermore, the compounds of the present invention can be also used to prevent the progression of the borderline type, impaired glucose tolerance, IFG (impaired fasting glucose) or IFG (impaired fasting glycemia) to diabetes mellitus.

Accordingly, another aspect of the invention provides methods of treating or preventing diseases or conditions described herein by administering to a mammal, such as a human, a therapeutically effective amount of a compound of Formula I in an amount effective to treat or prevent said disorder.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "mammal" refers to a warm-blooded animal that has or is at risk of developing a disease described herein and includes, but is not limited to, guinea pigs, dogs, cats, rats, mice, hamsters, and primates, including humans.

In certain embodiments, the methods of this invention are useful for treating diabetes mellitus. Diabetes mellitus is a condition where the fasting plasma glucose level (glucose concentration in venous plasma) is greater than or equal to 126 mg/dL (tested on two occasions) and the 2-hour plasma glucose level of a 75 g oral glucose tolerance test (OGTT) is greater than or equal to 200 mg/dL. Additional classic symptoms include polydipsia, polyphagia and polyuria.

In certain embodiments, the methods of this invention are useful for treating the syndrome of impaired glucose tolerance (IGT). IGT is diagnosed by the presentation of a fasting plasma glucose level of less than 126 mg/dL and a 2-hour post-oral glucose challenge lever greater than 140 mg/dL.

The compounds of the present invention can be also used as prophylactics or therapeutic agents of diabetic complications such as, but not limited to, neuropathy, nephropathy, retinopathy, cataract, macroangiopathy, osteopenia, diabetic hyperosmolar coma), infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance, etc.

The compounds of the present invention can be also used as prophylactics or therapeutic agents in the treatment of diseases and disorders such as, but not limited to, obesity, metabolic syndrome (syndrome X), hyperinsulinemia, hyperinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis, nephrotic syndrome, hypertensive nephrosclerosis, terminal renal disorder etc.), myocardiac infarction, angina pectoris, and cerebrovascular disease (e.g., cerebral infarction, cerebral apoplexy).

The compounds of the present invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarirtis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

This invention also provides the use of a compound of Formula I in the treatment of diseases or disorders mediated by deficient levels of glucokinase activity or which can be treated by activating glucokinase.

An additional aspect of the invention is the use of a compound of Formula I in the preparation of a medicament for the treatment or prevention of diseases or disorders mediated by deficient levels of glucokinase activity or which can be treated by activating glucokinase.

Combination Therapy

The compounds of the present invention can be used in combination with one or more additional drugs such as described below. The dose of the second drug can be appropriately selected based on a clinically employed dose. The proportion of the compound of the present invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of the present invention.

The second compound of the pharmaceutical combination formulation or dosing regimen preferably has complementary activities to the compound of this invention such that they do not adversely affect each other. Such drugs are suitably present in combination in amounts that are effective for the purpose intended. Accordingly, another aspect of the present invention provides a composition comprising a compound of this invention in combination with a second drug, such as described herein.

A compound of this invention and the additional pharmaceutically active agent(s) may be administered together in a unitary pharmaceutical composition or separately and, when administered separately this may occur simultaneously or sequentially in any order. Such sequential administration may be close in time or remote in time. The amounts of the compound of this invention and the second agent(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The compounds of the present invention can be used, for example, in combination with additional drug(s) such as a therapeutic agent for diabetes mellitus, and/or a therapeutic agent for diabetic complications, as defined above. Examples of known therapeutic agents for diabetes mellitus which can be used in combination with a compound of this invention include insulin preparations (e.g., animal insulin preparations extracted from the bovine or swine pancreas; human insulin preparations synthesized by a genetic engineering technique using *Escherichia coli* or a yeast), a fragment of insulin or derivatives thereof (e.g., INS-1), agents for improving insulin resistance (e.g., pioglitazone hydrochloride, troglitazone, rosiglitazone or its maleate, GI-262570, JTT-501, MCC-555, YM-440, KRP-297, CS-011, SK-614), alpha-glucosidase inhibitors (e.g., voglibose, acarbose, miglitol, emiglitate), biguanides (e.g., phenformin, metformin, buformin), insulin secretagogues[sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or its calcium salt hydrate, GLP-1], dipeptidylpeptidase IV inhibitors (e.g., NVP-DPP-278, PT-100), beta-3 agonists (e.g., CL-316243, SR-58611-A, UL-TG-307, SB-226552, AJ-9677, BMS-196085, AZ-40140, etc.), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), and the like.

Examples of known therapeutic agents for diabetic complications include aldose reductase inhibitors (e.g., tolrestat, epalrestat, zenarestat, zopolrestat, minalrestat, fidarestat (SNK-860), CT-112), neurotrophic factors (e.g., NGF, NT-3, BDNF), neurotrophic factor production secretion promoters, PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g., thioctic acid), and cerebral vasodilators (e.g., tiapuride, mexiletine).

The compounds of the present invention can also be used, for example in combination with antihyperlipidemic agents. Epidemiological evidence has firmly established hyperlipidemia as a primary risk factor in causing cardiovascular disease (CVD) due to atherosclerosis. In recent years, emphasis has been placed on lowering plasma cholesterol levels, and low density lipoprotein cholesterol in particular, as an essential step in prevention of CVD. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance. Examples of antihyperlipidemic agents include statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

The compounds of the present invention can also be used, for example, in combination with hypotensive agents. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension. Examples of hypotensive agents include angiotensin converting enzyme inhibitors (e.g., captopril, enalapril, delapril), angiotensin II antagonists (e.g., candesartan cilexetil, losartan, eprosartan, valsantan, termisartan, irbesartan, tasosartan), calcium antagonists (e.g., manidipine, nifedipine, nicardipine, amlodipine, efonidipine), and clonidine.

The compounds of the present invention can be used in combination with antiobesity agents. The term "obesity" implies an excess of adipose tissue. Obesity is a well-known risk factor for the development of many very common diseases such as diabetes, atherosclerosis, and hypertension. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding center that stimulate eating, and the satiety center modulates this process by sending inhibitory impulses to the feeding center. Several regulatory processes may influence these hypothalamic centers. The satiety center may be activated by the increases in plasma glucose and/or insulin that follow a meal. Examples of antiobesity agents include antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists (e.g., CL-316243, SR-58611-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-15849).

Routes of Administration

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with, for example, the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of this invention in association with a pharmaceutically acceptable diluent or carrier.

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

According to another embodiment, a kit may comprise (a) a first container with a compound of this invention contained therein; and (b) a second container with a second pharmaceutical formulation contained therein, wherein the second pharmaceutical formulation comprises a second compound useful for treating a disorder mediated by deficient levels, of glucokinase activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other glucokinase activators of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

The compounds of this invention also include the compounds of Examples 1-11, 14, 16, 18-19, 21, 25-29, 32-58, 60-63, 65-87, 89-90, and 92-202 described below. Compounds labeled "Reference Examples" were either found to be weakly active in the in vitro assays described below, or are included to exemplify the synthesis of intermediates used to prepare compounds of Formula I.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters). $^1$H NMR spectra were recorded on a Varian instrument operating at 400 MHz. $^1$H-NMR spectra were obtained as CDCl$_3$ or d$_6$-DMSO solutions (reported in ppm), using (7.25 ppm) or tetramethylsilane (0.00 ppm) as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2-(2-(4-Methylthiazol-2-ylamino)pyridin-4-yloxy)benzonitrile

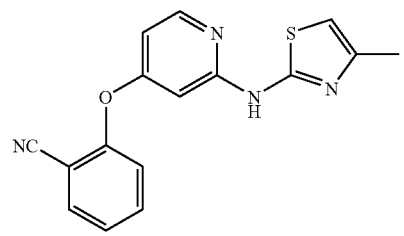

Step A: Preparation of 4-(benzyloxy-2-chloropyridine: A 250 mL round-bottomed flask was charged with 4-(benzyloxy)pyridin-2(1H)-one (10.0 g, 49.7 mmol) and phosphorus oxychloride (55.6 mL, 596 mmol). The reaction mixture was heated at 90° C. overnight, then cooled and carefully quenched with sodium carbonate and sodium hydroxide to pH 7. The aqueous layer was extracted with dichloromethane. The organic layer was dried over sodium sulfate, filtered and concentrated. The residue was purified by silica gel column chromatography with dichloromethane as eluent to afford 4-(benzyloxy)-2-chloropyridine (5.14 g, 47.1% yield) as white solid. $^1$H NMR (CDCl$_3$) δ 8.19 (d, 1H), 7.34-7.44 (m, 5H), 6.91 (d, 1H), 6.81 (dd, 1H), 5.10 (s, 2H). LC/MS: (5 to 95) $R_t$=2.64 min (ESI) m/z=220 (M+H) (40%).

Step B: Preparation of 4-(benzyloxy)-AN-(4-methylthiazol-2-yl)pyridin-2-amine: A 250 mL round-bottomed flask was charged with 2-amino-4-methylthiazole (43.8 mL, 17.5 mmol), 4-(benzyloxy)-2-chloropyridine (4.23 g, 19.3 mmol), potassium phosphate (4.09 g, 19.3 mmol), and toluene (44 mL), and the reaction mixture was degassed with nitrogen. Tris(dibenzylideneacetone)-dipalladium (0) (0.401 g, 0.438 mmol) and 9,9-dimethyl-4,5-bis(diphenyl-phosphino)-xanthene (0.279 g, 0.482 mmol) were added, and the reaction mixture was degassed with nitrogen. The reaction mixture was warmed to 90° C., degassed water (15 mL) was added, and reaction mixture was stirred at 90° C. overnight. Water was added, and the reaction mixture was extracted with ethyl acetate. The organic layer was dried over magnesium sulfate and filtered through a small plug of silica gel, and the filtrate was concentrated down to 50 mL of ethyl acetate and filtered to afford 4-(benzyloxy)-N-(4-methylthiazol-2-yl)pyridin-2-amine (2.50 g, 47.5% yield) as a white solid. $^1$H NMR (CDCl$_3$) δ 9.29 (bs, 1H), 8.15 (d, 1H), 7.39 (m, 4H), 7.35 (m, 1H), 6.53 (dd, 1H), 6.41 (d, 1H), 6.36 (d, 1H), 5.07 (s, 2H), 2.33 (s, 3H). Mass spectrum (esi) m/z=298 (M Step C: Preparation of 2-(4-methylthiazol-2-ylamino)pyridin-4-ol: Following the method of Example 3, Step A, 4-(benzyloxy)-N-(4-methylthiazol-2-yl)pyridin-2-amine (prepared according to Example 17) (2.3 g, 7.73 mmol), and HCl (38.7 mL, 116 mmol) (3M HCl) were reacted to provide 2-(4-methylthiazol-2-ylamino)pyridin-4-ol (0.620 g, 38.7% yield) as white solid. $^1$H NMR (CDCl$_3$) δ 7.38 (bs, 1H), 6.23 (m, 2H), 6.10 (bs, 1H), 2.28 (s, 3H). HPLC (5 to 95) $R_t$=1.82 min; Mass spectrum (esi) m/z=208 (M+H).

Step D: Preparation of 2-(2-(4-methylthiazol-2-ylamino)pyridin-4-yloxy)benzonitrile: 2-(4-Methylthiazol-2-ylamino)pyridin-4-ol (0.100 g, 0.483 mmol), 2-fluorobenzonitrile (0.064 g, 0.531-mmol) and potassium carbonate (0.167 g, 1.21 mmol) were combined in DMSO and heated at 90° C. overnight. The reaction mixture was partitioned between ethyl acetate and water. The organic layer was washed with water and brine, dried, and concentrated. The residue was purified by MPLC, eluting with 3:1 hexane:ethyl acetate to afford the free base. The free base was dissolved in THF (3 mL) and 1M HCl in ether (6 mL) was added. The solution was diluted with ether (15 mL), triturated for 10 minutes, and filtered to afford 2-(2-(4-methylthiazol-2-ylamino)pyridin-4-yloxy)benzonitrile (0.013 g, 8.65% yield) as white solid. $^1$H NMR (CDCl$_3$) δ 8.26 (d, 1H), 7.72 (dd, 1H), 7.60 (m, 1H), 7.32 (dt, 1H), 7.14 (d, 1H), 6.53 (dd, 1H), 6.42 (d, 1H), 6.33 (d, 1H), 2.23 (d, 3H); HPLC $R_t$=2.67 min; Mass spectrum (esi) m/z=309 (M+H).

Example 2

4-(2-(4-Methylthiazol-2-ylamino)pyridin-4-yloxy)benzonitrile

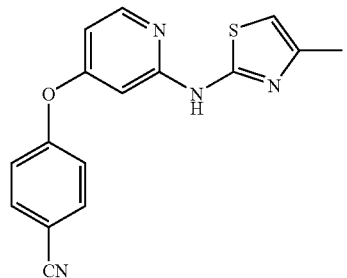

Following the method of Example 1, Step D, 2-(4-methylthiazol-2-ylamino)pyridin-4-ol (0.100 g, 0.483 mmol), 4-fluorobenzonitrile (0.064 g, 0.531 mmol) and potassium carbonate (0.167 g, 1.21 mmol) were reacted to provide 4-(2-(4-methylthiazol-2-ylamino)pyridin-4-yloxy)benzonitrile (0.033 g; 20.0% yield) as white solid. $^1$H NMR (CDCl$_3$) δ 8.27 (d, 1H), 7.72 (m, 1H), 7.70 (m, 1H), 7.18 (m, 1H), 7.16 (m, 1H), 6.52 (dd, 1H), 6.49 (m, 1H), 6.38 (s, 1H), 2.28 (d, 3H). HPLC (5 to 95) $R_t$=2.69 min; Mass spectrum (esi) m/z=309 (M+H).

Example 3

Methyl 3-(2-(4-methylthiazol-2-ylamino)pyridin-4-yloxy)benzoate

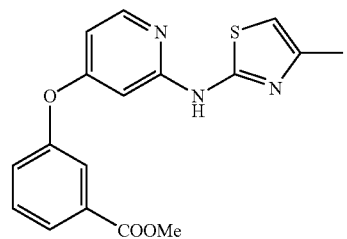

Step A: Preparation of methyl 3-(2-chloropyridin-4-yloxy)benzoate: Methyl 3-hydroxybenzoate (2.88 g, 18.9 mmol) was added to a mixture of 60% sodium hydride in mineral oil (0.757 g, 18.9 mmol) in DMF (20 mL). The reaction mixture was stirred for 20 minutes and then cooled in an ice bath. 2-Chloro-4-nitropyridine (3.00 g, 18.9 mmol) was added and the reaction mixture was stirred for 1 hour at 0° C., and then overnight at room temperature. The reaction mixture was partitioned between water and ethyl acetate. The organic layer was washed twice with water and brine, dried, and concentrated. The residue was purified by MPLC (Biotage) eluting with 5:1 hexane:ethyl acetate to afford methyl 3-(2-chloropyridin-4-yloxy)benzoate (4.49 g, 90.0% yield) as a thick oil. $^1$H NMR (CDCl$_3$) δ 8.26 (d, 1H), 7.98 (d, 1H), 7.77 (s, 1H), 7.54 (t, 1H), 7-31 (d, 1H), 6.82 (s, 1H), 6.79 (d, 1H).

Step B: Preparation of methyl 3-(2-(4-methylthiazol-2-ylamino)pyridin-4-yloxy)benzoate: Methyl 3-(2-chloropyridin-4-yloxy)benzoate (3.05 g, 11.6 mmol), 4-methylthiazol-2-amine (26.3 mL, 10.5 mmol), potassium phosphate (2.45 g, 11.6 mmol), tris(dibenzylideneacetone)dipalladium (0) (0.241 g, 0.263 mmol) and 9,9-dimethyl-4,5-bis(diphenylphosphino)xanthene (0.167 g, 0.289 mmol) were reacted in toluene (26 mL) and water (8 mL) according to Example 17, Step B to afford methyl 3-(2-(4-methylthiazol-2-ylamino)pyridin-4-yloxy)benzoate (2.65 g, 68.7% yield) as yellow solid. $^1$H NMR (CDCl$_3$) δ 8.15 (d, J=5.85 Hz, 1H), 7.89 (dt, J=1.17, 7.80 Hz, 1H), 7.70 (m, 1H), 7.45 (t, J=7.80 Hz, 1H), 7.24 (m, 1H), 6.44 (dd, J=1.95, 5.85 Hz, 1H), 6.25 (m, 2H), 3.88 (s, 3H), 2.14 (d, J=1.17 Hz, 3H). Mass spectrum (esi) m/z=342 (100) (M+H).

Example 4

Preparation of N-(4-(2-methoxyphenoxy)pyridin-2-yl)-4-methylthiazol-2-amine

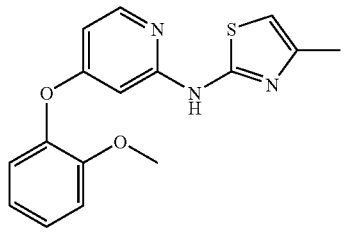

Step A: Preparation of 2-chloro-4-(2-methoxyphenoxy)pyridine:

Using the method of Example 3, Step A, 2-methoxyphenol (2.35 g, 18.9 mmol), 60% sodium hydride in mineral oil (0.757 g, 18.9 mmol), and 2-chloro-4-nitropyridine (3.00 g, 18.9 mmol) were reacted to provide 2-chloro-4-(2-methoxyphenoxy)pyridine (4.32 g, 96.9% yield) as a white powder. $^1$H NMR (CDCl$_3$) δ 8.20 (d, 1H), 7.27 (m, 1H), 7.10 (d, 1H), 6.99-7.06 (m, 2H), 6.72-6.75 (m, 2H), 3.79 (s, 3H).

Step B: Preparation of N-(4-(2-methoxy-henoxy)pyridin-2-yl)-4-methylthiazol-2-amine: Using the method of Example 3, step B, 2-chloro-4-(2-methoxyphenoxy)pyridine (2.95 g, 12.5 mmol), 4-methylthiazol-2-amine (28.5 mL, 11.4 mmol), potassium phosphate (2.66 g, 12.5 mmol), Pd$_2$(dba)$_3$ (0.261 g, 0.285 mmol) and 4,5-bis(diphenylphosphino)-9,9-dimethyl-9H-xanthene (0.181 g, 0.313 mmol) were reacted in toluene (30 mL) and water (8 mL) to provide 4-(2-methoxyphenoxy)-N-(4-methylthiazol-2-yl)pyridin-2-amine (3.12 g, 82.2% yield) as yellow solid. $^1$H NMR (CDCl$_3$) δ 8.10 (d, 1H), 7.19 (m, 1H), 7.04 (dd, 1H), 6.95 (m, 2H), 6.42 (dd, 1H), 6.24 (d, 1H), 6.14 (d, 1H), 3.71 (s, 1H), 2.12 (s, 3H); Mass spectrum (apci) m/z=314 (100) (4+H).

Example 5

N-(4-(3-Methoxyphenoxy)pyridin-2-yl)-4-methylthiazol-2-amine

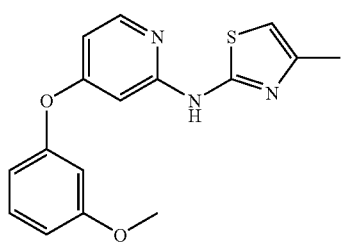

Step A: Preparation of 2-chloro-4-(3-methoxyphenoxy)pyridine: Using the method of Example 3, Step A, 3-methoxyphenol (2.35 g, 18.9 mmol), 60% sodium hydride in mineral oil (0.757 g, 18.9 mmol), and 2-chloro-4-nitropyridine (3.00 g, 18.9 mmol) were reacted to provide 2-chloro-4-(3-methoxyphenoxy)pyridine (4.24 g, 95.1% yield) as a thick oil. $^1$H NMR (CDCl$_3$) δ (8.23 (d, 1H), 7.34 (t, 1H), 6.80-6.85 (m, 3H), 6.63-6.69 (m, 2H), 3.82 (s, 3H).

Step B: Preparation of N-(4-(3-methoxyphenoxy)pyridin-2-yl)-4-methylthiazol-2-amine: Using the method of Example 3, Step B, 2-chloro-4-(3-methoxyphenoxy)pyridine (2.95 g, 12.5 mmol), 4-methylthiazol-2-amine (28.5 mL, 11.4 mmol), potassium phosphate (2.66 g, 12.5 mmol), Pd$_2$(dba)$_3$ (0.261 g, 0.285 mmol) and 4,5-bis(diphenylphosphino)-9,9-dimethyl-9H-xanthene (0.181 g, 0.313 mmol) were reacted in toluene (30 mL) and water (8 mL) to provide 4-(3-methoxyphenoxy)-N-(4-methylthiazol-2-yl)pyridin-2-amine (3.44 g, 88.7% yield) as yellow solid. $^1$H NMR (CDCl$_3$) δ 8.14 (d, 1H), 7.26 (t, 1H), 6.76 (m, 1H), 6.63 (m, 1H), 6.58 (t, 1H), 6.46 (dd, 1H), 6.27 (m, 2H), 3.75 (s, 3H), 2.17 (s, 3H); Mass spectrum (esi) m/z=314 (100) (M+H).

Example 6

N-(4-(4-Methoxyphenoxy)pyridin-2-yl)-4-methylthiazol-2-amine

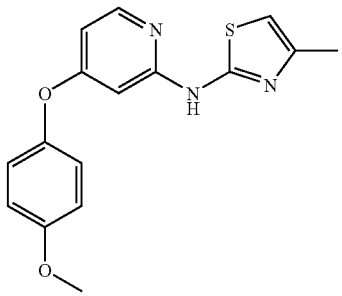

Step A: Preparation of 2-chloro-4-(4-methoxyphenoxy)pyridine: Using the method of Example 3, Step A, 4-methoxyphenol (2.35 g, 18.9 mmol), 60% sodium hydride in mineral oil (0.757 g, 18.9 mmol), and 2-chloro-4-nitropyridine (3.00 g, 18.9 mmol) were reacted to provide 2-chloro-4-(4-methoxyphenoxy)pyridine (4.44 g, 99% yield) as an oil. $^1$H NMR (CDCl$_3$) δ 8.20 (d, 1H), 7.01 (d, 2H), 6.95 (d, 2H), 6.75-6.77 (m, 2H), 3.84 (s, 3H).

Step B: Preparation of N-(4-(3-methoxyphenoxy)pyridin-2-yl)-4-methylthiazol-2-amine: Using the method of Example 3, Step B, 2-chloro-4-(4-methoxyphenoxy)pyridine (2.952 g, 12.53 mmol), 4-methylthiazol-2-amine (28.47 mL, 11.39 mmol), potassium phosphate (2.417 g, 11.39 mmol), Pd$_2$(dba)$_3$, (0.2607 g, 0.2847 mmol) and 9,9-dimethyl-4,5-bis(diphenylphosphino)xanthene (0.1812 g, 0.3131 mmol) were reacted in toluene (30 mL) and water (8 mL) to provide 4-(4-methoxyphenoxy)-N-(4-methylthiazol-2-yl)pyridin-2-amine (1.726 g, 44.50% yield) as yellow solid. $^1$H NMR (CDCl$_3$) δ 8.10 (d, 1H), 6.96 (m, 2H), 6.87 (m, 2H), 6.42 (dd, 1H), 6.26 (d, 1H), 6.18 (d, 1H), 3.80 (s, 3H), 2.15 (s, 3H); Mass spectrum (esi) m/z=314 (100) (+H).

Example 7

N-(4-Phenoxypyridin-2-yl)-4-methylthiazol-2-amine

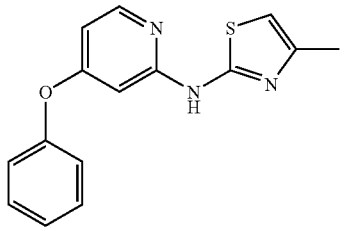

Step A: Preparation of 2-chloro-4-phenoxypyridine: Using the method of Example 3, Step A, phenol (494 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-phenoxypyridine (1.27 g, 98% yield) as an oil. $^1$H NMR (CDCl$_3$) δ 8.22 (d, 1H), 7.45 (t, 2H), 7.29 (t, 1H), 7.09 (d, 2H), 6.77-6.82 (m, 2H).

Step B: Preparation of N-(4-phenoxyridin-2-yl)-4-methylthiazol-2-amine: Using the method of Example 3, Step B, 2-chloro-4-phenoxypyridine (0.575 g, 2.79 mmol), 4-methylthiazol-2-amine (6.35 mL, 2.54 mmol), potassium phosphate (0.593 g, 2.79 mmol), Pd$_2$(dba)$_3$ (0.0582 g, 0.0635 mmol) and 4,5-bis(diphenylphosphino)-9,9-dimethyl-9H-xanthene (0.0404 g, 0.0699 mmol) in toluene (8 mL) and water (2 mL) afforded N-(4-methylthiazol-2-yl)-4-phenoxypyridin-2-amine (170 mg, 23% yield) as yellow solid. $^1$H NMR (CDCl$_3$) δ 9.72 (bs, 1H), 8.17 (d, 1H), 7.41 (m, 2H), 7.25 (m, 1H), 7.08 (m, 2H), 6.48 (dd, 1H), 6.30 (s, 1H), 6.28 (d, 1H), 2.19 (d, 3H); Mass spectrum (esi) m/z=284 (100) (M+H).

Example 8

4-Methyl-N-(4-(naphthalen-1-yloxy)pyridin-2-yl)thiazol-2-amine

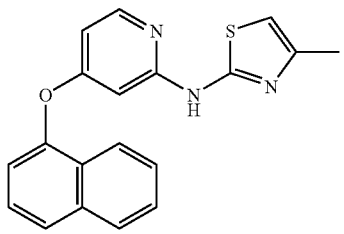

Step A: Preparation of 2-chloro-4-(naphthalen-1-yloxy)pyridine: Using the method of Example 3, Step A, naphthalen-1-ol (909 mg, 6.31 mmol), 60% sodium hydride in mineral oil (252 mg, 6.31 mmol), and 2-chloro-4-nitropyridine (1.00 g, 6.31 mmol) afforded 2-chloro-4-(naphthalen-1-yloxy)pyridine (1.53 g, 95% yield) as an oil. $^1$H NMR (CDCl$_3$) δ 8.22 (d, 1H), 7.93 (d, 1H), 7.86 (d, 1H), 7.81 (d, 1H), 7.48-7.56 (m, 3H), 7.21 (d, 1H), 6.79-6.83 (m, 2H).

Step B: Preparation of 4-methyl-N-(4-(naphthalen-1-yloxy)pyridin-2-yl)thiazol-2-amine: Using the method of Example 3, Step B, 2-chloro-4-phenoxypyridine (0.575 g, 2.79 mmol), 4-methylthiazol-2-amine (6.35 mL, 2.54 mmol), potassium phosphate (0.593 g, 2.79 mmol), Pd$_2$(dba)$_3$ (0.0582 g, 0.0635 mmol) and 4,5-bis(diphenylphosphino)-9,9-dimethyl-9H-xanthene (0.0404 g, 0.0699 mmol) were reacted in toluene (6 mL) and water (2 mL) to provide N-(4-methylthiazol-2-yl)-4-(naphthalen-1-yloxy)pyridin-2-amine (0.371 g, 77.8% yield) as off white solid. $^1$H NMR (CDCl$_3$) δ 8.13 (d, 1H), 7.90 (m, 2H), 7.76 (d, 1H), 7.53 (m, 1H), 7.46 (m, 2H), 7.18 (d, 1H), 6.49 (dd, 1H), 6.25 (m, 2H), 2.09 (s, 3H); Mass spectrum (esi) m/z=334 (100) (N+H).

Example 9

Methyl 2-(2-(4-methylthiazol-2-ylamino)pyridin-4-yloxy)benzoate

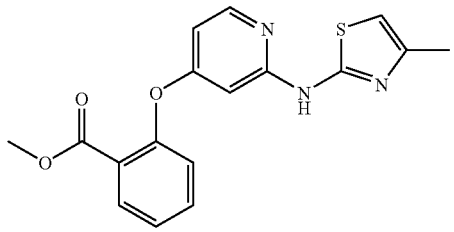

Step A: Preparation of methyl 2-(2-chloropyridin-4-yloxy)benzoate: Using the method of Example 3, Step A, methyl 2-hydroxybenzoate (2.88 mg, 18.9 mmol), 60% sodium hydride in mineral oil (757 mg, 18.9 mmol), and 2-chloro-4-nitropyridine (3.00 g, 18.9 mmol) were reacted to provide methyl 2-(2-chloropyridin-4-yloxy)benzoate (3.51 g, 70% yield) as an oil. $^1$H NMR (CDCl$_3$) δ 8.22 (d, 1H), 8.05 (d, 1H), 7.63 (t, 1H), 7.40 (t, 1H), 7.16 (d, 1H), 6.72-6.74 (m, 1H), 3.77 (s, 1H).

Step B: Preparation of methyl 2-(2-(4-methylthiazol-2-ylamino)pyridin-4-yloxy)benzoate: Using the method of Example 3, Step B, methyl 2-(2-chloropyridin-4-yloxy)benzoate (1.91 g, 7.23 mmol), 4-methylthiazol-2-amine (16.4 mL, 6.57 mmol), potassium phosphate (1.53 g, 7.23 mmol), 4,5-bis(diphenylphosphino)-9,9-dimethyl-9H-xanthene (0.105 g, 0.181 mmol) and Pd$_2$(dba)$_3$ (0.150 g, 0.164 mmol) were reacted in toluene (16 mL) and water (5 mL) to provide methyl 2-(2-(4-methylthiazol-2-ylamino)pyridin-4-yloxy)benzoate as yellow solid. $^1$H NMR (CDCl$_3$) δ 8.16 (d, 1H), 8.01 (dd, 1H), 7.57 (m, 1H), 7.35 (dt, 1H), 7.13 (d, 1H), 6.43 (dd, 1H), 6.29 (d, 1H), 6.21 (dc, 1H), 3.75 (s, 3H), 2.19 (d, 3H); Mass spectrum (esi) m/z=342 (100) (M+H).

Example 10

N-(4-(cyclohexyloxy)pyridin-2-yl)-4-methylthiazol-2-amine

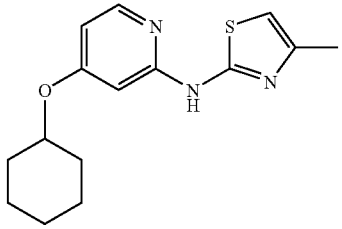

Step A: Preparation of 2-chloro-4-(cyclohexyloxy)pyridine:

Using the method of Example 3, Step A, cyclohexanol (948 mg, 9.46 mmol), 60% sodium hydride in mineral oil (378 mg, 9.46 mmol), and 2-chloro-4-nitropyridine (1.50 g, 9.46 mmol) were reacted to provide 2-chloro-4-(cyclohexyloxy)pyridine (1.78 g, 89% yield) as an oil. $^1$H NMR (CDCl$_3$) δ 8.15 (d; 1H), 6.80 (s, 1H), 6.71 (d, 1H), 4.32 (m, 1H), 1.94-1.99 (m, 2H), 1.79-1.85 (m, 2H), 1.26-1-62 (m, 6H).

Step B: Preparation of N-(4-(cyclohexyloxy)pyridin-2-yl)-4-methylthiazol-2-amine: Using the method of Example 3, Step B, 4-methylthiazol-2-amine (3.50 mL, 1.40 mmol), 2-chloro-4-(cyclohexyloxy)pyridine (0.326 g, 1.54 mmol), potassium phosphate (0.327 g, 1.54 mmol), tris(dibenzylideneacetone)dipalladium (0) (0.0321 g, 0.0350 mmol) and 9,9-dimethyl-4,5-bis(diphenylphosphino)xanthene (0.0223 g, 0.0385 mmol) were reacted in toluene (4 mL) and water (1.5 mL) to afford N-(4-(cyclohexyloxy)pyridin-2-yl)-4-methylthiazol-2-amine (0.127 g, 30.7% yield) as white solid. $^1$H NMR (CDCl$_3$) δ 8.12 (d, 1H), 6.43 (d, 1H), 6.35 (bs, 1H), 6.32 (d, 1H), 4.29 (m, 1H), 2.34 (d, 3H), 1.97 (m, 2H), 1.80 (m, 2H), 1.54 (m, 3H), 1.36 (m, 3H); Mass spectrum (apci) m/z=290 (100) (M+H).

Example 11

4-Methyl-N-(4-(phenylthio)pyridin-2-yl)thiazol-2-amine

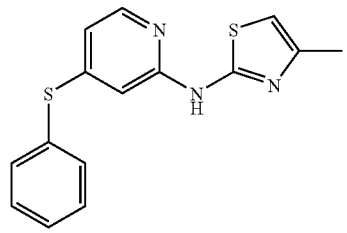

Step A: Preparation of 2-chloro-4-(phenylthio)pyridine: Using the method of Example 3, Step A, thiophenol (1.04 g, 9.46 mmol), 60% sodium hydride in mineral oil (378 mg, 9.46 mmol), and 2-chloro-4-nitropyridine (1.50 g, 9.46 mmol) were reacted to provide 2-chloro-4-(phenylthio)pyridine (1.97 g, 94% yield) as an oil. $^1$H NMR (CDCl$_3$) δ 8.11 (d, 1H), 7.45-7.58 (m, 5H), 6.90 (s, 1H), 6.85 (d, 1H).

Step B: Preparation of 4-methyl-N-(4-(2-benzylthio)pyridin-2-yl)thiazol-2-amine: Using the method of Example 3, Step B, 4-methylthiazol-2-amine (3.50 mL, 1.40 mmol), 2-chloro-4-(phenylthio)pyridine (0.342 g, 1.54 mmol), potassium phosphate (0.327 g, 1.54 mmol), tris(dibenzylideneacetone)dipalladium(0) (0.0321 g, 0.0350 mmol) and 4,5-bis(diphenylphosphino)-9,9-dimethyl-9H-xanthene (0.0223 g, 0.0385 mmol) were reacted in toluene (4 mL) and water (1.5 mL) to afford 4-methyl-N-(4-(phenylthio)pyridin-2-yl)thiazol-2-amine (0.296 g, 69.8% yield) as off white solid. $^1$H NMR (CDCl$_3$) δ 8.07 (d, 1H), 7.54 (m, 2H), 7.44 (m, 3H), 6.57 (dd, 1H), 6.45 (d, 1H), 6.32 (d, 1H), 2.24 (d, 3H); Mass spectrum (apci) m/z=300 (100) (M+H).

Example 12

Representative Example tert-Butyl 4-(2-(4-methylthiazol-2-ylamino)pyridin-4-yloxy)piperidine 1 carboxylate

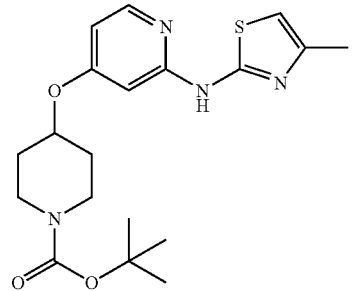

Step A: Preparation of tert-butyl 4-(2-chloropyridin-4-yloxy)piperidine-1-carboxylate: Using the method of Example 3, Step A, tert-butyl 4-hydroxypiperidine-1-carboxylate (1.90 g, 9.46 mmol), 60% sodium hydride in mineral oil (378 mg, 9.46 mmol), and 2-chloro-4-nitropyridine (1.50 g, 9.46 mmol) were reacted to provide tert-butyl 4-(2-chloropyridin-4-yloxy)piperidine-1-carboxylate (2.48 g, 84% yield) as an oil. $^1$H NMR (CDCl$_3$) δ 8.19 (d, 1H), 6.83 (s, 1H), 6.74 (d, 1H), 4.56 (m, 1H), 3.68 (ddd, 2H), 3.37 (ddd, 2H), 1.94 (dddd, 2H), 1.77 (dddd, 2H), 1.47 (s, 9H).

Step B: Preparation of tert-butyl 4-(2-(4-methylthiazol-2-ylamino)pyridin-4-yloxy)piperidine-1-carboxylate: Using the method of Example 3, Step B, 4-methylthiazol-2-amine (18.2 mL, 7.27 mmol), tert-butyl 4-(2-chloropyridin-4-yloxy)piperidine-1-carboxylate (2.50 g, 8.00 mmol), potassium phosphate (1.70 g, 8.00 mmol), tris(dibenzylideneacetone)dipalladium (0) (0.166 g, 0.182 mmol) and 4,5-bis(diphenylphosphino)-9,9-dimethyl-9H-xanthene (0.116 g, 0.200 mmol) were reacted in toluene (20 mL) and water (5 mL), to provide tert-butyl 4-(2-(4-methylthiazol-2-ylamino)pyridin-4-yloxy)piperidine-1-carboxylate (1.55 g, 54.1% yield) as white solid. $^1$H NMR (CDCl$_3$) δ 8.14 (d, 1H), 6.44 (d, 1H), 6.36 (bs, 2H), 4.51 (m, 1H), 3.68 (m, 2H), 3.34 (m, 2H), 2.34 (d, 3H), 1.92 (m, 2H), 1.75 (m, 2H), 1.47 (s, 9H); Mass spectrum (apci) m/z=291 (100) (M+H-Boc).

Example 13

Representative Example tert-butyl 3-(2-(4-methylthiazol-2-ylamino)pyridin-4-yloxy)piperidine-1-carboxylate

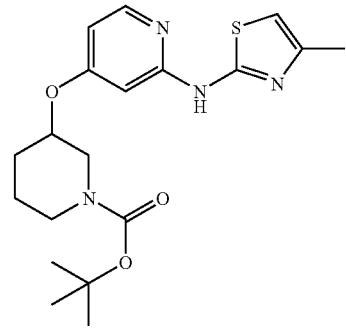

Step A: Preparation of tert-butyl 3-(2-chloropyridin-4-yloxy)piperidine-1-carboxylate: Using the method of Example 3, Step A, tert-butyl 3-hydroxypiperidine-1-carboxylate (1.90 g, 9.46 mmol), 60% sodium hydride in mineral oil (378 mg, 9-46 mmol), and 2-chloro-4-nitropyridine (1.50 g, 9.46 mmol) were reacted to provide tert-butyl 3-(2-chloropyridin-4-yloxy)piperidine-1-carboxylate (2.50 g, 84% yield) as an oil. $^1$H NMR (CDCl$_3$) δ 8.20 (d, 1H), 6.84 (s, 1H), 6.76 (d, 1H), 4.34 (m, 1H), 3.10-4.05 (bm, 4H), 1.50-2.05 (bm; 4H), 1.40 (bs, 9H).

Step B: Preparation of tert-butyl 3-(2-(4-methylthiazol-2-ylamino)pyridin-4-yloxy)piperidine-1-carboxylate: Using the method of Example 3, Step B, 4-methylthiazol-2-amine (18.2 mL, 7.27 mmol), tert-butyl 3-(2-chloropyridin-4-yloxy)piperidine-1-carboxylate (2.50 g, 8.00 mmol), potassium phosphate (1.70 g, 8.00 mmol), tris(dibenzylideneacetone)dipalladium (0) (0.166 g, 0.182 mmol) and 4,5-bis(diphenylphosphino)-9,9-dimethyl-9H-xanthene (0.116 g, 0.200 mmol) were reacted in toluene (20 mL) and water (5 mL) to provide tert-butyl 3-(2-(4-methylthiazol-2-ylamino)pyridin-4-yloxy)piperidine-1-carboxylate ((1.70 g, 53.3% yield) as yellow solid. $^1$H NMR (CDCl$_3$) δ 9.01 (bs, 1H), 8.15 (d, 1H), 6.46 (dd, 1H), 6.36 (s, 2H), 4.30 (m, 1H), 2.94-3.77 (m, 3H), 2.33 (d, 3H), 2.01 (bm, 1H), 1.79 (bm, 3H), 1.52 (m, 1H), 1.39 (bs, 9H); Mass spectrum (apci) m/z=391 (100) (M+H).

Example 14

N-(4-(3-(tert-butyldimethylsilyloxy)phenylthio)pyridin-2-yl)-4-methylthiazol-2-amine

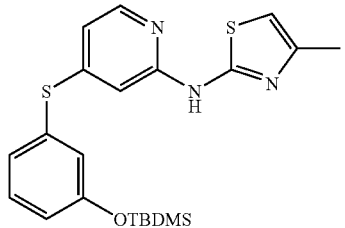

Step A: Preparation of 4-(3-(tert-butyldimethylsilyloxy)phenylthio)-2-chloropyridine: Using the method of Example 3, Step A, 3-(tert-butyldimethylsilyloxy)benzenethiol (1.52 g, 6.31 mmol), 60% sodium hydride in mineral oil (252 mg, 6.31 mmol), and 2-chloro-4-nitropyridine (1.00 g, 6.31 mmol) were reacted to provide 4-(3-(tert-butyldimethylsilyloxy)phenylthio)-2-chloropyridine (1.43 g, 64% yield) as an oil. $^1$H NMR (CDCl$_3$) δ 8.11 (d, 1H), 7.34 (t, 1H), 7.16 (d, 1H) 7.02 (s, 1H), 6.97 (d, 1H), 6.90 (s, 1H), 6.87 (d, 1H).

Step B: Preparation of N-(4-(3-(tert-butyldimethylsilyloxy)phenylthio)pyridin-2-yl)-4-methylthiazol-2-amine: Using the method of Example 3, Step B, 4-methylthiazol-2-amine (9.20 mL, 3.68 mmol), 4-(3-(tert-butyldimethylsilyloxy)phenylthio)-2-chloropyridine (1.42 g, 4.05 mmol), potassium phosphate (0.859 g, 4.05 mmol), tris(dibenzylideneacetone)-dipalladium (0) (0.0842 g, 0.0920 mmol) and 4,5-bis(diphenylphosphino)-9,9-dimethyl-9H-xanthene (0.0585 g, 0.101 mmol) were reacted in toluene (10 mL) and water (3 mL) to afford N-(4-(3-(tert-butyldimethylsilyloxy)phenylthio)pyridin-2-yl)-4-methylthiazol-2-amine (0.500 g, 28.5% yield) as yellow solid. $^1$H NMR (CDCl$_3$) δ 8.08 (d, 1H), 7.27 (t, 1H), 7.12 (dt, 1H), 7.00 (t, 1H), 6.90 (m, 1H), 6.56 (dd, 1H), 6.47 (d, 1H), 6.32 (d, 1H), 2.23 (d, 3H), 0.96 (s, 9H), 0.18 (s, 6H).

Example 15

Representative Example 4-(1-Methyl-1H-imidazol-2-ylthio)-N-(4-methylthiazol-2-yl)pyridin-2-amine dihydrochloride

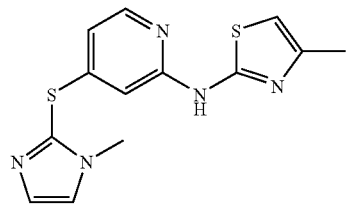

Step A: Preparation of 2-Chloro-4-(1-methyl-1H-imidazol-2-ylthio)pyridine: Using the method of Example 3, Step A, 1-methyl-1H-imidazole-2-thiol (720 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-(1-methyl-1H-imidazol-2-ylthio)pyridine (1.05 g, 74% yield) as an oil. $^1$H NMR (CDCl$_3$) δ 8.17 (d, 1H), 7.30 (d, 1H), 7.20 (d, 1H), 6.88 (s, 1H), 6.80 (d, 1H), 3.70 (s, 3H).

Step B: Preparation of 4-(1-methyl-1H-imidazol-2-ylthio)-N-(4-methylthiazol-2-yl)pyridin-2-amine dihydrochloride: Using the method of Example 3, Step B, 4-methylthiazol-2-amine (11.21 mL, 4.484 mmol), 2-chloro-4-(1-methyl-1H-imidazol-2-ylthio)pyridine (1.012 g, 4.484 mmol), potassium phosphate (0.9518 g, 4.484 mmol), Pd$_2$(dba)$_3$ (0.09332 g, 0.1019 mmol), and 4,5-bis(diphenylphosphino)-9,9-dimethyl-9H-xanthene (0.06486 g, 0.1121 mmol) were reacted to provide 4-(1-methyl-1H-imidazol-2-ylthio)-N-(4-methylthiazol-2-yl)pyridin-2-amine dihydrochloride (0.676 g, 44.07% yield) after salt formation. $^1$H NMR (d6-DMSO) δ 8.25 (d, 1H), 8.04 (d, 1H), 7.88 (d, 1H), 6.87 (s, 1H), 6.83 (dd, 1H), 6.70 (d, 1H), 3.83 (s, 3H), 2.26 (s, 3H); Mass spectrum (apci) m/z=304.1 (M+H-2HCl).

Example 16

N-(4-Methylthiazol-2-yl)-4-(5,6,7,8-tetrahydronaphthalen-1-yloxy)pyridin-2-amine hydrochloride

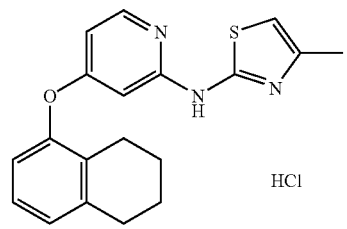

Step A: Preparation of 2-chloro-4-(5,6,7,8-tetrahydronaphthalen-1-yloxy)pyridine: Using the method of Example 3, Step A, 5,6,7,8-tetrahydronaphthalen-1-ol (935 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-(5,6,7,8-tetrahydronaphthalen-1-yloxy)pyridine (1.60 g, 98% yield) as an oil. $^1$H NMR (CDCl$_3$) δ 8.19 (d, 1H), 7.15 (t, 1H), 7.03 (d, 1H), 6.82 (d, 1H), 6.71-6.75 (m, 2H), 2.82 (t, 2H), 2.52 (t, 2H), 1.71-1.81 (m, 4H).

Step B: Preparation of N-(4-methylthiazol-2-yl)-4-(5,6,7,8-tetrahydronaphthalen-1-yloxy)pyridin-2-amine hydrochloride: Using the method of Example 3, Step B, 4-methylthiazol-2-amine (16.77 mL, 6.708 mmol), 2-chloro-4-(5,6,7,8-tetrahydronaphthalen-1-yloxy)pyridine (1.584 g, 6.099 mmol), potassium phosphate (1.424 g, 6.708 mmol), Pd$_2$(dba)$_3$ (0.1396 g, 0.1525 mmol) and 4,5-bis(diphenylphosphino)-9,9-dimethyl-9H-xanthene (0.09528 g, 0.1647 mmol) were reacted to provide N-(4-methylthiazol-2-yl)-4-(5,6,7,8-tetrahydronaphthalen-1-yloxy)pyridin-2-amine hydrochloride (1.035 g, 45.39% yield) after salt formation. $^1$H NMR (d$_6$-DMSO) δ 8.23 (d, 1H), 7.24 (t, 1H), 7.09 (d, 1H), 6.96 (d, 1H), 6.69 (s, 1H), 6-65 (m, 1H), 6.54 (m, 1H), 2.79 (m, 2H), 2.48 (m, 2H), 2.25 (s, 3H), 1.70 (m, 4H); Mass spectrum (apci) m/z=338.2 (M+H—HCl).

Example 17

Representative Example

N-(4-Methylthiazol-2-yl)-4-(1,2,3,4-tetrahydronaphthalen-1-yloxy)pyridin-2-amine

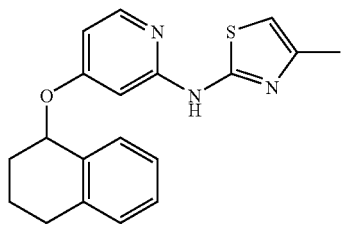

Step A: Preparation of 2-chloro-4-(1,2,3,4-tetrahydronaphthalen-1-yloxy)pyridine: Using the method of Example 3, Step A, 1,2,3,4-tetrahydronaphthalen-1-ol (935 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-(1,2,3,4-tetrahydronaphthalen-1-yloxy)pyridine (1.62 g, 99% yield) as an oil. $^1$H NMR (CDCl$_3$) δ 8.21 (d, 1H), 7.17-7.30 (m, 4H), 6.95 (s, 1H), 6.83 (d, 1H), 5.46 (t, 1H), 2.89 (ddd, 1H), 2.80 (ddd, 1H), 2.17 (m, 1H), 2.06 (m, 1H), 1.97 (m, 1H), 1.84 (m, 1H).

Step B: Preparation of N-(4-methylthiazol-2-yl)-4-(1,2,34-tetrahydronaphthalen-1-yloxy)pyridin-2-amine: Using the method of Example 3, Step B, 4-methylthiazol-2-amine (11.59 mL, 4.637 mmol), 2-chloro-4-(1,2,3,4-tetrahydronaphthalen-1-yloxy)pyridine (1.095 g, 4.216 mmol), potassium phosphate (0.9844 g, 4.637 mmol), Pd$_2$(dba)$_3$ (0.09651 g, 0.1054 mmol) and 4,5-bis(diphenylphosphino)-9,9-dimethyl-9H-xanthene (0.06586 g, 0.1138 mmol) were reacted to provide N-(4-methylthiazol-2-yl)-4-(1,2,3,4-tetrahydronaphthalen-1-yloxy)pyridin-2-amine (0.972 g, 68.33% yield). $^1$H NMR (d$_6$-DMSO) δ 10.96 (s, 1H), 8.14 (d, 1H), 7.27 (m, 2H), 7.19 (t, 2H), 6.68 (m, 1H), 6.66 (s, 1H), 6.50 (d, 1H), 5.56 (t, 1H), 2.84 (m, 1H), 2.74 (m, 1H), 2.23 (s, 3H), 2.03 (m, 2H), 1.81 (m, 2H); Mass spectrum (apci) m/z=338.0 (M+H).

Example 18

Ethyl 6-(4-methylthiazol-2-ylamino)-4-(naphthalen-1-yloxy)nicotinate

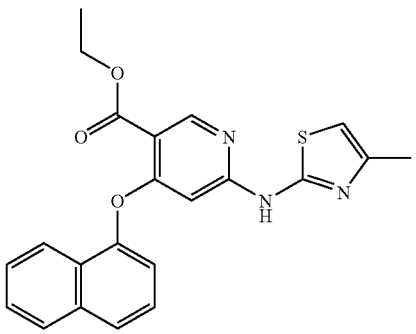

Step A: Preparation of ethyl 6-chloro-4-(naphthalen-1-yloxy)nicotinate: Using the method of Example 3, Step A, naphthalen-1-ol (2.62 g, 18.2 mmol), 60% sodium hydride in mineral oil (727 mg, 18.2 mmol), and ethyl 4,6-dichloronicotinate (4.00 g, 18.2 mmol) afforded ethyl 6-chloro-4-(naphthalen-1-yloxy)nicotinate (3.72 g, 62% yield) as an oil. $^1$H NMR (CDCl$_3$) δ 8.86 (s, 1H), 7.94 (d, 2H), 7.82 (d, 1H), 7.49-7.61 (m, 3H), 7.22 (d, 1H), 6.54 (s, 1H), 4.43 (q, 2H), 1.38 (t, 3H).

Step B: Preparation of ethyl 6-(4-methylthiazol-2-ylamino)-4-(naphthalen-1-yloxy)nicotinate: Using the method of Example 3, Step B, 4-methylthiazol-2-amine (25.2 mL, 10.1 mmol), ethyl 6-chloro-4-(naphthalen-1-yloxy)nicotinate (3.63 g, 11.1 mmol), potassium phosphate (2.35 g, 11.1 mmol), tris(dibenzylideneacetone)-dipalladium (0) (0.231 g, 0.252 mmol) and 4,5-bis(diphenylphosphino)-9,9-dimethyl-9H-xanthene (0.160 g, 0.277 mmol) were reacted in toluene (25 mL) and water (8 mL) to afford ethyl 6-(4-methylthiazol-2-ylamino)-4-(naphthalen-1-yloxy)nicotinate (3.30 g, 80.0% yield) as yellow solid. $^1$H NMR (CDCl$_3$) δ 9.90 (bs, 1H), 8.91 (s, 1H), 7.97 (d, 1H), 7.91 (d, 1H), 7.77 (d, 1H), 7.53 (m, 1H), 7.47 (m, 1H), 7.43 (m, 1H), 7.14 (d, 1H), 6.18 (s, 1H), 5.90 (s, 1H), 4.37 (quart, 2H), 1.76 (s, 3H), 1.33 (t, 3H); Mass spectrum (apci) m/z=406 (100) (M+H).

Example 19

3-(2-(4-Methylthiazol-2-ylamino)pyridin-4-yloxy)benzoate

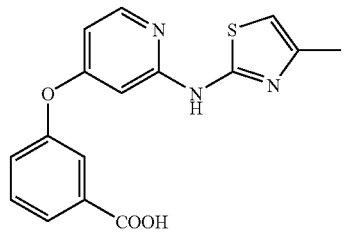

A 250 mL round bottom flask was charged with methyl 3-(2-(4-methylthiazol-2-ylamino)pyridin-4-yloxy)benzoate (2.0 g, 5.859 mmol) and methanol (100 mL) was added. To this solution was added 1M NaOH (30 mL). The reaction mixture was heated at 60° C. with stirring for 3 hours. The reaction mixture was cooled and concentrated. To the residue was added 1% HCl and 0.5 mL 6N HCl. The solution was filtered and the residue was collected to give 3-(2-(4-methylthiazol-2-ylamino)pyridin-4-yloxy)benzoic acid (1.499 g, 77.38% yield) as a tan solid. $^1$H NMR (CDCl$_3$) δ 8.24 (d, 1H), 7.94 (dt, 1H), 7.79 (t, 1H), 7.52 (t, 1H), 7.33 (ddd, 1H), 6.86 (bs, 1H), 6.68 (dd, 1H), 6.39 (d, 1H), 2.45 (d, 3H); Mass spectrum (apci) m/z=328 (100) (M+H).

Example 20

Representative Example 2-(2-(4-Methylthiazol-2-ylamino)pyridin-4-yloxy)benzoate

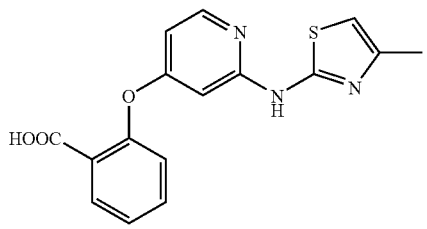

A 250 mL round bottom flask was charged with methyl 2-(2-(4-methylthiazol-2-ylamino)pyridin-4-yloxy)benzoate (1.50 g, 4.394 mmol) and methanol (100 mL) was added. To this solution was added 1M NaOH (20 mL). The reaction mixture was heated at 60° C. with stirring for 3 hours. The reaction mixture was cooled and concentrated. To the residue was added 1% HCl followed by 0.5 mL of 6N HCl to pH 1.0. The solution was filtered and the residue was collected to give 2-(2-(4-methylthiazol-2-ylamino)pyridin-4-yloxy)benzoate (1.246 g, 85.7% yield) as a an off white solid. $^1$H NMR (CDCl$_3$) δ 8.07 (dd, 1H), 8.03 (d, 1H), 7.57 (dt, 1H), 7.36 (dt, 1H), 7.25 (m, 1H), 6.96 (bs, 1H), 6.20 (m, 2H), 2.32 (d, 3H); Mass spectrum (esi) m/z 328 (100) (M+H).

Example 21

4-Methyl-N-(6-phenoxypyrimidin-4-yl)thiazol-2-amine

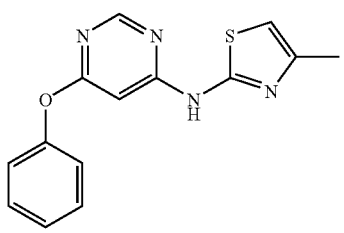

Using the method of Example 3, Step B, 4-chloro-6-phenoxypyrimidine (0.697 g, 3.37 mmol), 4-methylthiazol-2-amine (7.66 mL, 3.07 mmol), potassium phosphate (0.716 g, 3.37 mmol), Pd$_2$(dba)$_3$ (0.0702 g, 0.0766 mmol) and 4,5-bis(diphenylphosphino)-9,9-dimethyl-9H-xanthene (0.0488 g, 0.0843 mmol) in toluene (3 mL) and water (3 mL) to afford 4-methyl-N-(6-phenoxypyrimidin-4-yl)thiazol-2-amine (0.161 g, 18.5% yield) as off white solid. $^1$H NMR (CDCl$_3$), 8.56 (d, 1H), 7.43 (m, 2H), 7.28 (dt, 1H), 7.14 (m, 2H), 6.46 (d, 1H), 6.29 (s, 1H), 6.20 (m, 2H), 2.27 (d, 3H); Mass spectrum (esi) m/z=385 (100) (M+H).

Example 22

Representative Example

4-Methyl-N-(4-phenoxypyrimidin-2-yl)thiazol-2-amine

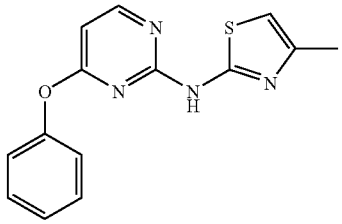

Using the method of Example 3, Step B, 4-methylthiazol-2-amine (7.66 mL, 3.07 mmol), 2-chloro-4-phenoxypyrimidine (0.697 g, 3.37 mmol), potassium phosphate (0.716 g, 3.37 mmol), Pd$_2$(dba)$_3$ (0.0702 g, 0.0766 mmol) and 4,5-bis(diphenylphosphino)-9,9-dimethyl-9H-xanthene (0.0488 g, 0.0843 mmol) were reacted in toluene (8 mL) and water (3 mL) to afford 4-methyl-N-(4-phenoxypyrimidin-2-yl)thiazol-2-amine (0.09 g, 9.40% yield) as a light yellow solid. $^1$H NMR (CDCl$_3$) δ 8.36 (d, 1H), 7.45 (m, 2H), 7.30 (m, 1H), 7.18 (m, 1H), 7.16 (m, 1H), 6.42 (d, 1H), 6.27 (bs, 1H), 2.30 (d, 3H); Mass spectrum (esi) m/z=385 (100) (M+H1).

Example 23

Representative Example

4-Methyl-N-(4-(piperidin-4-yloxy)pyridin-2-yl)thiazol-2-amine trifluoroacetate

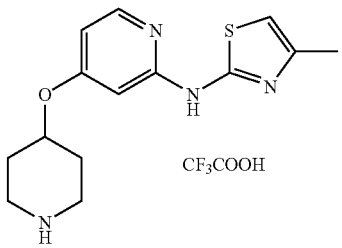

A 100 mL round bottom flask was charged with tert-butyl 4-(2-(4-methylthiazol-2-ylamino)pyridin-4-yloxy)piperidine-1-carboxylate (1.50 g, 3.84 mmol) in dichloromethane (10 mL) and added 2,2,2-trifluoroacetic acid (0.888 mL, 11.5 mmol). The reaction mixture was stirred at room temperature for 2 hours, then concentrated to provide 4-methyl-N-(4-(piperidin-4-yloxy)pyridin-2-yl)thiazol-2-amine TFA salt (1.6 g, 100%) as a light yellow solid. ¹H NMR (DMSO) δ 8.53 (bs, 2H), 8.15 (d, 1H), 6.67 (dd, 1H), 6.61 (m, 1H), 6.56 (d, 1H), 4.74 (m, 1H), 3.25 (bm, 2H), 3.11 (bm, 2H), 2.23 (d, 3H), 2.10 (bm, 2H), 1.84 (bm, 2H); Mass spectrum (apci) m/z=291 (100) (M+H).

Example 24

Representative Example

4-Methyl-N-(4-(piperidin-3-yloxy)pyridin-2-yl)thiazol-2-amine trifluoroacetate

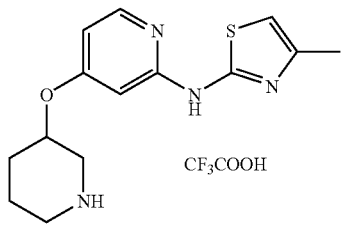

A 100 mL round bottom flask was charged with tert-butyl 3-(2-(4-methylthiazol-2-ylamino)pyridin-4-yloxy)piperidine-1-carboxylate (1.65 g, 4.23 mmol) in dichloromethane (10 mL), and 2,2,2-trifluoroacetic acid (0.977 mL, 12.7 mmol) was added. The reaction mixture was stirred at room temperature for 2 hours. A saturated solution of NaHCO₃ was added, and the solution was extracted with EtOAc and dichloromethane. The combined organic layers were filtered and concentrated to provide 4-methyl-N-(4-(piperidin-3-yloxy)pyridin-2-yl)thiazol-2-amine as a light yellow solid. (0.70 g, 53.6% yield). Mass spectrum (apci) m/z=291 (100) (+H).

Example 25

2-(2-(4-Methylthiazol-2-ylamino)pyridin-4-yloxy)phenol

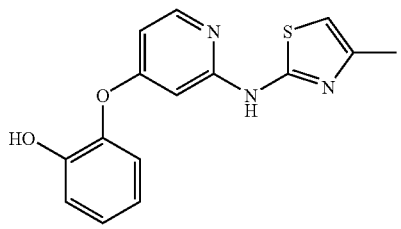

A 50 mL round bottom flask was charged with 4-(2-methoxyphenoxy)-N-(4-methylthiazol-2-yl)pyridin-2-amine (6.38 mL, 0.638 mmol) and dichloromethane (6 mL). The solution was cooled to 0° C., and tribromoborane (0.181 mL, 1.91 mmol) and 1 mL of 2-methyl-2-butene were added. The reaction mixture was stirred at 0° C. for 1 hour. Water and saturated solution of NaHCO₃ were added, and the reaction mixture was extracted with EtOAc. The organic layer was dried over magnesium sulfate, filtered and concentrated. The residue was purified on a prepacked silica gel column, eluting with 20-35% EtOAc in hexanes to give 2-(2-(4-methylthiazol-2-ylamino)pyridin-4-yloxy)phenol (0.130 g, 67.4% yield) as light yellow solid. ¹H NMR (DMSO) δ 10.90 (bs, 1H), 9.70 (bs, 1H), 8.10 (d, 1H), 7.11 (m, 2H), 7.01 (dd, 1H), 6.87 (dt, 1H), 6.49 (d, 1H), 6.43 (m, 2H), 2.19 (d, 3H); Mass spectrum (esi) m/z=300 (100) (M+H).

Example 26

3-(2-(4-Methylthiazol-2-ylamino)pyridin-4-yloxy)phenol

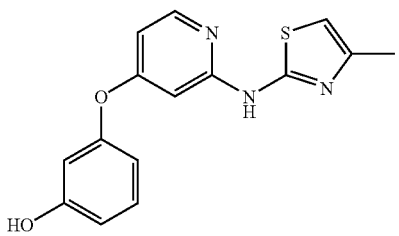

A 50 mL round bottom flask was charged with 4-(3-methoxyphenoxy)-N-(4-methylthiazol-2-yl)pyridin-2-amine (0.2 g, 0.638 mmol) and dichloromethane (6 mL). The solution was cooled to 0° C., and tribromoborane (0.181 mL, 1.91 mmol) and 1 mL of 2-methyl-2-butene were added. The reaction mixture was stirred at 0° C. for 1 hour. Water and saturated solution of NaHCO₃ were added, and the reaction mixture was extracted with EtOAc. The organic layer was dried over magnesium sulfate, filtered and concentrated. The residue was purified on a prepacked silica gel column eluting with 20-35% ethyl acetate in hexanes to give 3-(2-(4-methylthiazol-2-ylamino)pyridin-4-yloxy)phenol (0.124 g, 64.3% yield) as light orange solid. ¹H NMR (DMSO) δ 10.98 (bs, 1H), 9.78 (bs, 1H), 8.15 (d, 1H), 7.26 (t, 1H), 6.69 (ddd, 1H), 6.56 (m, 2H), 6.51 (m, 3H), 2.20 (d, 3H); Mass spectrum (esi) m/z 300 (100) (M+H).

Example 27

4-(2-(4-Methylthiazol-2-ylamino)pyridin-4-yloxy)phenol

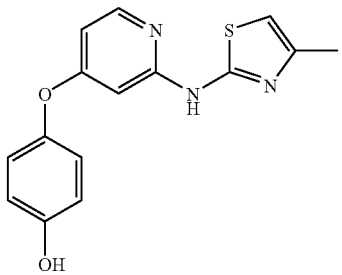

A 50 mL round bottom flask was charged with 4-(4-methoxyphenoxy)-N-(4-methylthiazol-2-yl)pyridin-2-amine (0.20 g, 0.638 mmol) and dichloromethane (6 mL). The solution was cooled to 0° C., and tribromoborane (0.181 mL, 1.91 mmol) and 1 mL of 2-methyl-2-butene were added. The reaction mixture was stirred at 0° C. for 1 hour. Water and saturated solution of NaHCO₃ were added, and the reaction mixture was extracted with EtOAc. The organic layer was dried over magnesium sulfate, filtered and concentrated. The residue was purified on a prepacked silica gel column eluting with 20-35% EtOAc in hexanes to give 4-(2-(4-methylthiazol-2-ylamino)pyridin-4-yloxy)phenol (0.07 g, 36.3% yield) as light orange solid. ¹H NMR (DMSO) δ 10.91 (s, 1H), 9.51 (s, 1H), 8.11 (dd, 1H), 6.99 (m, 2H), 6.83 (m, 2H), 6.50 (d, 1H), 6.46 (m, 2H), 2.19 (d, 3H); Mass spectrum (esi) m/z=300 (100) (M+H).

Example 28

4-Methyl-N-(4-(phenylsulfinyl)pyridin-2-yl)thiazol-2-amine

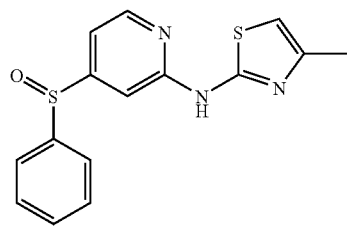

A 50 mL round bottom flask was charged with N-(4-methylthiazol-2-yl)-4-(phenylthio)pyridin-2-amine (0.050 g, 0.17 mmol) and dichloromethane (5 mL). The solution was cooled to 0° C., then MCPBA (0.029 g, 0.17 mmol) was added and the reaction mixture was stirred at room temperature for 2 hours. An additional 15 mg of MCPBA were added and the reaction mixture was stirred overnight. The reaction mixture was quenched with sodium bisulfite and extracted with dichloromethane. The organic layer was washed with a saturated solution of NaHCO₃. The organic layer was dried over magnesium sulfate, filtered and concentrated. The residue was purified using preparative TLC with 35% EtOAc in hexanes as the solvent system to afford 4-methyl-N-(4-(phenylsulfinyl)pyridin-2-yl)thiazol-2-amine as a light yellow solid. ¹H NMR (CDCl₃) δ 8.34 (d, 1H), 7.48-7.73 (m, 5H), 7.25 (s, 1H), 6.93 (dd, 1H), 6.41 (s, 1H), 2.36 (d, 3H); Mass spectrum (apci) m/z=316 (100) (M+H).

Example 29

4-Methyl-N-(4-(phenylsulfonyl)pyridin-2-yl thiazol-2-amine

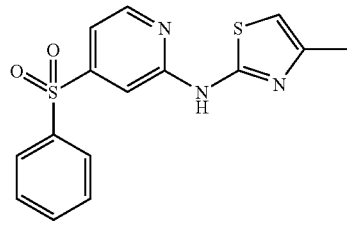

A 50 mL round bottom flask was charged with N-(4-methylthiazol-2-yl)-4-(phenylthio)pyridin-2-amine (0.050 g, 0.17 mmol) and dichloromethane (5 mL). The solution was cooled to 0° C., then MCPBA (0.086 g, 0.50 mmol) was added and the reaction mixture was stirred at room temperature overnight. An additional 86 mg of MCPA were added and the reaction mixture was stirred overnight. The reaction mixture was quenched with sodium bisulfite and extracted with dichloromethane. The organic layer was washed with a saturated solution of NaHCO₃. The organic layer was dried over magnesium sulfate, filtered and concentrated. The residue was purified using preparative TLC with 35% EtOAc in hexanes to afford 4-methyl-N-(4-(phenylsulfonyl)pyridin-2-yl)thiazol-2-amine as a light yellow solid. ¹H NMR (CDCl₃) δ 8.48 (d, 1H), 7.97 (m, 1H), 7.95 (m, 1H), 7.51-7.72 (m, 1H), 7.37 (s, 1H), 6.44 (s, 1H), 2.35 (d, 1H); Mass spectrum (apci) m/z=332 (100) (M+H).

Example 30

Representative Example

Methyl 3-(2-(4-methylthiazol-2-ylamino)pyridin-4-ylthio)benzoate

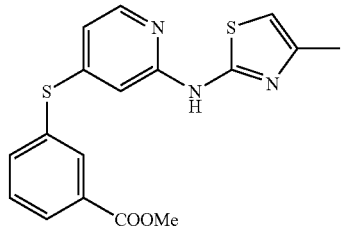

Step A: Preparation of methyl 3-(2-chloropyridin-4-ylthio)benzoate: Using the method of Example 3, Step A, 2-chloro-4-nitropyridine (4.00 g, 25.2 mmol), 60% sodium hydride in mineral oil (1.011 g, 25.2 mmol), and methyl 3-mercaptobenzoate (4.24 g, 25.2 mmol) were reacted to provide (2-chloropyridin-4-ylthio)benzoate (6.08 g, 86.1% yield). ¹H NMR (CDCl₃) δ 8.23 (t, 1H), 8.16 (m, 2H), 7.74 (m, 1H), 7.57 (t, 1H), 6.90 (m, 1H), 6.86 (dd, 1H), 3.95 (s, 3H); Mass spectrum (apci) m/z=280.1 (M+H).

Step B: Preparation of methyl 3-(2-(4-methylthiazol-2-ylamino)pyridin-4-ylthio)benzoate: Using the method of Example 3, Step B, 4-methylthiazol-2-amine (59.5 mL, 23.8 mmol), methyl 3-(2-chloropyridin-4-ylthio)benzoate (6.05 g, 21.6 mmol), potassium phosphate (5.05 g, 23.8 mmol), Pd₂(dba)₃ (0.495 g, 0.541 mmol) and 4,5-bis(diphenylphosphino)-9,9-dimethyl-9H-xanthene (0.338 g, 0.584 mmol) were reacted to provide methyl 3-(2-(4-methylthiazol-2-ylamino)pyridin-4-ylthio)benzoate (5.68 g, 73.5% yield). ¹H NMR (d₆-DMSO) δ 11.06 (s, 1H), 8.10 (m, 3H), 7.87 (m, 1H), 7.70 (t, 1H), 6.72 (s, 1H), 6.64 (dd, 1H), 6.53 (s, 1H), 3.88 (s, 1H), 2.19 (s, 3H); Mass spectrum (apci) m/z=358.1 (M+H).

Example 31

Representative Example 3-(2-(4-Methylthiazol-2-ylamino)pyridin-4-ylthio)benzoic acid hydrochloride

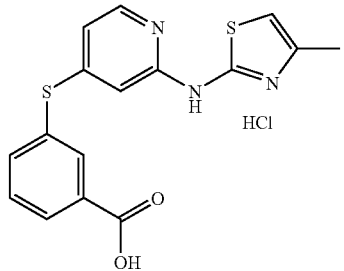

Methyl 3-(2-(4-methylthiazol-2-ylamino)pyridin-4-ylthio)benzoate (5.62 g, 15.72 mmol) was dissolved in MeOH (100 mL) and 1M NaOH (25 mL) and heated at 60° C. for 2 hours. The reaction mixture was cooled and MeOH was removed. 1N HCl was added to bring pH ~2. The reaction mixture was filtered and dried to provide 3-(2-(4-methylthiazol-2-ylamino)pyridin-4-ylthio)benzoic acid hydrochloride (5.379 g, 90.06% yield). $^1$H NMR (d$_6$-DMSO) δ 8.18 (d, 1H), 8.09 (m, 2H), 7.70 (t, 1H), 6.87 (s, 1H), 6.81 (dd, 1H), 6.72 (s, 1H), 2.26 (s, 3H); Mass spectrum (apci) m/z=344.1 (M+H—HCl).

Example 32

N-(2-(dimethylamino)ethyl)-3-(2-(4-methylthiazol-2-ylamino)pyridin-4-ylthio)benzamide dihydrochloride

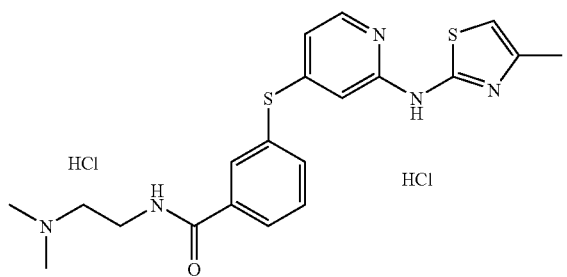

A 100 mL round-bottomed flask was charged with 3-(2-(4-methylthiazol-2-ylamino)pyridin-4-ylthio)benzoic acid (0.100 g, 0.2912 mmol) and THF (30 mL) and cooled to −5° C. Triethylamine (0.08840 g, 0.8736 mmol) and ethyl carbonochloridate (0.02784 mL, 0.2912 mmol) were added successively. The reaction mixture was stirred at −5° C. for 30 minutes. N1,N1-dimethylethane-1,2-diamine (0.07701 g, 0.8736 mmol) was added and stirred at −5° C. for 30 minutes and room temperature for 1 hour. An aqueous workup was done, the organic layer was dried and concentrated, and the residue was purified by silica gel chromatography to give the free base. The free base was dissolved in DCM, and 2M HCl was added. The solution was concentrated to provide N-(2-(dimethylamino)ethyl)-3-(2-(4-methylthiazol-2-ylamino)pyridin-4-ylthio)benzamide dihydrochloride (0.060 g, 42.36% yield). $^1$H NMR (d$_6$-DMSO) δ 11.34 (bs, 1H), 9.97 (bs, 1H), 8.94 (t, 1H), 8.13 (m, 2H), 8.07 (d, 1H), 7.79 (d, 1H), 7.67 (t, 1H), 6.80 (s, 1H), 6.66 (s, 1H), 6.58 (s, 1H), 3.63 (m, 2H), 2.26 (m, 2H), 2.82 (d, 6H), 2.21 (s, 3H); Mass spectrum (apci) m/z=414.0 (M+H-2HCl).

Example 33

(4-Methylpiperazin-1-yl)(3-(2-(4-methylthiazol-2-ylamino)pyridin-4-ylthio)phenyl)methanone dihydrochloride

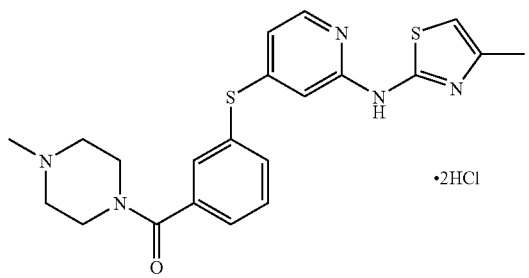

Using the method of Example 32, 3-(2-(4-methylthiazol-2-ylamino)pyridin-4-ylthio)benzoic acid (0.100 g, 0.2912 mmol), triethylamine (0.08840 g, 0.8736 mmol) ethyl carbonochloridate (0.02784 mL, 0.2912 mmol), and 1-methylpiperazine (0.08750 g, 0.8736 mmol) were reacted to provide (4-methylpiperazin-1-yl)(3-(2-(4-methylthiazol-2-ylamino)pyridin-4-ylthio)phenyl)methanone dihydrochloride (0.0253 g, 17.43% yield) after reverse phase purification and salt formation. $^1$H NMR (d$_6$-DMSO) δ 8.14 (m, 3H), 8.06 (d, 1H), 7.76 (d, 1H), 7.64 (t, 1H), 7.54 (s, 1H), 6.79 (s, 1H), 6.75 (d, 1H), 6.65 (s, 1H), 2.23 (m, 3H); Mass spectrum (apci) m/z=343.1 (M+H-2HCl).

Example 34

4-(3-Methoxyphenylthio)-N-(4-methylthiazol-2-yl)pyridin-2-amine

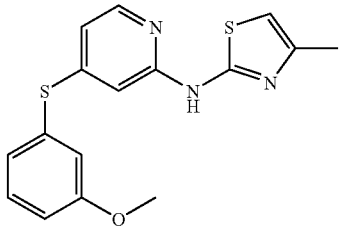

Step A: Preparation of 2-chloro-4-(3-methoxyphenylthio)pyridine: Using the method of Example 3, Step A, 3-methoxybenzenethiol (884 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-(3-methoxyphenylthio)pyridine (1.51 g, 95% yield) as an oil. $^1$H NMR (CDCl$_3$) δ 8.12 (d, 1H), 7.39 (t, 1H), 7.13 (d, 1H), 7.08 (s, 1H), 7.03 (d, 1H), 6.93 (s, 1H), 6.88 (d, 1H), 3.83 (s, 3H).

Step B: Preparation of 4-(3-methoxyphenylthio)-N-4-methylthiazol-2-yl)pyridin-2-amine: Using the method of Example 3, Step B, 4-methylthiazol-2-amine (10.8 mL, 4.32 mmol), 2-chloro-4-(3-methoxyphenylthio)pyridine (0.989 g, 3.93 mmol), potassium phosphate (0.917 g, 4.32 mmol), Pd$_2$(dba)$_3$ (0.0899 g, 0.0982 mmol), and 4,5-bis(diphenylphosphino)-9,9-dimethyl-9H-xanthene (0.0625 g, 0.108 mmol) were reacted to provide 4-(3-methoxyphenylthio)-N-(4-methylthiazol-2-yl)pyridin-2-amine (0.798 g, 61.7% yield). $^1$H NMR (d$_6$-DMSO) δ 11.08 (s, 1H), 8.09 (d, 1H), 7.45 (t, 1H), 7.14 (m, 2H), 7.11 (m, 1H), 6.77 (s, 1H), 6.61 (dd, 1H), 6.52 (s, 1H), 3.80 (s, 3H), 2.20 (s, 3H); Mass spectrum (apci) m/z=330.2 (M+H).

Example 35

N-(2-(isopropylamino)ethyl)-2-(2-(4-methylthiazol-2-ylamino)pyridin-4-yloxy)benzamide dihydrochloride

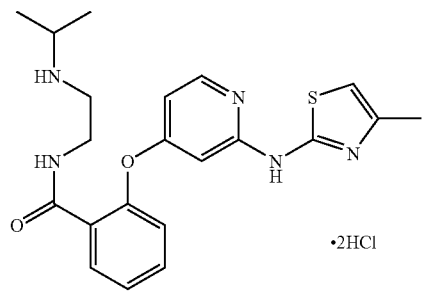

Using the method of Example 32, 2-(2-(4-methylthiazol-2-ylamino)pyridin-4-yloxy)benzoic acid (0.100 g, 0.3055 mmol), triethylamine (0.2129 mL, 1.527 mmol), ethyl chloroformate (0.03213 mL, 0.3360 mmol), N-isopropyl-ethylenediamine (0.1143 mL, 0.9164 mmol) in THF (2 mL) were reacted to provide N-(2-(isopropylamino)ethyl)-2-(2-(4-methylthiazol-2-ylamino)pyridin-4-yloxy)benzamide dihydrochloride (0.122 g, 81.62% yield) as an off white solid. ¹H NMR (DMSO) δ 8.63 (bs, 1H), 8.55 (m, 1H), 8.18 (d, 1H), 7.76 (dd, 1H), 7.62 (dt, 1H), 7.42 (dt, 1H), 7.27 (d, 1H), 6.59 (s, 1H), 6.56 (m, 1H), 6.53 (m, 1H), 3.42 (m, 2H), 3.25 (m, 1H), 2.86 (m, 2H), 2.23 (d, 3H), 1.17 (d, 6H); Mass spectrum (esi) m/z=412 (100) (M+H).

Example 36

2-(2-(4-Methylthiazol-2-ylamino)pyridin-4-yloxy)-N-(2-(pyrrolidin-1-yl)ethyl)benzamide dihydrochloride

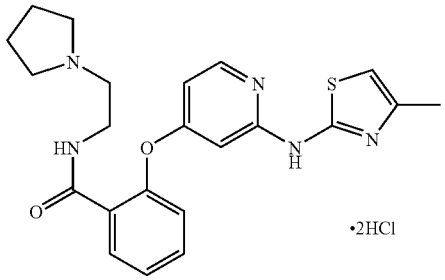

Using the method of Example 32, 2-(2-(4-methylthiazol-2-ylamino)pyridin-4-yloxy)benzoic acid (0.100 g, 0.3055 mmol), triethylamine (0.2129 mL, 1.527 mmol), ethyl carbonochloridate (0.03213 mL, 0.3360 mmol), 1-pyrroline ethanamine (0.1161 mL, 0.9164 mmol) in THF (2 mL) were reacted to provide 2-(2-(4-methylthiazol-2-ylamino)pyridin-4-yloxy)-N-(2-(pyrrolidin-1-yl)ethyl)benzamide dihydrochloride (0.125 g, 81.60% yield) as off white solid. ¹H NMR (DMSO) δ 8.616 (t, 1H), 8.20 (d, 1H), 7.77 (dd, 1H), 7.61 (dt, 1H), 7.41 (dt, 1H), 7.26 (d, 1H), 6.62 (s, 1H), 6.58 (m, 1H), 6.56 (m, 1H), 3.51 (m, 4H), 3.17 (quart, 2H), 2.92 (m, 2H), 2.23 (d, 3H), 1.93 (m, 2H), 1.82 (m, 2H); Mass spectrum (esi) m/z=424 (100) (M+H).

Example 37

2-(2-(4-Methylthiazol-2-ylamino)pyridin-4-yloxy)-N-(3-morpholinopropyl)benzamide dihydrochloride

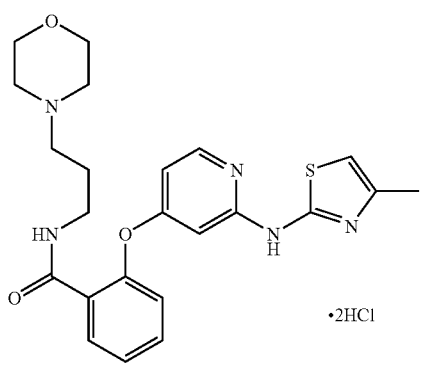

Using the method of Example 32, 2-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03213 mL, 0.3360 mmol), 4-(3-aminopropyl)morpholine (0.1339 mL, 0.9164 mmol) in THF (2 mL) were reacted to provide 2-(2-(4-methylthiazol-2-ylamino)pyridin-4-yloxy)-N-(3-morpholinopropyl)benzamide dihydrochloride (0.132 g, 81.26% yield) as an off white solid. ¹H NMR (DMSO) δ 8.44 (t, 1H), 8.18 (d, 1H), 7.68 (dd, 1H), 7.59 (dt, 1H), 7.40 (dt, 1H), 7.26 (d, 1H), 6.57 (s, 1H), 6.54 (d, 1H), 6.50 (dd, 1H), 3.89 (m, 2H), 3.29 (m, 2H), 3.20 (quart; 2H), 2.96 (m, 4H), 2.49 (m, 2H, under DMSO) 2.22 (d, 3H), 1.77 (m, 2H); Mass spectrum (esi) m/z=454(100) (M+H).

Example 38

(4-Ethylpiperazin-1-yl)(2-(2-(4-methylthiazol-2-ylamino)pyridin-4-yloxy)phenyl)methanone dihydrochloride

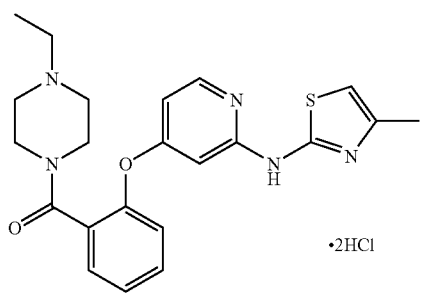

Using the method of Example 32, 2-(2-(4-methylthiazol-2-ylamino)pyridin-4-yloxy)-benzoic acid (0.1 g, 0.3055 mmol), triethylamine (0.2129 mL, 1.527 mmol), ethyl carbonochloridate (0.03213 mL, 0.3360 mmol), 1-ethylpiperazine (0.1164 mL, 0.9164 mmol) in THF (2 mL) were reacted to provide (4-ethylpiperazin-1-yl)(2-(2-(4-methylthiazol-2-ylamino)pyridin-4-yloxy)phenyl)methanone dihydrochloride (0.05 g, 32.64% yield). ¹H NMR (DMSO) δ 8.18 (d, 1H), 7.6859 (dt, 1H), 7.54 (d, 1H), 7.42 (t, 1H), 7.29 (d, 1H), 6.59 (m, 2H), 6.56 (m, 1H), 3.35-3.63 (m, 4H), 3.12 (m, 2H), 2.50 (m, 4H, under DMSO), 2.22 (d, 3H), 1.22 (t, 2H); Mass spectrum (esi) m/z=424(100) (M+H).

Example 39

N-(2-(dimethylamino)ethyl)-N-methyl-2-(2-(4-methylthiazol-2-ylamino)pyridin-4-yloxy)benzamide dihydrochloride

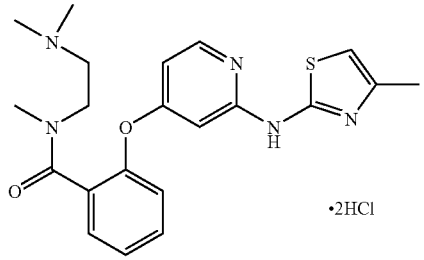

Using the method of Example 32, 2-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03213 mL, 0.3360 mmol), N,N,N-trimethylethylenediamine (0.1191 mL, 0.9164 mmol) in THF (2 mL) were reacted to provide N-(2-(dimethyl-amino)ethyl)-N-methyl-2-(2-(4-methylthiazol-2-ylamino)pyridin-4-yloxy)benzamide dihydrochloride (0.067 g, 44.82% yield) as off white solid. $^1$H NMR (CDCl$_3$) δ 8.20 (d, 1H), 7.57 (d, 1H), 7.50 (t, 1H), 7.38 (t, 1H), 7.13 (d, 1H), 6.79 (s, 1H), 6.59 (dd, 1H), 6.40 (d, 1H), 3.97 (m, 2H), 3.17 (m, 2H), 3.03 (s, 3H), 2.87 (s, 6H), 2.41 (s, 3H); Mass spectrum (esi) m/z=412 (100) (M+H).

Example 40

N-(2-(1H-imidazol-4-yl)ethyl)-2-(2-(4-methylthiazol-2-ylamino)pyridin-4-yloxy)benzamide dihydrochloride

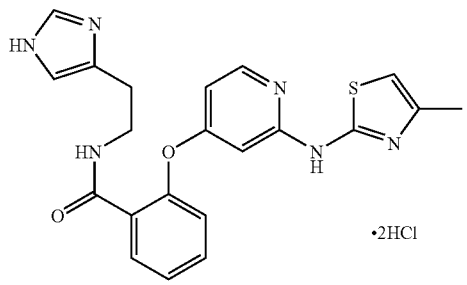

Using the method of Example 32, 2-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03213 mL, 0.3360 mmol), and histamine (0.1019 g, 0.9164 mmol) were reacted in THF (2 mL) to provide N-(2-(1H-imidazol-4-yl)ethyl)-2-(2-(4-methylthiazol-2-ylamino)pyridin-4-yloxy)benzamide dihydrochloride (0.084 g, 55.17% yield). $^1$H NMR (CDCl$_3$) δ 8.38 (s, 1H), 8.08 (d, 1H), 7.76 (d, 1H), 7.51 (t, 1H), 7.39 (t, 1H), 7.06 (s, 1H), 7.02 (m, 2H), 6.89 (s, 1H), 6.55 (m, 2H), 3.81 (m, 2H), 3.16 (m, 2H), 2.45 (s, 3H); Mass spectrum (esi) m/z=421 (100) (M+H).

Example 41

N-(2-(isopropylamino)ethyl)-3-(2-(4-methylthiazol-2-ylamino)pyridin-4-yloxy)benzamide dihydrochloride

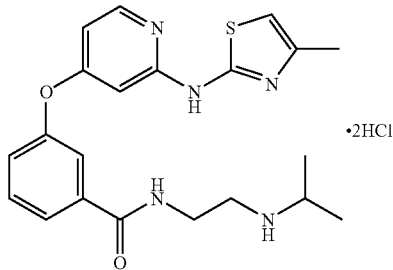

Using the method of Example 32, 3-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03359 mL, 0.3513 mmol), N1-isopropylethane-1,2-diamine (0.1143 mL, 0.9164 mmol) were reacted in THF (2 mL) to provide N-(2-(isopropylamino)ethyl)-3-(2-(4-methylthiazol-2-ylamino)pyridin-4-yloxy)benzamide dihydrochloride (0.063 g, 39.59% yield) as a light yellow solid. $^1$H NMR (CDCl$_3$) δ 9.51 (bs, 1H), 8.74 (s, 1H), 8.15 (d, 1H), 7.92 (d, 1H), 7.81 (s, 1H), 7.49 (t, 1H), 7.22 (d, 1H), 6.83 (d, 1H), 6.44 (s, 1H), 3.92 (m, 2H), 3.24 (m, 2H), 3.12 (m, 1H), 2.42 (s, 3H), 1.46 (d, 6H); Mass spectrum (esi) m/z=412 (100) (M+H).

Example 42

3-(2-(4-Methylthiazol-2-ylamino)pyridin-4-yloxy)-N-(2-(pyrrolidin-1-yl)ethyl)benzamide dihydrochloride

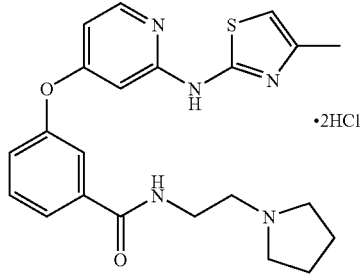

Using the method of Example 32, 3-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03359 mL, 0.3513 mmol), 2-(pyrrolidin-1-yl)ethanamine (0.1161 mL, 0.9164 mmol) were reacted in THF (2 mL) to provide 3-(2-(4-methylthiazol-2-ylamino)pyridin-4-yloxy)-N-(2-(pyrrolidin-1-yl)ethyl)benzamide dihydrochloride (0.088 g, 57.45% yield) as an off white solid. $^1$H NMR (CDCl$_3$) δ 8.88 (s, 1H), 8.17 (d, 1H), 8.02 (d, 1H), 7.96 (s, 1H), 7.54 (t, 1H), 7.24 (m, 1H), 6.76 (dd, 1H), 6.39 (s, 1H), 3.97 (m, 2H), 3.90 (m, 2H), 3.37 (m, 2H), 2.87 (m, 2H), 2.40 (d, 3H), 2.25 (m, 2H), 2.09 (m, 2H); Mass spectrum (esi) m/z=424 (100) (M+H).

Example 43

3-(2-(4-Methylthiazol-2-ylamino)pyridin-4-yloxy)-N-(3-morpholinopropyl)benzamide dihydrochloride

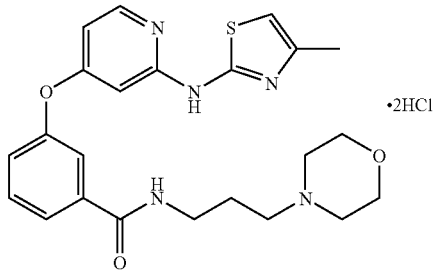

Using the method of Example 32, 3-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03359 mL, 0.3513 mmol), and 3-morpholinopropan-1-amine (0.1339 mL, 0.9164 mmol) were reacted in THF (2 mL) to provide 3-(2-(4-methylthiazol-2-ylamino)pyridin-4-yloxy)-N-(3-morpholinopropyl)benzamide dihydrochloride (0.098 g, 60.33% yield) as off white solid. $^1$H NMR (CDCl$_3$) δ 8.52 (s, 1H), 8.19 (d, 1H), 7.91 (d, 1H), 7.74 (s, 1H), 7.54 (t, 1H), 7.24 (d, 1H), 6.82 (dd, 1H), 6.41 (s, 1H), 4.26 (m, 2H), 3.99 (m, 2H), 3.65 (m, 2H), 3.52 (m, 2H), 3.19 (t, 2H), 2.89 (m, 2H), 2.41 (d, 3H), 2.26 (m, 2H); Mass spectrum (esi) m/z=454 (100) (M+H).

Example 44

N-(2-(Dimethylamino)ethyl)-N-methyl-3-(2-(4-methylthiazol-2-ylamino)pyridin-4-yloxy)benzamide dihydrochloride

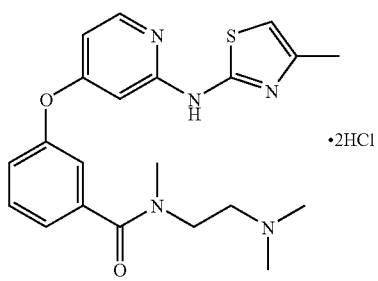

Using the method of Example 32, 3-(2-(4-methylthiazol-2-ylamino)pyridin-4-yloxy)benzoic acid (0.1 g, 0.3055 mmol), triethylamine (0.2129 mL, 1.527 mmol), ethyl carbonochloridate (0.03359 mL, 0.3513 mmol), and N1,N1,N2-trimethylethane-1,2-diamine (0.1191 mL, 0.9164 mmol) were reacted in THF (2 mL) to provide N-(2-(dimethylamino)ethyl)-N-methyl-3-(2-(4-methylthiazol-2-ylamino)pyridin-4-yloxy)benzamide dihydrochloride (0.052 g, 35.14% yield) as off white solid. $^1$H NMR (CDCl$_3$) δ 8.22 (d, 1H), 7.50 (m, 1H), 7.45 (m, 1H), 7.34 (bs, 1H), 7.19 (d, 1H), 6.69 (m, 2H), 6.39 (s, 1H), 4.05 (t, 2H), 3.31 (m, 2H), 3.19 (s, 3H), 2.91 (s, 6H), 2.38 (s, 3H); Mass spectrum (esi) m/z=412 (100) (M+H).

Example 45

N-(2-(Dimethylamino)ethyl)-3-(2-(4-methylthiazol-2-ylamino)pyridin-4-yloxy)benzamide dihydrochloride

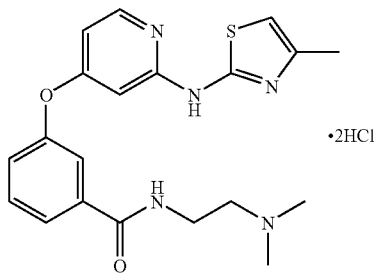

3-(2-(4-Methylthiazol-2-ylamino)pyridin-4-yloxy)benzoic acid (0.1 g, 0.3055 mmol), triethylamine (0.2129 mL, 1.527 mmol) and THF (2 mL) were combined according to the method of Example 32. The reaction mixture was cooled to 0° C., ethyl carbonochloridate (0.03359 mL, 0.3513 mmol) was added, and the reaction mixture was stirred at 0° C. for 30 minutes. N1,N1-dimethylethane-1,2-diamine (0.1006 mL, 0.9164 mmol) in THF (2 mL) was added to afford N-(2-(dimethylamino)ethyl)-3-(2-(4-methylthiazol-2-ylamino)pyridin-4-yloxy)benzamide dihydrochloride (0.07 g, 48.23% yield) as off white solid. $^1$H NMR (CDCl$_3$) δ 8.97 (bs, 1H), 8.16 (d, 1H), 7.99 (m, 2H), 7.52 (t, 1H), 7.23 (d, 1H), 6.92 (bs, 1H), 6.39 (s, 1H), 3.90 (m, 2H), 3.37 (m, 2H), 2.92 (s, 6H), 2.38 (s, 3H); Mass spectrum (esi) m/z=398 (100) (M+H).

Example 46

4-(2-Chlorophenylthio)-N-(4-methylthiazol-2-yl)pyridin-2-amine

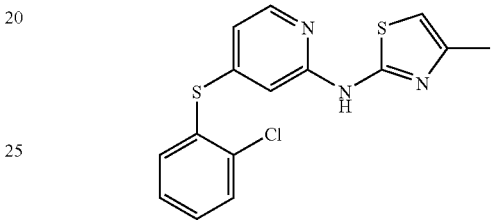

Step A: Preparation of 2-chloro-4-(2-chlorophenylthio)pyridine: Using the method of Example 3, Step A, 2-chlorobenzenethiol (912 mg, 6.31 mmol), 60% sodium hydride in mineral oil (252 mg, 6.31 mmol), and 2-chloro-4-nitropyridine (1.00 g, 6.31 mmol) were reacted to afford 2-chloro-4-(2-chlorophenylthio)pyridine (1.53 g, 95% yield) as an oil. $^1$H NMR (CDCl$_3$) δ 8.15 (d, 1H), 7.65 (d, 1H), 7.46 (t, 1H), 7.36 (t, 1H), 6.89 (s, 1H), 6.84 (d, 1H).

Step B: Preparation of 4-(2-chlorophenylthio)-N-(4-methylthiazol-2-yl)pyridin-2-amine: Using the method of Example 3, Step B, 4-methylthiazol-2-amine (7.88 mL, 5.52 mmol), 2-chloro-4-(2-chlorophenylthio)pyridine (1.55 g, 6.07 mmol), potassium phosphate (1.29 g, 6.07 mmol), tris(dibenzylideneacetone)dipalladium (0) (0.126 g, 0.138 mmol) and 4,5-bis(diphenylphosphino)-9,9-dimethyl-9H-xanthene (0.0878 g, 0.152 mmol) were reacted in toluene (8 mL) to afford 4-(2-chlorophenylthio)-N-(4-methylthiazol-2-yl)pyridin-2-amine (1.54 g, 82.8% yield) as yellow solid. $^1$H NMR (CDCl$_3$) δ 8.11 (d, 1H), 7.59 (dd, 1H), 7.53 (dd, 1H), 7.38 (dt, 1H), 7.29 (dt, 1H), 6.56 (dd, 1H), 6.48 (d, 1H), 2.23 (s, 3H); Mass spectrum (esi) m/z 334 (100) (M+H).

Example 47

4-(3-Chlorophenylthio)-N-(4-methylthiazol-2-yl)pyridin-2-amine

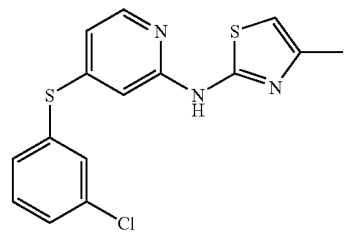

Step A: Preparation of 2-chloro-4-(3-chlorophenylthio)pyridine: Using the method of Example 3, Step A, 3-chlorobenzenethiol (912 mg, 6.31 mmol), 60% sodium hydride in mineral oil (252 mg, 6.31 mmol), and 2-chloro-4-nitropyridine (1.00 g, 6.31 mmol) were reacted to afford 2-chloro-4-(3-chlorophenylthio)pyridine (1.48 g, 92% yield) as an oil. $^1$H NMR (CDCl$_3$) δ 8.16 (d, 1H), 7.56 (s, 1H), 7.39-7.49 (m, 3H), 6.94 (s, 1H), 6.88 (d, 1H).

Step B: Preparation of 4-(2-chlorophenylthio)-N-(4-methylthiazol-2-yl)pyridin-2-amine: Using the method of Example 3, Step B, 4-methylthiazol-2-amine (7.007 mL, 4.905 mmol), 2-chloro-4-(3-chlorophenylthio)pyridine (1.382 g, 5.396 mmol), potassium phosphate (1.145 g, 5.396 mmol), tris(dibenzylideneacetone)dipalladium (0) (0.1123 g, 0.1226 mmol), 4,5-bis(diphenylphosphino)-9,9-dimethyl-9H-xanthene (0.07805 g, 0.1349 mmol) were reacted in toluene (7 mL) and water (2 mL) to afford 4-(3-chlorophenylthio)-N-(4-methylthiazol-2-yl)pyridin-2-amine (1.256 g, 75.93% yield) as off white solid. $^1$H NMR (CDCl$_3$) δ 8.11 (d, 1H), 7.51 (t, 1H), 7.38 (m, 2H), 7.30 (m, 1H), 6.58 (dd, 1H), 6.49 (s, 1H), 6.32 (d, 1H), 2.19 (d, 3H); Mass spectrum (esi) m/z=334 (100) (M+H).

Example 48

4-(4-Chlorophenylthio)-N-(4-methylthiazol-2-yl)pyridin-2-amine

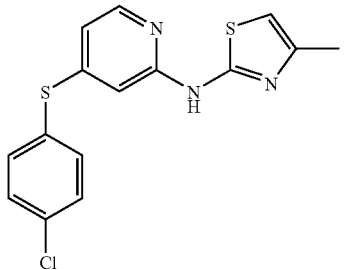

Step A: Preparation of 2-chloro-4-(4-chlorophenylthio)pyridine: Using the method of Example 3, Step A, 4-chlorobenzenethiol (912 mg, 6.31 mmol), 60% sodium hydride in mineral oil (252 mg, 6.31 mmol), and 2-chloro-4-nitropyridine (1.00 g, 6.31 mmol) were reacted to afford 2-chloro-4-(4-chlorophenylthio)pyridine (1.37 g, 85% yield) as an oil. $^1$H NMR (CDCl$_3$) δ 8.14 (d, 1H), 7.48 (d, 2H), 7.46 (d, 2H), 6.90 (s, 1H), 6.85 (d, 1H).

Step B: Preparation of 4-(2-chlorophenylthio)-N-(4-methylthiazol-2-yl)pyridin-2-amine: Using the method of Example 3, Step B, 4-methylthiazol-2-amine (7.01 mL, 4.91 mmol), 2-chloro-4-(4-chlorophenylthio)pyridine (1.38 g, 5.40 mmol), potassium phosphate (1.15 g, 5.40 mmol), tris(dibenzylideneacetone)dipalladium(0) (0.112 g, 0.123 mmol), 4,5-bis(diphenyl-phosphino)-9,9-dimethyl-9H-xanthene (0.0780 g, 0.135 mmol) were reacted in toluene (7 mL) and water (2 mL) to afford 4-(4-chlorophenylthio)-N-(4-methylthiazol-2-yl)pyridin-2-amine (0.781 g, 47.2% yield) as light yellow solid. $^1$H NMR (CDCl$_3$) δ 8.09 (d, 1H), 7.45 (m, 2H), 7.38 (m, 2H), 6.57 (dd, 1H), 6.44 (s, 1H), 6.34 (d, 1H), 2.17 (d, 3H); Mass spectrum (esi) m/z=334 (100) (M+H).

Example 49

2-(2-(3-Methyl-1,2,4-thiadiazol-5-ylamino)pyridin-4-yloxy)benzonitrile

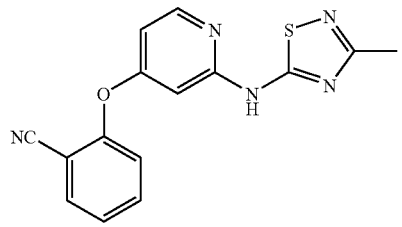

Using the method of Example 3, Step B, 2-(2-chloropyridin-4-yloxy)benzonitrile (0.330 g, 1.43 mmol), 3-methyl-1,2,4-thiadiazol-5-amine (3.26 mL, 1.30 mmol), potassium phosphate (0.304 g, 1.43 mmol), tris(dibenzylideneacetone) dipalladium (0) (0.0298 g, 0.0326 mmol) and 4,5-bis(diphenylphosphino)-9,9-dimethyl-9H-xanthene (0.0207 g, 0.0358 mmol) were reacted in toluene (5 mL) and water (1.5 mL) to afford 2-(2-(3-methyl-1,2,4-thiadiazol-5-ylamino)pyridin-4-yloxy)benzonitrile (10 mg) as off white solid. $^1$H NMR (CDCl$_3$) δ 8.35 (d, 1H), 7.76 (dd, 1H), 7.66 (dt, 1H), 7.37 (dt, 1H), 7.19 (d, 1H), 6.63 (dd, 1H), 6.45 (d, 1H), 2.49 (s, 3H); Mass spectrum (esi) m/z=310 (100) (M+H).

Example 50

4-Methyl-N-(4-(naphthalen-1-ylthio)pyridin-2-yl)thiazol-2-amine

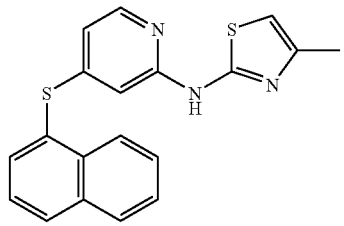

Step A: Preparation of 2-chloro-4-(naphthalen-1-ylthio)pyridine: Using the method of Example 3, Step A, naphthalen-1-thiol (909 mg, 6.31 mmol), 60% sodium hydride in mineral oil (252 mg, 6.31 mmol), and 2-chloro-4-nitropyridine (1.00 g, 6.31 mmol) were reacted to afford 2-chloro-4-(naphthalen-1-ylthio)pyridine (1.53 g, 95% yield) as an oil. $^1$H NMR (CDCl$_3$) δ 8.22 (d, 1H), 8.03-8.05 (m, 2H), 7.89-7.96 (m, 2H), 7.54-7.59 (m, 3H), 6.82 (s, 1H), 6.72 (d, 1H).

Step B: Preparation of 4-methyl-N-(4-(naphthalen-1-ylthio)pyridin-2-yl)thiazol-2-amine: Using the method of Example 3, Step B, 4-methylthiazol-2-amine (0.55 g, 4.82 mmol), 2-chloro-4-(naphthalen-1-ylthio)pyridine (1.44 g, 5.30 mmol), potassium phosphate (1.12 g, 5.30 mmol), Tris (dibenzylideneacetone)dipalladium (0) (0.110 g, 0.120 mmol) and 4,5-bis(diphenyl-phosphino)-9,9-dimethyl-9H-xanthene (0.0767 g, 0.132 mmol) were reacted in toluene (12 mL) and water (4 mL) to afford N-(4-methylthiazol-2-yl)-4-(naphthalen-1-ylthio)pyridin-2-amine (0.2 g, 11% yield) as yellow solid. $^1$H NMR (CDCl$_3$) δ 8.26 (m, 1H), 8.01 (m, 2H), 7.93 (m, 1H), 7.90 (dd, 1H), 7.54 (m, 3H), 6.49 (dd, 1H), 6.28 (d, 1H), 6.25 (d, 1H), 2.21 (d, 3H); Mass spectrum (esi) m/z 350 (100) (M+H).

Example 51

(6-(4-Methylthiazol-2-ylamino)-4-(naphthalen-1-yloxy)-pyridin-3-yl)methanol

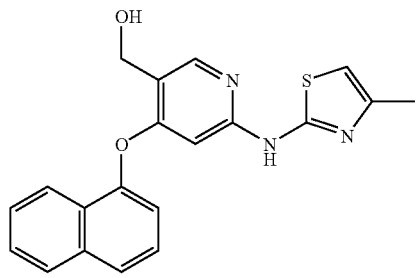

A solution of ethyl 6-(4-methylthiazol-2-ylamino)-4-(naphthalen-1-yloxy)nicotinate (1.50 g, 3.70 mmol) in THF (15 mL) was added to a 1.0 M solution of lithium aluminum hydride (18.5 mL, 18.5 mmol) in ether at 0° C. and stirred for 30 minutes. The reaction was quenched with sodium sulfate decahydrate, stirred 30 minutes, and filtered. The solids were washed with THF, filtered, and concentrated. The residue was partitioned between ethyl acetate and water. The organic layer was washed with brine, dried, and concentrated. The residue was triturated with hexanes and filtered to afford (6-(4-methylthiazol-2-ylamino)-4-(naphthalen-1-yloxy)pyridin-3-yl)methanol (1.10 g, 81.8% yield) as a white solid. $^1$H NMR (DMSO-d$_6$) δ 10.68 (bs, 1H), 8.25 (s, 1H), 8.05 (d, 1H), 7.92 (d, 2H), 7.53-7.64 (m, 3H), 7.36 (d, 1H), 6.47 (s, 1H), 6.19 (s, 1H), 5.20 (t, 1H), 4.71 (d, 2H), 2.13 (s, 3H); Mass spectrum (esi) m/z=364 (100) (M+H).

Example 52

(E)-methyl 3-(6-(4-methylthiazol-2-ylamino)-4-(naphthalen-1-yloxy)pyridin-3-yl)acrylate and (Z)-methyl 3-(6-(4-methylthiazol-2-ylamino)-4-(naphthalen-1-yloxy)pyridin-3-yl)acrylate

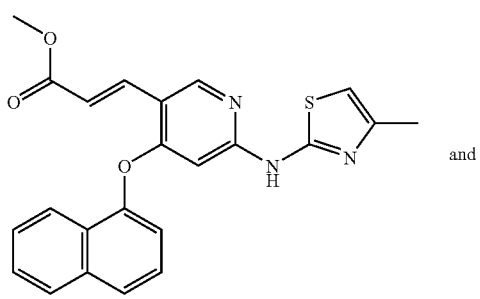 and

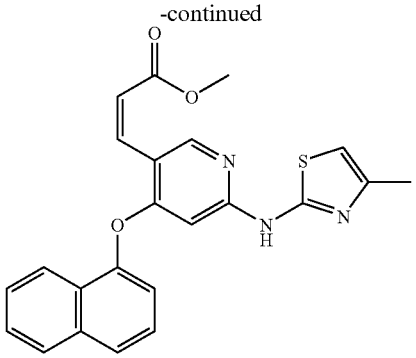

Step A: Preparation of 6-(4-methylthiazol-2-ylamino)-4-(naphthalen-1-yloxy)nicotinaldehyde: To a solution of Dess Martin periodane (1.30 g, 3.05 mmol) in THF (5 mL) at 0° C. was added a solution of (6-(4-methylthiazol-2-ylamino)-4-(naphthalen-1-yloxy)pyridin-3-yl)methanol (0.925 g, 2.55 mmol). The mixture was warmed to room temperature and stirred for 30 minutes, diluted with ether and hydrolyzed with 1N NaOH (40 mL). The mixture was extracted with ether, washed with brine, dried, and concentrated to afford 6-(4-methylthiazol-2-ylamino)-4-(naphthalen-1-yloxy)nicotinaldehyde (0.860 g, 93.5% yield) as a light yellow solid. $^1$H NMR (DMSO d6) δ 11.28 (bs, 1H), 10.40 (s, 1H), 8.75 (s, 1H), 8.09 (d, 1H), 7.98 (d, 1H), 7.92 (d, 1H), 7.55-7.68 (m, 3H), 7.49 (d, 1H), 6.62 (s, 1H), 6.26 (bs, 1H), 2.13 (s, 3H).

Step B: Preparation of (E)-methyl 3-(6-(4-methylthiazol-2-ylamino)-4-(naphthalen-1-yloxy)pyridin-3-yl)acrylate and (Z)-methyl 3-(6-(4-methylthiazol-2-ylamino)-4-(naphthalen-1-yloxy)pyridin-3-yl)acrylate: Carbomethoxymethylene triphenylphosphorane (0.517 g, 1.55 mmol) was added to a solution of 6-(4-methylthiazol-2-ylamino)-4-(naphthalen-1-yloxy)nicotinaldehyde (0.430 g, 1.19 mmol) in THF (5 mL). The reaction mixture was stirred for 2 hours and then concentrated, and the residue was purified via MPLC (Biotage), eluting with 1:1 hexane:ethyl acetate to provide (Z)-methyl 3-(6-(4-methylthiazol-2-ylamino)-4-(naphthalen-1-yloxy)pyridin-3-yl)acrylate (0.072 g, 14% yield) and (E)-methyl 3-(6-(4-methylthiazol-2-ylamino)-4-(naphthalen-1-yloxy)pyridin-3-yl)acrylate (0.216 g, 43% yield).

Example 53

(N-(5-((Dimethylamino)methyl)-4-(naphthalen-1-yloxy)pyridin-2-yl)-4-methylthiazol-2-amine dihydrochloride

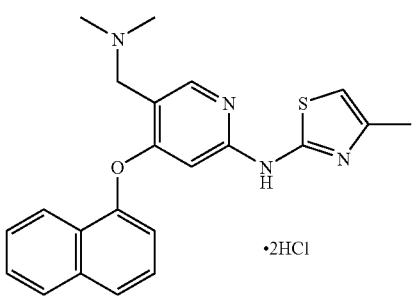

Dimethylamine (0.374 mL, 0.747 mmol) was added to a solution of 6-(4-methylthiazol-2-ylamino)-4-(naphthalen-1- yloxy)nicotinaldehyde (0.090 g, 0.249 mmol) in THF (3 mL) and stirred for 10 minutes. Sodium triacetoxyborohydride (0.264 g, 1.25 mmol) was added and the reaction mixture was stirred for an additional 30 minutes. The mixture was quenched with saturated sodium bicarbonate, partitioned between ethyl acetate and water, washed with brine, dried, and concentrated. The residue was dissolved in THF (2 mL), 1M HCl in ether was added, the solution was diluted in hexanes (5 mL), triturated for 15 minutes, filtered, dried to afford 5-((dimethylamino)methyl)-N-(4-methylthiazol-2-yl)-4-(naphthalen-1-yloxy)pyridin-2-amine (0.071 g, 73.0% yield) as a white solid. $^1$H NMR (DMSO d6) δ 10.88 (bs, 1H), 8.58 (s, 1H), 8.09 (d, 1H), 7.98 (d, 1H), 7.90 (d, 1H), 7.52-7.67 (m, 4H), 6.67 (s, 1H), 6.37 (s, 1H), 4.54 (s, 2H), 2.88 (s, 6H), 2.18 (s, 3H).

Example 54

4-Methyl-N-(4-(naphthalen-1-yloxy)-5-(piperidin-1-ylmethyl)pyridin-2-yl)thiazol-2-amine dihydrochloride

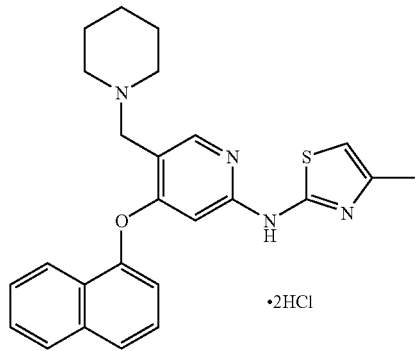

Using the method of Example 53, piperidine (0.0254 g, 0.299 mmol), 6-(4-methylthiazol-2-ylamino)-4-(naphthalen-1-yloxy)nicotinaldehyde (0.090 g, 0.249 mmol) and sodium triacetoxyborohydride (0.264 g, 1.25 mmol) were reacted to afford N-(4-methylthiazol-2-yl)-4-(naphthalen-1-yloxy)-5-(piperidin-1-ylmethyl)pyridin-2-amine dihydrochloride (0.091 g, 72.6% yield) as a white powder. $^1$H NMR (DMSO d6) δ 10.75 (bs, 1H), 8.65 (s, 1H), 8.09 (d, 1H), 7.98 (d, 1H), 7.88 (d, 1H), 7.52-7.68 (m, 4H), 6.66 (s, 1H), 6.31 (s, 1H), 4.48 (d, 2H), 3.55 (m, 2H), 3.08 (m, 2H), 2.16 (s, 3H), 1.20-1.92 (m, 6H).

Example 55

N1,N1-dimethyl-N2-((6-(4-methylthiazol-2-ylamino)-4-(naphthalen-1-yloxy)pyridin-3-yl)methyl)ethane-1,2-diamine dihydrochloride

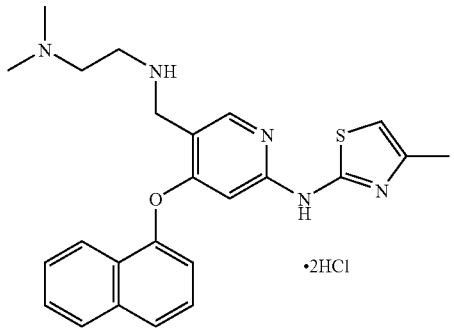

Using the method of Example 53, N,N-dimethylethane-1,2-diamine (0.0263 g, 0.299 mmol), 6-(4-methylthiazol-2-ylamino)-4-(naphthalen-1-yloxy)nicotinaldehyde (0.090 g, 0.249 mmol) and sodium triacetoxyborohydride (0.264 g, 1.25 mmol) were reacted to afford N1,N1-dimethyl-N2-((6-(4-methylthiazol-2-ylamino)-4-(naphthalen-1-yloxy)pyridin-3-yl)methyl)ethane-1,2-diamine dihydrochloride (0.079 g, 63% yield) as a white powder. $^1$H NMR (DMSO d6) δ 10.83 (bs, 1H), 8.45 (s, 1H), 8.08 (d, 1H), 7.97 (d, 2H), 7.50-7.67 (m, 4H), 6.52 (s, 1H), 6.18 (s, 1H), 4.39 (m, 2H), 3.30-3.55 (m, 4H), 2.73 (s, 6H), 2.13 (s, 3H).

Example 56

N-(5-(((Cyclohexylamino)methyl)-4-(naphthalen-1-yloxy)pyridin-2-yl)-4-methylthiazol-2-amine dihydrochloride

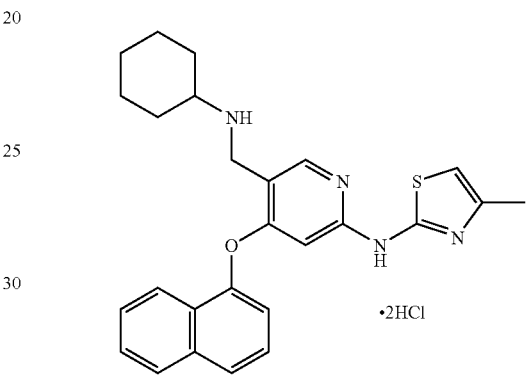

Using the method of Example 53, cyclohexylamine (0.0296 g, 0.299 mmol), 6-(4-methylthiazol-2-ylamino)-4-(naphthalen-1-yloxy)nicotinaldehyde (0.090 g, 0.249 mmol) and sodium triacetoxyborohydride (0.264 g, 1.25 mmol) were reacted to provide N-(5-((cyclohexylamino)methyl)-4-(naphthalen-1-yloxy)pyridin-2-yl)-4-methylthiazol-2-amine dihydrochloride (0.048 g, 37% yield) as a white powder. $^1$H NMR (DMSO d6) δ 9.48 (bs, 2H), 8.60 (s, 1H), 8.09 (d, 1H), 8.00 (d, 1H), 7.98 (d, 1H), 7.54-7.68 (m, 4H), 6.67 (s, 1H), 6.30 (s, 1H), 4.38 (s, 2H), 3.15 (m, 1H), 2.19 (s, 3H), 1.10-1.82 (m, 10H).

Example 57

Ethyl 6-(4-methylthiazol-2-ylamino)-4-phenoxynicotinate

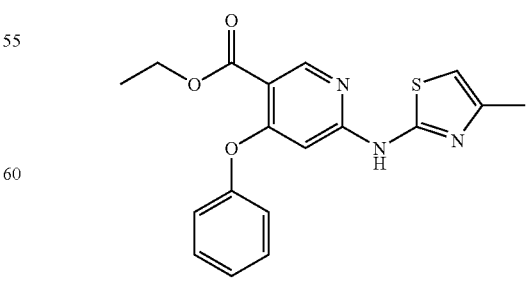

Using the method of Example 3, Step B, ethyl 6-chloro-4-phenoxynicotinate (12.0 g, 43.4 mmol), 4-methylthiazol-2- amine (4.49 g, 39.4 mmol), potassium phosphate (9.20 g, 43.4 mmol), tris(dibenzylideneacetone)-dipalladium (0) (0.902 g, 0.985 mmol) and 4,5-bis(diphenylphosphino)-9,9-dimethyl-9H-xanthene (0.627 g, 1.08 mmol) were combined in toluene (100 mL) and water (25 mL) to afford ethyl 6-(4-methylthiazol-2-ylamino)-4-phenoxynicotinate (9.6 g, 67.8% yield) as yellow solid. $^1$H NMR (CDCl$_3$) δ 8.88 (s, 1H), 7.40 (m, 2H), 7.25 (m, 1H), 7.08 (m, 1H), 7.07 (m, 1H), 6.30 (d, 1H), 6.06 (s, 1H), 4.35 (q, 2H), 2.04 (s, 3H), 1.35 (t, 3H); Mass spectrum (esi) m/z=356 (100)(M+H).

Example 58

(6-(4-Methylthiazol-2-ylamino)-4-phenoxypyridin-3-yl)methanol

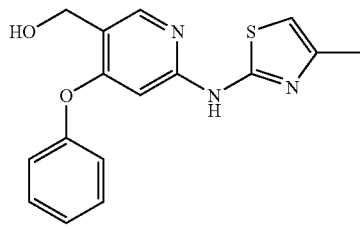

To a solution of 1M lithium aluminum hydride (70 mL, 70 mmol) in ether at 0° C. was added a solution of ethyl 6-(4-methylthiazol-2-ylamino)-4-phenoxynicotinate (14 mmol) in THF (50 mL). The reaction mixture was stirred for 1.5 hours, then slowly quenched with sodium sulfate decahydrate and stirred for 1 hour. The reaction mixture was filtered, the solids were washed with THF and the organic layer was concentrated. Water and ethyl acetate were added to the residue, and the aqueous layer was extracted with ethyl acetate. The organic layer was washed with brine, dried, concentrated to 50 mL of ethyl acetate, and filtered. The residue was purified using silica gel column chromatography with 30% ethyl acetate in hexanes as eluent to afford the desired product (3.0 g, 66% yield) as light yellow solid. $^1$H NMR (DMSO) δ 10.83 (s, 1H), 8.20 (s, 1H), 7.50 (m, 2H), 7.30 (m, 1H), 7.17 (m, 2H), 6.49 (d, 1H), 6.35 (s, 1H), 5.07 (t, 1H), 4.55 (d, 2H), 2.17 (d, 3H); Mass spectrum (esi) m/z=314 (100)(M+H).

Example 59

Representative Example 6-(4-Methylthiazol-2-ylamino)-4-phenoxynicotinic acid hydrochloride

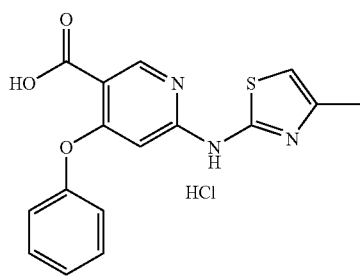

Ethyl 6-(4-methylthiazol-2-ylamino)-4-phenoxynicotinate (1.0 g, 2.81 mmol) was dissolved in THF (5 mL) and a solution of lithium hydroxide hydrate (0.236 g, 5.63 mmol) in water (1 mL) was added. The reaction mixture was stirred at room temperature overnight, then 2 mL of 2N NaOH was added and the reaction mixture was stirred for two days at room temperature. The reaction mixture was concentrated adjusted to about pH 3, then filtered and concentrated. The residue was dried overnight under high vacuum to yield the desired product (0.858 g, 83.0% yield) as off white solid. $^1$H NMR (DMSO) δ 8.70 (s, 1H), 7.50 (m, 2H), 7.30 (m, 1H), 7.18 (m, 2H), 6.59 (d, 1H), 6.44 (s, 1H), 2.18 (d, 3H); Mass spectrum (esi) m/z=328 (100) (M+H).

Example 60

3-(2-(4-Methylthiazol-2-ylamino)pyridin-4-ylthio)phenol

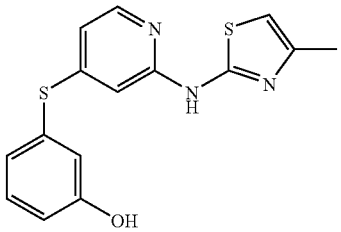

A 3 dram vial was charged with 4-(3-(tert-butyldimethylsilyloxy)phenylthio)-N-(4-methylthiazol-2-yl)pyridin-2-amine (0.470 g, 1.09 mmol and THF (2 mL) and 6M HCl (1 mL) were added. The reaction mixture was stirred at room temperature overnight, then diluted with water and extracted with ethyl acetate. The combined organic layers were dried over magnesium sulfate, filtered and concentrated to give desired product (0.309 g, 89.6% yield) as yellow solid. $^1$H NMR (DMSO) δ 11.07 (s, 1H), 9.84 (s, 1H), 8.08 (d, 1H), 7.32 (t, 1H), 6.98 (m, 1H), 6.92 (m, 2H), 6.76 (d, 1H), 6.59 (dd, 1H), 6.51 (d, 1H), 2.20 (d, 3H); Mass spectrum (esi) m/z=316 (100) (M+H).

Example 61 tert-Butyl 2-(3-(2-(4-methylthiazol-2-ylamino)pyridin-4-ylthio)phenoxy)acetate

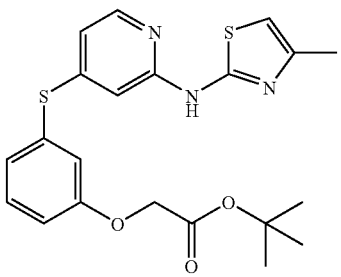

A mixture of potassium carbonate (1.08 g, 7.82 mmol), 3-(2-(4-methylthiazol-2-ylamino)pyridin-4-ylthio)phenol (0.274 g, 0.869 mmol), and tert-butyl 2-bromoacetate (0.169 g, 0.869 mmol) in DMF (5 mL). The reaction mixture was stirred at room temperature overnight, then diluted with water and extracted with ethyl acetate. The combined organic layers were dried over magnesium sulfate, filtered and concentrated. The residue was purified using prepacked silica gel column chromatography with 15-20% ethyl acetate to afford the desired product (0.224 g, 58.8% yield) as light yellow solid. $^1$H NMR (CDCl$_3$) δ 8.08 (d, 1H), 7.33 (t, 1H), 7.15 (m, 1H), 7.04 (t, 1H), 6.98 (m, 1H), 6.57 (dd, 1H), 6.49 (dd, 1H), 6.33 (d, 1H), 4.50 (s, 2H, 2.22 (d, 3H), 1.46 (s, 9H); Mass spectrum (esi) m/z=430 (100)(M+H).

Example 62

(4-Ethylpiperazin-1-yl)(3-(2-(4-methylthiazol-2-ylamino)pyridin-4-yloxy)phenyl)methanone dihydrochloride

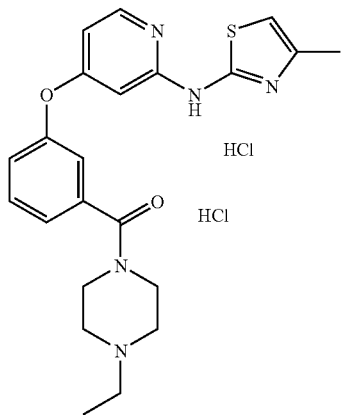

A 3 dram vial was charged with 3-(2-(4-methylthiazol-2-ylamino)pyridin-4-yloxy)benzoic acid (0.1 g, 0.3055 mmol), triethylamine (0.2129 mL, 1.527 mmol) and THF (2 mL), and the reaction mixture was cooled to 0° C. Ethyl carbonochloridate (0.03359 mL, 0.3513 mmol) was added and the reaction mixture was stirred at 0° C. for 30 minutes. 1-Ethylpiperazine (0.1164 mL, 0.9164 mmol) was added and the reaction mixture was warmed to room temperature and stirred for 1 hour, and then 2N NaOH was added. The reaction mixture was extracted with ethyl acetate, dried over magnesium sulfate, filtered and concentrated. The residue was purified using prepacked silica gel column with 5% methanol in DCM as eluent to afford the desired product (0.085 g, 56.05% yield) as off white solid. Mass spectrum (esi) m/z=424 (100) (M+H-2HCl).

Example 63

Ethyl 6-(4-isopropylthiazol-2-ylamino)-4-phenoxynicotinate

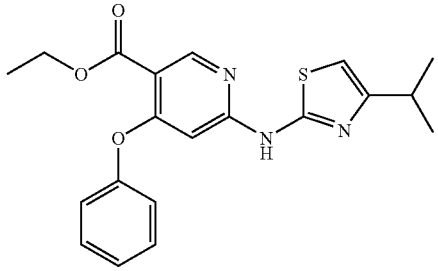

Using the method of Example 3, Step B, ethyl 6-chloro-4-phenoxynicotinate (4.296 g, 15.47 mmol), 4-isopropylthiazol-2-amine (2 g, 14.06 mmol), potassium phosphate (3.283 g, 15.47 mmol), tris(dibenzylideneacetone)dipalladium (0) (0.3219 g, 0.3516 mmol) and 4,5-bis(diphenylphosphino)-9,9-dimethyl-9H-xanthene (0.2238 g, 0.3867 mmol) were reacted in water (15 mL) and toluene (40 mL) to afford the desired product (4.447 g, 74.22% yield) as a yellow solid. $^1$H NMR (DMSO), 11.36 (s, 1H), 8.72 (s, 1H), 7.49 (m, 2H), 7.30 (m, 1H), 7.17 (m, 1H), 7.15 (m, 1H), 6.59 (m, 2H), 4.24 (q, 2H), 2.81 (m, 1H), 1.25 (t 3H), 1.15 (d, 6H); Mass spectrum (apci) m/z=384 (100) (M+H).

Example 64

Representative Example

N-(4-(3-(benzyloxy)phenoxy)pyridin-2-yl)-4-methylthiazol-2-amine

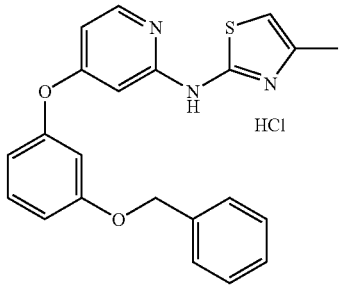

A mixture (2-(4-methylthiazol-2-ylamino)pyridin-4-yloxy)phenol (0.150 g, 0.501-mmol), potassium carbonate (0.208 g, 1.50 mmol), 1-(bromomethyl)benzene (0.0857 g, 0.501 mmol), and DMF (2 mL) was stirred overnight at room temperature. The reaction mixture was partitioned between ethyl acetate and water, and the ethyl acetate was washed with water and brine, dried and concentrated. The residue was purified via MPLC (Biotage) eluting with 7:3 hexane:ethyl acetate to afford the free base. The free base was dissolved in ether (4 mL) and 1M HCl in ether (1 mL) was added. The mixture was diluted with hexanes (5 mL) and triturated. The solids were collected by filtration, washed with hexanes, and dried to afford the desired product (0.075 g, 35.1% yield) as a white powder. $^1$H NMR (d$_6$-DMSO) δ 10.5 (bs, 1H), 8.24 (d, 1H), 7.33-7.47 (m, 6H), 6.98 (d, 1H), 6.90 (s, 1H), 6.80 (d, 1H), 6.58-6.60 (m, 3H), 5.13 (s, 2H), 2.25 (s, 3H).

Example 65 tert-Butyl 2-(3-(2-(4-methylthiazol-2-ylamino)-pyridin-4-yloxy)phenoxy)acetate

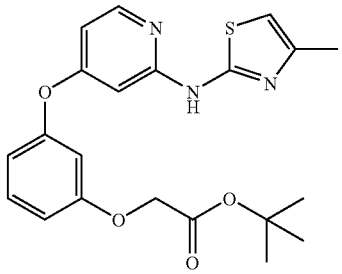

A mixture of potassium carbonate (3.00 g, 21.7 mmol), 3-(2-(4-methylthiazol-2-ylamino)pyridin-4-yloxy)phenol (0.750 g; 2.51 mmol), and tert-butyl 2-bromoacetate (0.489 g, 2.51 mmol) was stirred in DMF (20 mL) overnight at room temperature. The reaction mixture was partitioned between ethyl acetate and water, and the ethyl acetate was washed with water and brine, dried and concentrated. The residue was purified via MPLC (Biotage) eluting with 3:2 hexane:ethyl acetate to afford the desired product as a white powder. ¹H NMR (d₆-DMSO) δ 11.01 (s, 1H), 8.16 (d, 1H), 7.38 (t, 1H), 6.85 (d, 1H), 6.79 (d, 1H), 6.74 (s, 1M), 6.56 (s, 1H), 6.49-6.52 (m, 2H), 4.68 (s, 2H), 2.21 (s, 3H), 0.90 (s, 9H).

Example 66

2-(3-(2-(4-Methylthiazol-2-ylamino)pyridin-4-yloxy)phenoxy)acetic acid hydrochloride

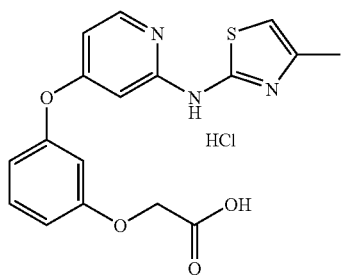

tert-Butyl 2-(3-(2-(4-methylthiazol-2-ylamino)pyridin-4-yloxy)phenoxy)acetate (0.530 g, 1.28 mmol) was dissolved in dichloromethane (5 mL), and trifluoroacetic acid (5 mL) was added. The reaction mixture was stirred at room temperature for one hour, the concentrated. The TFA salt was dissolved in ether (15 mL). 1M HCl in ether (6 mL) was added, and the solids were collected by filtration, washed with hexanes and dried to afford the desired product as a white solid. ¹H NMR (d₆-DMSO) δ 11.85 (bs, 1H), 8.25 (d, 1H), 7.41 (t, 1H), 6.88 (d, 1H), 6.80-6.83 (m, 2H), 6.67-6.70 (m, 2H), 4.72 (s, 2H), 2.26 (s, 3H).

Example 67

6-(4-Methylthiazol-2-ylamino)-4-(naphthalen-1-yloxy)nicotinic acid

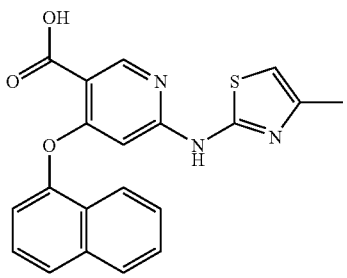

Ethyl 6-(4-methylthiazol-2-ylamino)-4-(naphthalen-1-yloxy)nicotinate (1.00 g, 2.47 mmol) was dissolved in THF (5 mL). A solution of lithium hydroxide hydrate (0.207 g, 4.93 mmol) in water (1 mL) was added, and the reaction mixture was stirred at room temperature overnight. The reaction mixture was concentrated, 2M HCl was added to adjust the pH to 3. The reaction mixture was filtered to obtain the desired product (0.61 g, 65.5% yield) as a white solid. ¹H NMR (d₆-DMSO) δ 10.85 (bs, 1H), 8.76 (s, 1H), 8.06 (d, 1H), 7.88-7.93 (m, 2H), 7.55-7.65 (m, 3H), 7.35 (d, 1H), 6.58 (s, 1H), 6.32 (s, 1H), 2.14 (s, 3H).

Example 68

N-(4-(2-chlorophenoxy)pyridin-2-yl)-4-methylthiazol-2-amine

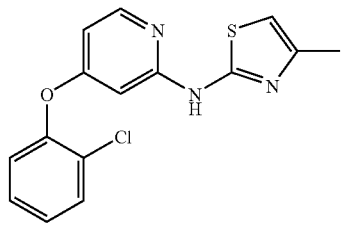

Step A: Preparation of 2-chloro-4-(2-chlorophenoxy)pyridine: Using the method of Example 3, Step A, 2-chlorophenol (811 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-(2-chlorophenoxy)pyridine (0.98 g, 95% yield) as an oil. ¹H NMR (CDCl₃) δ 8.25 (d, 1H), 7.52 (d, 1H), 7.36 (t, 1H), 7.28 (t, 1H), 7.17 (d, 1H), 6.74-6.77 (m, 2H).

Step B: Preparation of N-(4-(2-chloro-phenoxypyridin-2-yl)-4-methylthiazol-2-amine: Using the method of Example 3, Step B, 4-methylthiazol-2-amine (0.238 g, 2.08 mmol), 2-chloro-4-(2-chlorophenoxy)pyridine (0.500 g, 2.08 mmol), potassium phosphate (0.486 g, 2.29 mmol), Pd₂(dba)₃ (0.095 g, 0.104 mmol), and 4,5-bis(diphenylphosphino)-9,9-dimethyl-9H-xanthene (0.060 g, 0.104 mmol) were reacted to provide N-(4-(2-chlorophenoxy)pyridin-2-yl)-4-methylthiazol-2-amine (0.293 g, 44% yield). ¹H NMR (d₆-DMSO) δ 11.00 (bs, 1H), 8.18 (d, 1H), 7.68 (d, 1H), 7.49 (t, 1H), 7.36-7.40 (m, 2H), 6.47-6.53 (m, 3H), 2.20 (s, 3H).

Example 69

N-(4-(2,6-difluorophenoxy)pyridin-2-yl)-4-methylthiazol-2-amine

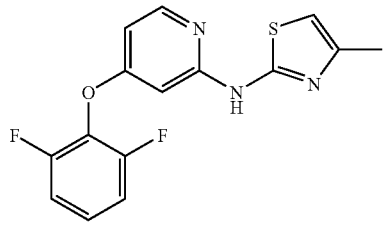

Step A: Preparation of 2-chloro-4-(2,6-difluorophenoxy)pyridine: Using the method of Example 3, Step A, 2,6-difluorophenol (821 mg, 6.31 mmol), 60% sodium hydride in mineral oil (252 mg, 6.31 mmol), and 2-chloro-4-nitropyridine (1.00 g, 6.31 mmol) were reacted to provide 2-chloro-4-(2,6-difluorophenoxy)pyridine (1.44 g, 94% yield) as an oil. ¹H NMR (CDCl₃) δ 8.27 (d, 1H), 7.26 (m, 1H), 7.04-7.10 (m, 2H), 6.80-6.86 (m, 2H).

Step B: Preparation of N-(4-(2,6-difluorophenoxy)pyridin-2-yl)-4-methylthiazol-2-amine: Using the method of Example 3, Step B, 4-methylthiazol-2-amine (0.284 g, 2.48 mmol), 2-chloro-4-(2,6-difluorophenoxy)pyridine (0.600 g, 2.48 mmol), potassium phosphate (0.580 g, 2.73 mmol), Pd$_2$(dba)$_3$ (0.114 g, 0.124 mmol), and 4,5-bis(diphenylphosphino)-9,9-dimethyl-9H-xanthene (0.072 g, 0.124 mmol) were reacted to provide N-(4-(2,6-difluorophenoxy)pyridin-2-yl)-4-methylthiazol-2-amine (0.312 g, 39% yield). $^1$H NMR (d6-DMSO) δ 11.03 (s, 1H), 8.20 (d, 1H), 7.36-7.50 (m, 3H), 6.60-6.63 (m, 2H), 6.54 (s, 1H), 2.20 (s, 3H).

Example 70

N-(4-(2,6-dichlorophenoxy)pyridin-2-yl)-4-methylthiazol-2-amine

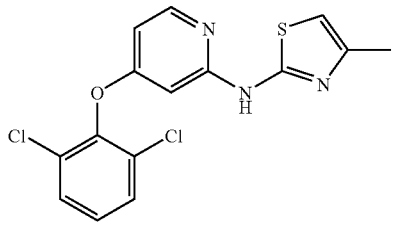

Step A: Preparation of 2-chloro-4-(2,6-dichlorophenoxy)pyridine: Using the method of Example 3, Step A, 2,6-dichlorophenol (2.06 g, 12.6 mmol), 60% sodium hydride in mineral oil (505 mg, 12.6 mmol), and 2-chloro-4-nitropyridine (2.00 g, 12.6 mmol) were reacted at 80° C. overnight to provide 2-chloro-4-(2,6-dichlorophenoxy)pyridine (2.23 g, 64% yield) as an oil. $^1$H NMR (CDCl$_3$) δ 8.27 (d, 1H), 7.44 (d, 2H), 7.24 (t, 1H), 6.71-6.75 (m, 2H).

Step B: Preparation of N-(4-(2,6-dichlorophenoxypyridin-2-yl)-4-methylthiazol-2-amine: Using the method of Example 3, Step B, 4-methylthiazol-2-amine (0.291 g, 2.55 mmol), 2-chloro-4-(2,6-difluorophenoxy)pyridine (0.700 g, 2.55 mmol), potassium phosphate (0.595 g, 2.80 mmol), Pd$_2$(dba)$_3$ (0.117 g, 0.127 mmol), and 4,5-bis(diphenylphosphino)-9,9-dimethyl-9H-xanthene (0.074 g, 0.127 mmol) were reacted to provide N-(4-(2,6-dichlorophenoxy)pyridin-2-yl)-4-methylthiazol-2-amine (0.450 g, 50% yield). $^1$H NMR (d-DMSO) δ 10.99 (s, 1H), 8.20 (d, 1H), 7.71 (d, 2H), 7.45 (t, 1H), 6.50-6.54 (m, 2H), 6.47 (s, 1H), 2.20 (s, 3H).

Example 71

4-Methyl-N-(4-(o-tolylthio)pyridin-2-yl)thiazol-2-amine

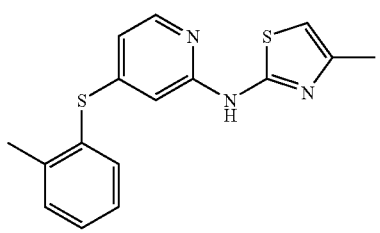

Step A: Preparation of 2-chloro-4-(o-tolylthio)pyridine: Using the method of Example 3, Step A, 2-methylbenzenethiol (0.783 g, 6.31 mmol), 60% sodium hydride in mineral oil (252 mg, 6.31 mmol), and 2-chloro-4-nitropyridine (1.00 g, 12.6 mmol) to provide 2-chloro-4-(o-tolylthio)pyridine (1.32 g, 89% yield) as an oil. $^1$H NMR (CDCl$_3$) δ 8.09 (d, 1H), 7.55 (d, 1H), 7.37-7.44 (m, 2H), 7.29 (t, 1H), 6.81 (s, 1H), 6.75-6.78 (m, 2H), 2.38 (s, 3H).

Step B: Preparation of 4-methyl-N-(4-(o-tolylthio)pyridin-2-yl)thiazol-2-amine: Using the method of Example 3, Step B, 4-methylthiazol-2-amine (0.291 g, 2.55 mmol), 2-chloro-4-(o-tolylthio)pyridine (0.600 g, 2.55 mmol), potassium phosphate (0.595 g, 2.80 mmol), Pd$_2$(dba)$_3$ (0.117 g, 0.127 mmol), and 4,5-bis(diphenylphosphino)-9,9-dimethyl-9H-xanthene (0.074 g, 0.127 mmol) were reacted to provide 4-methyl-N-(4-(o-tolylthio)pyridin-2-yl)thiazol-2-amine (0.401 g, 50% yield). $^1$H NMR (d$_6$-DMSO) δ 11.04 (s, 1H), 8.07 (d, 1H), 7.57 (d, 1H), 7.47 (d, 2H), 7.34 (m, 1H), 6.63 (s, 1H), 6.50 (s, 1H), 6.48 (m, 1H), 2.34 (s, 3H), 2.19 (s, 3H).

Example 72

N-(4-(2-isopropylphenylthio)pyridin-2-yl)-4-methylthiazol-2-amine hydrochloride

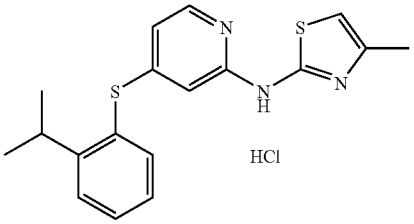

Step A: Preparation of 2-chloro-4-(2-isopropylphenylthio)pyridine: Using the method of Example 3, Step A, 2-isopropylbenzenethiol (0.749 g, 4.92 mmol), 60% sodium hydride in mineral oil (197 mg, 4.92 mmol), and 2-chloro-4-nitropyridine (0.780 g, 12.6 mmol) to provide 2-chloro-4-(o-tolylthio)pyridine (1.18 g, 91% yield) as an oil. $^1$H NMR (CDCl$_3$) δ 8.08 (d, 1H), 7.46-7.55 (m, 3H), 7.28 (t, 1H), 6.82 (s, 1H), 6.77 (d, 1H), 3.42 (heptet, 1H), 1.19 (d, 6H).

Step B: Preparation of N-(4-(2-isopropylphenylthio)pyridin-2-yl)-4-methylthiazol-2-amine hydrochloride salt: Using the method of Example 3, Step B, 4-methylthiazol-2-amine (0.260 g, 2.27 mmol), 2-chloro-4-(2-isopropylphenylthio)pyridine (0.600 g, 2.27 mmol), potassium phosphate (0.531 g, 2.50 mmol), Pd$_2$(dba)$_3$ (0.104 g, 0.114 mmol), and 4,5-bis(diphenylphosphino)-9,9-dimethyl-9H-xanthene (0.066 g, 0.114 mmol) were reacted to provide N-(4-(2-isopropylphenylthio)pyridin-2-yl)-4-methylthiazol-2-amine hydrochloride salt (0.301 g, 35% yield). $^1$H NMR (d6-DMSO) δ 11.1

(bs, 1H), 8.15 (d, 1H), 7.57-7.61 (m, 3H), 7.37 (m, 1H), 6.76 (s, 1H), 6.71-6.73 (m, 2H), 3.37 (heptet, 1H), 2.26 (s, 3H), 1.17 (d, 6H).

Example 73

Preparation of 4-methyl-N-(4-(2-(trifluoromethyl)phenylthio)pyridin-2-yl)thiazol-2-amine

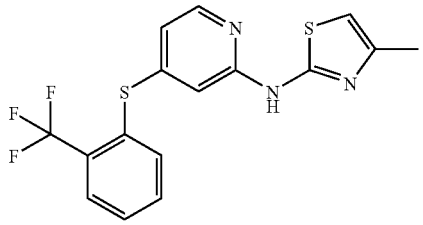

Step A: Preparation of 2-chloro-4-(2-(trifluoromethyl)phenylthio)pyridine: Using the method of Example 3, Step A, 2-(trifluoromethyl)benzenethiol (1.12 g, 6.31 mmol), 60% sodium hydride in mineral oil (252 mg, 6.31 mmol) and 2-chloro-4-nitropyridine (1.00 g, 12.6 mmol) were reacted to provide 2-chloro-4-(2-(trifluoromethyl)phenylthio)pyridine (1.70 g, 93% yield) as an oil. $^1$H NMR (CDCl$_3$) δ 8.13 (d, 1H), 7.88 (m, 1H), 7.61-7.72 (m, 4H), 6.85 (s, 1H), 6.80 (m, 1H).

Step B: Preparation of 4-methyl-N-(4-(2-(trifluoromethyl)phenylthio)-pyridin-2-yl)thiazol-2-amine: Using the method of Example 3, Step B, 4-methylthiazol-2-amine (0.236 g, 2.07 mmol), 2-chloro-4-(2-(trifluoromethyl)phenylthio)pyridine (0.600 g, 2.07 mmol), potassium phosphate (0.484 g, 2.28 mmol), Pd$_2$(dba)$_3$ (0.095 g, 0.104 mmol), and 4,5-bis(diphenylphosphino)-9,9-dimethyl-9H-xanthene (0.060 g, 0.104 mmol) were reacted to provide 4-methyl-N-(4-(2-(trifluoromethyl)phenylthio)pyridin-2-yl)thiazol-2-amine (0.568 g, 75% yield). $^1$H NMR (d$_6$-DMSO) δ 11.06 (s, 1H), 8.10 (d, 1H), 7.99 (d, 1H), 7.76-7.83 (m, 3H), 6.66 (s, 1H), 6.59 (m, 1H), 6.52 (s, 1H), 2.19 (s, 3H).

Example 74

Ethyl 2-(2-(4-(phenylthio)pyridin-2-yl-amino)thiazol-4-yl)acetate

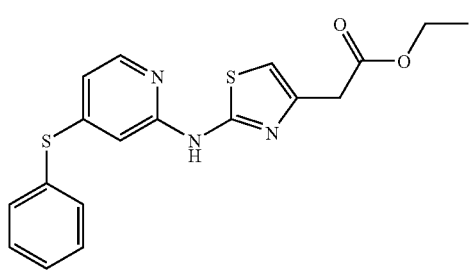

Using the method of Example 3, Step B, ethyl 2-(2-aminothiazol-4-yl)acetate (1.334 g, 7.16 mmol), 2-chloro-4-(phenylthio)pyridine (1.588 g, 7.16 mmol), potassium phosphate (1.672 g, 7.88 mmol); Pd$_2$(dba)$_3$ (0.328 g, 0.358 mmol), and 4,5-bis(diphenylphosphino)-9,9-dimethyl-9H-xanthene (0.207 g, 0.358 mmol) were reacted to provide 4-methyl-N-(4-(2-(trifluoromethyl)phenylthio)pyridin-2-yl)thiazol-2-amine (1.71 g, 64% yield). $^1$H NMR (d$_6$-DMSO) δ 11.23 (s, 1H), 8.09 (d, 1H), 7.52-7.60 (m, 5H), 6.75 (s, 1H), 6.71 (s, 1H), 6.52 (m, 1H), 4.07 (quartet, 2H), 3.61 (s, 2H), 1.18 (t, 3H).

Example 75

2-(2-(4-(Phenylthio)pyridin-2-ylamino)thiazol-4-yl)ethanol

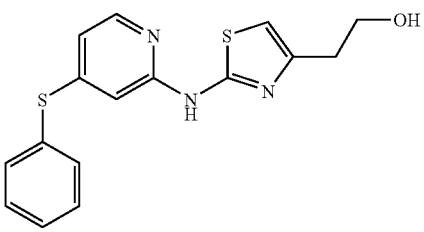

Ethyl 2-(2-(4-(phenylthio)pyridin-2-ylamino)thiazol-4-yl)acetate (1.20 g, 3.23 mmol) in THF was added to a solution of 1.0 M lithium aluminum hydride (9.69 mL, 9.69 mmol) in ether and THF (50 mL) at 0° C. The reaction mixture was stirred for 40 minutes, and cooled while carefully quenching with an excess of sodium sulfate decahydrate. A small amount of anhydrous magnesium sulfate was added and the reaction mixture was stirred overnight. The reaction mixture was filtered, and the cake was washed with THF several times. The combined filtrates were concentrated and the residue was recrystallized from 3:1 ethyl acetate:hexanes (50 mL). The crystals were filtered, washed with hexanes and dried to afford 2-(2-(4-(phenylthio)pyridin-2-ylamino)thiazol-4-yl)ethanol (0.501 g, 47.1% yield) as light pink crystals/needles. $^1$H NMR (d$_6$-DMSO) δ 11.11 (s, 1H), 8.08 (d, 1H), 7.53-7.61 (t, 6H), 6.73 (s, 1H), 6.57 (s, 1H), 6.56 (m, 1H), 4.58 (t, 1H), 3.65 (m, 2H), 2.69 (t, 2H).

Example 76

N-(4-(2,3-dichlorophenylthio)pyridin-2-yl)-4-methylthiazol-2-amine

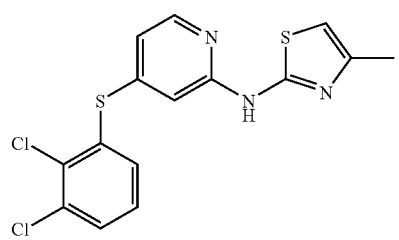

Step A: Preparation of 2-chloro-4-(2-3-dichlorophenylthio)pyridine: Using the method of Example 3, Step A, 2,3-dichlorobenzenethiol (1.69 g, 9.46 mmol), 60% sodium hydride in mineral oil (378 mg, 9.46 mmol), and 2-chloro-4-nitropyridine (1.50 g, 9.46 mmol) were reacted to provide 2-chloro-4-(2,3-dichlorophenylthio)pyridine (1.55 g, 56% yield) as a white powder. $^1$H NMR (CDCl$_3$) δ 8.19 (d, 1H), 7.61 (d, 1H), 7.54 (d, 1H), 7.29 (t, 1H), 6.95 (s, 1H), 6.87 (d, 1H).

Step B: Preparation of N-(4-(2,3-dichlorophenylthio)pyridin-2-yl)-4-methylthiazol-2-amine: Using the method of Example 3, Step B, 4-methylthiazol-2-amine (0.196 g, 1.72 mmol), 2-chloro-4-(2,3-dichlorophenylthio)pyridine (0.500 g, 1.72 mmol), potassium phosphate (0.402 g, 1.89 mmol), Pd$_2$(dba)$_3$ (0.079 g, 0.086 mmol), and 4,5-bis(diphenylphosphino)-9,9-dimethyl-9H-xanthene (0.050 g, 0.086 mmol) were reacted to provide N-(4-(2,3-dichlorophenylthio)pyridin-2-yl)-4-methylthiazol-2-amine (0.480 g, 76% yield). $^1$H NMR (d$_6$-DMSO) δ 11.10 (s, 1H), 8.15 (d, 1H), 7.82 (d, 1H), 7.66 (d, 1H), 7.49 (t, 1H), 6.71 (s, 1H), 6.69 (d, 1H), 6.54 (s, 1H), 2.20 (s, 3H).

Example 77

N-(4-(2,6-dimethylphenylthio)pyridin-2-yl)-4-methylthiazol-2-amine

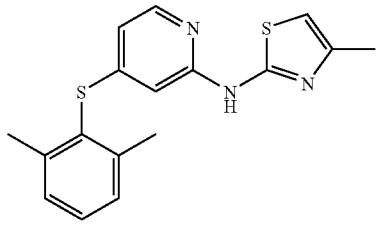

Step A: Preparation of 2-chloro-4-(2,6-dimethylphenylthio)pyridine: Using the method of Example 3, Step A, 2,6-dimethylbenzenethiol (0.872 g, 6.31 mmol), 60% sodium hydride in mineral oil (252 mg, 6.31 mmol), and 2-chloro-4-nitropyridine (1.00 g, 6.31 mmol) were reacted to provide 2-chloro-4-(2,6-dimethylphenylthio)pyridine (1.35 g, 86% yield) as a white solid. $^1$H NMR (CDCl$_3$) δ 8.07 (d, 1H), 7.22-7.34 (m, 3H), 6.75 (s, 1H), 6.71 (d, 1H), 2.40 (s, 6H).

Step B: Preparation of N-(4-(2,6-dimethylphenylthio)pyridin-2-yl)-4-methylthiazol-2-amine: Using the method of Example 3, Step B, 4-methylthiazol-2-amine (0.274 g, 2.40 mmol), 2-chloro-4-(2,6-dimethylphenylthio)pyridine (0.600 g, 2.40 mmol), potassium phosphate (0.561 g, 2.64 mmol), Pd$_2$(dba)$_3$ (0.110 g, 0.120 mmol), and 4,5-bis(diphenylphosphino)-9,9-dimethyl-9H-xanthene (0.070 g, 0.120 mmol) were reacted to provide N-(4-(2,6-dimethylphenylthio)pyridin-2-yl)-4-methylthiazol-2-amine (0.375 g, 48% yield). $^1$H NMR (d$_6$-DMSO) δ 11.01 (s, 1H), 8.03 (d, 1H), 7.31-7.40 (m, 3H), 6.57 (s, 1H), 6.50 (s, 1H), 6.41 (d, 1H), 2.40 (s, 6H), 2.20 (s, 3H).

Example 78

N-(4-(2,6-dichlorophenylthio)pyridin-2-yl)-4-methylthiazol-2-amine

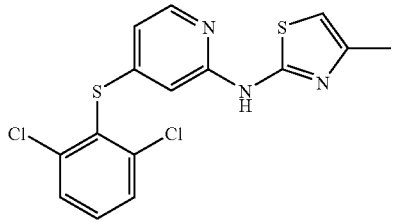

Step A: Preparation of 2-chloro-4-(2,6-dichlorophenylthio)pyridine: Using the method of Example 3, Step A, 2,6-dichlorobenzenethiol (1.69 g, 9.46 mmol), 60% sodium hydride in mineral oil (378 mg, 9.46 mmol), and 2-chloro-4-nitropyridine (1.50 g, 9.46 mmol) were reacted to provide 2-chloro-4-(2,6-dichlorophenylthio)pyridine (1.37 g, 50% yield) as a white powder. $^1$H NMR (CDCl$_3$) δ 8.15 (d, 1H), 7.53 (d, 2H), 7.41 (t, 1H), 6.84 (s, 1H), 6.79 (d, 1H).

Step B: Preparation of N-(4-(2,6-dichlorophenylthio)pyridin-2-yl)-4-methylthiazol-2-amine: Using the method of Example 3, Step B, 4-methylthiazol-2-amine (0.196 g, 1.72 mmol), 2-chloro-4-(2,6-dichlorophenylthio)pyridine (0.500 g, 1.72 mmol), potassium phosphate (0.402 g, 1.89 mmol), Pd$_2$(dba)$_3$ (0.079 g, 0.086 mmol), and 4,5-bis(diphenylphosphino)-9,9-dimethyl-9H-xanthene (0.050 g, 0.86 mmol) were reacted to provide N-(4-(2,6-dichlorophenylthio)pyridin-2-yl)-4-methylthiazol-2-amine (0.413 g, 65% yield) as a white powder. $^1$H NMR (d$_6$-DMSO) δ 11.03 (s, 1H), 8.09 (d, 1H), 7.77 (d, 2H), 7.64 (t, 1H), 6.58 (s, 1H), 6.57 (d, 1H), 6.52 (s, 1H), 2.19 (s, 3H).

Example 79

N-(4-(2,6-dichlorophenylthio)pyridin-2-yl)-4-isopropylthiazol-2-amine

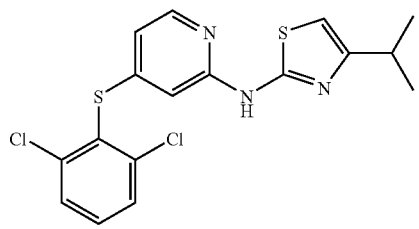

Using the method of Example 3, Step B, 4-isopropylthiazol-2-amine (0.245 g, 1.72 mmol), 2-chloro-4-(2,6-dichlorophenylthio)pyridine (0.500 g, 1.72 mmol), potassium phosphate (0.402 g, 1.89 mmol), Pd$_2$(dba)$_3$ (0.079 g, 0.086 mmol), and 4,5-bis(diphenylphosphino)-9,9-dimethyl-9H-xanthene (0.050 g, 0.086 mmol) were reacted to provide N-(4-(2,6-dichlorophenylthio)pyridin-2-yl)-4-isopropylthiazol-2-amine (0.260 g, 38% yield) as a white powder. $^1$H NMR (d$_6$-DMSO) δ 11.07 (s, 1H), 8.10 (d, 1H), 7.76 (d, 2H), 7.64 (t, 1H), 6.57 (s, 1H), 6.56 (d, 1H), 6.51 (s, 1H), 2.82 (hextet, 1H), 1.18 (d, 6H).

Example 80

N-(4-(2,6-dimethylphenoxy)pyridin-2-yl)-4-methylthiazol-2-amine

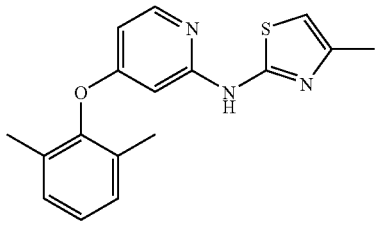

Step A: Preparation of 2-chloro-4-(2,6-dimethylphenoxy)pyridine: Using the method of Example 3, Step A, 2,6-dimethylphenol (0.771 g, 6.31 mmol), 60% sodium hydride in mineral oil (252 mg, 6.31 mmol), and 2-chloro-4-nitropyridine (1.00 g, 6.31 mmol) were reacted to provide 2-chloro- 4-(2,6-dimethylphenoxy)pyridine (1.42 g, 96% yield) as a white solid. $^1$H NMR (CDCl$_3$) δ 8.20 (d, 1H), 7.12 (s, 4H), 6.65-6.68 (m, 2H), 2.11 (s, 6H).

Step B: Preparation of N-(4-(2,6-dimethylphenoxy)pyridin-2-yl)-4-methylthiazol-2-amine: Using the method of Example 3, Step B, 4-methylthiazol-2-amine (0.244 g, 2.14 mmol), 2-chloro-4-(2,6-dimethylphenoxy)pyridine (0.500 g, 2.14 mmol), potassium phosphate (0.500 g, 2.35 mmol), Pd$_2$(dba)$_3$ (0.098 g, 0.107 mmol), and 4,5-bis(diphenylphosphino)-9,9-dimethyl-9H-xanthene (0.062 g, 0.107 mmol) were reacted to provide N-(4-(2,6-dimethylphenoxy)pyridin-2-yl)-4-methylthiazol-2-amine (0.290 g, 44% yield). $^1$H NMR (d$_6$-DMSO) δ 10.93 (s, 1H), 8.13 (d, 1H), 7.15-7.22 (m, 3H), 6.50 (s, 1H), 6.40 (d, 1H), 6.39 (s, 1H), 2.19 (s, 3H), 2.08 (s, 6H).

Example 81

Ethyl 4-chloro-3-(2-(4-methylthiazol-2-ylamino)pyridin-4-yloxy)benzoate

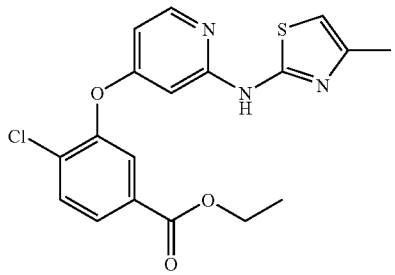

Step A: Preparation of ethyl 4-chloro-3-(2-chloropyridin-4-yloxy)benzoate: Using the method of Example 3, Step A, ethyl 4-chloro-3-hydroxybenzoate (0.759 g, 3.78 mmol), 60% sodium hydride in mineral oil (151 mg, 3.78 mmol), and 2-chloro-4-nitropyridine (0.600 g, 3.78 mmol) were reacted to provide ethyl 4-chloro-3-(2-chloropyridin-4-yloxy)benzoate (0.904 g, 76% yield) as a white solid. $^1$H NMR (CDCl$_3$) δ 8.27 (d, 1H), 7.96 (d, 1H), 7.84 (s, 1H), 7.60 (d, 1H), 6.77 (s, 1H), 6.76 (d, 1H), 4.39 (quartet, 2H), 1.41 (t, 2H).

Step B: Preparation of ethyl 4-chloro-3-(2-(4-methylthiazol-2-ylamino)pyridin-4-yloxy)benzoate: Using the method of Example 3, Step B, 4-methylthiazol-2-amine (0.329 g, 2.88 mmol), ethyl 4-chloro-3-(2-chloropyridin-4-yloxy)benzoate (0.900 g, 2.88 mmol), potassium phosphate (0.673 g, 3.17 mmol), Pd$_2$(dba)$_3$ (0.132 g, 0.144 mmol), and 4,5-bis(diphenylphosphino)-9,9-dimethyl-9H-xanthene (0.083 g, 0.144 mmol) were reacted to provide ethyl 4-chloro-3-(2-(4-methylthiazol-2-ylamino)pyridin-4-yloxy)benzoate (0.631 g, 56% yield). $^1$H NMR (d$_6$-DMSO) δ 10.99 (s, 1H), 8.20 (d, 1H), 7.92 (d, 1H), 7.83-7.87 (m, 2H), 6.51-6.57 (m, 3H), 4.32 (quartet, 2H), 2.20 (s, 3H), 1.31 (t, 2H).

Example 82

4-Chloro-3-(2-(4-methylthiazol-2-ylamino)pyridin-4-yloxy)benzoic acid hydrochloride

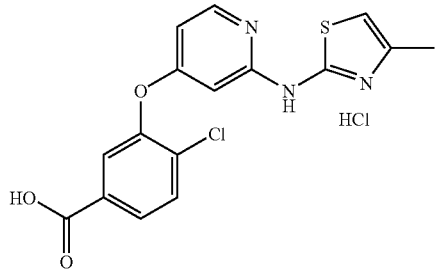

A 100 mL round bottom flask was charged with ethyl 4-chloro-3-(2-(4-methylthiazol-2-ylamino)pyridin-4-yloxy)benzoate (0.600 g, 1.54 mmol) and ethanol (30 mL) and 1M NaOH (10 mL) were added. The reaction mixture was stirred and heated at 60° C. for 3 hours. The reaction mixture was w concentrated and water and 6N HCl (1 mL) were added. The resulting solids were filtered and dried to yield 4-chloro-3L(2-(4-methylthiazol-2-ylamino)pyridin-4-yloxy)benzoic acid hydrochloride (0.565 g, 89.4% yield). $^1$H NMR (DMSO) δ 8.25 (d, 1H), 7.91 (dd, 1H), 7.83 (d, 1H), 7.81 (d, 1H), 6.66 (dd, 1H), 6.64 (d, 1H), 6.61 (d, 1H), 2.23 (d, 3H); Mass spectrum (apci) m/z=362 (100) (M+H).

Example 83

4-Chloro-N-(2-(dimethylamino)ethyl)-3-(2-(4-methylthiazol-2-ylamino)pyridin-4-yloxy)benzamide hydrochloride

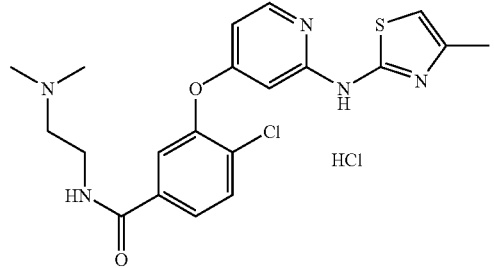

A 3 dram vial was charged with 4-chloro-3-(2-(4-methylthiazol-2-ylamino)pyridin-4-yloxy)benzoic acid hydrochloride (0.100 g, 0.2511 mmol), triethylamine (0.1016 g, 1.004 mmol) and DMF (3 mL). The reaction mixture was cooled to 0° C. and ethyl carbonochloridate (0.02641 mL, 0.2762 mmol) was added. The reaction mixture was at 0° C. for 3 hours. N,N-dimethylethylenediamine (0.04427 g, 0.5022 mmol) was added and the reaction mixture was stirred at room temperature overnight, and then 2N NaOH was added. The reaction mixture was extracted with ethyl acetate, dried over magnesium sulfate, filtered and concentrated. The residue was purified using prepacked silica gel column with 50% ethyl acetate in hexanes followed by 15% (ammoniated)

methanol in ethyl acetate. 2M HCl in ether was added and the resulting solids were dried over high vacuum to afford 4-chloro-N-(2-(dimethylamino)ethyl)-3-(2-(4-methylthiazol-2-ylamino)pyridin-4-yloxy)benzamide hydrochloride (0.017 g, 13.01% yield) as an off white solid. $^1$H NMR (DMSO) δ 11.21 (bs, 1H), 9.82 (bs, 1H), 8.95 (t, 1H), 8.24 (d, 1H), 7.90 (dd, 1H), 7.86 (d, 1H), 7.84 (d, 1H), 6.57 (m, 3H), 3.61 (q, 2H), 3.24 (q, 2H), 2.82 (s, 3H), 2.81 (s, 3H), 2.21 (d, 3H); Mass spectrum (esi) m/z=432 (100) (M+H—HCl).

Example 84

4-Chloro-3-(2-(4-methylthiazol-2-ylamino)pyridin-4-yloxy)-N-(3:—morpholinopropyl)benzamide hydrochloride

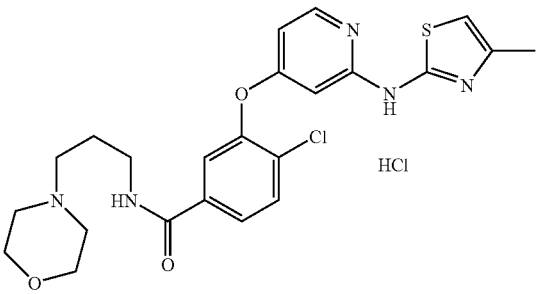

Following procedure of Example 83, 4-chloro-3-(2-(4-methylthiazol-2-ylamino)pyridin-4-yloxy)benzoic acid hydrochloride (0.100 g, 0.2511 mmol), triethylamine (0.1016 g, 1.004 mmol), (DMF (3 mL), ethyl carbonochloridate (0.02641 mL, 0.2762 mmol) and 4-(3-aminopropyl)morpholine (0.07242 g, 0.5022 mmol) were reacted to afford 4-chloro-3-(2-(4-methylthiazol-2-ylamino)pyridin-4-yloxy)-N-(3-morpholinopropyl)benzamide hydrochloride (0.030 g, 20.50% yield) as off white solid. $^1$H NMR (DMSO) δ 11.20 (bs, 1H), 10.37 (bs, 1H), 8.83 (t, 1H), 8.23 (d, 1H), 7.87 (dd, 1H), 7.84 (d, 1H), 7.82 (d, 1H), 6.58 (m, 2H), 6.55 (d, 1H), 3.94 (d, 2H), 3.72 (t, 2H), 3.40 (d, 2H), 3.32 (q, 2H), 3.12 (m, 2H), 3.03 (m, 2H), 2.21 (d, 3H), 1.93 (m, 2H); Mass spectrum (esi) m/z=488 (100) (M+H—HCl).

Example 85

4-Chloro-3-(2-(4-methylthiazol-2-ylamino)pyridin-4-yloxy)-N-(2-(pyrrolidin-1-yl)ethyl)benzamide

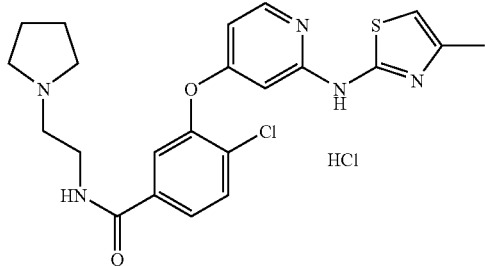

Following procedure of Example 83, 4-chloro-3-(2-(4-methylthiazol-2-ylamino)pyridin-4-yloxy)benzoic acid hydrochloride (0.1 g, 0.2511 mmol), triethylamine (0.1016 g, 1.004 mmol), DMF (3 mL), added ethyl carbonochloridate (0.02641 mL, 0.2762 mmol), N-(2-aminoethyl)pyrrolidine (0.05734 g, 0.5022 mmol) were reacted to afford 4-chloro-3-(2-(4-methylthiazol-2-ylamino)pyridin-4-yloxy)-N-(2-(pyrrolidin-1-yl)ethyl)benzamide hydrochloride (0.021 g, 15.22% yield) as off white solid. $^1$H NMR (DMSO) δ 11.26 (bs, 1H), 10.18 (bs, 1H), 8.98 (t, 1H), 8.23 (d, 1H), 7.92 (dd, 1H), 7.89 (d, 1H), 7.83 (d, 1H), 6.58 (m, 3H), 3.61 (m, 4H), 3.31 (q, 2H), 3.02 (m, 2H), 2.21 (d, 3H), 2.00 (m, 2H), 1.86 (m, 2H); Mass spectrum (esi) m/z 458 (100) (M+H—HCl).

Example 86

(2-(4-Methylthiazol-2-ylamino)pyridin-4-yl)(phenyl)methanol

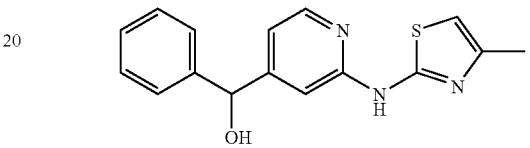

Step A: Preparation of ethyl 2-(4-methylthiazol-2-ylamino)isonicotinate: Using the method of Example 3, Step B, 2-chloroisonicotinic acid, methyl ester (4.734 g, 27.59 mmol), 2-amino-4-methylthiazole (3.0 g, 26.28 mmol), potassium phosphate (2.393 ml, 28.90 mmol), Pd$_2$(dba)$_3$ (0.6016 g, 0.6569 mmol), 4,5-bis(diphenylphosphino)-9,9-dimethyl-9H-xanthene (0.4181 g, 0.7226 mmol) in toluene (20 mL) and water (0.5 mL) were reacted to afford methyl 2-(4-methylthiazol-2-ylamino)isonicotinate (4.682 g, 71.48% yield) as a white solid. $^1$H NMR (CDCl$_3$) δ 10.25 (bs, 1H), 8.47 (dd, 1H), 7.40 (m, 1H), 7.39 (dd, 1H), 6.45 (d, 1H), 3.94 (s, 3H), 2.39 (d, 3H); Mass spectrum (apci) m/z=250 (100) (M+H).

Step B: Preparation of (2-(4-methylthiazol-2-ylamino)pyridin-4-yl)methanol: Charged a flask with methyl 2-(4-methylthiazol-2-ylamino)isonicotinate (0.5 g, 2.01 mmol) and added ether (10 mL). The reaction mixture was cooled to 0° C. and diisobutylaluminum hydride (8.01 mL, 8.01 mmol) was added. The reaction mixture was stirred at 0° C. for 8 hours and then stirred overnight at room temperature. The reaction mixture was quenched with water, extracted with ethyl acetate, dried over magnesium sulfate, filtered, and concentrated. The residue was purified using silica gel column chromatography with ethyl acetate as the eluent to afford (2-(4-methylthiazol-2-ylamino)pyridin-4-yl)methanol (0.347 g, 76.6% yield) as white solid. $^1$H NMR (CD$_3$OD) δ 8.20 (d, 1H), 7.01 (m, 1H), 6.86 (m, 1H), 6.42 (m, 1H), 4.60 (s, 2H), 2.27 (d, 3H); Mass spectrum (apci) m/z=222 (55) (M+H).

Step C: Preparation of 2-(4-methylthiazol-2-ylamino)isonicotinaldehyde: A solution of (2-(4-methylthiazol-2-ylamino)pyridin-4-yl)methanol (0.210 g, 0.949 mmol) in THF (5 mL) was added to a solution of Dess-Martin periodinane (0.604 g, 1.42 mmol) in THF (5 mL) at 0° C. The reaction mixture was warmed to room temperature and stirred for 30 minutes, then diluted with ether and 1N NaOH (40 mL). The reaction mixture was stirred for 30 minutes, then extracted with ether, washed with water, brine, dried and concentrated to afford 2-(4-methylthiazol-2-ylamino)isonicotinaldehyde (0.197 g, 94.7% yield) as a yellow wax/powder. The crude product was used in the next step without purification.

Step D: Preparation of (2-(4-methylthiazol-2-ylamino)pyridin-4-yl)(phenyl)methanol: 3.0 M Phenylmagnesium bromide (0.9982 mL, 2.995 mmol) in ether was added to THF (2 mL) at 0° C., and then 2-(4-methylthiazol-2-ylamino)isonicotinaldehyde (0.197 g, 0.8985 mmol) in THF (3 mL) was added. The reaction mixture was stirred for 30 minutes, then partitioned between saturated ammonium chloride and ethyl acetate. The organic layer was washed with brine, dried, and concentrated. The residue was purified via MPLC (Biotage) eluting with 2:3 hexane:ethyl acetate to afford (2-(4-methylthiazol-2-ylamino)pyridin-4-yl)(phenyl)methanol (0.107 g, 40.05% yield) as a white solid. $^1$H NMR (d$_6$-DMSO) δ 11.10 (s, 1H), 8.14 (d, 1H), 7.24-7.37 (m, 5H), 7.11 (s, 1H), 6.81 (d, 1H), 6.50 (s, 1H), 6.09 (d, 1H), 5.64 (d, 1H), 2.22 (s, 3H).

Example 87

(2-(4-Methylthiazol-2-ylamino)pyridin-4-yl)(phenyl)methanone hydrochloride

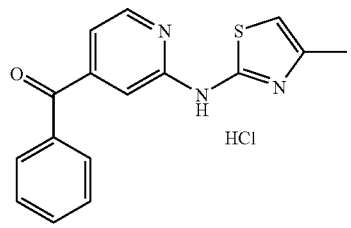

A solution of (2-(4-methylthiazol-2-ylamino)pyridin-4-yl)(phenyl)methanol (0.100 g, 0.336 mmol) in THF (5 mL) was added to a solution of Dess-Martin periodinane (0.214 g, 0.504 mmol) in THF (5 mL) at 0° C. The reaction mixture was warmed to room temperature and stirred for 30 minutes. The reaction mixture was diluted with ether and 1N NaOH (40 mL) and stirred for 4 hours. The reaction mixture was extracted with ether, washed with water, brine, dried, concentrated, and filtered through silica with 1:1 hexane:ethyl acetate. The filtrate was concentrated, dissolved in ether (4 mL), and 1M HCl in ether (2 mL) was added. The solids were filtered, washed with hexanes, and dried to afford (2-(4-methylthiazol-2-ylamino)pyridin-4-yl)(phenyl)methanone hydrochloride (0.071 g, 63.6% yield). $^1$H NMR (d$_6$-DMSO) δ 11.75 (bs, 1H), 8.50 (d, 1H), 7.82 (d, 2H), 7.75 (t, 1H), 7.61 (t, 2H), 7.36 (s, 1H), 7.17 (d, 1H), 6.68 (s, 1H), 2.27 (s, 3H).

Example 88

Representative Example

Ethyl 4-methyl-3-(2-(4-methylthiazol-2-ylamino)pyridin-4-yloxy)benzoate

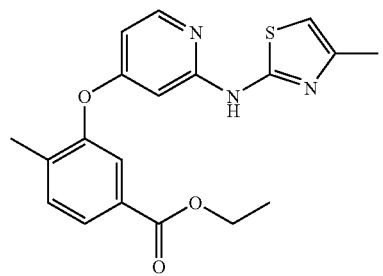

Step A: Preparation of ethyl 4-methyl-3-(2-chloropyridin-4-yloxy)benzoate: Using the method of Example 3, Step A, ethyl 4-methyl-3-hydroxybenzoate (1.70 g, 9.46 mmol), 60% sodium hydride in mineral oil (378 mg, 9.48 mmol), and 2-chloro-4-nitropyridine (1.50 g, 9.46 mmol) were reacted to provide ethyl 4-methyl-3-(2-chloropyridin-4-yloxy)benzoate (2.59 g, 94% yield) as a clear oil. $^1$H NMR (CDCl$_3$) δ 8.24 (d, 1H), 7.90 (d, 1H), 7.69 (s, 1H), 7.38 (d, 1H), 6.73 (d, 2H), 4.37 (quartet, 2H), 2.23 (s, 3H), 1.39 (t, 3H).

Step B: Preparation of ethyl 4-methyl-3-(2-(4-methylthiazol-2-ylamino)pyridin-4-yloxy)benzoate: Using the method of Example 3, Step B, 4-methylthiazol-2-amine (0.50 g, 4.38 mmol), ethyl 4-methyl-3-(2-chloropyridin-4-yloxy)benzoate (1.41 g, 4.38 mmol), potassium phosphate (1.02 g, 4.82 mmol), Pd$_2$(dba)$_3$ (0.100 g, 0.109 mmol), and 4,5-bis(diphenylphosphino)-9,9-dimethyl-9H-xanthene (0.070 g, 0.109 mmol) were reacted to provide ethyl 4-chloro-3-(2-(4-methylthiazol-2-ylamino)pyridin-4-yloxy)benzoate (1.20 g, 70% yield) as a light yellow solid. $^1$H NMR (CDCl$_3$) δ 9.03 (bs, 1H), 8.17 (d, 1H), 7.86 (dd, 1H), 7.67 (d, 1H), 7.35 (d, 1H), 6.41 (dd, 1H), 6.31 (d, 1H), 6.21 (d, 1H), 4.36 (q, 2H), 2.22 (s, 3H), 2.21 (d, 3H), 1.37 (t, 3H), Mass spectrum (esi) m/z=370 (100) (M+H).

Example 89

Ethyl 2-methyl-3-(2-(4-methylthiazol-2-ylamino)pyridin-4-yloxy)benzoate

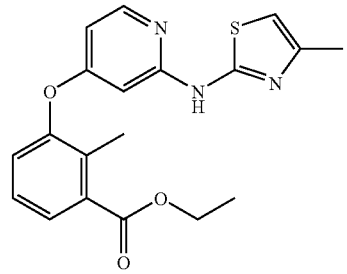

Step A: Preparation of ethyl 2-methyl-3-(2-chloropyridin-4-yloxy)benzoate: Using the method of Example 3, Step A, ethyl 2-methyl-3-hydroxybenzoate (2.27 g, 12.6 mmol), 60% sodium hydride in mineral oil (505 mg, 12.6 mmol), and 2-chloro-4-nitropyridine (2.00 g, 12.6 mmol) were reacted to provide ethyl 2-methyl-3-(2-chloropyridin-4-yloxy)benzoate (3.31 g, 90% yield) as a clear oil. $^1$H NMR (CDCl$_3$) δ 8.22 (d, 1H), 7.83 (d, 1H), 7.33 (t, 1H), 7.18 (d, 1H), 6.70-6.72 (m, 2H), 4.39 (quartet, 2H), 2.38 (s, 3H), 1.41 (t, 3H).

Step B: Preparation of ethyl 2-methyl-3-(2-(4-methylthiazol-2-ylamino)pyridin-4-yloxy)benzoate: Using the method of Example 3, Step B, 4-methylthiazol-2-amine (0.50 g, 4.38 mmol), ethyl 4-methyl-3-(2-chloropyridin-4-yloxy)benzoate (1.55 g, 4.82 mmol), potassium phosphate (1.02 g, 4.82 mmol), Pd$_2$(dba)$_3$ (0.100 g, 0.109 mmol), and 4,5-bis(diphenylphosphino)-9,9-dimethyl-9H-xanthene (0.070 g, 0.109 mmol) were reacted to provide ethyl 2-methyl-3-(2-(4-methylthiazol-2-ylamino)pyridin-4-yloxy)benzoate (1.40 g, 86% yield) as a yellow solid. $^1$H NMR (CDCl$_3$) δ 9.61 (bs, 1H), 8.16 (d, 1H), 7.78 (d, 1H), 7.29 (d, 1H), 7.16 (d, 1H), 6.40 (dd, 1H), 6.30 (d, 1H), 6.16 (d, 1H), 4.39 (q, 2H), 2.37 (s, 3H), 2.19 (d, 3H), 1.41 (t, 3H); Mass spectrum (esi) m/z=370 (100) (M+H).

Example 90

Ethyl 4-fluoro-3-(2-(4-methylthiazol-2-ylamino) pyridin-4-yloxy)benzoate

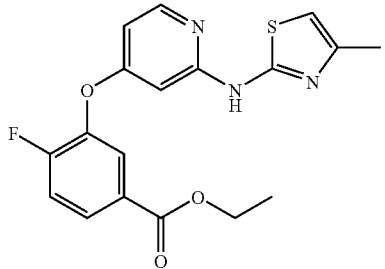

Step A: Preparation of ethyl 4-fluoro-3-(2-chloropyridin-4-yloxy)benzoate: Using the method of Example 3, Step A, ethyl 4-fluoro-3-hydroxybenzoate (2.90 g, 15.8 mmol), 60% sodium hydride in mineral oil (631 mg, 15.8 mmol), and 2-chloro-4-nitropyridine (2.50 g, 15.8 mmol) were reacted to provide ethyl 4-fluoro-3-(2-chloropyridin-4-yloxy)benzoate (4.15 g, 89% yield) as a clear oil. $^1$H NMR-(CDCl$_3$) δ 8.27 (d, 1H), 8.02 (m, 1H), 7.90 (d, 1H), 7.30 (t, 1H), 6.78-6.83 (m, 2H), 4.39 (q, 2H), 1.40 (t, 3H).

Step B: Preparation of ethyl 4-fluoro-3-(2-(4-methylthiazol-2-ylamino)pyridin-4-yloxy)benzoate: Using the method of Example 3, Step B, 4-methylthiazol-2-amine (0.600 g, 5.26 mmol), ethyl 4-fluoro-3-(2-chloropyridin-4-yloxy)benzoate (1.55 g, 5.26 mmol), potassium phosphate (1.23 g, 5.78 mmol), Pd$_2$(dba)$_3$ (0.120 g, 0.131 mmol), and 4,5-bis(diphenylphosphino)-9,9-dimethyl-9H-xanthene (0.084 g, 0.131 mmol) were reacted to provide ethyl 4-fluoro-3-(2-(4-methylthiazol-2-ylamino)pyridin-4-yloxy)benzoate (1.60 g, 77% yield). $^1$H NMR (CDCl$_3$) δ 10.16 (bs, 1H), 8.20 (d, 1H), 7.97 (m, 1H), 7.86 (dd, 1H), 7.26 (t, 1H), 6.48 (dd, 1H), 6.29 (d, 1H), 6.28 (d, 1H), 4.38 (q, 2H), 2.18 (s, 3H), 1.38 (t, 3H); Mass spectrum (esi) m/z 374 (100) (M+H).

Example 91

Representative Example

4-Methyl-N-(4-(pyridin-2-ylthio)pyridin-2-yl)thiazol-2-amine hydrochloride

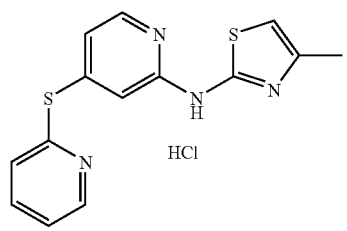

Step A: Preparation of 2-chloro-4-(pyridin-2-ylthio)pyridine: Using the method of Example 3, Step A, pyridine-2-thiol (0.526 g, 4.73 mmol), 60% sodium hydride in mineral oil (189 mg, 4.73 mmol), and 2-chloro-4-nitropyridine (0.750 g, 4.73 mmol) were reacted to provide 2-chloro-4-(pyridin-2-ylthio)pyridine (0.93 g, 88% yield) as a clear oil. $^1$H NMR (CDCl$_3$) δ 8.61 (d, 1H), 8.25 (d, 1H), 7.71 (d, 1H), 7.44 (d, 1H), 7.31 (s, 1H), 7.25 (m, 1H), 7.19 (d, 1H).

Step B: Preparation of 4-methyl-N-(4-(pyridin-2-ylthio)pyridin-2-yl)thiazol-2-amine hydrochloride: Using the method of Example 3, Step B, 4-methylthiazol-2-amine (0.477 g, 4.18 mmol), 2-chloro-4-(pyridin-2-ylthio)pyridine (0.930 g, 4.18 mmol), potassium phosphate (0.975 g, 4.59 mmol), Pd$_2$(dba)$_3$ (0.191 g, 0.209 mmol), and 4,5-bis(diphenylphosphino)-9,9-dimethyl-9H-xanthene (0.121 g, 0.209 mmol) were reacted to provide 4-methyl-N-(4-(pyridin-2-ylthio)pyridin-2-yl)thiazol-2-amine hydrochloride (0.310 g, 44% yield). $^1$H NMR (d$_6$-DMSO) δ 11.55 (bs, 1H), 8.62 (d, 1H), 8.31 (d, 1H), 7.89 (t, 1H), 7.59 (d, 1H), 7.44 (m, 1H), 7.36 (s, 1H), 7.08 (d, 1H), 6.83 (s, 1H), 2.31 (s, 3H).

Example 92

4-Methyl-N-(4-(pyridin-3-yloxy)pyridin-2-yl)thiazol-2-amine

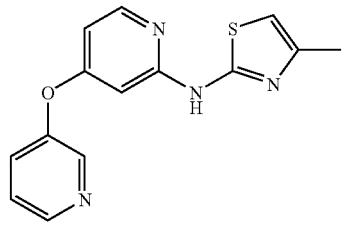

Step A: Preparation of 2-chloro-4-(pyridin-3-yloxy)pyridine: Using the method of Example 3, Step A, pyridin-3-ol (0.450 g, 4.73 mmol), 60% sodium hydride in mineral oil (189 mg, 4.73 mmol), and 2-chloro-4-nitropyridine (0.750 g, 4.73 mmol) were reacted to provide 2-chloro-4-(pyridin-3-yloxy)pyridine (0.938 g, 96% yield) as a clear oil. $^1$H NMR (CDCl$_3$) δ 8.57 (d, 1H), 8.49 (d, 1H), 8.28 (d, 1H), 7.39-7.48 (m, 2H), 6.86 (s, 1H), 6.82 (d, 1H).

Step B: Preparation of 4-methyl-N-(4-(pyridin-3-yloxy)pyridin-2-yl)thiazol-2-amine: Using the method of Example 3, Step B, 4-methylthiazol-2-amine (0.518 g, 4.54 mmol), 2-chloro-4-(pyridin-3-yloxy)pyridine (0.938 g, 4.54 mmol), potassium phosphate (1.06 g, 4.99 mmol), Pd$_2$(dba)$_3$ (0.208 g, 0.227 mmol), and 4,5-bis(diphenylphosphino)-9,9-dimethyl-9H-xanthene (0.131 g, 0.227 mmol) were reacted to provide 4-methyl-N-(4-(pyridin-3-yloxy)pyridin-2-yl)thiazol-2-amine (0.704 g, 55% yield). $^1$H NMR (d$_6$-DMSO) δ 11.05 (s, 1H), 8.54 (m, 2H), 8.20 (d, 1H), 7.72 (d, 1H), 7.55 (d, 1H), 6.53-6.59 (m, 3H), 2.21 (s, 3H).

Example 93

N-(6-chloro-4-(2,6-difluorophenoxy)pyridin-2-yl)-4-methylthiazol-2-amine

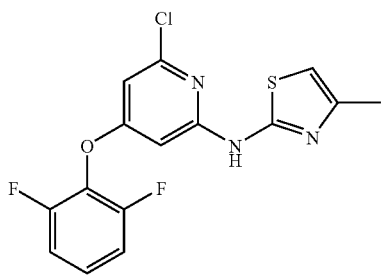

Step A: Preparation of 2,6-dichloro-4-(2,6-difluorophenoxy)pyridine: 2,6-Difluorophenol (10.0 mmol) is added to a mixture of sodium hydride (240 mg, 10 mmol) in DMF (6 mL). The reaction mixture is stirred for 30 minutes at room temperature. The reaction mixture is cooled to 0° C., and 2,4,6-trichloropyridine is added. The reaction mixture is stirred at 0° C. for 1 hour, then at room temperature for 4 hours. The reaction mixture is partitioned between ethyl acetate and water, the organic layer is washed with 2N NaOH, water, brine, dried, and concentrated. The residue is purified via chromatography eluting with 5:1 hexane:ethyl acetate to afford 2,6-dichloro-4-(2,6-difluorophenoxy)pyridine.

Step B: Preparation of 5N-(6-chloro-4-(2,6-difluorophenoxy)pyridin-2-yl)-4-methylthiazol-2-amine: A mixture of 2,6-dichloro-4-(2,6-difluorophenoxy)pyridine (552 mg, 2.0 mmol), 4-methylthiazol-2-amine (228 mg, 2.0 mmol), potassium phosphate (466 mg, 2.20 mmol), tris(dibenzylideneacetone)dipalladium (0) (0.092 g, 0.100 mmol) and 9,9-dimethyl-4,5-bis(diphenylphosphino)xanthene (0.167 g, 0.100 mmol) in degassed toluene (5 mL) and water (2 mL) is heated at 90° C. for 12 hours and then cooled to room temperature. The reaction mixture is partitioned between water and ethyl acetate to afford N-(6-chloro-4-(2,6-difluorophenoxy)pyridin-2-yl)-4-methylthiazol-2-amine.

Example 94

N-(5-Bromo-4-(2,6-difluorophenoxy)pyridin-2-yl)-4-methylthiazol-2-amine

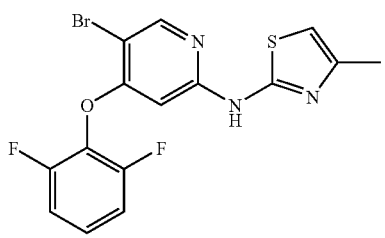

Step A: Preparation of 4-(2,6-difluorophenoxy)pyridin-2-amine: A mixture of 2-chloro-4-(2,6-difluorophenoxy)pyridine (4.82 g, 20.0 mmol), Pd₂dba₃ (221 mg, 0.24 mmol), BINAP (0.24 mmol), potassium tert-butoxide (20.0 mmol), benzophenone imine (4.53 g, 25.0 mmol), and degassed toluene (40 mL) is heated under nitrogen overnight. The reaction mixture is cooled, and 1N HCl (200 mL) and THF (100 mL) are added. The reaction mixture is heated for 3 hours at 40° C. The reaction mixture is cooled, partitioned between ethyl acetate and 2N NaOH, wash with water, brine, dry, and concentrated. The residue is purified via column chromatography to afford difluorophenoxy)pyridin-2-amine.

Step B: Preparation of 5-bromo-4-(2,6-difluorophenoxy)pyridin-2-amine: A mixture of difluorophenoxy)pyridin-2-amine (2.22 g, 10 mmol) and N-bromosuccinimide (11 mmol) in acetonitrile (50 mL) is stirred at room temperature for one hour then reflux for 4 hours. The reaction mixture is cooled, concentrated, and the residue is purified via column chromatography to afford 5-bromo-4-(2,6-difluorophenoxy)pyridin-2-amine.

Step C: Preparation of N-(5-bromo-4-(2,6-difluorophenoxy)pyridin-2-ylcarbamothioyl)benzamide: Benzoyl isothiocyanate (1.63 g, 10.0 mmol) is added to a solution of 5-bromo-4-(2,6-difluorophenoxy)pyridin-2-amine (3.01 g, 10 mmol) in dichloromethane (20 mL) at 0° C. The reaction mixture is warmed to room temperature and stirred for one hour. The reaction mixture is diluted with hexanes and filtered to afford N-(5-bromo-4-(2,6-difluorophenoxy)pyridin-2-ylcarbamothioyl)benzamide.

Step D: Preparation of 1-(5-bromo-4-(2,6-difluorophenoxy)pyridin-2-yl) thiourea. A mixture of N-(5-bromo-4-(2,6-difluorophenoxy)pyridin-2-ylcarbamothioyl)benzamide (4.41 g, 9.5 mmol) and 3M NaOH (10 ml, 30 mmol) in ethanol (40 mL) is heated. The reaction mixture is cooled, concentrated to 15 mL, diluted with water, and filtered to afford 1-(5-bromo-4-(2,6-difluorophenoxy)pyridin-2-yl) thiourea.

Step E: Preparation of N-(5-bromo-4-(2,6-difluorophenoxy)pyridin-2-yl)-4-methylthiazol-2-amine: A mixture of 1-chloropropan-2-one (1.01 g, 11 mmol), 1-(5-bromo-4-(2,6-difluorophenoxy)pyridin-2-yl)thiourea (3.24 g, 9.0 mmol), triethylamine (1.41 g, 14 mmol) and ethanol (15 mL) is heated at reflux for 16 hours. The reaction mixture is cooled and partitioned between ethyl acetate and water. The organic layer is washed with water and brine, dried and concentrated. The residue is purified via chromatography to afford N-(5-bromo-4-(2,6-difluorophenoxy)pyridin-2-yl)-4-methylthiazol-2-amine.

Example 95

N-(5-Bromo-3-chloro-4-(2,6-difluorophenoxy)pyridin-2-yl)-4-methylthiazol-2-amine

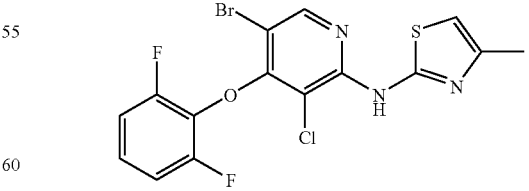

Step A: Preparation of 5-bromo-3-chloro-4-(2,6-difluorophenoxy)pyridin-2-amine: A mixture of 5-bromo-4-(2,6-difluorophenoxy)pyridin-2-amine (301 mg, 1.0 mmol) and N-chlorosuccinimide (1.1 mmols) in acetonitrile (50 mL) is stirred at room temperature for one hour then heated at reflux for 24 hours. The reaction mixture is cooled and concentrated. The residue is purified via column chromatography to afford 5-bromo-3-chloro-4-(2,6-difluorophenoxy)pyridin-2-amine.

Step B: Preparation of N-(5-bromo-3-chloro-4-(2,6-difluorophenoxy)pyridin-2-ylcarbamothioyl)benzamide: Benzoyl isothiocyanate (163 mg, 1.0 mmol) is added to a solution of 5-bromo-3-chloro-4-(2,6-difluorophenoxy)pyridin-2-amine (336 mg, 1.0 mmol) in dichloromethane (20 mL) at 0° C. The reaction mixture is warmed to room temperature and stirred for one hour. The reaction mixture is diluted with hexanes and filtered to afford N-(5-bromo-3-chloro-4-(2,6-difluorophenoxy)pyridin-2-ylcarbamothioyl)benzamide.

Step C: Preparation of 11-(5-bromo-3-chloro-4-(2,6-difluorophenoxy)pyridin-2-yl)thiourea. A mixture of N-(5-bromo-3-chloro-4-(2,6-difluorophenoxy)pyridin-2-ylcarbamothioyl)benzamide (474 mg, 0.95 mmol) and 3M NaOH (1 mL, 30 mmol) in ethanol (4 mL) is heated. The reaction mixture is cooled, concentrated to 2 mL, diluted with water, and filtered to afford 1-(5-bromo-3-chloro-4-(2,6-difluorophenoxy)pyridin-2-yl)thiourea.

Step D: Preparation of N-(5-bromo-3-chloro-4-(2,6-difluorophenoxy)pyridin-2-yl)-4-methylthiazol-2-amine: A mixture of 1-chloropropan-2-one (102 mg, 1.1 mmol), 11-(5-bromo-3-chloro-4-(2,6-difluorophenoxy)pyridin-2-yl)thiourea. (355 mg, 0.90 mmol), triethylamine (141 mg, 1.4 mmol) and ethanol (3 mL) is heated at reflux for 16 hours. The reaction mixture is cooled and partitioned between ethyl acetate and water. The organic layer is washed with water, brine, dried, and concentrated. The residue is purified via chromatography to afford N-(5-bromo-3-chloro-4-(2,6-difluorophenoxy)pyridin-2-yl)-4-methylthiazol-2-amine.

Example 96

Methyl 3-(4-(2,6-difluorophenoxy)-6-(4-methylthiazol-2-ylamino)pyridin-3-ylthio)propanoate

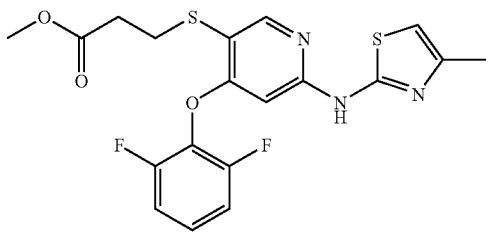

A 25 mL round-bottomed flask is charged with N-(5-bromo-4-(2,6-difluorophenoxy)pyridin-2-yl)-4-methylthiazol-2-amine (398 mg, 1.00 mmol), Pd$_2$dba$_3$ (22.1 mg, 0.024 mmol), 4,5-bis(diphenylphosphino)-9,9-dimethyl-9H-xanthene (27.9 mg, 0.048 mmol), N-ethyl-N-isopropylpropan-2-amine (0.33 mL, 1.9 mmol), methyl 3-mercaptopropanoate (0.12 mL, 1.1 mmol), and dioxane (10 mL). The reaction mixture is heated at 100° C. under nitrogen for 2 hours, then cooled to room temperature, filtered and concentrated. The residue is purified via chromatography, eluting with 40% EtOAc in hexanes, to afford methyl 3-(4-(2,6-difluorophenoxy)-6-(4-methylthiazol-2-ylamino)pyridin-3-ylthio)propanoate.

Example 97

Ethyl 4-chloro-3-(2-(4-methylthiazol-2-ylamino)-5-(Pyridin-2-ylmethylthio)pyridin-4-yloxy)benzoate

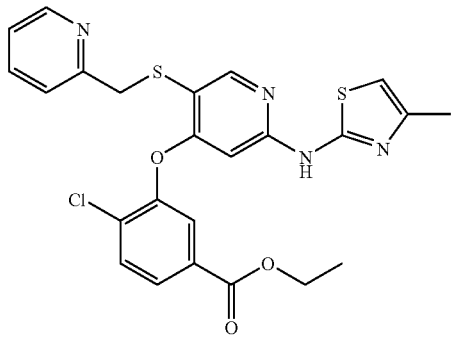

A 20 mL vial is charged with ethyl 4-chloro-3-(5-(3-methoxy-3-oxopropylthio)-2-(4-methylthiazol-2-ylamino)pyridin-4-yloxy)benzoate (0.33 mmol) and THF (0.5 mL). 1M KOtBu in THF (1.184 ml, 1.184 mmol) is added and the reaction mixture is stirred at room temperature for 30 seconds. 2-(Bromomethyl)pyridine hydrobromide (85.55 mg, 0.3382 mmol) is added and the reaction mixture is stirred at room temperature for 30 minutes. Saturated aqueous ammonium chloride is added and extracted with EtOAc. The reaction mixture is purified via column chromatography on silica gel to afford ethyl 4-chloro-3-(2-(4-methylthiazol-2-ylamino)-5-(pyridin-2-ylmethylthio)pyridin-4-yloxy)benzoate.

Example 98

Ethyl 3-(2-(4-(2,6-difluorophenoxy)-3,3'-bipyridin-6-ylamino)thiazol-4-yl)propanoate

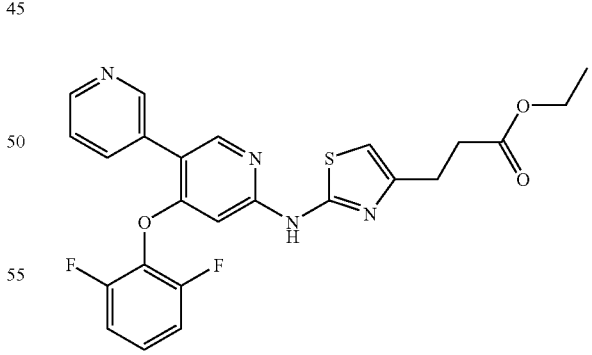

Ethyl 3-(2-(5-bromo-4-(2,6-difluorophenoxy)pyridin-2-ylamino)thiazol-4-yl)propanoate (0.1932 mmol), pyridin-3-ylboronic acid (0.02850 g, 0.2319 mmol), Pd(PPh$_3$)$_4$ (0.02233 g, 0.01932 mmol), in DME (10 mL), and 2M sodium bicarbonate (2 mL) are combined and heated to 80° C. overnight. The reaction mixture is cooled and partitioned between CH$_2$Cl$_2$ and water. The combined organic layers are dried, filtered, and concentrated. The residue is purified by silica gel, eluting with 30-40% EtOAc in hexane, to afford ethyl 3-(2-(4-(2,6-difluorophenoxy)-3,3'-bipyridin-6-ylamino)thiazol-4-yl)propanoate.

Example 99

4-(2,6-Difluorophenoxy)-6-(4-methylthiazol-2-ylamino)pyridin-3-ol

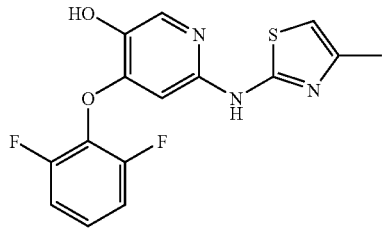

N-(5-bromo-4-(2,6-difluorophenoxy)pyridin-2-yl)-4-methylthiazol-2-amine (2.66 mmol) is dissolved in THF (30 mL) and cooled to −78° C. MeLi (2.07 mL, 3.32 mmol) is slowly added and the reaction mixture is stirred for 10 minutes. n-Butyllithium (1.33 mL, 3.32 mmol) is added and the reaction mixture is stirred for 15 minutes. Triisopropylborate (0.613 mL, 2.66 mmol) is added and the reaction mixture is stirred for 30 minutes. The reaction mixture is warmed to 0° C., and methanol (5 mL), 10% aqueous NaOH (5.1 mL, 12.8 mmol), and 30% aqueous $H_2O_2$ (1.27 mL, 13.3 mmol) are added. The reaction mixture is stirred at 0° C. for 1 hour, then purified by silica gel chromatography (10-20% EtOAc in hexanes) to afford 4-(2,6-difluorophenoxy)-6-(4-methylthiazol-2-ylamino)pyridin-3-ol.

Example 100

4-(2,6-Dichlorophenylthio)-6-(4-methylthiazol-2-Ylamino)pyridin-3-ol

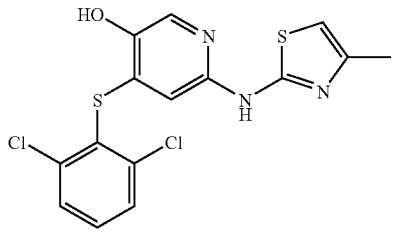

A degassed mixture of N-(5-bromo-4-(2,6-dichlorophenylthio)pyridin-2-yl)-4-methylthiazol-2-amine (1.18 g, 2.66 mmol), 4,4,4',4',5,5,5',5'-octamethyl-2,2'-bi(1,3,2-dioxaborolane) (1.35 g, 5.32 mmol), Pd(OAc)$_2$ (60 mg, 0.27 mmol), tricyclopentylphosphine (93 mg. 0.40 mmol) and cesium fluoride (3.64 g, 23.9 mmol) in acetonitrile is heated at 90° C. for 5 hours. The reaction mixture is cooled and partitioned between ether and water. The crude product is dissolved in THF. N-morpholine N-oxide (1.40 g, 12.0 mmol) is added and the reaction mixture is heated at reflux for 12 hours. The reaction mixture is cooled and partitioned between ether and water. The organic layer is washed with water and brine, dried and concentrated. The residue is purified by silica gel chromatography, eluting with 10-20% EtOAc in hexanes to afford 4-(2,6-dichlorophenylthio)-6-(4-methylthiazol-2-ylamino)pyridin-3-ol.

Example 101

N-(4-(2,6-difluorophenoxy)-5-methoxypyridin-2-yl)-4-methylthiazol-2-amine

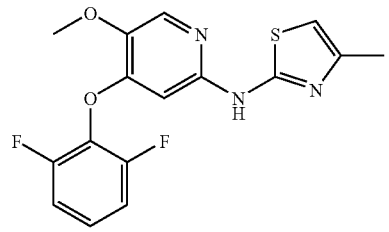

Iodomethane (0.0362 g, 0.255 mmol) is added to a mixture of 4-(2,6-difluorophenoxy)-6-(4-methylthiazol-2-ylamino) pyridin-3-ol (0.255 mmol and potassium carbonate (0.0794 g, 0.574 mmol) in DMF (3 mL) and stirred overnight at room temperature. The reaction mixture is partitioned between water and ether. The organic layer is washed with water, dried, and concentrated. The residue is purified by silica gel chromatography, eluting with 15-20% EtOAc in hexanes, to afford N-(4-(2,6-difluorophenoxy)-5-methoxypyridin-2-yl)-4-methylthiazol-2-amine.

Example 102

Methyl 3-(4-(2,6-difluorophenoxy)-6-(4-methylthiazol-2-ylamino)pyridin-3-yl)propanoate

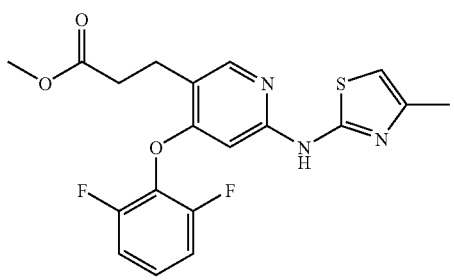

Step A: N-(5-bromo-4-(2,6-difluorophenoxy)pyridin-2-yl)-4-methylthiazol-2-amine (1.06 g, 2.66 mmol) is dissolved in THF (30 mL) and cooled to −78° C. MeLi (2.07 mL, 3.32 mmol) is added slowly, and stir for 10 minutes. n-Butyllithium (1.33 mL, 3.32 mmol) is added and the reaction mixture is stirred for 15 minutes. DMF (0.413 mL, 5.32 mmol) is added, and the reaction mixture is stirred for 30 minutes. The reaction mixture is warmed to room temperature and AcOH (2 mL) is added. The reaction mixture is stirred at room temperature for 1 hour, poured into saturated aqueous sodium bicarbonate and extracted with ethyl acetate. The combined organic layers are dried over sodium sulfate, filtered and concentrated in vacuo. The residue is purified by silica gel (10-20% EtOAc in hexanes) to afford 4-(2,6-difluorophenoxy)-6-(4-methylthiazol-2-ylamino)nicotinaldehyde.

Step B: A 25 mL round-bottomed flask is charged with 4-(2,6-difluorophenoxy)-6-(4-methylthiazol-2-ylamino) nicotinaldehyde (534 mg, 1.54 mmol) and THF (10 mL). Methyl(triphenylphosphoranylidene)acetate (668 mg, 2.00 mmol) is added and the reaction mixture is stirred at room temperature. After 4 hours, additional methyl(triphenylphosphoranylidene)acetate (668 mg, 2.00 mmol) is added and the reaction mixture is and stirred overnight. The precipitate is filtered, concentrated, and purified by silica gel chromatography (1:1 EtOAc in hexanes) to afford (E)-methyl 3-(4-(2,6-difluorophenoxy)-6-(4-methylthiazol-2-ylamino)pyridin-3-yl)acrylate.

Step C: A 25 mL round-bottomed flask is charged with (E)-methyl 3-(4-(2,6-difluorophenoxy)-6-(4-methylthiazol-2-ylamino)pyridin-3-yl)acrylate (455 mg, 1.13 mmol), 4-methylbenzenesulfonohydrazide (1050 mg, 5.64 mmol), and toluene (10 mL). The reaction mixture is heated at reflux for 12 hours, then cooled to room temperature and concentrated in vacuo. The residue is purified by silica gel (20 to 30% EtOAc in hexanes) to afford methyl 3-(4-(2,6-difluorophenoxy)-6-(4-methylthiazol-2-ylamino)pyridin-3-yl)propanoate.

Example 103

Methyl 3-(2-(4-isopropylthiazol-2-ylamino)pyridin-4-yloxy)benzoate

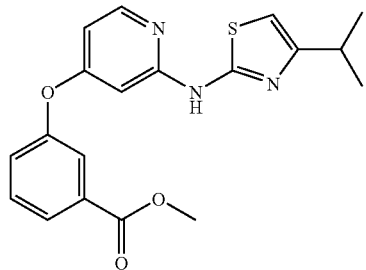

Following the method of Example 1, Step B, 4-isopropylthiazol-2-amine (10.55 mL, 4.219 mmol), methyl 3-(2-chloropyridin-4-yloxy)benzoate (1.224 g, 4.641 mmol), potassium phosphate (0.9850 g, 4.641 mmol), tris(dibenzylideneacetone)dipalladium (0). (0.09658 g, 0.1055 mmol), and 9,9-dimethyl-4,5-bis(diphenylphosphino)xanthene (0.06713 g, 0.1160 mmol) were reacted in water (3 mL) and toluene (11 mL) to give the title compound (1.297 g, 81.55% yield) as yellow solid. $^1$H NMR (CDCl$_3$) δ 8.19 (d, 1H), 7.93 (dt, 1H), 7.76 (m, 1H), 7.50 (t, 1H), 7.30 (m, 1H), 6.50 (m, 1H), 6.48 (dd, 1H), 6.33 (s, 1H), 3.92 (s, 3H), 2.87 (m, 1H), 1.22 (d, 6H).

Example 104

4-Chloro-3-(2-(4-methylthiazol-2-ylamino)pyridin-4-yloxy)benzoic acid hydrochloride

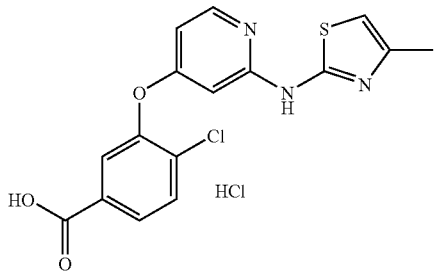

Step A: Preparation of ethyl 4-chloro-3-(2-chloropyridin-4-yloxy)benzoate: Following the method of Example 3, Step A, ethyl 4-chloro-3-hydroxybenzoate (5.75 g, 28.7 mmol), sodium hydride (0.724 g, 28.7 mmol), DM (30 mL), and 2-chloro-4-nitropyridine (4.54 g, 28.7 mmol) were combined to give the desired product (4.75 g, 47.8% yield) as a yellow oil.

Step B: Preparation of ethyl 4-chloro-3-(2-(4-methylthiazol-2-ylamino)pyridin-4-yloxy)benzoate: Following the method of Example 3, Step B, ethyl 4-chloro-3-(2-chloropyridin-4-yloxy)benzoate (1.64 g, 5.26 mmol), 4-methylthiazol-2-amine (0.60 g, 5.26 mmol), potassium phosphate (1.23 g, 5.78 mmol), tris(dibenzylideneacetone)dipalladium (0) (0.241 g, 0.263 mmol), 4,5-bis(diphenylphosphino)-9,9-dimethyl-9H-xanthene (0.228 g, 0.394 mmol), water (4 mL) and toluene (13 mL) were combined to give the desired product (1.84 g, 89.8% yield) as a yellow solid.

Step C: Preparation of 4-chloro-3-(2-(4-methylthiazol-2-ylamino)pyridin-4-yloxy)benzoic acid hydrochloride: Following the method of Example 31, ethyl 4-chloro-3-(2-(4-methylthiazol-2-ylamino)pyridin-4-yloxy)benzoate (0.600 g, 1.54 mmol), ethanol (30 ml), 1M NaOH (10 mL) were combined to give the desired product (0.565 g, 89.4% yield) as a light green solid. $^1$H NMR (d$_6$-DMSO) δ 8.25 (d, 1H), 7.91 (dd, 1H), 7.83 (d, 1H), 7.81 (d, 1H), 6.66 (dd, 1H), 6.64 (m, 1H), 6.61 (d, 1H), 2.23 (d, 3H).

Example 105

4-Chloro-N-(2-(dimethylaminoethyl)-3-(2-(4-methylthiazol-2-ylamino)pyridin-4-yloxy)benzamide dihydrochloride

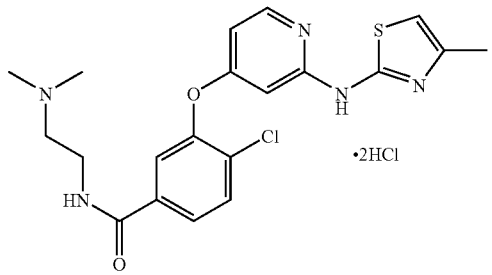

Following the method of Example 32, 4-chloro-3-(2-(4-methylthiazol-2-ylamino)pyridin-4-yloxy)benzoic acid hydrochloride (Example 104, step C), triethylamine, DMF, ethyl carbonochloridate, and N,N-dimethylethylenediamine were combined to give the title compound (0.017 g, 11% yield) as an off white solid. $^1$H NMR (d$_6$-DMSO) δ 11.21 (bs, 1H), 9.82 (bs, 1H), 8.94 (t, 1H), 8.22 (d, 1H), 7.90 (dd, 1H), 7.86 (d, 1H), 7.83 (d, 1H), 6.57 (m, 3H), 3.61 (m, 2H), 3.25 (m, 2H), 2.82 (s, 3H), 2.81 (s, 3H), 2.21 (d, 3H).

Example 106

2-methyl-3-(2-(4-methylthiazol-2-ylamino)pyridin-4-yloxy)benzoic acid hydrochloride

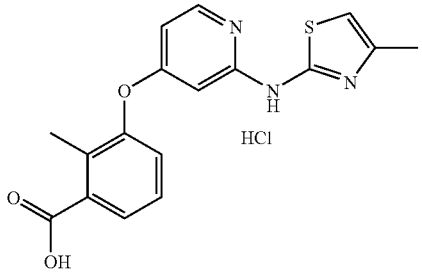

The title compound was prepared according to the method of Example 31 from ethyl 2-methyl-3-(2-(4-methylthiazol-2-ylamino)pyridin-4-yloxy)benzoate (Example 89). Yield: 0.630 g, 72.8%. $^1$H NMR (d$_6$-DMSO) δ 8.24 (d, 1H), 7.78 (dd, 1H), 7.44 (t, 1H), 7.38 (dd, 1H), 6.67 (m, 2H), 6.53 (d, 1H), 2.31 (s, 3H), 2.25 (d, 3H).

Example 107

4-fluoro-3-(2-(4-methylthiazol-2-ylamino)pyridin-4-yloxy)benzoic acid hydrochloride

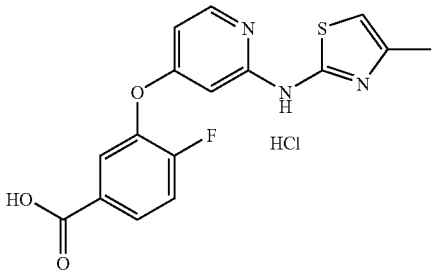

The title compound was prepared according to Example 31 from ethyl 4-fluoro-3-(2-(4-methylthiazol-2-ylamino)pyridin-4-yloxy)benzoate (Example 90). Yield: 0.667 g, 79.9%. $^1$H NMR (DMSO) δ 8.24 (d, 1H), 7.95 (m, 1H), 7.86 (dd, 1H), 7.62 (dd, 1H), 6.68 (dd, 1H), 6.64 (d, 1H), 6.61 (d, 1H), 7.22 (d, 3H).

Example 108

4-methyl-3-(2-(4-methylthiazol-2-ylamino)pyridin-4-yloxy)benzoic acid hydrochloride

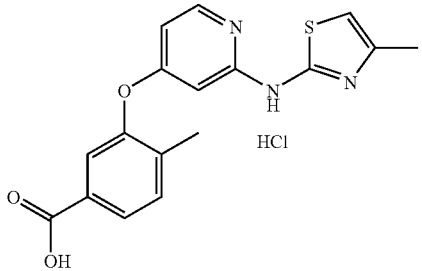

The title compound was prepared according to Example 31 from ethyl 4-methyl-3-(2-(4-methylthiazol-2-ylamino)pyridin-4-yloxy)benzoate (Example 88). Yield: 0.483 g, 60.0%. $^1$H NMR (d$_6$-DMSO) δ 8.18 (d, 1H); 7.80 (dd, 1H), 7.57 (d, 1H), 7.53 (d, 1H), 6.52 (m, 2H), 6.47 (d, 1), 2.21 (s, 3H), 2.2 (d, 3H).

Example 109

4-fluoro-3-(2-(4-methylthiazol-2-ylamino)pyridin-4-yloxy)-N-(2-(pyrrolidin-1-yl)ethyl)benzamide dihydrochloride

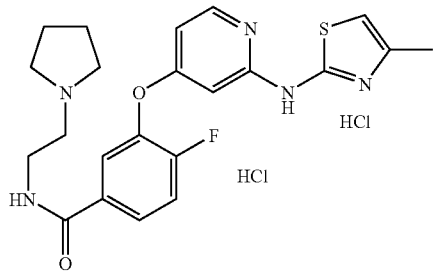

A 3 dram vial was charged with bromo-tris-pyrrolidino-phosphonium hexafluorophosphate (0.488 g, 1.05 mmol), 4-fluoro-3-(2-(4-methylthiazol-2-ylamino)pyridin-4-yloxy)benzoic acid hydrochloride (Example 107; 0.200 g, 0.524 mmol), N-(2-aminoethyl)pyrrolidine (0.179 g, 1.57 mmol) and DMF (3 mL). The reaction was stirred for 1 hour at ambient temperature. Water was added and the reaction was extracted with ethyl acetate, dried over sodium sulfate, filtered and concentrated. The residue was purified by flash column chromatography. 2M HCl in ether was added to the isolated material and the collected solids were dried over high vacuum to give the title compound (0.078 g, 28.9% yield) as a white solid. $^1$H NMR (d$_6$-DMSO) δ 11.21 (bs, 1H), 9.75 (bs, 1H), 8.86 (t, 1H), 8.23 (m, 1H), 7.92 (m, 2H), 7.64 (dd, 1H), 6.62 (m, 2H), 6.58 (d, 1H), 3.60 (m, 4H), 3.32 (quart, 2H), 3.03 (m, 2H), 2.21 (d, 3H), 2.00 (d, 2H), 1.85 (m, 2H).

Example 110

N-(2-(dimethylamino)ethyl)-4-methyl-3-(2-(4-methylthiazol-2-ylamino)pyridin-4-yloxy)benzamide dihydrochloride

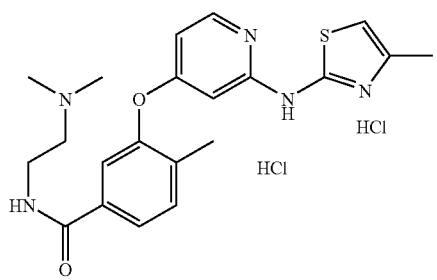

The title compound was prepared according to the method of Example 107 from 4-methyl-3-(2-(4-methylthiazol-2-ylamino)pyridin-4-yloxy)benzoic acid hydrochloride (Example 108) and N,N-dimethylethylenediamine. Yield: 0.065 g, 25%. $^1$H NMR (CDCl$_3$), 8.84 (bs, 1H), 8.16 (d, 1H), 7.90 (d, 1H), 7.86 (bs, 1H), 7.37 (d, 1H), 6.80 (bs, 1H), 6.71 (dd, 1H), 6.38 (s, 1H), 3.89 (m, 2H), 3.35 (m, 2H), 2.91 (s, 6H), 2.37 (s, 3H), 2.22 (s, 3H).

Example 111

(3-(2-(4-methylthiazol-2-ylamino)pyridin-4-yloxy)phenyl)(pyrrolidin-1-yl)methanone hydrochloride

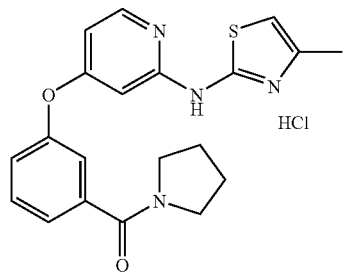

Prepared according to the method of Example 109. $^1$H NMR (CDCl$_3$) δ 10.33 (bs, 1H), 8.18 (d, 1H), 7.38-7.46 (m, 2H), 7.23 (m, 1H), 7.13 (m, 1H), 6.48 (dd, 1H), 6.34 (d, 1H), 6.32 (d, 1H), 3.62 (t, 2H), 3.37 (t, 2H), 2.21 (d, 3H), 1.94 (q, 2H), 1.85 (q, 2H).

Example 112

(4-ethylpiperazin-1-yl)(6-(4-methylthiazol-2-ylamino)-4-phenoxypyridin-3-yl)methanone hydrochloride

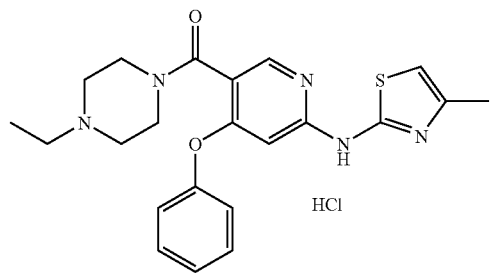

Prepared according to the method of Example 32 from 1-ethylpiperazine and 6-(4-methylthiazol-2-ylamino)-4-phenoxynicotinic acid hydrochloride (Example 59). Yield: 0.055 g, 43.07%. $^1$H NMR (CDCl$_3$) δ 8.34 (s, 1H), 7.47 (t, 2H), 7.33 (t, 1H), 7.06 (s, 1H), 7.04 (s, 1H), 6.38 (s, 1H), 6.26 (s, 1H), 3.97 (m, 3H), 2.97 (m, 7H), 2.27 (s, 3H), 1.46 (t, 3H).

Example 113

N-(2-(dimethylamino)ethyl)-6-(4-methylthiazol-2-ylamino)-4-phenoxynicotinamide hydrochloride

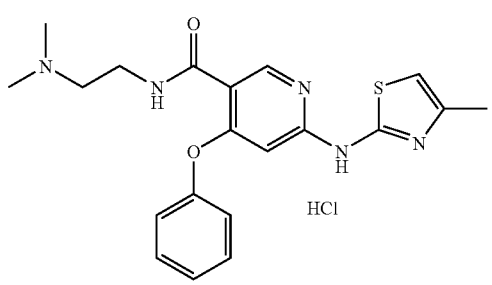

Prepared according to Example 32 from 6-(4-methylthiazol-2-ylamino)-4-phenoxynicotinic acid hydrochloride (Example 59). Yield: 0.083 g, 68.89%. $^1$H NMR (CDCl$_3$) δ 8.93 (s, 1H), 8.28 (m, 1H), 7.48 (t, 2H), 7.33 (t, 1H), 7.26 (m, 1H, under CDCl$_3$), 7.23 (bs, 1H), 6.38 (m, 1H), 6.24 (s, 1H), 3.96 (m, 2H), 3.32 (t, 2H), 2.87 (s, 6H), 2.27 (s, 3H).

Example 114

Ethyl 3-(5-bromo-2-(4-phenethylthiazol-2-ylamino)pyridin-4-yloxy)-4-chlorobenzoate

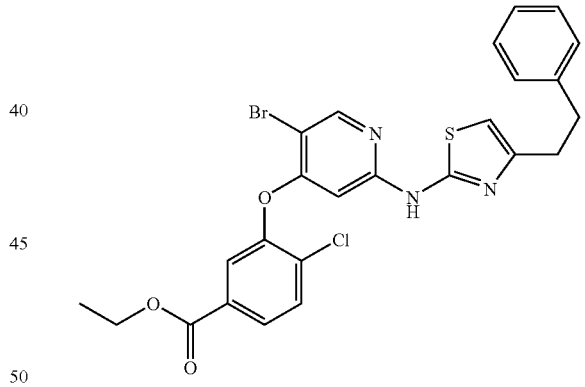

Step A: Preparation of ethyl 3-(2-aminopyridin-4-yloxy)-4-chlorobenzoate: A flask was charged with ethyl 4-chloro-3-(2-chloropyridin-4-yloxy)benzoate (16.347 g, 52.369 mmol), tert-butyl carbamate (18.405 g, 157.11 mmol), potassium phosphate (12.228 g, 57.606 mmol), and toluene (150 mL). The flask was degassed with nitrogen, and 9,9-dimethyl-4,5-bis(diphenylphosphino)xanthene (3.0302 g, 5.2369 mmol) and tris(dibenzylideneacetone)dipalladium (0) (2.3978 g, 2.6185 mmol) were added. The flask was degassed again, and degassed water (40 mL) was added. The reaction was heated at 90° C. overnight. Water was added and the reaction mixture was extracted with ethyl acetate and concentrated. TFA (100 mL) was added and the mixture was stirred overnight, then concentrated, treated with sodium bicarbonate, and extracted with ethyl acetate. The organic layer was dried and concentrated. The residue was purified by silica gel column chromatography eluting with 20-25% ethyl acetate in hexanes and then ethyl acetate to provide the desired product (5.75 g, 37.510% yield) as yellow oily semi solid.

Step B: Preparation of ethyl 3-(2-amino-5-bromopyridin-4-yloxy)-4-chlorobenzoate: A flask was charged with ethyl 3-(2-aminopyridin-4-yloxy)-4-chlorobenzoate (5.50 g, 18.8 mmol) and acetic acid (50 mL), and bromine (0.943 ml, 18.4 mmol) was added. The reaction was stirred at ambient temperature for 30 minutes and then concentrated. The residue was purified by silica gel column chromatography, eluting with 20%-35% ethyl acetate in hexanes to give the desired product (4.20 g, 58.9% yield) as light yellow solid.

Step C: Preparation of ethyl 3-(2-(3-benzoylthioureido)-5-bromopyridin-4-yloxy)-4-chlorobenzoate: A flask was charged with ethyl 3-(2-amino-5-bromopyridin-4-yloxy)-4-chlorobenzoate (2.76 g, 7.43 mmol), benzoyl isothiocyanate (1.05 ml, 7.80 mmol) and THF (100 mL). The reaction mixture was stirred at ambient temperature overnight and then concentrated. The residue was purified by silica gel column chromatography using 20% ether in hexanes to give the desired product (1.35 g, 34% yield) as light yellow solid.

Step D: Preparation of ethyl 3-(5-bromo-2-thioureidopyridin-4-yloxy)-4-chlorobenzoate: A flask was charged with ethyl 3-(2-(3-benzoylthioureido)-5-bromopyridin-4-yloxy)-4-chlorobenzoate (1.37 g, 2.56 mmol), Potassium carbonate (0.496 g, 3.59 mmol) and ethanol (50 mL). The reaction mixture was stirred at 40° C. for 6 hours and then concentrated. The crude material was purified by silica gel column chromatography eluting with 10% ethyl acetate in hexanes to give the desired product (0.61 g, 54% yield) as white solid.

Step E: Preparation of ethyl 3-(5-bromo-2-(4-phenethylthiazol-2-ylamino)-Pyridin-4-yloxy)-4-chlorobenzoate: A flask was charged with ethyl 3-(5-bromo-2-thioureidopyridin-4-yloxy)-4-chlorobenzoate (0.200 g, 0.464 mmol), 1-bromo-4-phenylbutan-2-one (0.105 g, 0.464 mmol) and triethylamine (0.0470 g, 0.464 mmol). Ethanol (5 mL) was added and the reaction was heated at 70° C. for 6 hours, and then concentrated to provide ethyl the desired product (0.250 g, 95 yield) as white solid. LC/MS (apci) M+2H: 560 (100%).

The following compounds were also prepared according to the method of Example 114.

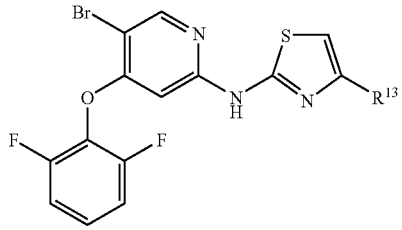

| Example # | R13 | Name |
|---|---|---|
| 115 | cyclopropyl | 4-cyclopropyl-N-(4-(2,6-difluorophenoxy)pyridin-2-yl)thiazol-2-amine: $^1$H NMR (DMSO-$d_6$) δ 0.64 (m, 2 H), 0.77 (m, 2 H), 1.87 (m, 1 H), 6.60 (s, 1 H), 6.67 (s, 1 H), 7.40-7.57 (m, 3 H), 8.44 (s, 1 H), 11.03 (s, 1 H). |
| 116 | Ph | N-(4-(2,6-difluorophenoxy)pyridin-2-yl)-4-phenylthiazol-2-amine: $^1$H NMR (DMSO-$d_6$) δ 6.82 (s, 1 H), 7.30 (t, 1 H), 7.40 (t, 2 H), 7.44-7.60 (m, 4 H), 7.75 (d, 2 H), 8.50 (s, 1 H), 11.25 (s, 1 H). |
| 117 | PhCH$_2$CH$_2$— | N-(4-(2,6-difluorophenoxy)pyridin-2-yl)-4-phenethylthiazol-2-amine: $^1$H NMR (DMSO-$d_6$) δ 2.79 (m, 2 H), 2.86 (m, 2 H), 6.59 (s, 1 H), 6.66 (s, 1 H), 7.15-7.19 (m, 3 H), 7.26 (t, 2 H), 7.40-7.52 (m, 3 H), 8.45 (s, 1 H), 11.11 (s, 1 H). |
| 118 | Bu | 4-butyl-N-(4-(2,6-difluorophenoxy)pyridin-2-yl)thiazol-2-amine: $^1$H NMR (DMSO-$d_6$) δ 0.87 (t, 3 H), 1.27 (hextet, 2 H), 1.52 (pentet, 2 H), 2.47 (t, 2 H), 6.58 (s, 1 H), 6.68 (s, 1 H), 7.40-7.57 (m, 3 H), 8.44 (s, 1 H), 11.05 (s, 1 H). |
| 119 | cyclohexyl | 4-cyclohexyl-N-(4-(2,6-difluorophenoxy)pyridin-2-yl)thiazol-2-amine: $^1$H NMR (DMSO-$d_6$) δ 1.23-1.35 (m, 6 H), 1.63-1.76 (m, 4 H), 2.43 (m, 1 H), 6.53 (s, 1 H), 6.82 (s, 1 H), 7.41-7.56 (m, 3 H), 8.44 (s, 1H), 11.03 (s, 1 H). |
| 120 | isobutyl | N-(4-(2,6-difluorophenoxy)pyridin-2-yl)-4-isobutylthiazol-2-amine: $^1$H NMR (DMSO-$d_6$) δ 0.85 (d, 6 H), 1.85 (m, 1 H), 2.35 (d, 2 H), 6.58 (s, 1 H), 6.76 (s, 1 H), 7.42-7.55 (m, 3 H), 8.45 (s, 1 H), 11.05 (s, 1H). |
| 121 | 4-pyridyl | N-(4-(2,6-difluorophenoxy)pyridin-2-yl)-4-(pyridin-4-yl)thiazol-2-amine: $^1$H NMR (DMSO-$d_6$) δ 6.80 (s, 1 H), 7.42-7.55 (m, 3 H), 7.67 (s, 1 H), 8.00 (d, 2 H), 8.45 (s, 1 H), 8.70 (d, 2 H), 11.30 (s, 1 H). |
| 122 | 2-pyridyl | N-(4-(2,6-difluorophenoxy)pyridin-2-yl)-4-(pyridin-2-yl)thiazol-2-amine: $^1$H NMR (DMSO-$d_6$) δ 6.84 (s, 1 H), 7.30 (m, 1 H), 7.46-7.60 (m, 3 H), 7.67 (m, 1 H), 7.68 (s, 1 H), 7.89 (t, 1 H), 8.51 (s, 1 H), 8.57 (d, 1 H), 11.29 (s, 1 H). |

-continued

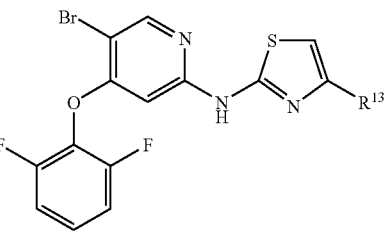

| Example # | R[13] | Name |
|---|---|---|
| 123 | 3-pyridyl | N-(4-(2,6-difluorophenoxy)pyridin-2-yl)-4-(pyridin-3-yl)thiazol-2-amine: $^1$H NMR (DMSO-$d_6$) δ 6.77 (s, 1 H), 7.42-7.58 (m, 4 H), 7.66 (s, 1 H), 8.08 (d, 1 H), 8.49-8.52 (m, 2 H), 9.02 (s, 1 H), 11.33 (s, 1 H). |
| 124 | 3-thiophene | N-(4-(2,6-difluorophenoxy)pyridin-2-yl)-4-(thiophen-3-yl)thiazol-2-amine: $^1$H NMR (DMSO-$d_6$) δ 6.80 (s, 1 H), 7.30 (s, 1 H), 7.44-7.60 (m, 6 H), 8.49 (s, 1 H), 11.26 (s, 1 H). |
| 125 | Et | N-(4-(2,6-difluorophenoxy)pyridin-2-yl)-4-ethylthiazol-2-amine: $^1$H NMR (DMSO-$d_6$) δ 1.12 (t, 3 H), 2.51 (q, 2 H), 6.58 (s, 1 H), 6.68 (s, 1 H), 7.41-7.55 (m, 3 H), 8.45 (s, 1 H), 11.05 (s, 1 H). |
| 126 | t-Bu | 4-tert-butyl-N-(4-(2,6-difluorophenoxy)pyridin-2-yl)thiazol-2-amine: $^1$H NMR (DMSO-$d_6$) δ 1.15 (s, 9 H), 6.54 (s, 1 H), 6.88 (s, 1 H), 7.40-7.55 (m, 3 H), 8.44 (s, 1 H), 11.06 (s, 1 H). |
| 127 | CF$_3$ | N-(4-(2,6-difluorophenoxy)pyridin-2-yl)-4-(trifluoromethyl)thiazol-2-amine: $^1$H NMR (DMSO-$d_6$) δ 6.50 (s, 1 H), 7.43-7.54 (m, 3 H), 7.77 (s, 1 H), 8.55 (s, 1 H), 11.57 (s, 1 H). |
| 128 | Me | 5-bromo-4-(2,6-difluorophenoxy)-N-(4-methylthiazol-2-yl)pyridin-2-amine (2.249 g, 67.13% yield) as off white solid. $^1$H NMR (CDCl$_3$) δ 10.04 (bs, 1 H), 8.37 (s, 1 H), 7.26 (m, 1 H), 7.05 (t, 2 H), 6.26 (s, 1 H), 6.13 (s, 1 H), 2.08 (s, 3 H). |
| 129 | CH$_2$CH$_2$COOMe | methyl 3-(2-(5-bromo-4-(2,6-difluorophenoxy)pyridin-2-ylamino)thiazol-4-yl)propanoate (1.210 g, 61.99% yield) as off white solid. $^1$H NMR (CDCl$_3$) δ 8.97 (bs, 1 H), 8.36 (s, 1 H), 7.26 (m, 1 H), 7.08 (t, 2 H), 6.40 (s, 1 H), 6.37 (s, 1 H), 3.66 (s, 3 H), 2.81 (t, 2 H), 2.56 (t, 2 H). |

The following compounds were also prepared according to the method of Example 114.

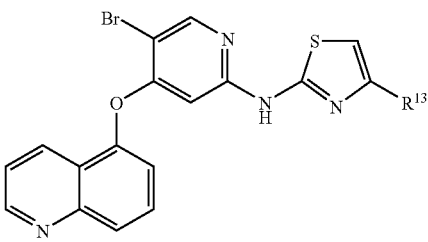

| Example # | R[13] | Name |
|---|---|---|
| 130 | 2-Pyridyl | N-(5-bromo-4-(quinolin-5-yloxy)pyridin-2-yl)-4-(pyridin-2-yl)thiazol-2-amine: $^1$H NMR (DMSO-$d_6$) δ 11.16 (s, 1 H), 9.02 (dd, 1 H), 8.54 (m, 2 H), 8.26 (m, 1 H), 8.10 (d, 1 H), 7.91 (t, 1 H), 7.82 (dt, 1H), 7.62 (m, 2 H), 7.56 (d, 1 H), 7.51 (m, 1 H), 7.28 (m, 1 H), 6.69 (s, 1 H). |
| 131 | Phenyl | N-(5-bromo-4-(quinolin-5-yloxy)pyridin-2-yl)-4-phenylthiazol-2-amine: $^1$H NMR (DMSO-$d_6$) δ |

-continued

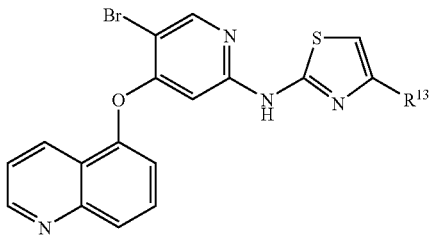

| Example # | R13 | Name |
|---|---|---|
|  |  | 11.13 (s, 1 H), 9.02 (dd, 1 H), 8.53 (s, 1 H), 8.26 (m, 1 H), 8.08 (dt, 1 H), 7.90 (t, 1 H), 7.67 (m, 2 H), 7.62 (dd, 1 H), 7.55 (dd, 1 H), 7.43 (s, 1 H), 7.36 (m, 2 H), 7.27 (m, 1 H), 6.67 (s, 1 H) |
| 132 | Me | N-(5-bromo-4-(quinolin-5-yloxy)pyridin-2-yl)-4-methylthiazol-2-amine: $^1$H NMR (DMSO-$d_6$) δ 10.88 (s, 1 H), 9.01 (dd, 1 H), 8.48 (s, 1 H), 8.24 (m, 1 H), 8.05 (d, 1 H), 7.88 (t, 1 H), 7.61 (dd, 1 H), 7.51 (d, 1 H), 6.54 (s, 1 H), 6.44 (s, 1 H), 2.13 (d, 3 H). |
| 133 | —CH$_2$CH$_2$Ph | N-(5-bromo-4-(quinolin-5-yloxy)pyridin-2-yl)-4-phenethylthiazol-2-amine: $^1$H NMR (DMSO-$d_6$) δ 10.99 (s, 1 H), 9.01 (dd, 1 H), 8.49 (s, 1 H), 8.25 (m, 1 H), 8.03 (d, 1 H), 7.86 (t, 1 H), 7.61 (dd. 1 H), 7.50 (d, 1 H), 7.23 (m, 2 H), 7.15 (m, 2 H), 7.13 (m, 1 H), 6.55 (s, 1 H), 6.50 (s, 1 H), 2.81 (m, 2 H), 2.75 (m, 2 H). |
| 134 | (CH$_2$)$_2$COOMe | methyl 3-(2-(5-bromo-4-(quinolin-5-yloxy)pyridin-2-ylamino)thiazol-4-yl)propanoate: $^1$H NMR (DMSO-$d_6$) δ 10.93 (s, 1 H), 9.01 (dd, 1 H), 8.49 (s, 1 H), 8.24 (m, 1 H), 8.04 (d, 1 H), 7.87 (t, 1 H), 7.61 (dd, 1 H), 7.50 (d, 1 H), 6.59 (s, 1 H), 6.47 (s, 1 H), 3.56 (s, 3 H), 2.73 (t, 2 H), 2.54 (t, 2 H). |
| 135 | (CH$_2$)$_2$COONa | Sodium 3-(2-(5-bromo-4-(quinolin-5-yloxy)pyridin-2-ylamino)thiazol-4-yl)propanoate: $^1$H NMR (DMSO-$d_6$) δ 9.00 (dd, 1 H), 8.46 (s, 1 H), 8.26 (d, 1 H), 8.01 (d, 1 H), 7.85 (t, 1 H), 7.60 (dd, 1 H), 7.44 (d, 1 H), 6.50 (s, 1 H), 6.43 (s, 1 H), 2.61 (t, 2 H), 2.05 (t, 2 H). |

Example 136

3-2-(5-bromo-4-(2,6-difluorophenoxy)pyridin-2-ylamino)thiazol-4-yl)propanoic acid dihydrochloride

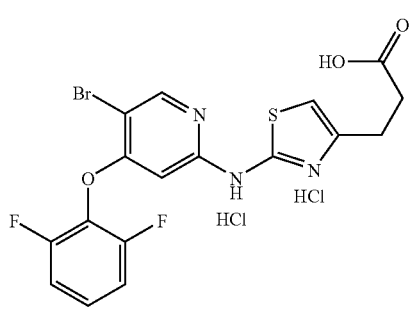

The title compound was prepared from methyl 3-(2-(5-bromo-4-(2,6-difluorophenoxy)pyridin-2-ylamino)thiazol-4-yl)propanoate (Example 129) according to the method of Example 31. Yield: 0.160 g, 70.4%. $^1$H NMR (d$_6$-DMSO) δ 8.45 (s, 1H), 7.45 (m, 3H), 6.64 (bs, 1H), 6.61 (m, 1H), 3.32 (m, 2H), 2.73 (t, 2H).

Example 137

Methyl 3-(4-(2,6-difluorophenoxy)-6-(4-methylthiazol-2-ylamino)pyridin-3-ylthio)propanoate

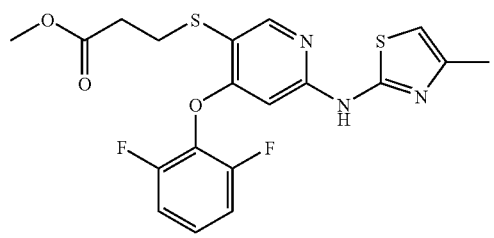

Tris(dibenzylideneacetone)dipalladium (0) (0.05749 g, 0.06278 mmol), 5-bromo-4-(2,6-difluorophenoxy)-N-(4-methylthiazol-2-yl)pyridin-2-amine (Example 128; 1.0 g, 2.511 mmol), 4,5-bis(diphenylphosphino)-9,9-dimethyl-9H-xanthene (0.07265 g, 0.1256 mmol), methyl-3-mercaptopropanoate (0.2920 ml, 2.637 mmol), N-ethyl-N-isopropylpropan-2-amine (0.8748 ml, 5.022 mmol) and dioxane (50 mL)

were heated under argon at 80° C. overnight and then concentrated. The residue was purified by column chromatography to provide the desired product (0.375 g, 33.79% yield) as a yellow solid. ¹H NMR (CDCl₃) δ 10.97 (s, 1H), 8.37 (s, 1H), 7.26 (m, 1H), 7.03 (t, 2H), 6.26 (s, 1H), 6.03 (s, 1H), 3.67 (s, 3H), 3.12 (t, 2H), 2.62 (t, 2H), 2.06 (s, 3H).

Example 138

(2-methyl-3-(2-(4-methylthiazol-2-ylamino)pyridin-4-yloxy)phenyl)methanol hydrochloride

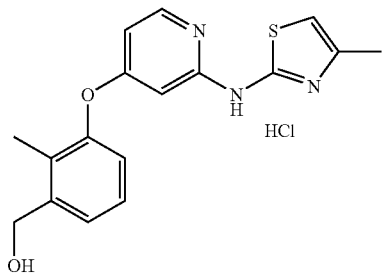

To a solution of lithium tetrahydroaluminate. (2.46 mL, 2.46 mmol) in ether at 0° C. was added a solution of ethyl 2-methyl-3-(2-(4-methylthiazol-2-ylamino)pyridin-4-yloxy)benzoate (Example 89; 0.182 g, 0.493 mmol) in THF (5 mL). Sodium sulphate decahydrate was added and the reaction mixture was stirred for 1 hour. Water was added and the reaction was extracted with ethyl acetate. The organic layer was dried, concentrated and purified by silica gel column chromatography eluting with 50% ethyl acetate in hexanes and 1% methanol in DCM to give the title compound (0.145 g, 74.4% yield) as white solid. ¹H NMR (CDCl₃) δ 8.18 (d, 1H), 7.34 (d, 1H), 7.27 (d, 1H), 6.97 (d, 1H), 6.67 (dd, 1H), 6.56 (m, 1H), 6.38 (d, 1H), 4.75 (s, 2H), 2.39 (d, 3H), 2.15 (s, 314).

Example 139

(4-fluoro-3-(2-(4-methylthiazol-2-ylamino)pyridin-4-yloxy)phenyl)methanol hydrochloride

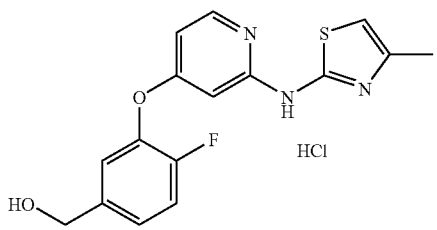

The title compound was prepared from ethyl 4-fluoro-3-(2-(4-methylthiazol-2-ylamino)pyridin-4-yloxy)benzoate (Example 90) according to the method of Example 138; (0.119 g, 59.8% yield) as white solid. ¹H NMR (CDCl₃) δ 8.21 (d, 1H), 7.27 (m, 1H), 7.21 (m, 2H), 6.74 (dd, 1H), 6.66 (bs, 1H), 6.39 (d, 1H), 4.70 (s, 2H), 2.37 (d, 3H).

Example 140

(4-methyl-3-(2-(4-methylthiazol-2-ylamino)-pyridin-4-yloxy)phenyl)methanol hydrochloride

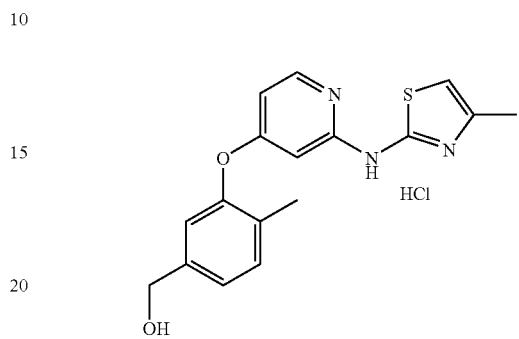

The title compound was prepared from ethyl 4-methyl-3-(2-(4-methylthiazol-2-ylamino)pyridin-4-yloxy)benzoate (Example 88) according to the method of Example 138; (0.127 g, 63.8% yield) as white solid. ¹H NMR (CDCl₃) δ 8.17 (d, 1H), 7.27 (d, 1H), 7.18 (d, 1H), 7.09 (s, 1H), 6.67 (d, 1H), 6.61 (m, 1H), 6.38 (s, 1H), 4.69 (s, 2H), 2.38 (s, 3H), 2.15 (s, 3H).

Example 141

N-(4-(2,6-difluorophenoxy)-5-phenylpyridin-2-yl)-4-methylthiazol-2-amine hydrochloride

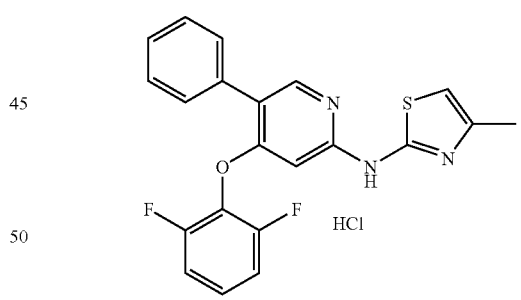

A vial was charged with phenylboronic acid (0.0367 g, 0.301 mmol), 5-bromo-4-(2,6-difluorophenoxy)-N-(4-methylthiazol-2-yl)pyridin-2-amine (Example 128; 0.100 g, 0.251 mmol), tetrakis(triphenylphosphine)palladium (0) (0.0290 g, 0.0251 mmol), sodium carbonate (0.0798 g, 0.753 mmol), DME (5 mL) and water (3 mL). The reaction mixture was stirred at 80° C. overnight. Water was added and the reaction was extracted with ethyl acetate, dried, filtered and concentrated. The crude material was purified by silica gel column chromatography eluting with 10-20% ethyl acetate/hexanes. The isolated product was treated with 2M HCl and dried to the title compound (0.1 g, 83% yield) as a yellow solid. ¹H NMR (CDCl₃) δ 8.34 (s, 1H), 7.63 (m, 2H), 7.48 (m, 2H), 7.42 (m, 1H), 7.24 (m, 1H), 7.07 (t, 2H), 6.39 (m, 2H), 2.40 (s, 3H).

Example 142

N-(4-(2,6-difluorophenoxy)-5-(phenylthio)pyridin-2-yl)-4-methylthiazol-2-amine hydrochloride

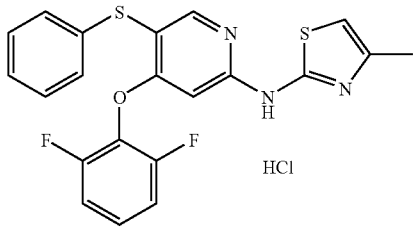

A flask was charged with 5-bromo-4-(2,6-difluorophenoxy)-N-(4-methylthiazol-2-yl)pyridin-2-amine (Example 128; 0.150 g, 0.377 mmol) and THF (10 mL) and cooled to −78° C. Methyllithium (0.294 ml, 0.471 mmol) was slowly added and the reaction was stirred for 5 minutes. Butyllithium (0.188 ml, 0.471 mmol) was added and the reaction was stirred for 5 minutes. 1,2-Diphenyldisulfane (0.0822 g, 0.377 mmol) was added and the reaction was stirred for 5 minutes. The reaction was warmed to ambient temperature and saturated NH₄Cl was added. The reaction was extracted with DCM, and the organic layer was dried, filtered and concentrated. The crude material was purified by preparative TLC eluting with 25% ethyl acetate/DCM. The isolated material was treated with 2M HCl in ether to provide the title compound (0.011 g, 6.23% yield) as a yellow solid. ¹H NMR (CDCl₃) δ 8.40 (s, 1H), 7.28 (m, 4H), 7.19 (m, 2H), 7.02 (m, 2H), 6-35 (Us, 1H), 6.21 (Us, 1H), 2.24 (s, 3H).

Example 143

Sodium 2-(3-(2-(4-methylthiazol-2-ylamino)pyridin-4-ylthio)phenoxy)acetate

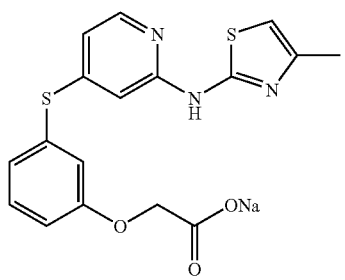

A 3 dram vial was charged with tert-butyl 2-(3-(2-(4-methylthiazol-2-ylamino)pyridin-4-ylthio)phenoxy)acetate (0.200 g, 0.466 mmol) and DCM (5 mL). Trifluoroacetic acid (3 mL) was added, and the reaction was stirred at ambient temperature overnight, then concentrated. Saturated aqueous sodium bicarbonate was added and the solids were collected by filtration to give the title compound (0.120 g, 65.2% yield) as a yellow solid. ¹H NMR (d₆-DMSO) δ 11.25 (s, 1H), 8.06 (d, 1H), 7.35 (t, 1H), 7.03 (dt, 1H), 6.95 (m, 2H), 6.86 (d, 1H), 6.61 (dd, 1H), 6.49 (d, 1H), 4.13 (s, 2H), 2.19 (d, 3H).

Example 144

N-(5-(cyclohexylthio)-4-(2,6-difluorophenoxy)pyridin-2-yl)-4-methylthiazol-2-amine hydrochloride

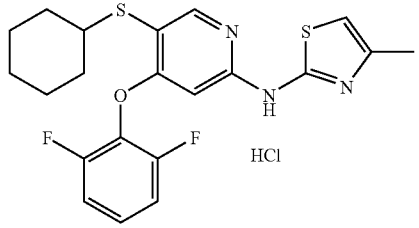

The title compound was prepared from 5-bromo-4-(2,6-difluorophenoxy)-N-(4-methylthiazol-2-yl)pyridin-2-amine (Example 128) and cyclohexanethiol according to the method of Example 137; (0.067 g, 56.2% yield. ¹H NMR (CDCl₃) δ 8.42 (s, 1H), 7.29 (m, 1H), 7.09 (t, 2H), 6.40 (d, 1H), 6.29 (s, 1H), 3.25 (m, 1H), 2.41 (d, 3H), 1.95 (m, 2H), 1.79 (m, 2H), 1.33 (m, 6H).

Example 145

N-(4-(2,6-difluorophenoxy)-5-(pyridin-4-ylthio)pyridin-2-yl)-4-methylthiazol-2-amine dihydrochloride

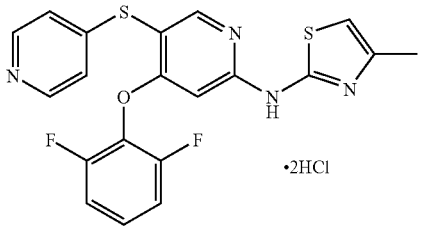

The title compound was prepared from 5-bromo-4-(2,6-difluorophenoxy)-N-(4-methylthiazol-2-yl)pyridin-2-amine (Example 128) and Aldrithiol-4 according to the method of Example 142; (0.097 g, 46.2% yield). ¹H NMR (DMSO) δ 8.64 (m, 1H), 8.62 (m, 1H), 8.58 (s, 1H), 7.70 (m, 1H), 7.68 (m, 1H), 7.49 (m, 1H), 7.41 (m, 2H), 6.71 (bs, 1H), 6.68 (d, 1H), 2.20 (s, 3H).

Example 146

4-(2,6-Difluorophenoxy)-6-(4-methylthiazol-2-ylamino)nicotinaldehyde

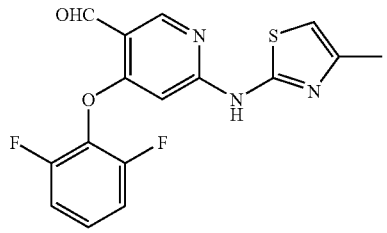

A flask was charged with 5-bromo-4-(2,6-difluorophenoxy)-N-(4-methylthiazol-2-yl)pyridin-2-amine (Example 128; 1.0 g, 2.51 mmol) and THF (50 mL) and cooled to −78° C. Methyllithium (1.96 ml, 3.14 mmol) was added slowly and the reaction mixture was stirred for 5 minutes. Butyllithium (1.26 ml, 3.14 mmol) was added and the reaction mixture was stirred for 5 minutes. N,N-dimethylformamide (0.551 g, 7.53 mmol) was added and the reaction mixture was stirred for 5 minutes. Water was added and the reaction mixture was extracted with ethyl acetate. The organic layer was dried, filtered, and concentrated. The residue was titurated with a mixture of hexanes, ether, and DCM and filtered to give the title compound (0.480 g, 51.2% yield) as yellow solid. $^1$H NMR (d$_6$-DMSO) δ 11.48 (s, 1H), 10.23 (s, 1H), 8.73 (s, 1H), 7.48 (m, 3H), 6.68 (s, 1H), 6.53 (bs, 1H), 2.19 (s, 3H).

Example 147

N-(4-(2,6-difluorophenoxy)-5-(4-(dimethylamino)but-1-enyl)pyridin-2-yl)-4-methylthiazol-2-amine dihydrochloride

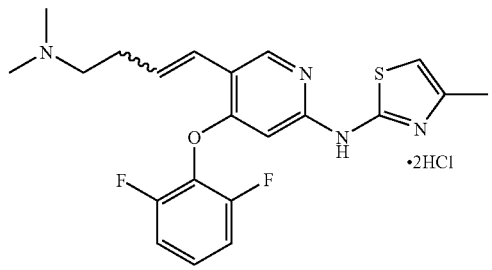

A flask was charged with (3-(dimethylamino)propyl)triphenylphosphonium bromide (0.555 g, 1.30 mmol) and THF (5 mL) and cooled to 0° C. Butyllithium (0.518 mL, 1.30 mmol) was added. The reaction was stirred at 0° C. for 20 minutes, and then 4-(2,6-difluorophenoxy)-6-(4-methylthiazol-2-ylamino)nicotinaldehyde (Example 146; 0.150 g, 0.432 mmol) was added. The reaction was stirred at ambient temperature overnight. Water and saturated NH$_4$Cl were added, and the reaction was extracted with ethyl acetate and dichloromethane. The organic layer was dried, filtered and concentrated, and the crude material was purified by silica gel column chromatography eluting with DCM-2-5% methanol/DCM. The isolated material was treated with 2M HCl in ether and dried over high vacuum to give the title compound (0.165 mg, 78% yield) as a white solid. $^1$H NMR (CDCl$_3$) δ 8.43 (s, 0.5H), 8.22 (s, 0.5H), 7.29 (m, 1H), 7.25 (m, 1H), 7.08 (m, 2H), 6.95 (d, 0.5H), 6.68 (d, 0.5H), 6.38 (d, 1H), 6.31 (d, 1H), 3.16 (dt, 2H), 2.87 (s, 6H), 2.79 (m, 2H), 2.32 (d, 3H).

Example 148

N-(4-(2,6-difluorophenoxy)-5-(pyrimidin-2-ylthio)pyridin-2-yl)-4-methylthiazol-2-amine dihydrochloride

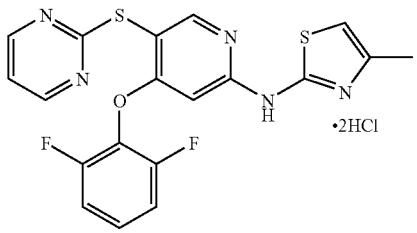

The title compound was prepared according to the method of Example 142 from 5-bromo-4-(2,6-difluorophenoxy)-N-(4-methylthiazol-2-yl)pyridin-2-amine (Example 128) and 2-(2-(pyrimidin-2-yl)disulfanyl)pyrimidine. Yield: 0.012 g, 9.04%. $^1$H NMR (CDCl$_3$) δ 8.56 (s, 1H), 8.50 (d, 2H), 7.23 (m, 1H), 7.02 (m, 3H), 6.45 (s, 1H), 6.39 (s, 1H), 2.42 (s, 3H).

Example 149

N-(4-(2,6-difluorophenoxy)-5-(pyridin-2-ylthio)pyridin-2-yl)-4-methylthiazol-2-amine dihydrochloride

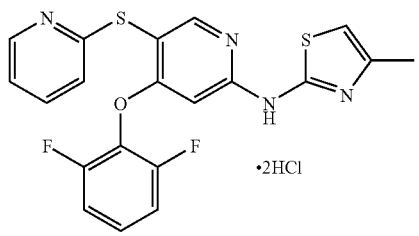

The title compound was prepared according to the method of Example 142 from 5-bromo-4-(2,6-difluorophenoxy)-N-(4-methylthiazol-2-yl)pyridin-2-amine (Example 128) and 2-(2-(pyridin-2-yl)disulfanyl)pyridine; (0.072 g, 34.3% yield). $^1$H NMR (CDCl$_3$) δ 8.61 (s, 1H), 8.44 (m, 1H), 7.61 (dt, 1H), 7.23 (m, 1H), 7.12 (m, 2H), 7.03 (t, 2H), 6.46 (d, 1H), 6.39 (s, 1H), 2.44 (d, 3H).

Example 150

N-(4-(2,6-difluorophenoxy)-5-(thiazol-2-ylthio)pyridin-2-yl)-4-methylthiazol-2-amine dihydrochloride

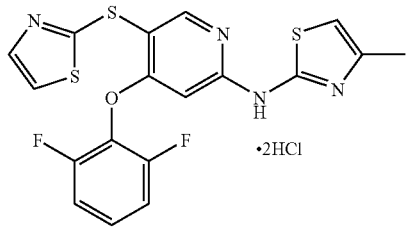

The title compound was prepared according to the method of Example 142 from 5-bromo-4-(2,6-difluorophenoxy)-N-(4-methylthiazol-2-yl)pyridin-2-amine (Example 128) and 2-(2-(thiazol-2-yl)disulfanyl)thiazole; (0.014 g, 13.7% yield). $^1$H NMR (CDCl$_3$) δ 8.61 (s, 1H), 7.70 (d, 1H), 7.27 (m, 2H), 7.05 (t, 2H), 6.44 (s, 1H), 6.35 (s, 1H), 2.39 (s, 3H).

Example 151

N-(4-(quinolin-5-yloxy)pyridin-2-yl)thiazolo[5,4-b]pyridin-2-amine

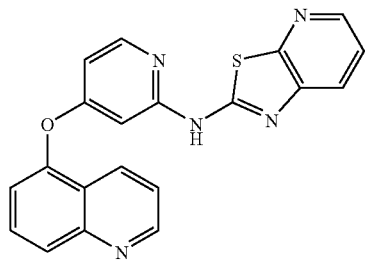

The title compound was prepared according to the method of Example 180 from 4-(quinolin-5-yloxy)pyridin-2-amine and 2-chloro-3-isothiocyanatopyridine; (0.006 g, 3.83% yield) as a light yellow solid. $^1$H NMR (d$_6$-DMSO) δ 11.47 (s, 1H), 9.00 (dd, 1H), 8.32 (m, 3H), 8.04 (d, 1H), 7.88 (t, 2H), 7.59 (dd, 1H), 7.51 (d, 1H), 7.38 (dd, 1H), 6.77 (dd, 1H), 6.66 (d, 1H).

Example 152

N-(4-methylthiazol-2-yl)-5-(pyridin-2-ylthio)-4-(quinolin-5-yloxy)pyridin-2-amine

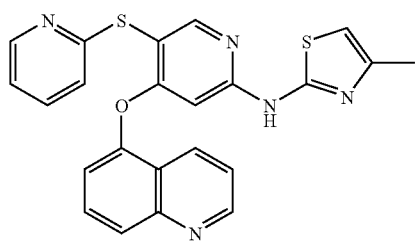

The title compound was prepared according to the method of Example 142 from N-(5-bromo-N-(4-methylthiazol-2-yl)-4-(quinolin-5-yloxy)pyridin-2-amine (Example 132) and 2-(2-(pyridin-2-yl)disulfanyl)pyridine (0.107 g, 0.484 mmol); (0.033 g, 30.7% yield. $^1$H NMR (DMSO-d$_6$) δ 10.99 (s, 1H), 8.96 (dd, 1H), 8.48 (m, 2H), 8.11 (m, 1H), 8.00 (dt, 1H), 7.84 (t, 1H), 7.72 (dt, 1H), 7.53 (dd, 1H), 7.42 (dd, 1H), 7.31 (dt, 1H), 7.18 (m, 1H), 6.57 (s, 1H), 6.36 (s, 1H), 2.14 (d, 3H).

Example 153

N-(5-benzyl-4-(quinolin-5-yloxy)pyridin-2-yl)-4-methylthiazol-2-amine

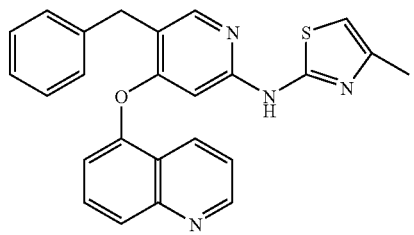

A vial was charged with 1,1'-bis(diphenylphosphino)ferrocene-dichloropalladium(II) (0.0199 g, 0.0242 mmol), N-(5-bromo-4-(quinolin-5-yloxy)pyridin-2-yl)-4-methylthiazol-2-amine (0.100 g, 0.242 mmol), 9-benzyl-9-bora-bicyclo[3.3.1]nonane (1.45 ml, 0.726 mmol), cesium carbonate (0.237 g, 0.726 mmol), DMF (5 mL), and water (1.5 mL). The reaction mixture was heated at 80° C. for three days. Water was added and the reaction mixture was extracted with ethyl acetate. The organic layer was dried and concentrated. The crude material was purified by reverse phase column chromatography to give the title compound (0.010 g, 9.25% yield) as a white solid. $^1$H NMR (CDCl$_3$) δ 8.85 (dd, 1H), 8.17 (s, 1H), 7.96 (d, 1H), 7.60 (t, 1H), 7.56 (d, 1H), 7.25 (m, 3H), 7.22 (s, 1H), 7.19 (m, 1H), 7.15 (dd, 1H), 7.04 (d, 1H), 6.05 (s, 1H), 5.75 (s, 1H), 4.04 (s, 2H), 1-69 (s, 3H).

Example 154

N-(4-phenylthiazol-2-yl)-5-(piperidin-4-ylmethylthio)-4-(quinolin-5-yloxy)pyridin-2-amine dihydrochloride

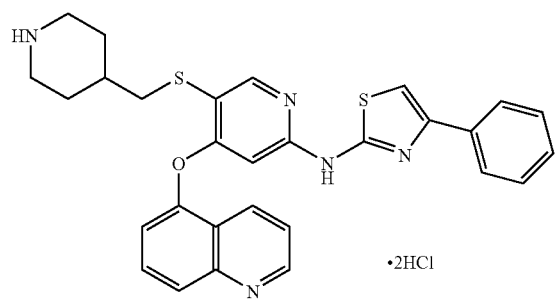

A flask was charged with tert-butyl 4-((6-(4-phenylthiazol-2-ylamino)-4-(quinolin-5-yloxy)pyridin-3-ylthio)methyl)piperidine-1-carboxylate (prepared according to the method of Example 202) (0.150 g, 0.240 mmol) and 4 mL DCM. TFA (4 mL) was added and the reaction was stirred at ambient temperature for 2 hours and then concentrated. The crude material was purified on a SCX ion exchange column using DCM, methanol and ammoniated methanol as eluent. The isolated material was treated with 2M HCl (2 mL) in ether and dried to give the title compound (0.057 g, 39.3% yield) as light yellow solid. $^1$H NMR (DMSO-d$_6$) δ 11.14 (s, 1H), 9.06 (dd, 1H), 8.67 (m, 1H), 8.43 (s, 1H), 8.34 (d, 1H), 8.09 (d, 1H), 7.91 (t, 1H), 7.71 (s, 1H), 7.70 (s, 1H), 7.67 (dd, 1H), 7.50 (d, 1H), 7.43 (s, 1H), 7.31 (t, 2H), 7.28 (m, 1H) 6.58 (s, 1H), 3.25 (m, 2H), 2.95 (d, 2H), 2.86 (m, 2H), 2.01 (m, 2H), 1.80 (m, 1H), 1.40 (m, 2H).

Example 155

N-(4-methylthiazol-2-yl)-5-(piperidin-4-ylmethylthio)-4-(quinolin-5-yloxy)pyridin-2-amine dihydrochloride

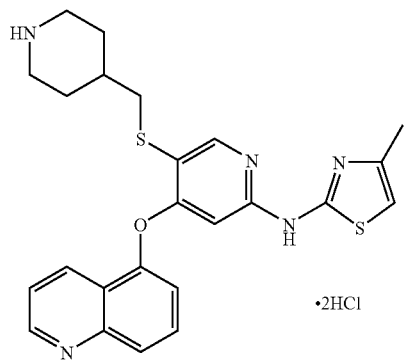

The title compound was prepared according to the method of Example 154 from tert-butyl-4-((6-(4-methylthiazol-2-ylamino)-4-(quinolin-5-yloxy)pyridin-3-ylthio)methyl)piperidine-1-carboxylate (prepared according to the method of Example 201). Yield: 0.110 g, 90.6%. $^1$H NMR (DMSO-$d_6$) δ 9.12 (dd, 1H), 8.47 (d, 1H), 8.44 (s, 1H), 8.12 (d, 1H), 7.95 (t, 1H), 7.75 (dd, 1H), 7.51 (d, 1H), 6.65 (d, 1H), 6.50 (s, 1H), 3.23 (m, 2H), 2.95 (d, 2H), 2.83 (m, 2H), 2.18 (d, 3H), 1.98 (m, 2H), 1.79 (m, 1H), 1.41 (quart, 2H).

Example 156

3-(5-bromo-2-(4-phenethylthiazol-2-ylamino)pyridin-4-yloxy)-4-chlorobenzoic acid

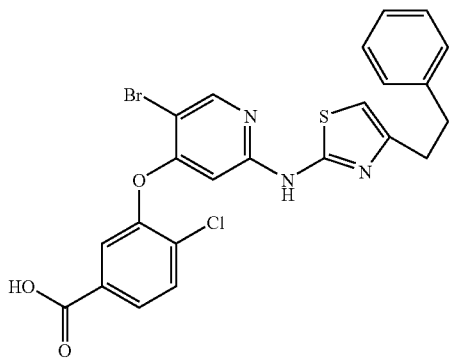

The title compound was prepared according to the method of Example 31 from ethyl 3-(5-bromo-2-(4-phenethylthiazol-2-ylamino)pyridin-4-yloxy)-4-chlorobenzoate (Example 114); (0.225 g, 83.8% yield). $^1$H NMR (DMSO-$d_6$) δ 11.10 (s, 1H), 8.44 (s, 1H), 7.85 (dd, 1H), 7.73 (m, 1H), 7.68 (d, 1H), 7.25 (m, 2H), 7.17 (m, 3H), 6.56 (s, 1H), 6.47 (s, 1H), 2.87 (m, 2H), 2.81 (m, 2H).

Example 157

3-(5-bromo-2-(4-phenethylthiazol-2-ylamino)pyridin-4-yloxy)-4-chloro-N-(2-(pyrrolidin-1-yl)ethyl)benzamide dihydrochloride

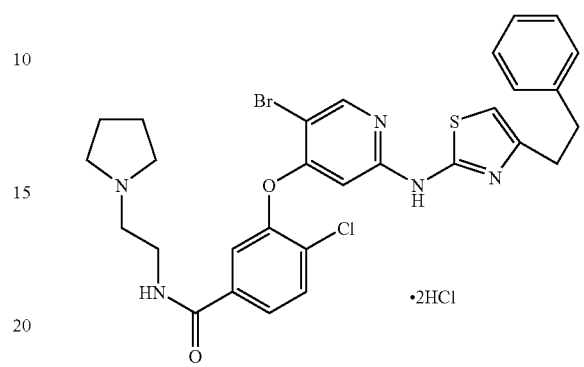

A vial was charged with 3-(5-bromo-2-(4-phenethylthiazol-2-ylamino)pyridin-4-yloxy)-4-chlorobenzoic acid (0.050 g, 0.0942 mmol), 1-pyrrolidine ethanamine (0.013 g, 0.113 mmol), N,N-diisopropylethylamine (0.0328 mL, 0.188 mmol), and THF (3 mL). Diethyl cyanophosphononate (0.0239 g, 0.132 mmol) was added and the reaction was stirred for 4 hours at ambient temperature. The reaction mixture was concentrated and the residue was partitioned between water and ethyl acetate. The organic later was dried and concentrated, and the crude material was purified by preparative TLC using 5% ammoniated methanol in DCM. The isolated material was treated with 2M HCl in ether and the isolated solids were dried in vacuum to give the title compound (0.035 g, 51.5% yield) as a light yellow solid. $^1$H NMR (CDCl$_3$) δ 8.99 (s, 1H), 8.36 (s, 1H), 7.96 (m, 2H), 7.57 (m, 1H), 7.25 (m, 1H), 7.15 (m, 3H), 6.70 (s, 1H), 6.30 (s, 1H), 3.85 (m, 4H), 3.35 (m, 2H), 2.93 (m, 6H), 2.14 (m, 4H).

The following compounds were also prepared according to the method of Example 4.

| Example # | R$^2$ | L | R$^{13}$ | Name |
|---|---|---|---|---|
| 158 | 2,4-diFPh | O | Me | N-(4-(2,4-difluorophenoxy)pyridin-2-yl)-4-methylthiazol-2-amine: $^1$H NMR (DMSO-$d_6$) δ 2.20 (s, 3 H), 6.53-6.57 (m, 3 H), 7.23 (m, 1 H), 7.50 (m, 1 H), 7.58 (m, 1 H), 8.18 (d, 1 H), 10.99 (s, 1 H). |
| 159 | 2-Me-6-Cl-Ph | S | Me | N-(4-(2-chloro-6-methylphenylthio)pyridin-2-yl)-4-methylthiazol-2-amine: $^1$H NMR (DMSO-$d_6$) δ 2.19 (s, 3 H), 2.34 (s, 3 H), 6.48-6.51 (m, 2 H), 6.57 (s, 1 H), 7.49-7.59 (m, 3 H), 8.07 (d, 1 H), 11.02 (s, 1 H). |
| 160 | 2-Me-6-Cl-Ph | O | Me | N-(4-(2-chloro-6-methylphenoxy)pyridin-2-yl)-4-methylthiazol-2-amine: $^1$H NMR (DMSO-$d_6$) δ 2.15 (s, 3 H), 2.20 (s, 3 H), 6.42-6.46 (m, 2 H), 6.52 (s, |

-continued

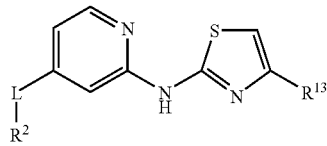

| Example # | R² | L | R¹³ | Name |
|---|---|---|---|---|
| 161 | 2,4-diClPh | S | Me | 1 H), 7.30 (t, 1 H), 7.39 (d, 1 H), 7.50 (d, 1 H), 8.16 (d, 1 H), 10.97 (s, 1 H). N-(4-(2,4-dichlorophenylthio)pyridin-2-yl)-4-methylthiazol-2-amine: ¹H NMR (DMSO-d₆) δ 2.20 (s, 3 H), 6.53 (s, 1 H), 6.65-6.67 (m, 2 H), 7.58 (d, 1 H), 7.73 (d, 1 H), 7.94 (s, 1 H), 8.12 (d, 1 H), 11.05 (s, 1 H). |
| 162 | 2-F-Ph | S | Me | N-(4-(2,4-dichlorophenylthio)pyridin-2-yl)-4-methylthiazol-2-amine: ¹H NMR (DMSO-d₆) δ 2.19 (s, 3 H), 6.52 (s, 1 H); 6.60 (d, 1 H), 6.71 (s, 1 H), 7.38 (t, 1 H), 7.47 (t, 1 H), 7.65-7.71 (m, 2 H), 8.10 (d, 1 H), 11.07 (s, 1 H). |
| 163 | cyclopentyl | S | Me | N-(4-(cyclopentylthio)pyridin-2-yl)-4-methylthiazol-2-amine: ¹H NMR (DMSO-d₆) δ 1.48-1.75 (m, 6 H), 2.15-2.24 (m, 2 H), 2.23 (s, 3 H), 3.74 (m, 1 H), 6.52 (s, 1 H), 6.76 (d, 1 H), 6.95 (s, 1 H), 8.06 (d, 1 H), 11.04 (s, 1 H). |
| 164 | 4-pyridyl | S | Me | 4-methyl-N-(4-(pyridin-4-ylthio)pyridin-2-yl)thiazol-2-amine: ¹H NMR (DMSO-d₆) δ 2.22 (s, 3 H), 6.57 (s, 1 H), 6.87 (d, 1 H), 7.02 (s, 1 H), 7.41 (d, 2 H), 8.25 (d, 1 H), 8.56 (d, 2 H), 11.22 (s, 1 H). |
| 165 | 2-Cl-5-(COOEt)-Ph | S | Me | ethyl 4-chloro-3-(2-(4-methylthiazol-2-ylamino)pyridin-4-ylthio)benzoate: ¹H NMR (DMSO-d₆) δ 1.31 (t, 3 H), 2.19 (s, 3 H), 4.33 (q, 2 H), 6.53 (s, 1 H), 6.67-6.69 (m, 2 H), 7.89 (d, 1 H), 8.08 (d, 1 H), 8.13-8.15 (m, 2 H), 11.06 (s, 1 H). |
| 166 | cyclohexyl | S | Me | N-(4-(cyclohexylthio)pyridin-2-yl)-4-methylthiazol-2-amine: ¹H NMR (DMSO-d₆) δ 1.22-1.48 (m, 5 H), 1.62(m, 1 H), 1.71-1.76 (m, 2 H), 2.00-2.03 (m, 2 H), 2.23 (s, 3 H), 3.42 (m, 1 H), 6.53 (s, 1 H), 6.77 (d, 1 H), 6.95 (s, 1 H), 8.06 (d, 1 H), 11.04 (s, 1 H). |
| 167 | (trans)-2-Me-cyclohexyl | O | Me | 4-methyl-N-(4-((trans)-2-methylcylohexyloxy)pyridin-2-yl)thiazol-2-amine: ¹H NMR (DMSO-d₆) δ 0.94 (d, 3 H), 1.08-1.40 (m, 4 H), 1.58-1.80 (m, 4 H), 2.07 (m, 1 H), 2.22 (s, 3 H), 3.92 (m, 1 H), 6.49 (s, 1 H), 6.52-6.57 (m, 2 H), 8.05 (d, 1 H), 10.88 (s, 1 H). |
| 168 | 2-methyl-3-furyl | S | Me | 4-methyl-N-(4-(2-methylfuran-3-ylthio)pyridin-2-yl)thiazol-2-amine: ¹H NMR (DMSO-d₆) δ 2.15 (s, 3 H), 2.26 (s, 3H), 6.46 (s, 1H), 6.52 (s, 1 H), 6.55 (d, 1 H), 6.66 (s, 1 H), 7.74 (s, 1 H), 8.01 (d, 1 H), 10.99 (s, 1 H). |
| 169 | 2,6-diF | S | Me | N-(4-(2,6-difluorophenylthio)pyridin-2-yl)-4-methylthiazol-2-amine: ¹H NMR (DMSO-d₆) δ 2.19 (s, 3 H), 6.53 (s, 1 H), 6.65 (d, 1 H), 6.69 (s, 1 H), 7.40 (t, 2 H), 7.75 (m, 1 H), 8.11 (d, 1 H), 11.06 (s, 1 H). |

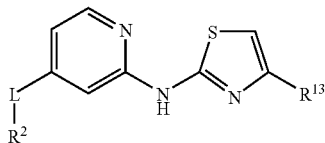

| Example # | R² | L | R¹³ | Name |
|---|---|---|---|---|
| 170 | 2,6-diClPh | S | COOEt | ethyl 2-(4-(2,6-dichlorophenylthio)pyridin-2-ylamino)thiazole-4-carboxylate: ¹H NMR (DMSO-d₆) δ 1.29 (t, 3 H), 4.24 (q, 2 H), 6.49 (s, 1 H), 6.61 (d, 1 H), 7.65 (t, 1 H), 7.79 (d, 2 H), 7.85 (s, 1 H), 8.14 (d, 1 H), 11.58 (s, 1 H). |
| 171 | quinolin-5-yl | O | Me | 4-methyl-N-(4-(quinolin-5-yloxy)pyridin-2-yl)thiazol-2-amine: ¹H NMR (DMSO-d₆) δ 2.18 (s, 3 H), 6.52 (m, 2 H), 6.61 (d, 1 H), 7.46 (d, 1 H), 7.57 (dd, 1 H), 7.85 (t, 1 H), 8.01 (d, 1 H), 8.20 (d, 1 H), 8.30 (d, 1 H), 8.99 (m, 1 H), 10.94 (s, 1 H). |
| 172 | quinolin-6-yl | O | Me | 4-methyl-N-(4-(quinolin-6-yloxy)pyridin-2-yl)thiazol-2-amine: ¹H NMR (DMSO-d₆) δ 2.18 (s, 3 H), 6.52 (s, 1 H), 6.61 (s, 1 H), 6.64 (d, 1 H), 7.57 (dd, 1 H), 7.63 (d, 1 H), 7.79 (s, 1 H), 8.14 (d, 1 H), 8.22 (d, 1 H), 8.38 (d, 1 H), 8.92 (d, 1 H), 10.97 (s, 1 H). |
| 173 | isoquinolin-7-yl | O | Me | N-(4-(isoquinolin-7-yloxy)pyridin-2-yl)-4-methylthiazol-2-amine: ¹H NMR (DMSO-d₆) δ 2.13 (s, 3 H), 6.48 (s, 1 H), 6.56 (s, 1 H), 6.59 (d, 1 H), 7.62 (d, 1 H), 7.85-7.88 (m, 2 H), 8.08 (d, 1 H), 8.17 (d, 1 H), 8.48 (d, 1 H), 9.27 (s, 1 H), 10.93 (s, 1 H). |
| 174 | 7-quinolinyl | O | Me | 4-methyl-N-(4-(quinolin-7-yloxy)pyridin-2-yl)thiazol-2-amine hydrochloride: ¹H NMR (DMSO-d₆) δ 2.30 (s, 3 H), 6.81 (s, 1 H), 6.97 (d, 1 H), 7.07 (s, 1 H), 7.82 (d, 1 H), 7.99 (dd, 1 H), 8.07 (s, 1 H), 8.42 (d, 1 H), 8.47 (d, 1 H), 9.10 (d, 1 H), 9.27 (d, 1 H). |
| 175 | 5-isoquinolinyl | O | Me | N-(4-(isoquinolin-5-yloxy)pyridin-2-yl)-4-methylthiazol-2-amine: ¹H NMR (DMSO-d₆) δ 2.18 (s, 3 H), 6.50-6.62 (m, 3 H), 7.63-7.80 (m, 3 H), 8.12 (d, 1 H), 8.19 (d, 1 H), 8.54 (d, 1 H), 9.45 (s, 1 H), 10.94 (s, 1 H). |

Example 176

2-(2-(4-(Naphthalen-1-yloxy)pyridin-2-ylamino)thiazol-4-yl)ethanol

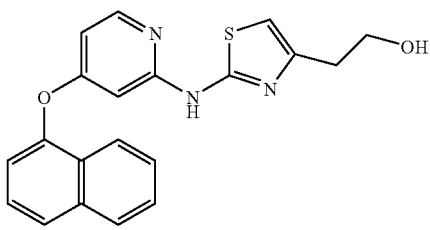

A solution of ethyl 2-(2-(4-(naphthalen-1-yloxy)pyridin-2-ylamino)thiazol-4-yl)acetate (prepared from 2-chloro-4-(naphthalen-1-yloxy)pyridine (1.18 g, 4.61 mmol) and ethyl 2-(2-aminothiazol-4-yl)acetate according to the method of example 1 step B; 0.370 g, 0.913 mmol) in THF (4 ml) was added to a 1M solution of lithium aluminum hydride in THF (5 mL) at 0° C. The reaction mixture was stirred at ambient temperature for one hour, then cooled in an ice bath and quenched carefully with an excess of sodium sulfate decahydrate and stirred overnight. The reaction mixture was filtered, the solids were washed with THF several times, and the combined filtrate was concentrated. The crude material was purified via MPLC, eluting first with 1:1 hexane:ethyl acetate, followed by ethyl acetate. The component which eluted with ethyl acetate was concentrated and triturated with hexanes:dichloromethane (4:1, 15 mL), filtered, washed with hexanes, and dried to afford the title compound (0.125 g, 37.7% yield). ¹H NMR (d₆-DMSO) δ 2.67 (t, 2H), 3.63 (q, 2H), 4.57 (t, 1H), 6.51 (s, 1H), 6.57 (m, 214), 7.36 (d, 1H), 7.55-7.63 (m, 3H), 7.85 (d, 1H), 7.92 (d, 1H), 8.05 (d, 1H), 8.17 (d, 1H), 10.97 (s, 1H).

Example 177

4-Chloro-3-(2-(4-methylthiazol-2-ylamino)pyridin-4-ylthio)benzoic acid hydrochloride

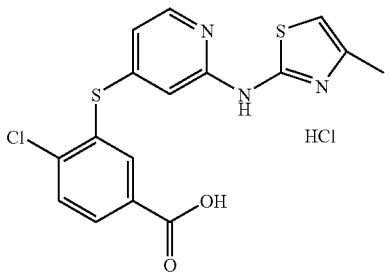

Prepared according to the method of Example 31. $^1$H NMR ($d_6$-DMSO) δ 2.25 (s, 3H), 6.69 (s, 1H), 6.81 (d, 1H), 6.82 (s, 1H), 7.88 (d, 1H), 8.08 (d, 1H), 8.15 (s, 1H), 8.21 (d, 1H).

Example 178

2-(3-(2-(4-Methylthiazol-2-ylamino)pyridin-4-yloxy)phenoxy)ethanol

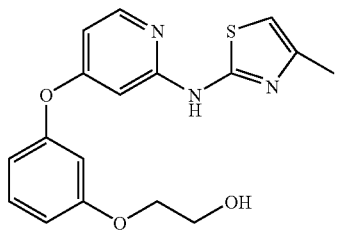

Lithium aluminum hydride in ether (1.0 M, 3.86 ml, 3.86 mmol) was added to a solution of THF (50 mL) at 0° C., 2-(3-(2-(4-methylthiazol-2-ylamino)pyridin-4-yloxy)phenoxy)acetic acid hydrochloride (Example 66; 0.380 g, 0.965 mmol) was added portionwise. The reaction was stirred for one hour, and then quenched with an excess of solid saturated sodium sulfate decahydrate. The reaction was stirred overnight and filtered, and the solid cake was washed several times with THF. The combined filtrates were concentrated and the residue was purified by MPLC (Biotage), eluting with ethyl acetate to afford the product as the free base. The free base was dissolved in ether, and 1M HCl in ether was added. The mixture was diluted with hexanes, filtered, and washed with hexanes to afford the title compound (0.065 g, 17.7% yield) as a white powder. $^1$H NMR ($d_6$-DMSO) δ 2.22 (s, 3H), 3.66 (t, 2H), 3.95 (t, 2H), 6.60-6.76 (m, 5H), 6.85 (d, 1H), 7.35 (t, 1H), 8.19 (d, 1H).

Example 179

N-(3-fluoro-4-(phenylthio)pyridin-2-yl)-4-methylthiazol-2-amine

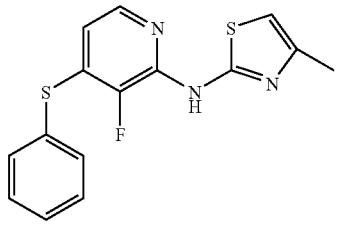

Step A: Preparation of 2-chloro-3-fluoro-4-(phenylthio)pyridine: 2-Chloro-3-fluoropyridine (3.00 g, 22.8 mmol) was added to a mixture of 1.8 M lithium diisopropyl amide (19.0 ml, 34.2 mmol) and THF (50 mL) at −78° C. The reaction was stirred for an hour at −78° C., and then a solution of 1,2-diphenyldisulfane (9.96 g, 45.6 mmol) in THF (5 mL) was added. The reaction was stirred for an hour at −78° C. and then quenched with saturated ammonium chloride and partitioned between ether and water. The organic layer was washed with 2N NaOH, 2N HCl, brine, dried (MgSO$_4$), and concentrated. The crude material was purified via MPLC (Biotage) eluting with 10:1 hexane:ethyl acetate to afford the desired product (3.95 g, 72.3% yield) as a pale yellow oil.

Step B: Preparation of N-(3-fluoro-4-(phenylthio)pyridin-2-yl)-4-methylthiazol-2-amine: Degassed toluene (10 mL) was added to a mixture of 2-chloro-3-fluoro-4-(phenylthio)pyridine (0.500 g, 2.09 mmol), 4-methylthiazol-2-amine (0.238 g, 2.09 mmol), tris(dibenzylideneacetone)dipalladium (0) (0.0955 g, 0.104 mmol) and potassium phosphate (0.487 g, 2.29 mmol), and then degassed water (3 mL) was added. The reaction was stirred overnight at 90° C., then partitioned between ethyl acetate and water, washed with brine, dried, and concentrated. The crude material was purified by MPLC (Biotage), eluting with 3:1 hexane:ethyl acetate to afford the desired product (0.364 g, 55.0% yield) as white crystals. $^1$H NMR ($d_6$-DMSO) δ 2.24 (s, 3H), 6.21 (t, 1H), 6.56 (s, 1H), 7.52-7.61 (m, 5H), 7.93 (d, 1H), 11.35 (bs, 1H).

Example 180

N-(4-(2,6-difluorophenoxy)pyridin-2-yl)-5-methylthiazolo[5,4-b]pyridin-2-amine hydrochloride

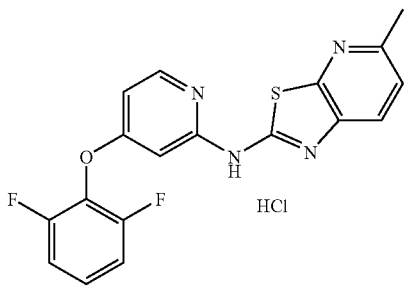

Step A: Preparation of 2-chloro-3-isothiocyanato-6-methylpyridine: A solution of thiophosgene (3.871 g, 33.66 mmol) in dichloromethane (10 mL) was added to a mixture of 2-chloro-6-methylpyridin-3-amine (4.00 g, 28.05 mmol) and sodium carbonate (5.947 g, 56.11 mmol) in dichloromethane (200 mL). The reaction was stirred overnight at ambient temperature, then washed with water, brine, dried, and concentrated to afford the desired product (5.2 g, 100.4% yield) as a tan powder.

Step B: Preparation of N-(4-(2,6-difluoro-phenoxy)pyridin-2-yl)-5-methylthiazolo[5,4-b]pyridin-2-amine hydrochloride: A mixture of 2-chloro-3-isothiocyanato-6-methylpyridine (0.0831 g, 0.450 mmol) and 4-(2,6-difluorophenoxy)pyridin-2-amine (0.100 g, 0.450 mmol) in DMF (2 mL) was stirred at 80° C. for 3 hours and then at 120° C. overnight. The reaction was cooled and partitioned between ethyl acetate and 2N NaOH. The organic layer was washed with water and brine, dried, and concentrated. The crude material was purified via MPLC (Biotage) eluting with 3:2 hexane:ethyl acetate. The isolated product was dissolved in ether (5 mL), followed by the addition of 1N HCl in ether (3 mL) and then hexanes (4 mL). The resulting solids were filtered and washed with hexanes to provide the desired product (0.095 g, 51.9% yield) as a white powder: $^1$H NMR (d6-DMSO) δ 2.64 (s, 3H), 6.71 (s, 1H), 6.81 (d, 1H), 7.38-7.53 (m, 4H), 8.05 (d, 1H), 8.36 (d, 1H).

Example 181

N-(4-(2,6-difluorophenoxy)pyridin-2-yl)thiazolo[5,4-b]pyridin-2-amine hydrochloride

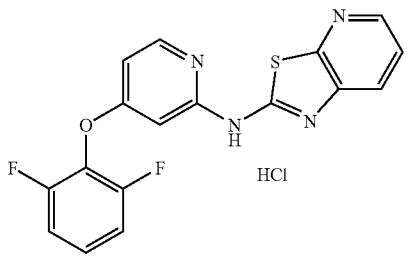

Prepared according to the method of Example 180. $^1$H NMR (d$_6$-DMSO) δ 6.76 (s, 1H), 6.77 (d, 1H), 7.38-7.52 (m, 4H), 7.92 (d, 1H), 8.32-8.35 (m, 2H), 11.58 (s, 1H).

Example 182

N-(4-(2,6-dichlorophenylthio)pyridin-2-yl)thiazolo[5,4-b]pyridin-2-amine

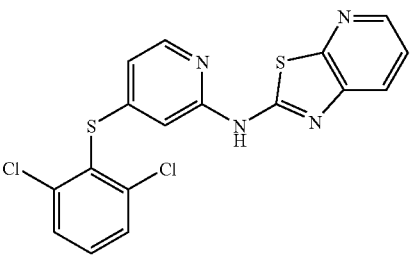

Prepared according to the method of Example 180. $^1$H N (d$_6$-DMSO) δ 6.72 (s, 1H), 6.77 (d, 1H), 7.38 (dd, 1H), 7.68 (t, 1H), 7.80 (d, 2H), 7.89 (d, 1H), 8.22 (d, 1H), 8.33 (d, 1H), 11.58 (s, 1H).

Example 183

N-(4-(2,6-dichlorophenylthio)pyridin-2-yl)-3-methyl-1,2,4-thiadiazol-5-amine

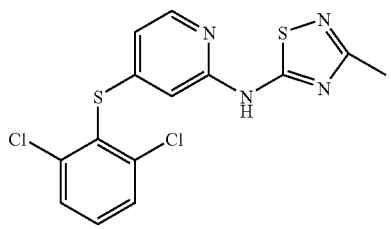

Prepared according to the method of Example 4, step B. $^1$H NMR (d$_6$-DMSO) δ 2.35 (s, 3H), 6.57 (s, 1H), 6.74 (d, 1H), 7.66 (t, 1H), 7.79 (d, 2H), 8.22 (d, 1H), 11.86 (s, 1H).

Example 184

N-(4-(2,6-dichlorophenylthio)pyridin-2-yl)-3-phenyl-1,2,4-thiadiazol-5-amine

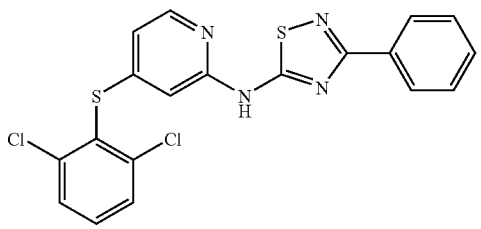

Prepared according to the method of Example 4, step B. $^1$H NMR (d$_6$-DMSO) δ 6.64 (s, 1H), 6.77 (d, 1H), 7.47-7.50 (m, 3H), 7.68 (t, 1H), 7.81 (d, 2H), 8.14 (d, 2H), 8.28 (d, 1H), 12.15 (s, 1H).

Example 185

3-(5-bromo-2-(4-phenethylthiazol-2-ylamino)pyridin-4-ylthio)-5-chloroisonicotinonitrile

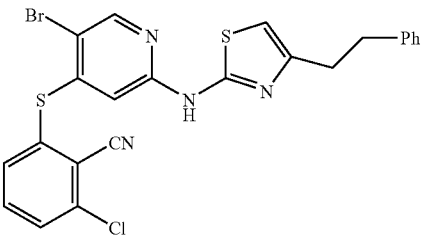

Step A: Preparation of 4-(4-methoxybenzylthio)-2-chloropyridine: A flask was charged with 2-chloro-4-nitropyridine (12.75 g, 80.4 mmol), (4-methoxyphenyl)methanethiol (12.40 g, 80.4 mmol) and DMF (100 mL). Cesium carbonate (31.43 g, 96.48 mmol) was added in portions, and the mixture was stirred for 2 hours at ambient temperature. The solution was diluted with dichloromethane (250 mL) and washed with diluted sodium bicarbonate solution, dried over magnesium sulfate, filtered and evaporated. The resulting yellowish residue was triturated with hexanes and the solid was filtered to obtain the desired product (18.1 g, 85%) as a pale yellow powder.

Step B: Preparation of 4-(4-methoxybenzylthio)pyridine-2-amine: 4-(4-methoxybenzylthio)-2-chloropyridine (12 g, 45.2 mmol) and diphenylmethanimine (8.7 ml, 52.0 mmol) were dissolved in toluene (300 mL). The solution was evacuated and purged with nitrogen. Pd(OAc)$_2$ (0.51 g, 2.3 mmol), rac-Binap (1.41 g, 2.26 mmol), and NaOtBu (6.1 g, 63.2 mmol) were added. The mixture stirred under N$_2$ at 100° C. for 90 minutes. After cooling to ambient temperature, the mixture was quenched with water and the material was extracted with EtOAc, dried, and concentrated to afford the 4-(4-methoxybenzylthio)-N-(diphenylmethylene)pyridine-2-amine crude intermediate (18.5 g). The crude imine was dissolved in MeOH (200 mL) and hydroxylamine hydrochloride (11.0 g, 158 mmol) and sodium acetate trihydrate (30.7 g, 226 mmol) were added. The reaction was stirred at ambient temperature for 2 hours, then diluted with 1N HCl and extracted with EtOAc. The aqueous layer was basified to pH 9 and extracted with EtOAc. This second EtOAc layer was dried and concentrated to provide 4.7 g of the desired product. An additional 4.3 g of product was isolated by concentrating the first EtOAc layer extraction and purified via flash chromatography (70% EtOAc/hexanes) to provide the desired product (Total yield: 9.0 g, 80%) was isolated as a yellow solid.

Step C: Preparation of 4-(4-methoxybenzylthio)-5-bromopyridin-2-amine: 4-(4-methoxybenzylthio)pyridine-2-amine (2.4 g, 9.7 mmol) was dissolved in acetic acid (30 mL). Bromine (1M in AcOH, 9.8 ml, 9.8 mmol) was added dropwise at ambient temperature and the reaction stirred for 30-minutes. The solution was concentrated and the residue was neutralized with saturated NaHCO$_3$ solution. The solution was extracted with EtOAc and the organic layer was dried and concentrated. The residue was purified by flash chromatography (70% EtOAc/hexanes) to obtain the desired product (1.71 g, 54% yield) as a yellow solid.

Step D: Preparation of 1-(4-(4-methoxybenzylthio)-5-bromopyridin-2-yl)-3-benzoylthiourea: 4-(4-methoxybenzylthio)-5-bromopyridin-2-amine (7.45 g, 22.9 mmol) was dissolved in THF (80 mL). Benzoyl isothiocyanate (3.4 ml, 25 mmol) was added, and the reaction was stirred overnight at ambient temperature. The solution was diluted in 9:1 hexanes:EtOAc and stirred for 5 minutes, then filtered and dried to provide the desired product (8.5 g, 76% yield) as a brown solid.

Step E: Preparation of 1-(4-(4-methoxybenzylthio)-5-bromopyridin-2-yl)thiourea: 1-(4-(4-methoxybenzylthio)-5-bromopyridin-2-yl)-3-benzoylthiourea (8.50 g, 17.4 mmol) was suspended in THF (150 mL). NaOH (116 ml, 348 mmol) was added, and the reaction was stirred at 65° C. overnight. The solution was cooled and filtered, and the solids were washed with cold water. The solids were then triturated in EtOH and filtered to provide the desired product (5.3 g, 79% yield) as a tan solid.

Step F: Preparation of 4-(4-methoxybenzylthio)-5-bromo-N-(4-phenethylthiazol-2-yl)pyridine-2-amine: 1-(4-(4-methoxybenzylthio)-5-bromopyridin-2-yl)thiourea (3.0 g, 7.8 mmol) and 1-bromo-4-phenylbutan-2-one (1.77 g, 7.8 mmol) were diluted in EtOH (120 mL). Triethylamine (2.2 ml, 15.6 mmol) was added, and the solution was heated at 75° C. for 3 hours. The solution was cooled and concentrated to half the amount of solvent. The solid was filtered and rinsed with cold EtOH to provide the desired product (2.44 g, 61% yield) as a tan solid.

Step G: Preparation of 5-bromo-2-(4-phenethylthiazol-2-ylamino)pyridine-4-thiol: 4-(4-methoxybenzylthio)-5-bromo-N-(4-phenethylthiazol-2-yl)pyridine-2-amine (1.23 g, 2.4 mmol) was dissolved in TFA (10 mL):anisole (2 mL) (5:1). The reaction mixture was stirred at 75° C. overnight, then neutralized with solid NaHCO$_3$, extracted with EtOAc, dried, and concentrated. The crude material was triturated in MeOH and filtered. The filtrate was further concentrated and triturated again with MeOH. The solids were combined and dried to give the desired product (0.68 g, 72% yield).

Step H: Preparation of 3-(5-bromo-2-(4-phenethylthiazol-2-ylamino)pyridin-4-ylthio)-5-chloroisonicotinonitrile: A flask was charged with 5-bromo-2-(4-phenethylthiazol-2-ylamino)pyridine-4-thiol (0.040 g, 0.10 mmol), 3,5-dichloroisonicotinonitrile (0.019 g, 0.11 mmol), Cs$_2$CO$_3$ (0.037 g, 0.11 mmol), and DMSO (2 mL). The reaction mixture was stirred at ambient temperature overnight, then quenched with water, extracted with EtOAc, dried, and concentrated. The crude material was purified by flash chromatography to provide the desired product (0.026 g, 48% yield) as a yellow solid. $^1$H NMR (CDCl$_3$) δ 8.74 (d, 2H), 8.39 (s, 1H), 7.16-7.30 (m, 5H), 6.68 (s, 1H), 6.33 (s, 1H), 2.85-2.92 (m, 4H).

The following compounds were also prepared by the procedure listed in example 185, step H.

| Example # | R$^2$ | Name |
|---|---|---|
| 186 | 2-nitropyridin-3-yl | 5-bromo-4-(2-nitropyridin-3-ylthio)-N-(4-phenethylthiazol-2-yl)pyridin-2-amine: $^1$H NMR (CDCl$_3$) δ 8.52 (s, 1 H), 8.45 (d, 1 H), 7.52 (d, 1 H), 7.42-7.45 (m, 1 H), 7.09-7.26 (m, 6 H), 6.41 (s, 1 H), 2.91-2.95 (m, 4 H). |
| 187 | 2-chloropyridin-4-yl | 5-bromo-4-(2-chloropyridin-4-ylthio)-N-(4-phenethylthiazol-2-yl)pyridin-2-amine: $^1$H NMR (CDCl$_3$) δ 8.45 (s, 1 H), 8.34 (d, 1 H), 7.13-7.29 (m, 7 H), 6.86 (s, 1 H), 6.37 (s, 1 H), 2.85-2.96 (m, 4 H). |
| 188 | 5-bromo-2-chloropyridin-4-yl | 5-bromo-4-(5-bromo-2-chloropyridin-4-ylthio)-N-(4-phenethyliazol-2-yl)pyridin-2-amine: $^1$H NMR(d$_6$-DMSO) δ 11.70 (s, 1 H), 8.86 (s, 1 H), 8.63 (s, 1 H), 7.42 (s, 1 H), 7.17-7.29 (m, 6 H), 6.68 (s, 1 H), 2.86-2.97 (m, 4 H). |

-continued

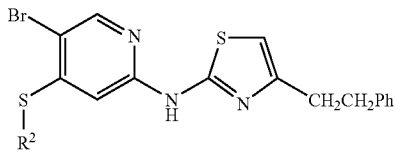

| Example # | R² | Name |
|---|---|---|
| 189 | 3-methylisoxazolo[5,4-b]pyridin-4-yl | 5-bromo-4-(3-methylisoxazolo[5,4-b]pyridin-4-ylthio)-N-(4-phenethylthiazol-2-yl)pyridin-2-amine: ¹H NMR (CDCl₃) δ 8.49 (s, 1 H), 8.43 (d, 1 H), 7.02-7.26 (m, 5 H), 7.02 (d, 1 H), 6.84 (s, 1 H), 6.35 (s, 1 H), 2.65-2.82 (m, 2 H), 2.87-2.91 (m, 2 H), 2.65 (s, 3 H). |
| 190 | 6-Boc-5,6,7,8-tetrahydropyrido[4,3-d]pyrimidin-4-yl | tert-butyl 4-(5-bromo-2-(4-phenethylthiazol-2-ylamino)pyridin-4-ylthio)-7,8-dihydropyrido[4,3-d]pyrimidine-6(5 H)-carboxylate: ¹H NMR (d₆-DMSO) δ 11.50 (s, 1 H), 8.78 (s, 1 H), 8.54.(s, 1 H), 7.17-7.29 (m, 6 H), 6.65 (s, 1 H), 4.52 (s, 2 H), 3.71 (t, 2 H), 2.85-2.94 (m, 6 H), 1.42 (s, 9 H). |
| 191 | thieno[3,2-b]pyridin-7-yl | 5-bromo-N-(4-phenethylthiazol-2-yl)-4-(thieno[3,2-b]pyridin-7-ylthio)pyridin-2-amine: ¹H NMR (d₆-DMSO) δ 11.06 (bs, 1 H), 8.83 (d, 1 H), 8.42 (s, 1 H), 8.23 (d, 1 H). 7.73 (d, 1 H), 7.66 (d, 1 H), 7.22-7.26 (m, 3 H), 7.16 (d, 2 H), 6.56 (s, 1 H), 6.49 (s. 1 H), 2.75-2.87 (m, 4 H). |
| 192 | 2,5-dimethylpyrazolo[1,5-a]pyrimidin-7-yl | 5-bromo-4-(2,5-dimethylpyrazolo[1,5-a]pyrimidin-7-ylthio)-N-(4-phenethylthiazol-2-yl)pyridin-2-amine: ¹H NMR (CDCl₃) δ 8.59 (s, 1 H), 7.08-7.26 (m, 9 H), 6.41 (s, 1 H), 6.38 (s, 1 H), 6.08 (s, 1 H), 2.89-2.93 (m, 4 H), 2.52 (s, 3 H), 2.43 (s, 3 H). |

The following compounds were also prepared according to the method of Example 185.

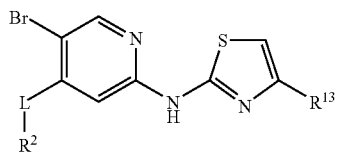

| Example # | R² | L | R¹³ | Name |
|---|---|---|---|---|
| 193 | 3-cyanopyridin-4-yl | S | CH₂CH₂Ph | 4-(5-bromo-2-(4-phenethylthiazol-2-ylamino)pyridin-4-ylthio)nicotinonitrile: ¹H NMR (CDCl₃) δ 8.84 (m, 1 H), 8.60 (d, 1 H), 8.53 (s, 1 H), 7.27 (m, 2 H), 7.19 (m, 1 H), 7.17 (m, 1 H), 7.15 (m, 1 H), 7.10 (s, 1 H), 7.06 (dd, 1 H), 6.39 (s, 1 H), 2.92 (m, 4 H). |
| 194 | 3-(trifluoromethyl)pyridin-4-yl | S | CH₂CH₂Ph | N-(5-bromo-4-(3-(trifluoromethyl)-pyridin-4-ylthio)pyridin-2-yl)-4-phenethylthiazol-2-amine: ¹H NMR (CDCl₃) δ 8.94 (m, 1 H), 8.65 (d, 1 H), 8.50 (s, 1 H), 7.27 (m, 2 H), 7.18 (m, 3 H), 7.11 (d, 1 H), 6.98 (s, 1 H), 6.35 (s, 1 H), 2.92 (m, 4 H). |

Example 195

3-(5-bromo-2-(4-phenethylthiazol-2-ylamino)pyridin-4-yloxy)-5-chloroisonicotinonitrile

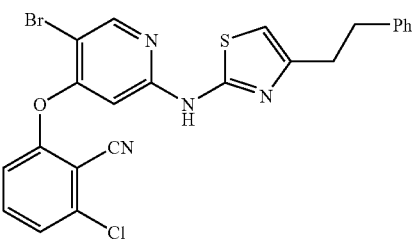

Step A: Preparation of 4-(benzyloxy)pyridin-2-amine: 4-(benzyloxy)-2-chloropyridine (18.6 g, 84.7 mmol), XPHOS (4.04 g, 8.47 mmol), and Pd$_2$dba3 (3.88 g, 4.23 mmol) were mixed in THF (250 mL). LHMDS (93.1 ml, 93.1 mmol) was added and the reaction was heated at 50° C. for 1.5 hours. The solution was cooled and diluted with 1N HCl (50 mL) and stirred at ambient temperature for 2 hours. The reaction was concentrated and the residue was extracted with EtOAc. The aqueous layer was basified with saturated K$_2$CO$_3$ and the aqueous layer was extracted with EtOAc. The combined organic layers were dried and concentrated to give the desired product (11.9 g, 70.2% yield) as a brown solid.

Step B: Preparation of 4-(benzyloxy)-5-bromopyridin-2-amine: A flask was charged with 4-(benzyloxy)pyridin-2-amine (10.69 g, 53.39 mmol) and 20 mL acetic acid was added. Bromine (2.735 ml, 53.39 mmol) and the reaction was stirred for 10 minutes. The reaction mixture was concentrated and purified using silica gel column chromatography eluting with 50%-100% ethyl acetate/hexane provide the desired product (7.0 g, 42.28% yield) as brown solid Step C: Preparation of 1-benzoyl-3-(4-(benzyloxy)-5-bromopyridin-2-yl)thiourea: A flask was charged with 4-(benzyloxy)-5-bromopyridin-2-amine (6.90 g, 24.7 mmol), and THF (250 mL). Benzoyl isothiocyanate (4.24 g, 26.0 mmol) was added and the reaction was stirred at ambient temperature overnight. The reaction mixture was concentrated, and 9:1 Hexanes:ethyl acetate (400 mL) was added to the residue. The suspension was filtered to give the desired product (10 g, 82.3% yield) as light brown solid.

Step D: Preparation of 1-(4-(benzyloxy)-5-bromopyridin-2-yl)thiourea: A flask was charged with 1-benzoyl-3-(4-(benzyloxy)-5-bromopyridin-2-yl)thiourea (9.8 g, 22.2 mmol) and THF (200 mL). 6N NaOH (100 mL) and NaOH (5 g) were added. The reaction was stirred at 60° C. for 3 hours, then concentrated and filtered to give the desired product (2.54 g, 33.9% yield) as off white solid.

Step E: Preparation of 4-(benzyloxy)-5-bromo-N-(4-phenethylthiazol-2-yl)pyridin-2-amine: A flask was charged with 1-(4-(benzyloxy)-5-bromopyridin-2-yl)thiourea (2.34 g, 6.92 mmol), 1-bromo-4-phenylbutan-2-one (1.65 g, 7.26 mmol), and triethylamine (1.93 ml, 13.8 mmol). Ethanol (100 mL) was added and the reaction was stirred at 75° C. for 8 hours. The reaction was cooled and filtered, and the collected solids were washed with water to give the desired product (2.54 g, 77.9% yield) as a white solid.

Step F: Preparation of 5-bromo-2-(4-phenethylthiazol-2-ylamino)pyridin-4-ol hydrochloride: A flask was charged with 4-(benzyloxy)-5-bromo-N-(4-phenethylthiazol-2-yl)pyridin-2-amine (1.0 g, 2.1 mmol), dioxane (20 mL), concentrated HCl (70 mL) and 6N HCl (10 mL). The reaction was stirred at 95° C. overnight. The reaction was filtered and the collected solids were washed with water and under high vacuum overnight to give the desired product (0.80 g, 89% yield) as light yellow solid.

Step G: Preparation of 3-(5-bromo-2-(4-phenethylthiazol-2-ylamino)pyridin-4-yloxy)-5-chloroisonicotinonitrile: A mixture of 5-bromo-2-(4-phenethylthiazol-2-ylamino)pyridin-4-ol (0.060 g, 0.16 mmol), 3,5-dichloroisonicotinonitrile (0.030 g, 0.18 mmol) and Cs$_2$CO$_3$ (0.057 g, 0.18 mmol) was stirred in DMSO (2 mL) at 100° C. overnight. The solution was cooled, quenched with water, extracted with EtOAc, dried, and concentrated. The crude material was purified by flash chromatography gave the desired product (0.006 g, 7% yield) as a white solid. $^1$H NMR (CDCl$_3$) δ 8.55 (s, 1H), 8.50 (s, 1H), 8.27 (s, 1H), 7.12-7.26 (m, 5H), 6.87 (s, 1H), 6.37 (s, 1H), 2.89 (bs, 4H).

Example 196

5-bromo-N-(4-phenethylthiazol-2-yl)-4-(5,6,7,8-tetrahydropyrido[4,3-d]pyrimidin-4-ylthio)pyridin-2-amine

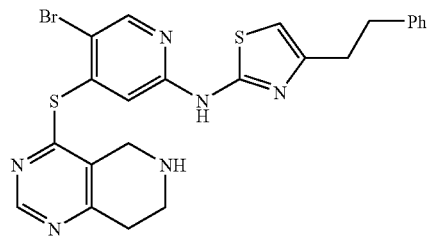

tert-Butyl 4-(5-bromo-2-(4-phenethylthiazol-2-ylamino)pyridin-4-ylthio)-7,8-dihydropyrido[4,3-d]pyrimidine-6(5H)-carboxylate (0.023 g, 0.037 mmol) was dissolved in TFA (2 mL) and stirred at ambient temperature for 2 hours. The solution was neutralized with saturated NaHCO$_3$ and extracted with EtOAc. The organic layer was washed with brine, dried, and concentrated to afford the desired product (0.010 g, 52% yield) as a white solid. $^1$H NMR (CDCl$_3$) δ 8.66 (s, 1H), 8.51 (s, 1H), 7.14-7.27 (m, 6H), 6.38 (s, 1H), 3.99 (s, 2H), 3.22 (t, 2H), 2.89-2.96 (m, 6H).

Example 197

N-(5-bromo-4-((3-methyl-1,2,4-oxadiazol-5-yl)methyl)pyridin-2-yl)-4-phenethylthiazol-2-amine

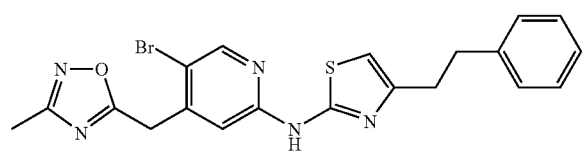

A vial was charged with 2-(5-bromo-2-(4-phenethylthiazol-2-ylamino)pyridin-4-yl)acetic acid (0.0863 g, 0.2063 mmol) in 5 ml of DMF and DIEA (0.03953 ml, 0.2269 mmol), and tetramethylfluoroformamidinium hexafluorophosphate (TFFH) (0.060 g, 0.227 mmol) were added consecutively. The mixture was stirred for 30 minutes and N-hydroxyacetamidine (0.0168 g, 0.227 mmol) was added. The mixture was heated at 100° C. overnight. The mixture was then cooled, diluted with dichloromethane, and washed with aqueous sodium bicarbonate, dried over magnesium sulfate, filtered and evaporated. The residue was purified by silica gel chromatography, eluting with 20% ethyl acetate/hexane to provide N-(5-bromo-4-((3-methyl-1,2,4-oxadiazol-5-yl)methyl)pyridin-2-yl)-4-phenethylthiazol-2-amine (11 mg, 11.58% yield) as a yellow solid. $^1$H NMR (CDCl$_3$) δ 2.37 (s, 3H), 2.94-2.98 (m, 4H), 4.25 (s, 2H), 6.39 (s, 1H), 6.89 (s, 1H), 7.14-7.26 (m, 5H), 8.45 (s, 1H).

Example 198

N-(5-bromo-4-((5-methyl-1,3,4-oxadiazol-2-yl)methylpyridin-2-yl)-4-phenethylthiazol-2-amine

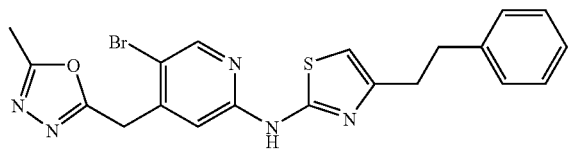

Step A: Preparation of ethyl 2-(2-chloropyridin-4-yl)acetate: In a 1000 mL round-bottom flask, diisopropylamine (80.21 mL, 567.5 mmol) was combined with THF (250 mL) and cooled to −78° C. Butyllithium (227.0 mL, 567.5 mmol) (2.5M in hexane) was added and the mixture was stirred for 30 minutes. 2-Chloro-4-methylpyridine (36.20 g, 283.8 mmol) in THF (100 mL) was added, and the mixture was stirred for 2 hours. A mixture of diethyl carbonate (37.82 mL, 312.1 mmol) and hexamethylphosphoramide (54.31 mL, 312.1 mmol) was added, and the mixture was stirred at −78° C. for one hour and then stirred at ambient temperature. The reaction was quenched with 25% ammonium chloride solution and extracted twice with ethyl acetate. The combined organic extracts were washed with brine, dried and evaporated. The crude oil was purified by silica gel chromatography, eluting with 5% ethyl acetate/hexane to provide the desired product as clear oil (42.75 g, 75.47% yield).

Step B: Preparation of ethyl 2-(2-(tert-butoxycarbonylamino)pyridin-4-yl)acetate: A flask was charged with ethyl 2-(2-chloropyridin-4-yl)acetate (20.00 g, 100.2 mmol), tert-butyl carbamate (35.21 g, 300.5 mmol), 9,9-dimethyl-4,5-bis(diphenylphosphino)xanthene (2.90 g, 5.01 mmol), tris(dibenzylideneacetone)dipalladium(0) (2.29 g, 2.51 mmol), cesium carbonate (48.96 g, 150 mmol) and THF (400 mL). The mixture was heated at reflux under nitrogen for 24 hours. Upon cooling, the reaction was quenched with 10% ammonium acetate solution and extracted with ethyl acetate. The combined organic extracts were washed with water and brine, dried and concentrated. The residue was purified by silica gel chromatography, eluting with 20% ethyl acetate/hexane to yield 20.80 g (72.6% yield) of the desired product as white solid.

Step C: Preparation of ethyl 2-(2-aminopyridin-4-yl)acetate: A flask was charged with ethyl 2-(2-(tert-butoxycarbonyl)pyridin-4-yl)acetate (20.00 g, 69.21 mmol) and dichloromethane (100 mL) and the mixture was cooled to 0° C. Trifluoroacetic acid (100 mL) was added and the mixture was stirred overnight. The solvent and excess trifluoroacetic acid were removed in vacuo to provide the desired product (36.05 g, containing 3 equivalents of TFA) as an oil, which was used without purification in the next step. LC/MS (APCI-pos) m/z 181 (M+H)$^+$ Step D: Preparation of ethyl 2-(2-amino-5-bromopyridin-4-yl)acetate: A flask was charged with ethyl 2-(2-aminopyridin-4-yl)acetate (12.45 g, 69.09 mmol) and acetic acid (100 mL). Bromine (3.550 ml, 69.09 mmol) was added, and the reaction mixture was stirred for 3 hours. The solvent was evaporated in vacuo and the residue was mixed with ice, basified with ammonium hydroxide, and extracted with ethyl acetate. The combined organic layers were washed with brine and concentrated. The residual brown oil was purified by silica gel chromatography, eluting with 1-2% methanol/dichloromethane to provide the desired product (8.15 g, 45.53% yield) as pale yellow solid.

Step E: Preparation of ethyl 2-(2-(3-benzoylthioureido)-5-bromopyridin-4-yl)acetate: A flask was charged with ethyl 2-(2-amino-5-bromopyridin-4-yl)acetate (2.700 g, 10.42 mmol) and THF (20 mL), and benzoyl isothiocyanate (1.546 mL, 11.46 mmol) was added. The mixture was stirred overnight at ambient temperature. The thick slurry was diluted with 50 mL of 10% ethyl acetate/hexane and filtered. The filter cake was washed with 10% ethyl acetate/hexane and dried to afford the desired product (3.75 g, 85.22%) as a pale yellow fluffy solid.

Step F: Preparation of ethyl 2-(5-bromo-2-thioureidopyridin-4-yl)acetate: A flask was charged with ethyl 2-(2-(3-benzoylthioureido)-5-bromopyridin-4-yl)acetate (2.940 g, 6.962 mmol) and ethanol (100 mL), and potassium carbonate (4.811 g, 34.81 mmol) was added. The mixture was heated at 70° C. for 2 hours, then filtered hot. The filter cake was washed with a small amount of ethanol, and the filtrate was concentrated to provide the desired product (2.205 g, 99.54%) as a yellow solid.

Step G: Preparation of ethyl 2-(5-bromo-2-(4-phenethylthiazol-2-ylamino)pyridin-4-yl)acetate: A flask was charged with ethyl 2-(5-bromo-2-thioureidopyridin-4-yl)acetate (2.200 g, 6.914 mmol), 1-bromo-4-phenylbutan-2-one (1.884 g, 8.297 mmol), DIEA (1.806 mL, 10.37 mmol) and ethanol (100 mL). The mixture was heated stirred at 70° C. for 2 hours, then cooled. The reaction was concentrated, and the residue was partitioned between chloroform and dilute sodium bicarbonate solution. The organic phase was washed with dilute sodium bicarbonate solution, dried over magnesium sulfate, filtered and evaporated. The solid residue was recrystallized from hexane/ethyl acetate to give the desired product (1.815 g, 58.81% yield) as a yellow solid.

Step H: Preparation of 2-(5-bromo-2-(4-phenethylthiazol-2-ylamino)pyridin-4-yl)acetic acid: A flask was charged with ethyl 2-(5-bromo-2-(4-phenethylthiazol-2-ylamino)pyridin-4-yl)acetate (1.123 g, 2.516 mmol) and THF (40 mL), and 1M sodium hydroxide (7.548 mL, 7.548 mmol) was added. The mixture was heated at 55° C. for 2 hours, and then diluted with THF and acidified with 1M HCl (8 mL). The reaction mixture was concentrated and the resulting slurry was filtered. The solids were washed with water and dried to give the desired product (1.035 g, 98.38% yield).

Step I: N-(5-bromo-4-((5-methyl-1,34-oxadiazol-2-yl)methyl)pyridin-2-yl)-4-phenethylthiazol-2-amine: A vial was charged with 2-(5-bromo-2-(4-phenethylthiazol-2-ylamino)pyridin-4-yl)acetic acid (0.098 g, 0.2343 mmol) in 3 ml of DMF, and 1,1'-carbonyldiimidazole (0.05698 g, 0.3514 mmol) was added. The mixture was stirred overnight, and then diisopropylethylamine (0.06121 mL, 0.3514 mmol), followed by acetohydrazide (0.02603 g, 0.3514 mmol) were added. The mixture was stirred for 4 hours at ambient temperature, diluted with ethyl acetate, washed with water and brine, dried over magnesium sulfate, filtered and evaporated. Crude yellowish solid was suspended in acetonitrile (5 mL), and phosphorous oxychloride (0.07237 mL, 0.7905 mmol) was added. The mixture was heated at 80° C. for 1 hour. The solvent was evaporated and the residue was partitioned between aqueous sodium bicarbonate and chloroform. The organic phase was washed with 1M NaOH and sodium bicarbonate, dried over magnesium sulfate, filtered and evaporated. The residue was purified by silica gel chromatography, eluting with 50-70% ethyl acetate/hexane to provide the desired product (17 mg, 23.84% yield) as pale yellow glassy solid. $^1$H NMR (CDCl$_3$) δ 2.48 (s, 3H), 2.92-2.96 (m, 4H), 4.24 (s, 2H), 6.39 (s, 1H), 6.86 (s, 1H), 7.12-7.26 (m, 5H), 8.44 (s, 1H).

Example 199

N-(5-bromo-4-((5-methyloxazol-2-yl)methyl)pyridin-2-yl)-4-phenethylthiazol-2-amine

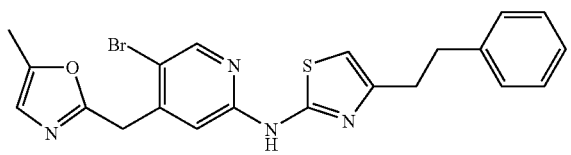

Prepared according to the method of Example 198, substituting 2-(5-bromo-2-(4-phenethylthiazol-2-ylamino)pyridin-4-yl)acetic acid for 2-(5-bromo-2-(4-phenethylthiazol-2-ylamino)pyridin-4-yl)acetic acid to provide the desired product (16 mg, 16.38% yield) as pale yellow glassy solid. $^1$H NMR (CDCl$_3$) δ 2.25 (s, 3H), 2.92-2.98 (m, 4H), 4.12 (s, 2H), 6.36 (s, 1H), 6.65 (s, 1H), 6.76 (s, 1H), 7.12-7.26 (m, 5H), 8.41 (s, 1H).

Example 200

3-((5-bromo-2-(4-phenethylthiazol-2-ylamino)pyridin-4-yl)methyl)-1H-pyrazol-5(4H)-one

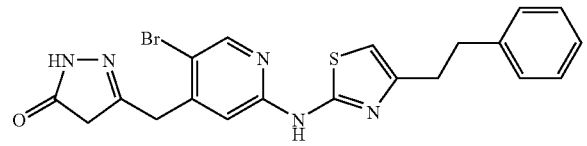

Step A: Preparation of ethyl 4-(5-bromo-2-(4-phenethylthiazol-2-ylamino)pyridin-4-yl)-3-oxobutanoate: A flask was charged with 2-(5-bromo-2-(4-phenethylthiazol-2-ylamino)pyridin-4-yl)acetic acid (0.576 g, 1.377 mmol) and THF (20 mL), and carbonyl diimidazole (0.3014 g, 1.859 mmol) was added. The mixture was heated at 50° C. for 2 hours. In a separate 50 mL scintillation vial, mono-ethyl malonate (0.2845 ml, 2.410 mmol) was dissolved in THF (15 mL) and cooled to 0° C., and isopropyl magnesium chloride (2.410 mL, 4.819 mmol) was added. This second mixture was stirred at ambient temperature for 30 minutes, then heated to 50° C. and stirred another 30 minutes. Both solutions were cooled to 0° C. and the second mixture was added to the first mixture. The combined mixture was stirred at ambient temperature overnight, then quenched with saturated ammonium chloride solution and extracted with ethyl acetate. The combined extracts were washed with water and brine, dried and evaporated. The residue was purified by silica gel chromatography, eluting with 20% ethyl acetate/hexane to provide the desired product (0.337 g, 46-10% yield) as white solid.

Step B: Preparation of 3-((5-bromo-2-(4-phenethylthiazol-2-ylamino)pyridin-4-yl)methyl)-1H-pyrazol-5(4H)-one: A flask was charged with ethyl 4-(5-bromo-2-(4-phenethylthiazol-2-ylamino)pyridin-4-yl)-3-oxobutanoate (0.0500 g, 0.1024 mmol) and ethanol (2 mL), and hydrazine hydrate (0.007471 mL, 0.1536 mmol) was added. The mixture was stirred at 45° C. for 4 hours. THF (2 mL) was added, and the mixture was stirred for 18 hours at 60° C. The mixture was concentrated and the residue was triturated with 50% ethyl acetate/hexane to afford the desired product (26 mg, 55.65% yield) as a white solid. $^1$H NMR (d$_6$-DMSO) δ 2.83-2.96 (m, 4H), 3.87 (s, 2H), 5.27 (s, 1H), 6.59 (s, 1H), 6.94 (s, 1H), 7.17-7.29 (m, 5H), 8.38 (s, 1H).

Example 201 tert-Butyl 4-((6-(4-methylthiazol-2-ylamino)-4-(quinolin-5-yloxy)pyridin-3-ylthio)methyl)piperidine-1-carboxylate

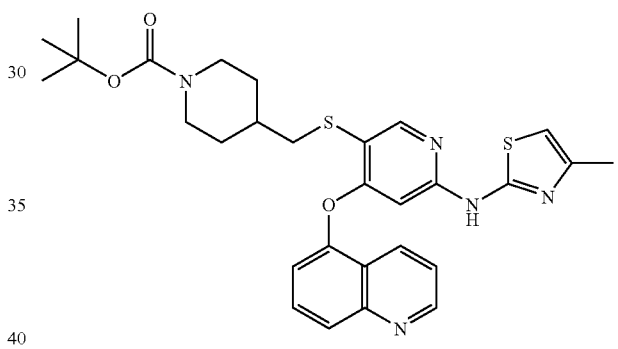

Step A: Preparation of N-(5-bromo-4-(quinolin-5-yloxy)pyridin 2-yl)-4-methylthiazol-2-amine: A mixture of 1-(5-bromo-4-(quinolin-5-yloxy)pyridin-2-yl)thiourea (2.00 g, 5.330 mmol), 1-chloropropan-2-one (0.6366 ml, 7.995 mmol), triethylamine (1.486 ml, 10.66 mmol), and ethanol (25 ml) was heated at reflux for two days. The organic solvents were concentrated, and hexanes:ethyl acetate (9:1) were added and the reaction was filtered. The residue was washed with water and ethyl acetate, and dried over high vacuum overnight to give the desired compound (1.70 g, 76.40% yield) as very light yellow solid.

Step B: Preparation of methyl 3-(6-(4-methylthiazol-2-ylamino)-4-(quinolin-5-yloxy)pyridin-3-ylthio)propanoate: A flask was charged with tris(dibenzylideneacetone)dipalladium (0) (0.05539 g, 0.06049 mmol), 5-bromo-N-(4-methylthiazol-2-yl)-4-(quinolin-5-yloxy)pyridin-2-amine (0.500 g, 1.210 mmol), 4,5-bis(diphenylphosphino)-9,9-dimethyl-9H-xanthene (0.05250 g, 0.09074 mmol), methyl 3-mercaptopropanoate (0.5360 ml, 4.839 mmol), and N-ethyl-N-isopropylpropan-2-anine (0.4215 ml, 2.420 mmol), and degassed dioxane (40 mL) was added. The reaction was stirred at 93° C. overnight. Water was added and the reaction was extracted with ethyl acetate. The organic layer was dried, filtered and concentrated. The residue was purified using silica gel column chromatography with 20-30-40-60-80% ethyl acetate in hexanes and then with ethyl acetate to give the desired product (0.469 g, 85% yield) as yellow solid. $^1$H NMR (CDCl$_3$) δ 8.93 (m, 1H), 8.37 (d, 1H), 8.19 (m, 1H), 8.02 (dd, 1H), 7.66 (t, 1H), 7.36 (dd, 1H), 7.19 (d, 2H), 6.11 (s, 1H), 3.60 (s, 3H), 2.60 (t, 2H), 1.71 (s, 3H), 1.22 (t, 2H).

Example 202 tert-Butyl 4-((6-(4-phenylthiazol-2-ylamino)-4-(quinolin-5-yloxy)pyridin-3-ylthio)methyl)piperidine-1-carboxylate

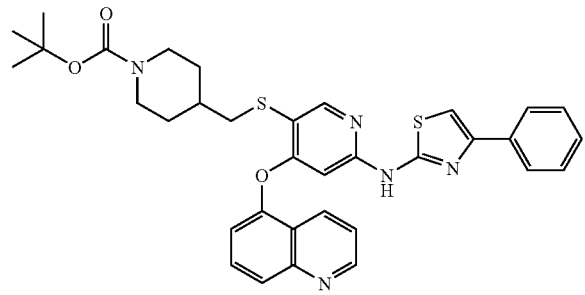

Following the procedure of Example 201, methyl 3-(6-(4-phenylthiazol-2-ylamino)-4-(quinolin-5-yloxy)pyridin-3-ylthio)propanoate (0.200 g, 0.389 mmol) (prepared as in Example 137), THF (10 mL), potassium 2-methylpropan-2-olate (1.36 ml, 1.36 mmol), tert-butyl 4-(bromomethyl)piperidine-1-carboxylate (0.108 g, 0.389 mmol) were combined to give tert-butyl 4-((6-(4-phenylthiazol-2-ylamino)-4-(quinolin-5-yloxy)pyridin-3-ylthio)methyl)piperidine-1-carboxylate (0.15 g, 61% yield) as yellow solid. $^1$H NMR (CDCl$_3$) δ 8.94 (dd, 1H), 8.36 (s, 1H), 8.17 (d, 1H), 7.98 (dd, 1H), 7.55 (t, 1H), 7.49 (s, H), 7.47 (s, 1H), 7.35 (dd, 1H), 7.12 (m, 3H), 6.94 (d, 1H), 6.84 (s, 1H), 6.02 (s, 1H), 2.18 (d, 2H), 2.61 (t, 2H), 1.81 (m, 2H), 1.60 (m, 1H), 1.40 (s, 9H), 1.22 (t, 2H), 1.12 (m, 2H).

Example 203

3-(5-bromo-2-(3-(tetrahydrofuran-2-yl)-1,2,4-thiadiazol-5-ylamino)pyridin-4-yloxy)-4-chloro-N-(2-(dimethylamino)ethyl)benzamide

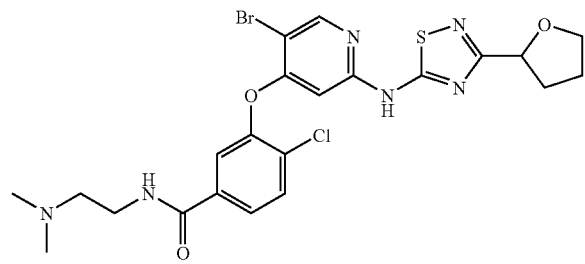

Step A: Preparation of tetrahydrofuran-2-carbaldehyde oxime: Tetrahydrofuran-2-carbaldehyde (100 g, 500 mmol, 50 wt % in water) was dissolved in methanol:water (1:1, 1500 mL) and cooled in an ice bath. Sodium carbonate (26.5 g, 250 mmol) and hydroxylamine hydrochloride (41.6 g, 600 mmol) were added and the reaction was stirred overnight at ambient temperature. The reaction was concentrated to half volume and extracted with EtOAc. The organic layer was dried over magnesium sulfate, filtered and concentrated to afford tetrahydrofuran-2-carbaldehyde oxime (44.3 g, 80%) as a colorless oil.

Step B: Preparation of tetrahydrofuran-2-carbonyl chloride oxime: A 250 mL round-bottomed flask was charged with tetrahydrofuran-2-carbaldehyde oxime (2.0 g, 17 mmol) and DMF (100 mL). 1-Chloropyrrolidine-2,5-dione (2.3 g, 17 mmol) was added and stirred at ambient temperature overnight. The reaction was poured into 1:1 brine:water (800 mL) and extracted with EtOAc). The organic layer was washed with water, dried over sodium sulfate, filtered and concentrated to afford tetrahydrofuran-2-carbonyl chloride oxime (2.6 g, 100%).

Step C: Preparation of N-(methylsulfonyloxy)tetrahydrofuran-2-carbimidoyl chloride: A 500 mL round-bottomed flask was charged with tetrahydrofuran-2-carbonyl chloride oxime (2.6 g, 17.4 mmol), methanesulfonyl chloride (1.4 ml, 17.4 mmol), and Et$_2$O (200 mL). Triethylamine (2.4 ml, 17.4 mmol) was added dropwise over about 1 minute and stirred at ambient temperature for 10 minutes. The resultant solids were filtered and the filtrate was concentrated. The resultant residue was purified on silica gel (100% DCM) to afford N-(methylsulfonyloxy)tetrahydrofuran-2-carbimidoyl chloride (2.1 g, 53.07% yield) as a white solid.

Step D: Preparation of ethyl 3-(5-bromo-2-(3-(tetrahydrofuran-2-yl)-1,2,4-thiadiazol-5-ylamino)pyridin-4-yloxy)-4-chlorobenzoate: A mixture of N-(methylsulfonyloxy)tetrahydrofuran-2-carbimidoyl chloride (0.18 g, 0.81 mmol), pyridine (0.20 ml, 2.4 mmol), and NaSCN (0.065 g, 0.81 mmol) was dissolved in acetonitrile (8 mL). The mixture was heated at 40° C. for 40 minutes. Ethyl 3-(2-amino-5-bromopyridin-4-yloxy)-4-chlorobenzoate (prepared according Example 114, steps A and B; 0.20 g, 0.54 mmol) was then added. The reaction stirred at 60° C. overnight. The solution was cooled, quenched with NaHCO$_3$ solution. The solution was then extracted with EtOAc and the organic layer was dried, and concentrated. Flash chromatography gave the desired product (0.29 g, 100%).

Step E: Preparation of 3-(5-bromo-2-(3-(tetrahydrofuran-2-yl)-1,2,4-thiadiazol-5-ylamino)pyridin-4-yloxy)-4-chloro-N-(2-(dimethylamino)ethyl)benzamide: Ethyl 3-(5-bromo-2-(3-(tetrahydrofuran-2-yl)-1,2,4-thiadiazol-5-ylamino)pyridin-4-yloxy)-4-chlorobenzoate (0.090 g, 0.17 mmol) was diluted in ethanol (2 mL), and NaOH (1N in H$_2$O, 0.36 ml, 0.36 mmol) was then added. The reaction was stirred at 60° C. for 1 hour and then cooled and concentrated to give the crude carboxylic acid as a yellow solid (sodium salt). The crude material was dissolved in DMF (2 mL) and was charged with N,N-diisopropylethylamine (0.024 ml, 0.22 mmol), 1-[3-(dimethylamino)propyl]-3-ethylcarbodiimide hydrochloride (0.035 g, 0.18 mmol) and HOBT-H$_2$O (0.028 g, 0.18 mmol), and the reaction was stirred at 50° C. overnight. The solution was cooled to room temperature, diluted with water (15 mL), stirred for 5 minutes and then filtered. The solid was dried under vacuum and recrystallized in EtOAc/hexanes to provide 3-(5-bromo-2-(3-(tetrahydrofuran-2-yl)-1,2,4-thiadiazol-5-ylamino)pyridin-4-yloxy)-4-chloro-N-(2-(dimethylamino)ethyl)benzamide (0.011 g, 12%) as a white solid. $^1$H NMR (400 MHz, CDCl$_3$) δ 2.17 (s, 6H), 2.25-2.29 (m, 2H), 2.52-2.56 (m, 2H), 3.50-3.56 (m, 2H), 3.87-3.97 (m, 4H), 4.04 (t, 1H), 5.91 (s, 1H), 7.46-7.59 (m, 4H), 8.47 (s, 1H).

Example 204

3-(2-(4-(1-Acetylpiperidin-4-yl)thiazol-2-ylamino)pyridin-4-yloxy)isonicotinonitrile hydrochloride

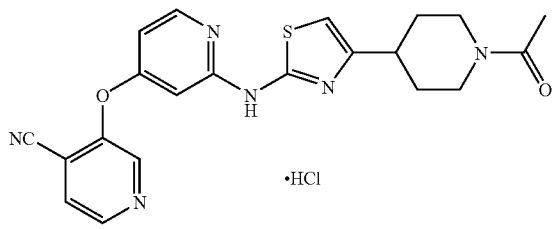

Step A: Preparation of 1-acetyl-N-methoxy-N-methylpiperidine-4-carboxamide: To a solution of 1-acetylpiperidine-4-carboxylic acid (58.50 g, 341.7 mmol) in dichloromethane (700 ml) was added di(1H-imidazol-1-yl)methanone (58.18 g, 358.8 mmol) in portions. The mixture was agitated for two hours and N-methoxymethanamine hydrochloride (35.00 g, 358.8 mmol) was added at once. The mixture was stirred overnight at ambient temperature, and then 4M HCl in dioxane (75 ml) was added slowly. The slurry was agitated for 30 minutes and then filtered. The filtrate was washed twice with sodium bicarbonate solution, dried and concentrated in vacuo to give the desired product (59.10 g, 80.72% yield) as a white solid.

Step B: Preparation of 1,1'-(piperidine-1,4-diyl)diethanone: 1-Acetyl-N-methoxy-N-methylpiperidine-4-carboxamide (59.10 g, 275.8 mmol) was dissolved in tetrahydrofuran (800 ml) and cooled to 0° C. Methylmagnesium bromide (110.3 ml, 331.0 mmol) (3.0 M in diethyl ether) was added slowly and the resulting white slurry was agitated for 1 hour. The reaction was quenched with 300 ml of 2M HCl and organic solvent was evaporated. The resulting aqueous slurry was extracted three times with 20:80 isopropanol/chloroform. The resulting extracts were washed with brine and evaporated to produce the desired product (38.40 g, 82.27% yield) as amber oil.

Step C: Preparation of 1-(1-acetylpiperidin-4-yl)-2-bromoethanone: 1,1'-(Piperidine-1,4-diyl)diethanone (38.00 g, 224.6 mmol) was dissolved in methanol (700 ml) and bromine (12.11 ml, 235.8 mmol) was added in portions. The resulting mixture was agitated 3 hours and the solvent was removed in vacuo. The resulting solid was triturated with ethyl acetate and partitioned between ethyl acetate and sodium carbonate solution. The organic phase was separated, washed with brine, dried and evaporated to give the desired product (44.70 g, 80.23% yield) as yellow solid.

Step D: Preparation of 1-(4-(2-aminothiazol-4-yl)piperidin-1-yl)ethanone: 1-(1-acetylpiperidin-4-yl)-2-bromoethanone (2.372 g, 9.561 mmol) and thiourea (0.7278 g, 9.561 mmol) were dissolved in ethanol (40 ml) and agitated at ambient temperature for 30 minutes. The mixture was heated to 80° C. and agitated an additional 1 hour. Upon cooling solvent was evaporated and the residue was distributed between 20 ml of 2M NaOH and 20 ml of chloroform. The organic phase was separated and discarded. The remaining aqueous phase (white slurry) was extracted with chloroform until all solids were extracted (4×200 ml). The organic extracts were combined, dried over magnesium sulfate and evaporated to give the desired product (1.600 g, 74.27% yield) as white solid.

Step E: Preparation of 3-(2-(4-(1-acetylpipieridin-4-yl)thiazol-2-ylamino)pyridin-4-yloxy)isonicotinonitrile hydrochloride: 3-(2-Chloropyridin-4-yloxy)isonicotinonitrile (0.0650 g, 0.2806 mmol) (prepared as in Example 205), 1-(4-(2-aminothiazol-4-yl)piperidin-1-yl)ethanone (0.08219 g, 0.3648 mmol), potassium phosphate (0.1371 g, 0.4209 mmol), tris(dibenzylideneacetone)dipalladium (0) (0.006424 g, 0.007015 mmol) and 9,9-dimethyl-4,5-bis(diphenylphosphino)xanthene (0.008118 g, 0.01403 mmol) were combined and the vessel was capped with rubber septum. The vessel was evacuated and purged with nitrogen three times. Toluene (2 ml) and degassed water (2 ml) were added and the resulting mixture was heated to 90° C. and agitated overnight. After cooling the mixture was diluted with 50 ml of ethyl acetate and washed with sodium bicarbonate, brine, dried and evaporated. The crude product was purified by preparative HPLC (Parallex) and converted to HCl salt by treatment with 2M HCl in ether to provide the title compound (0.0150 g, 12.71% yield) as white solid. $^1$H NMR (CDCl$_3$) δ 1.52-1.62 (m, 2H), 1.98-2.06 (m, 2H), 2.10 (s, 3H), 2.65 (t, 1H), 2.80 (t, 1H), 3.13 (t, 1H), 3.85 (d, 1H), 4.66 (d, 1H), 6.35 (s, 1H), 6.45 (s, 1H), 6.50 (d, 1H), 7.15 (s, 1H), 7.40 (d, 1H), 8.05 (s, 1H), 9.01 (bs, 1H).

Example 205

Representative Example 3-(2-chloropyridin-4-yloxy isonicotinonitrile

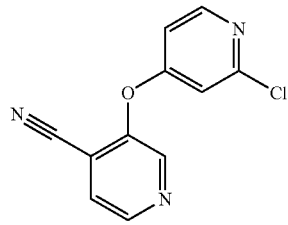

Step A: Preparation of 3-chloroisonicotinonitrile: In a 4 neck 3L round bottom flask equipped with mechanical stirrer and condenser, was added 4-cyanopyridine-n-oxide (50 g, 416 mmol), phosphoryl trichloride (153 ml, 1665 mmol), and phosphorous pentachloride (121 g, 583 mmol). The reaction was stirred at 105° C. overnight. The reaction mixture was cooled and then slowly added in portions to 2 kg ice. The pH was adjusted to about 8 by slow addition of 50% NaOH. The mixture was extracted with ethyl acetate. The organic layer was dried and concentrated. The residue was purified by silica gel chromatography, eluting with 5-10% ethyl acetate to give the desired product (23 g, 39.9% yield) as light yellow solid.

Step B: Preparation of 32-(trimethylsilyl)ethoxy)isonicotinonitrile: A flask was charged with 2-(trimethylsilyl)ethanol (1.02 g, 8.66 mmol) and added THF (20 mL). Sodium hydride (0.219 g, 8.66 mmol) was added and the reaction was stirred at ambient temperature for 1 hour. 3-Chloroisonicotinonitrile (1.00 g, 7.22 mmol) was added, and the reaction mixture was stirred at ambient temperature for 1 hour and then at 50° C. overnight. A saturated solution of ammonium chloride was added. The reaction mixture was extracted with ethyl acetate, dried and concentrated to give the desired product (1.30 g, 81.7% yield) as light brown semi solid material.

Step C: Preparation of 3-hydroxyisonicotinonitrile: A flask was charged with 3-(2-(trimethylsilyl)ethoxy)isonicotinonitrile (1.30 g, 5.90 mmol), THF (5 mL) and N,N-dibutyl-N-propylbutan-1-aminium fluoride (11.8 ml, 11.8 mmol) in THF was added. The reaction mixture was stirred at ambient temperature for 1 hour and then concentrated. The crude product was purified by silica gel chromatography, eluting with DCM and 5% methanol in DCM to give the desired product (0.7 g, 99% yield) as dark brown oil.

Step D: Preparation of 3-(2-chloropyridin-4-yloxy)isonicotinonitrile: A flask was charged with sodium hydride (3.99 g, 158 mmol) and DMF (50 mL), and 3-hydroxyisonicotinonitrile (15.8 g, 132 mmol) was added. The reaction was stirred for 2 hours at ambient temperature. 2-Chloro-4-nitropyridine (21.9 g, 138 mmol) was added and the reaction was and stirred overnight. Water was added and the reaction was extracted with ethyl acetate. The organic layer was dried and concentrated. The crude product was purified by silica gel chromatography, eluting with DCM, 5% ammoniated methanol in DCM to give the desired product (0.250 g, 0.820% yield) as yellow solid.

Example 206

1-(4-(2-(4-(2,6-dichlorophepylthio)pyridin-2-ylamino)thiazol-4-yl)piperidin-1-yl)ethanone hydrochloride

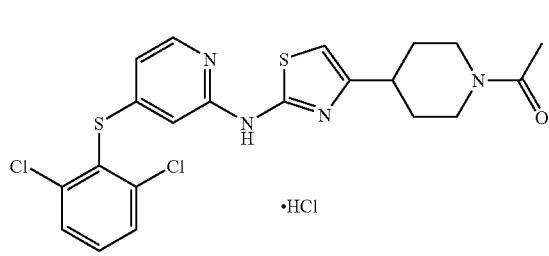

Prepared according to the method of Example 204, Step E. $^1$H NMR (CDCl$_3$) δ 1.52-1.62 (m, 2H), 1.98-2.06 (m, 2H), 2.10 (s, 3H), 2.65 (t, 1H), 2.80 (t, 1H), 3.13 (t, 1H), 3.85 (d, 1H), 4.66 (d, 1H), 6.35 (s, 1H), 6.45 (s, 1H), 6.50 (d, 1H), 7.34 (t, 1H), 7.50 (d, 1H), 8.10 (d, 1H), 9.01 (bs, 1H).

Example 207

1-(4-(2-(4-(2-chlorophenoxy)pyridin-2-ylamino)thiazol-4-ylpiperidin-1-yl)ethanone hydrochloride

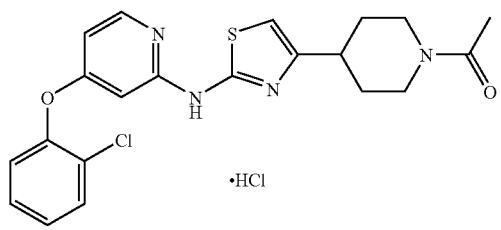

Prepared according to the method of Example 204, Step E. $^1$H NMR (CDCl$_3$) δ 1.52-1.62 (m, 2H), 1.98-2.06 (m, 2H), 2.10 (s, 3H), 2.65 (t, 1H), 2.80 (t, 1H), 3.13 (t, 1H), 3.85 (d, 1H), 4.66 (d, 1H), 6.35 (s, 1H), 6.45-6.47 (m, 2H), 7.16-7.52 (m, 4H), 8.18 (d, 1H), 8.91 (bs, 1H).

Example 208

1-(4-2-(4-(2,6-dimethylphenoxy)pyridin-2-ylamino thiazol-4-yl)piperidin-1-yl)ethanone hydrochloride

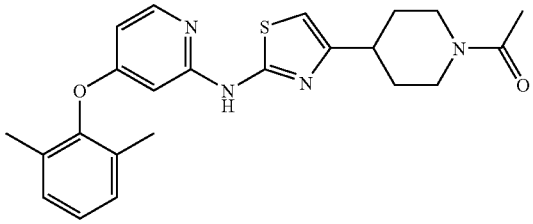

Prepared according to the method of Example 204, Step E. $^1$H NMR (CDCl$_3$) 1.52-1.62 (m, 2H), 1.98-2.06 (m, 2H), 2.10 (s, 3H), 2.12 (s, 6H) 2.65 (t, 1H), 2.80 (t, 1H), 3.13 (t, 1H), 3.85 (d, 1H), 4.66 (d, 1H), 6.25 (s, 1H), 6.35 (s, 1H), 6.42 (d, 1H), 7.11 (d, 2H), 7.34-7.45 (m, 2H), 8.18 (m, 2H).

Example 209

1-(4-(2-(4-(2-chloro-6-methylphenoxy)pyridin-2-ylamino)thiazol-4-yl)piperidin-1-yl)ethanone hydrochloride

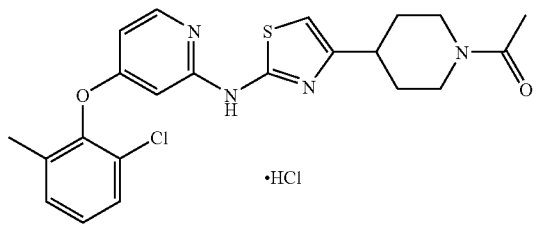

Prepared according to the method of Example 204, Step E. $^1$H NMR (CDCl$_3$) δ 1.52-1.62 (m, 2H), 1.98-2.06 (m, 2H), 2.10 (s, 3H), 2.15 (s, 3H), 2.65 (t, 1H), 2.80 (t, 1H), 3.13 (t, 1H), 3.85 (d, 1H), 4.66 (d, 1H), 6.35 (s, 1H), 6.45 (s, 1H), 6.50 (d, 1H), 7.34 (t, 1H), 7.50 (d, 1H), 8.10 (d, 1H), 9.01 (bs, 1H).

Example 210 ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate

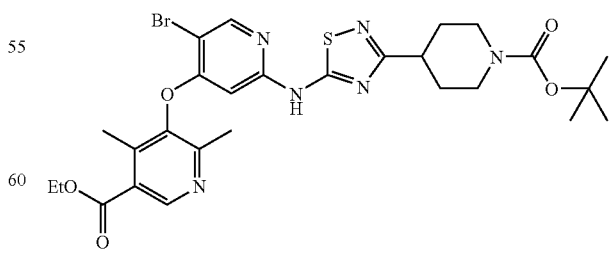

Step A: Preparation of (5-(2-chloropyridin-4-yloxy)-4,6-dimethylpyridin-3-yl)methanol: A suspension of sodium hydride (5.27 g, 209 mmol) in DMF (100 mL) was carefully charged with 5-(hydroxymethyl)-2,4-dimethylpyridin-3-ol hydrochloride (18 g, 95 mmol). The mixture stirred at room temperature for 2 hours. 2-chloro-4-nitropyridine (15 g, 95 mmol) was then added and the reaction stirred overnight at room temperature. The material was diluted with water and extracted with ethylacetate. The organic layer was dried, and concentrated. Flash chromatography (dichloromethane/methanol 20:1) gave (5-(2-chloropyridin-4-yloxy)-4,6-dimethylpyridin-3-yl)methanol (19.8 g, 79%) as colorless oil.

Step B: Preparation of 5-(2-chloropyridin-4-yloxy)-4,6-dimethylnicotinic acid: (5-(2-chloropyridin-4-yloxy)-4,6-dimethylpyridin-3-yl)methanol (5.00 g, 18.9 mmol) was charged with NaOH (0.1N in H$_2$O, 19 ml, 1.9 mmol). 3% Aqueous KMnO4 (119 ml, 22.7 mmol) was then added. The reaction stirred at room temperature overnight. The solution was diluted with dichloromethane, filtered through celite, and acidified with citric acid. The organic layer was separated and the aqueous layer was extracted with DCM. The combined organic layers were dried and concentrated to give 5-(2-chloropyridin-4-yloxy)-4,6-dimethylnicotinic acid (2.66 g, 51%).

Step C: Preparation of ethyl 5-(2-chloropyridin-4-yloxy)-4,6-dimethylnicotinate: A three necked round bottom flask containing 5-(2-chloropyridin-4-yloxy)-4,6-dimethylnicotinic acid (11.7 g, 42.0 mmol) was charged with ethanol (250 mL), benzene (300 mL) and sulphuric acid (10 mL). The flask was fitted with Dean Stark apparatus and the reaction stirred at reflux overnight. The solution was cooled and carefully neutralized with saturated NaHCO$_3$ solution. The material was extracted with EtOAc, dried, and concentrated to afford ethyl 5-(2-chloropyridin-4-yloxy)-4,6-dimethylnicotinate (8.6 g, 67%) as an oil which solidified to a white solid upon standing in a refrigerator (4° C.) overnight.

Step D: Preparation of ethyl 5-(2-aminopyridin-4-yloxy)-4,6-dimethylnicotinate: A round bottom flask containing ethyl 5-(2-chloropyridin-4-yloxy)-4,6-dimethylnicotinate (7.5 g, 25 mmol), tert-butyl carbamate (8.6 g, 73 mmol), potassium phosphate (tribasic) (5.7 g, 27 mmol), tris(dibenzylideneacetone)dipalladium (1.1 g, 1.2 mmol), and 9,9-Dimethyl-4,5-bis(diphenylphosphino)xanthene (1.1 g, 1.8 mmol) was suspended in toluene (200 mL) and water (40 mL). The solution was degassed with nitrogen and then stirred at 90 C for 4 hours. The solution was filtered through GF/F paper and diluted with water. The material was then extracted with EtOAc and the organic layer was dried, and concentrated. The residue was then slowly diluted in TFA (50 mL) and stirred at room temperature for 6 hours. The solution was concentrated, diluted with water, and neutralized with saturated NaHCO$_3$ solution. The material was extracted with EtOAc and the organic layer was dried, and concentrated. Flash chromatography (10% MeOH/EtOAc) gave ethyl 5-(2-aminopyridin-4-yloxy)-4,6-dimethylnicotinate (3.8 g, 54%).

Step E: Preparation of ethyl 5-(2-amino-5-bromopyridin-4-yloxy)-4,6-dimethylnicotinate: Ethyl 5-(2-aminopyridin-4-yloxy)-4,6-dimethylnicotinate (2.5 g, 8.7 mmol) in AcOH (30 mL) was charged with dropwise addition of bromine (1M in AcOH, 8.7 ml, 8.7 mmol). The solution was stirred at room temperature for 30 minutes. The solution was then concentrated and neutralized with saturated NaHCO$_3$ solution. The material was then extracted with EtOAc and the organic layer was dried, and concentrated. Flash chromatography gave ethyl 5-(2-amino-5-bromopyridin-4-yloxy)-4,6-dimethylnicotinate (1.88 g, 59%) as a yellow solid.

Step F: Preparation of ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate:tert-Butyl 4-(chloro(methylsulfonyloxyimino)methyl)piperidine-1-carboxylate (2.57 g, 7.5 mmol, was dissolved in acetonitrile (50 mL). Pyridine (1.8 ml, 23 mmol) and NaSCN (0.61 g, 7.5 mmol) were then added and the reaction stirred at 40° C. for 40 minutes. Ethyl 5-(2-amino-5-bromopyridin-4-yloxy)-4,6-dimethylnicotinate (1.84 g, 5.0 mmol) was then added and the reaction stirred at 60° C. overnight. The solution was then cooled and quenched with saturated NaHCO$_3$ solution. The material was extracted with EtOAc and the organic layer was dried and concentrated. Flash chromatography gave ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate (2.53 g, 80% yield) as a yellow solid. $^1$H NMR (400 MHz, CDCl$_3$) δ 1.44 (s, 9H), 1.44 (t, 3H), 1.72-1.79 (m, 2H), 1.96-1.99 (m, 2H), 2.41 (s, 3H), 2.43 (s, 3H), 2.85-2.92 (m, 3H), 4.07-4.13 (m, 2H), 4.42 (q, 2H), 5.79 (s, 1H), 8.55 (s, 1H), 8.90 (s, 1H).

Example 211

5-(2-(3-(1-(tert-butoxycarbonyl)piperidin-4-yl)-1,2,4-thiadiazol-5-ylamino)-5-bromopyridin-4-yloxy-4,6-dimethylnicotinic acid

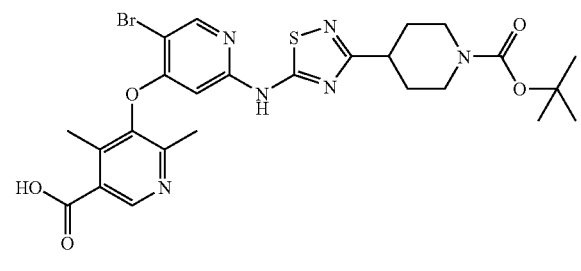

Ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate (0.050 g, 0.08 mmol) was dissolved in EtOH (2 mL). NaOH (1N in H$_2$O, 0.28 ml, 0.28 mmol) was added. The reaction stirred at 60° C. for 1 hour. The solution was cooled and concentrated. The material was acidified with saturated NH$_4$Cl solution and extracted with dichloromethane. The organic layer was washed with water, dried and concentrated to give 5-(2-(3-(1-(tert-butoxycarbonyl)piperidin-4-yl)-1,2,4-thiadiazol-5-ylamino)-5-bromopyridin-4-yloxy)-4,6-dimethylnicotinic acid (0.012 g, 25% yield) as an off white solid. $^1$H NMR (400 MHz, DMSO-d$_6$) δ 1.39 (s, 9H), 1.52-1.55 (m, 2H), 1.89-1.93 (m, 2H), 2.34 (s, 6H), 2.84-2.93 (m, 3H), 3.90-3.94 (m, 2H), 6.20 (s, 1H), 8.62 (s, 1H), 8.89 (s, 1H), 11.69 (s, 1H), 13.09 (s, 1H).

Example 212 tert-butyl 4-(5-(4-(5-((2-(dimethylamino)ethylcarbamoyl)-2,4-dimethylpyridin-3-yloxy)-5-bromopyridin-2-ylamino)-1,2,4-thiadiazol-3-yl)piperidine-1-carboxylate

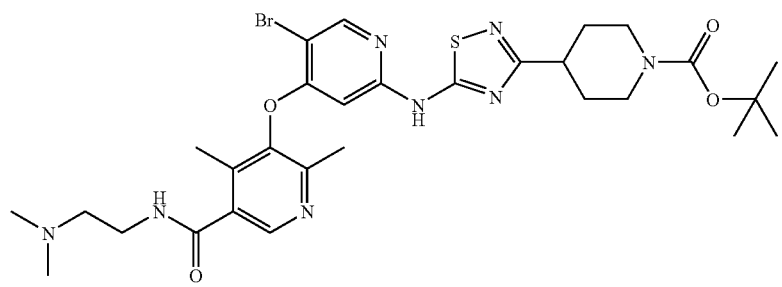

Ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate (0.50 g, 0.79 mmol) was dissolved in EtOH (10 mL). NaOH (1N in H$_2$O, 2.0 ml, 2.0 mmol) was added. The reaction stirred at 60° C. for 3 hours. The solution was cooled and concentrated to give the hydrolyzed product as a yellow salt. This residue was re-dissolved in DMF (2 mL). N1,N1-dimethylethane-1,2-diamine (0.31 ml, 2.8 mmol), 1-[3-(dimethylamino)propyl]-3-ethylcarbodiimide hydrochloride (0.45 g, 2.4 mmol) and HOBT-H$_2$O (0.36 g, 2.4 mmol) were added. The reaction stirred at 50° C. for 2 hours. The solution was cooled, diluted with water (15 mL), extracted with EtOAc, dried, and concentrated. Flash chromatography (DCM-15% MeOH/DCM/0.1-1% NH4OH) gave tert-butyl 4-(5-(4-(5-((2-(dimethylamino)ethyl)carbamoyl)-2,4-dimethylpyridin-3-yloxy)-5-bromopyridin-2-ylamino)-1,2,4-thiadiazol-3-yl)piperidine-1-carboxylate (0.30 g, 56%) as an off-white solid. $^1$H NMR (400 MHz, CDCl$_3$) δ 1.45 (s, 9H), 1.70-1.77 (m, 2H), 1.95-1.99 (m, 2H), 2.25 (s, 3H), 2.29 (s, 6H), 2.39 (s, 3H), 2.56-2.62 (m, 2H), 2.85-2.89 (m 3H), 3.52-2.64 (m, 2H), 4.08-4.15 (m, 2H), 5.95 (s, 1H), 7.07 (s, 1H), 8.30 (s, 1H), 8.53 (s, 1H), 10.15 (s, 1H).

Example 213

5-(5-bromo-2-(3-(piperidin-4-yl)-1,2,4-thiadiazol-5-ylamino)pyridin-4-yloxy)-N-(2-(dimethylamino)ethyl)-4,6-dimethylnicotinamide dihydrochloride

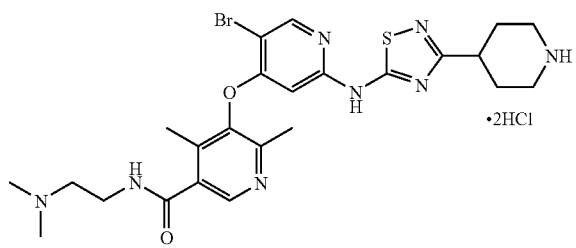

tert-Butyl 4-(5-(4-(5-((2-(dimethylamino)ethyl)carbamoyl)-2,4-dimethylpyridin-3-yloxy)-5-bromopyridin-2-ylamino)-1,2,4-thiadiazol-3-yl)piperidine-1-carboxylate (0.025 g, 0.037 mmol) was dissolved in a mixture of methanol:dichloromethane (1 mL each). HCl (4N in dioxane, 0.5 mL, 2.0 mmol) was added. The reaction stirred overnight. The solution was concentrated to give 5-(5-bromo-2-(3-(piperidin-4-yl)-1,2,4-thiadiazol-5-ylamino)pyridin-4-yloxy)-N-(2-(dimethylamino)ethyl)-4,6-dimethylnicotin-amide dihydrochloride (0.028 g, 100% yield) as an off-white solid. $^1$H NMR (400 MHz, DMSO-d$_6$) δ 1.87-1.93 (m, 2H), 2.06-2.14 (m, 2H), 2.22 (s, 3H), 2.34 (s, 3H), 2.83 (s, 3H), 2.84 (s, 3H), 2.96-3.08 (m, 2H), 3.23-3.32 (m, 4H), 3.44-2.52 (m, 1H), 3.62-3.73 (m, 2H), 6.37 (s, 1H), 8.64 (s, 1H), 8.67 (s, 1H), 8.70 (s, 1H), 9.0 (s, 1H), 9.03 (t, 1H), 10.50 (s, 1H), 11.88 (s, 1H).

Example 214 tert-butyl 4-(5-(5-bromo-4-(2-chloro-5-((2-(dimethylamino)ethyl)carbamoyl)phenoxy)pyridin-2-ylamino)-1,2,4-thiadiazol-3-yl)piperidine-1-carboxylate

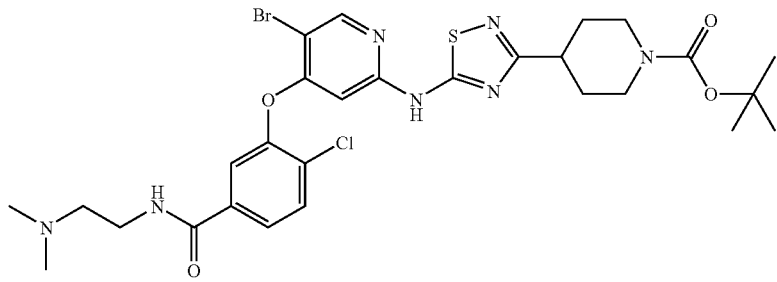

Prepared from ethyl 3-(2-amino-5-bromopyridin-4-yloxy)-4-chlorobenzoate utilizing the procedure found in example 210 (step F) and 212. $^1$H NMR (400 MHz, CDCl$_3$) δ 1.45 (s, 9H), 1.69-1.76 (m, 2H), 1.94-1.97 (m, 2H), 2.20 (s, 6H), 2.57 (t, 2H), 2.82-2.89 (m, 3H), 3.54-3.58 (m, 2H), 4.07-4.11 (m, 2H), 5.95 (s, 1H), 7.39 (s, 1H), 7.52 (d, 1H), 7.54 (s, 1H), 7.62 (dd, 1H), 8.48 (s, 1H).

Example 215

Pr 3-(5-bromo-2-(3-(piperidin-4-yl)-1,2,4-thiadiazol-5-ylamino)pyridin-4-yloxy)-4-chloro-N-(2-(dimethylamino)ethyl)benzamide dihydrochloride

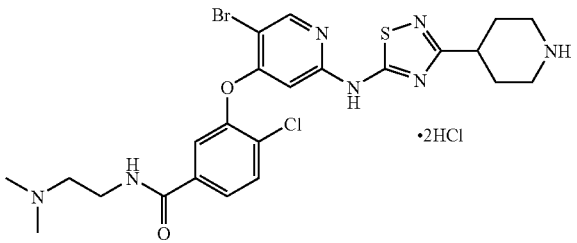

Prepared from tert-butyl 4-(5-(S-bromo-4-(2-chloro-5-((2-(dimethylamino)ethyl)carbamoyl)phenoxy)pyridin-2-ylamino)-1,2,4-thiadiazol-3-yl)piperidine-1-carboxylate utilizing the procedure in Example 213. $^1$H NMR (400 MHz, DMSO-d$_6$) δ 1.88-1.92 (m, 2H), 2.08-2.14 (m, 2H), 2.81 (s, 3H), 2.82 (s, 3H), 2.96-3.16 (m, 2H), 3.24-3.32 (m, 4H), 3.44-3.52 (m, 1H), 3.61-3.72 (m, 2H), 6.44 (s, 1H), 7.89 (d, 1H), 7.98 (d, 1H), 7.98 (s, 1H), 8.64 (s, 1H), 8.70 (s, 1H), 8.85 (s, 1H), 9.05 (s, 1H), 10.10 (s, 1H), 11.95 (s, 1H).

Example 216

3-(2-(3-(1-acetylpiperidin-4-yl)-1,2,4-thiadiazol-5-ylamino)-5-bromopyridin-4-yloxy)-4-chloro-N-(2-(dimethylamino)ethyl)benzamide

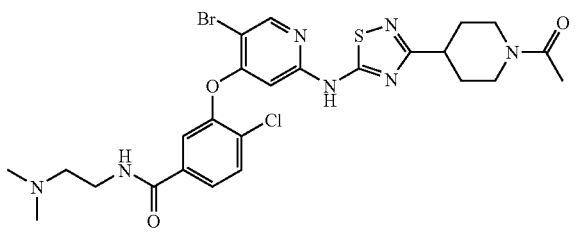

3-(5-bromo-2-(3-(piperidin-4-yl)-1,2,4-thiadiazol-5-ylamino)pyridin-4-yloxy)-4-chloro-N-(2-(dimethylamino)ethyl)benzamide dihydrochloride (0.12 g, 0.18 mmol) was dissolved in DMF (2 mL) and the solution was cooled to 0° C. DIEA (0.13 ml, 0.73 mmol) was added followed by acetyl chloride (0.017 mL, 0.24 mmol). The solution was warmed to RT. After 15 minutes, the solution was quenched with water, extracted with EtOAc, dried, and concentrated. HPLC purification gave 3-(2-(3-(1-acetylpiperidin-4-yl)-1,2,4-thiadiazol-5-ylamino)-5-bromopyridin-4-yloxy)-4-chloro-N-(2-(dimethylamino)ethyl)benzamide (0.0066 g, 6%) as a white solid. $^1$H NMR (400 MHz, CDCl$_3$) 01.69-1.76 (m, 1H), 1.81-1.88 (m, 1H), 1.86-2.12 (m, 2H), 2.04 (s, 3H), 2.26 (s, 6H) 2.60 (t, 2H), 2.78-2.85 (m, 1H), 2.95-3.04 (m, 1H), 3.13-3.21 (m, 1H), 3.54-3.60 (m, 2H), 3.78-3.84 (m, 1H), 4.41-4.46 (m, 1H), 6.15 (s, 1H), 7.40 (s, 1H), 7.53 (d, 1H), 7.59-7.64 (m, 3H), 8.49 (s, 1H).

Example A

In Vitro Glucokinase Assays

The in vitro efficacy of glucokinase activators of the present invention was assessed in two separate assays: an EC$_{50}$ assay to evaluate the potency of each compound at a fixed, physiologically relevant concentration of glucose, and a glucose S$_{0.5}$ assay at a fixed, near saturating (if possible) concentration of compound to evaluate its effect on the V$_m$ and S$_{0.5}$ for glucose. For each of these assays, glucokinase activity was estimated by monitoring the increase in absorbance at 340 nm in a coupled assay system containing NAD$^+$ and glucose 6-phosphate dehydrogenase. Assays were conducted at 30° C. using a thermostatically controlled absorbance plate reader (Spectramax 340PC, Molecular Devices Corp.) and clear, 96-well, flat bottom, polystyrene plates (Costar 3695, Corning). Each 50-μL assay mixture contained 10 mM K$^+$ MOPS, pH 7.2, 2 mM MgCl$_2$, 50 mM KCl, 0.01% Triton X-100, 2% DMSO, 1 mM DTT, 1 mM ATP, 1 mM NAD$^+$, 5 U/mL glucose 6-phosphate dehydrogenase, approximately 5 nM human glucokinase and (depending on the assay) varying concentrations of glucose and test compound. The absorbance at 340 nm was monitored kinetically over a period of 5 minutes (10 s/cycle), and rates were estimated from the slopes of linear fits to the raw data.

Glucokinase $EC_{50}$ Assay:

For this assay, the glucose concentration was fixed at 5 mM, while the control or test compound was varied over a 10-point, 3-fold dilution series and typically ranged from a high dose of 50 µM to a low dose of approximately 2.5 nM. A standard, four-parameter logistic model (Equation 1) was fit to the raw data (rate versus concentration of compound):

$$y = A + \frac{B-A}{1+\left[\frac{C}{x}\right]^{D}} \quad (1)$$

where x is the concentration of compound, y is the estimated rate, A and B are the lower and upper asymptotes, respectively, C is the $EC_{50}$ and D is the Hill slope. The $EC_{50}$ is defined as the midpoint or inflection point between the upper and lower asymptotes. A compound was identified as a glucokinase activator if it stimulated the activity of glucokinase 25 percent or more above that observed in the absence of the compound.

Glucose $S_{0.5}$ Assay:

For this assay, the concentration of control or test compound was fixed at or near a saturating concentration, if possible, typically 50 µM, while the glucose concentration was varied over a 10-point, 2-fold dilution series ranging from 80 to approximately 0.16 mM. The same four-parameter logistic model used for the $EC_{50}$ assay (Equation 1) was employed to estimate the relevant kinetic parameters. In this assay, the definitions for the variables and parameters are similar except that x represents the concentration of glucose, B is the rate at saturating glucose ($V_m$), C is the $S_{0.5}$ for glucose (the concentration of glucose at $V_m/2$) and D is the Hill Coefficient. The $S_{0.5}$ for compounds of Examples 1-11, 14, 16, 18-19, 21, 25-2932-58, 60-63, 65-87, 89-90, 92-202 is in the range of 1.5 and 7.5 mM. For certain compounds of the invention, the $S_{0.5}$ is in the range of 1.5 and 4.0 mM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound selected from the Formula I

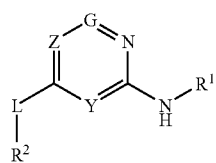

and salts thereof, wherein:
L is O, S, S(=O), S(=O)$_2$, $NR^{14}$, $CR^{14}R^{15}$, or C(=O);
Y is CH;
G is CH or CCl;
Z is $CR^3$;
$R^1$ is a heteroaryl ring represented by the formula

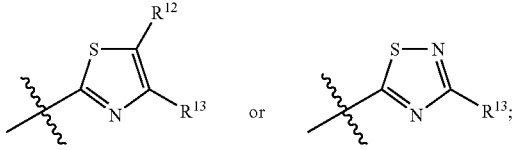

$R^2$ is
(i) phenyl optionally substituted with one or more groups independently selected from F, Cl, CN, $C_1$-$C_6$ alkyl (optionally substituted with OH), $CF_3$, $OR^6$, $CO_7R^6$, $O(CH_2)C(=O)OR^6$, and $C(=O)NR^6R^7$;
(ii) a 5-6 membered heteroaryl ring having 1-3 heteroatoms independently selected from N and O (provided the ring does not contain a O—O bond) wherein said heteroaryl is optionally substituted with one or two groups independently selected from $NO_2$, Cl, Br, CN, CF) and $C_1$-$C_6$ alkyl;
(iii) a partially unsaturated 5 membered azacyclic ring optionally substituted with oxo;
(iv) 9-10 membered heteroaryl ring having a nitrogen atom and optionally having 1 to 2 additional ring heteroatoms independently selected from N, O and S and optionally substituted with $C_1$-$C_6$ alkyl or a partially unsaturated 10 membered bicyclic heterocyclic ring having 1-3 nitrogen atoms and optionally substituted with C(O)O-tBu; or
(v) a 5-6 membered cycloalkyl ring optionally substituted with $C_1$-$C_6$ alkyl;
$R^3$ is H, alkyl, alkenyl, alkynyl, heteroalkyl, saturated or partially unsaturated cycloalkyl, saturated or partially unsaturated heterocyclyl, aryl, heteroaryl, F, Cl, Br, I, CN, $OR^6$, C(=O)$R^6$, C(=O)$OR^6$, OC(=O)$R^6$, C(=O)$NR^6R^7$, OC(=O)$NR^6R^7$, OC(=S)$NR^6R^7$, $NR^6R^7$, $NR^6C(=O)R^7$, $SR^6$, S(O)$R^6$, S(O)$_2R^6$ or S(O)$_2NR^6R^7$, wherein said alkyl, alkenyl, alkynyl, heteroalkyl, cycloalkyl, heterocyclyl, aryl and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_nC(=O)R^8$, $V_n$—C(=O)$OR^8$, $V_n$—OC(=O)$R^8$, $V_n$—C(=O)$NR^8R^9$, $V_n$—$NR^8R^9$, $V_n$—$NR^8C(=O)R^9$, $V_n$—$SR^8$, $V_n$—S(O)$R^8$, $V_n$—S(O)$_2R^8$ and $V_n$—S(O)$_2NR^8R^9$;
$R^6$ and $R^7$ are independently H, alkyl, alkenyl, alkynyl, saturated or partially unsaturated cycloalkyl, saturated or partially unsaturated heterocyclyl, aryl, heteroaryl, $OR^8$, $NR^8R^9$, C(=O)$NR^8R^9$, C(=O)$R^8$, or C(=O)$OR^8$, wherein said alkyl, alkenyl, alkynyl, cycloalkyl, heterocyclyl, aryl and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl optionally substituted with C(O)O($C_1$-$C_6$ alkyl), $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—C(=O)$R^8$, $V_n$—C(=O)$OR^8$, $V_n$—OC(=O)$R^8$, $V_n$—C(=O)$NR^8R^9$, $V_n$—$NR^8R^9$, $V_n$—$NR^8$C(=O)$R^9$, $V_n$—$SR^8$, $V_n$—S(O)$R^8$, $V_n$—S(O)$_2R^8$, and $V_n$—S(O)$_2NR^8R^9$, or $R^6$ and $R^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $V_n$—F, $V_n$—$C_1$, $V_n$—Br, $V_n$—I, $V_n$—$OR^8$, $V_n$—C(=O)$OR^8$, $V_n$—C(=O)$NR^8R^9$, $V_n$—$NR^8R^9$, $V_n$—$NR^8$C(=O)$R^9$, $V_n$—$NR^8$C(=O)$NR^9R^{10}$, alkyl, alkenyl, and alkynyl;

$R^8$, $R^9$ and $R^{10}$ are independently H, alkyl, alkenyl, alkynyl, saturated or partially unsaturated cycloalkyl, saturated or partially unsaturated heterocyclyl, aryl or heteroaryl, wherein said alkyl, alkenyl, alkynyl, cycloalkyl, heterocyclyl, aryl and heteroaryl are optionally substituted with one or more groups independently selected from oxo, alkyl, alkenyl, alkynyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—Cl, $V_n$—Br, $V_n$—I, $V_n$—$OR^a$, $V_n$—$NR^aR^b$, $V_n$—C(=O)$OR^a$, $V_n$—C(=O)$NR^aR^b$, and $V_n$—$NR^a$C(=O)$R^b$, or $R^8$ and $R^9$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, $V_n$—F, $V_n$—Cl, $V_n$—Br, $V_n$—I, $V_n$—$OR^a$, and $V_n$—CN, or $R^9$ and $R^{10}$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, $V_n$—F, $V_n$—Cl, $V_n$—Br, $V_n$—I, $V_n$—$OR^a$, and $V_n$—CN;

$R^{12}$ is H;

$R^{13}$ is H, alkyl, alkenyl, alkynyl, heteroalkyl, saturated or partially unsaturated cycloalkyl, saturated or partially unsaturated heterocyclyl, aryl, heteroaryl, F, Cl, Br, I, $CF_3$, CN, $OR^6$, C(=O)$R^6$, C(=O)$OR^6$, OC(=O)$R^6$, C(=O)$NR^6R^7$, $NR^6R^7$, $NR^6$C(=O)$R^7$, $SR^6$, S(O)$R^6$ or S(O)$_2R^6$, wherein said alkyl, alkenyl, alkynyl, cycloalkyl, heterocyclyl, aryl and heteroaryl are optionally substituted with one or more groups independently selected from oxo, $V_n$—F, $V_n$—$C_1$, $V_n$—Br, $V_n$—I, $V_n$—$CF_3$, $V_n$—CN, $V_n$—$OR^8$, $V_n$—C(=O)$OR^8$, $V_n$—OC(=O)$R^8$, $V_n$—C(=O)$NR^8R^9$, $V_n$—$NR^8R^9$, $V_n$—$NR^8$C(=O)$R^9$, alkyl, alkenyl, alkynyl, saturated and partially unsaturated $V_n$-cycloalkyl, saturated and partially unsaturated $V_n$-heterocyclyl, $V_n$-aryl, and $V_n$-heteroaryl, wherein said heterocyclyl is optionally substituted with one or more oxo $R^{14}$ and $R^{15}$ are independently H, methyl, ethyl, F, Cl, Br, I, $CF_3$, $CHF_2$, $CH_2F$, OH, O—($C_1$-$C_4$ alkyl), or $NH_2$;

$R^a$ and $R^b$ are independently H, alkyl, alkenyl, alkynyl, saturated or partially unsaturated $V_n$-cycloalkyl, saturated or partially unsaturated $V_n$-heterocyclyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocyclyl, $V_n$-aryl, and $V_n$-heteroaryl are optionally substituted with one or more OH;

V is alkylene having from 1 to 12 carbons, or alkenylene or alkynylene each having from 2 to 12 carbons, wherein said alkylene, alkenylene, or alkynylene are optionally substituted with one or more groups independently selected from alkyl, alkenyl, alkynyl, heteroalkyl, saturated and partially unsaturated cycloalkyl, saturated and partially unsaturated heterocyclyl, aryl, heteroaryl, F, Cl, Br, I, $CF_3$, cyano, $OR^8$, C(=O)$OR^8$, OC(=O)$R^8$, C(=O)$NR^8R^9$, $NR^8R^9$, and $NR^8$C(=O)$R^9$; and n is 0 or 1.

2. The compound of claim 1 wherein:

$R^6$ and $R^7$ are independently H, alkyl, alkenyl, alkynyl, saturated or partially unsaturated cycloalkyl, saturated or partially unsaturated heterocyclyl, aryl, heteroaryl, $OR^8$, $NR^8R^9$, C(=O)$NR^8R^9$, C(=O)$R^8$, or C(=O)$OR^8$, wherein said alkyl, alkenyl, alkynyl, cycloalkyl, heterocyclyl, aryl and heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocyclyl, $V_n$-aryl, $V_n$-heteroaryl, $V_n$—F, $V_n$—$C_1$, $V_n$—Br, $V_n$—I, $V_n$—$CF_3$, $V_n$—CN, $V_n$—$OR^8$, $V_n$—C(=O)$R^8$, $V_n$—C(=O)$OR^8$, $V_n$—OC(=O)$R^8$, $V_n$—C(=O)$NR^8R^9$, $V_n$—$NR^8R^9$, $V_n$—$NR^8$C(=O)$R^9$, $V_n$—$SR^8$, $V_n$—S(O)$R^8$, $V_n$—S(O)$_2R^8$, and $V_n$—S(O)$_2NR^8R^9$, or $R^6$ and $R^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $V_n$—F, $V_n$—$C_1$, $V_n$—Br, $V_n$—I, $V_n$—$OR^8$, $V_n$—C(=O)$OR^8$, $V_n$—C(=O)$NR^8R^9$, $V_n$—$NR^8R^9$, $V_n$—$NR^8$C(=O)$R^9$, $V_n$—$NR^8$C(=O)$NR^9R^{10}$, alkyl, alkenyl, and alkynyl.

3. The compound of claim 1 having the Formula Ia

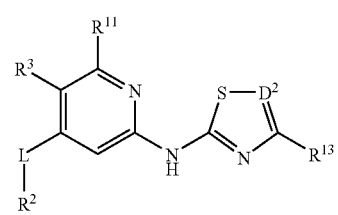

Ia wherein:

L is O, S, SO, $SO_2$, CHOH, C(O), or $CH_2$;

$D^2$ is $CR^{12}$ or N;

$R^3$ is H, Br, $OR^6$, $SR^6$, C(O)$OR^6$, C(O)$NR^6R^7$, C(O)$R^6$, heteroaryl, or $C_1$-$C_6$ alkyl substituted with one or more groups independently selected from $V_n$-aryl, $V_nOR^8$, $V_nC$(=O)$OR^8$ and $V_n$—$NR^8R^9$;

$R^6$ and $R^7$ are independently H, $C_1$-$C_6$ alkyl, saturated or partially unsaturated cycloalkyl, aryl, or heteroaryl, wherein said alkyl is optionally substituted with one or more groups independently selected from $V_n$-heterocyclyl [optionally substituted with C(O)O($C_1$-$C_6$ alkyl)], $V_n$-heteroaryl, $V_n$—C(=O)$OR^8$, or R⁶ and R⁷ together with the atoms to which they are attached form a saturated or partially unsaturated heterocyclic ring, wherein said heterocyclic ring optionally comprises one or more additional ring nitrogen heteroatoms, wherein said heterocyclic ring is optionally substituted with one or more groups independently selected from $C_1$-$C_6$ alkyl;

$R^8$, $R^9$ and $R^{10}$ are independently H or alkyl;

$R^{11}$ is H or Cl;

$R^{12}$ is H;

$R^{13}$ is H, $C_1$-$C_6$ alkyl (optionally substituted with one or more groups independently selected from $V_n$—$OR^8$ or $V_n$—C(=O)$OR^8$), saturated or partially unsaturated cycloalkyl, saturated or partially unsaturated heterocyclyl, aryl, or heteroaryl (optionally substituted with $C_1$-$C_6$ alkyl);

each V is independently alkylene having from 1 to 4 carbons or alkenylene having from 2 to 4 carbons; and each n is independently 0 or 1.

4. The compound of claim 1, wherein $R^{13}$ is selected from H, $CF_3$, $C_1$-$C_6$ alkyl [optionally substituted with $V_n$—$OR^8$, $V_n$—C(=O)$OR^8$ or $V_n$-aryl], $C_3$-$C_6$ cycloalkyl, a 5-6 membered heterocyclyl having a ring oxygen atom, heteroaryl, and $CO_2R^6$.

5. The compound of claim 4, wherein $R^{13}$ is H, methyl, ethyl, isopropyl, butyl, isobutyl, t-butyl, $CF_3$, cyclopropyl, cyclohexyl, —$CH_2CH_2OH$, —$(CH_2)_2CO_2H$, —$(CH_2)_2CO_2Me$, —$(CH_2)CO_2Et$, $CH_2CH_2Ph$, phenyl, 2-pyridyl, 3-pyridyl, 4-pyridyl, 3-thienyl, 2-tetrahydrofuranyl or $CO_2Et$.

6. The compound of claim 1, wherein $R^2$ is (i) phenyl optionally substituted with one or more groups independently selected from Cl, F, CN, Me, iPr, $CF_3$, —$OCH_3$, —OH, —$OCH_2CH_2OH$, —$CH_2OH$, —$OCH_2CO_2H$, —$OCH_2CO_2(t$-Bu$)$, —$CO_2Me$, —$CO_2Et$, —$CO_2H$, —$C(O)NHCH_2CH_2NMe_2$, —$C(O)NHCH_2CH_2CH_2N(CH_3)_2$, —$C(O)N(Me)CH_2CH_2N(CH_3)_2$, —$C(O)NHCH_2CH_2NHCH(CH_3)_2$, —$C(O)NH(CH_2)_3$(N-morpholinyl), —$C(O)$(N-pyrrolidinyl), —$C(O)NHCH_2CH_2$(imidazolyl), —$OCH_2C(O)OC(CH_3)_2$, —$OCH_2C(O)OH$,

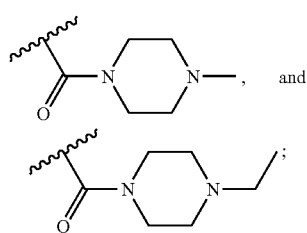

and (ii) 2-pyridyl, 3-pyridyl, 4-pyridyl, 2-imidazolyl, 3-furyl, 1,2,4-oxadiazol-5-yl, 1,3,4-oxadiazol-2-yl or 2-oxazolyl optionally substituted with one or two groups independently selected from $NO_2$, Cl, Br, CN, $CF_3$, and $C_1$-$C_6$ alkyl;

(iii) 1H-pyrazol-5(4H)-one;

(iv) quinolyl, isoxazolo[5,4-b]pyridyl, thienopyridyl, pyrazolopyrimidyl or 5,6,7,8-tetrahydropyrido[4,3-d]pyrimidyl optionally substituted with $C_1$-$C_6$ alkyl or —C(O)O(t-Bu);

(v) cyclohexyl or cyclopentyl optionally substituted with methyl.

7. The compound of claim 6, wherein $R^2$ is selected from the structures:

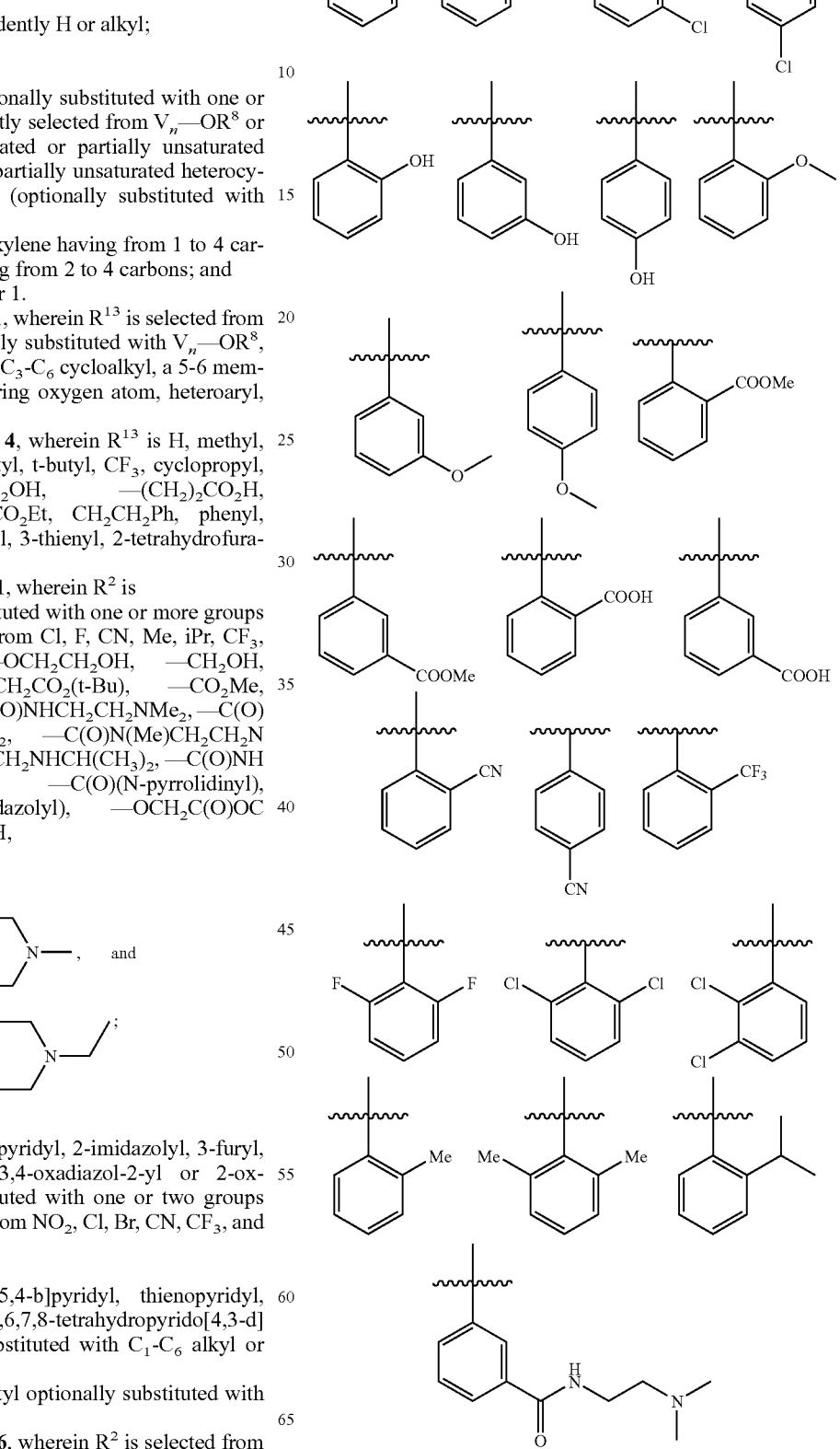

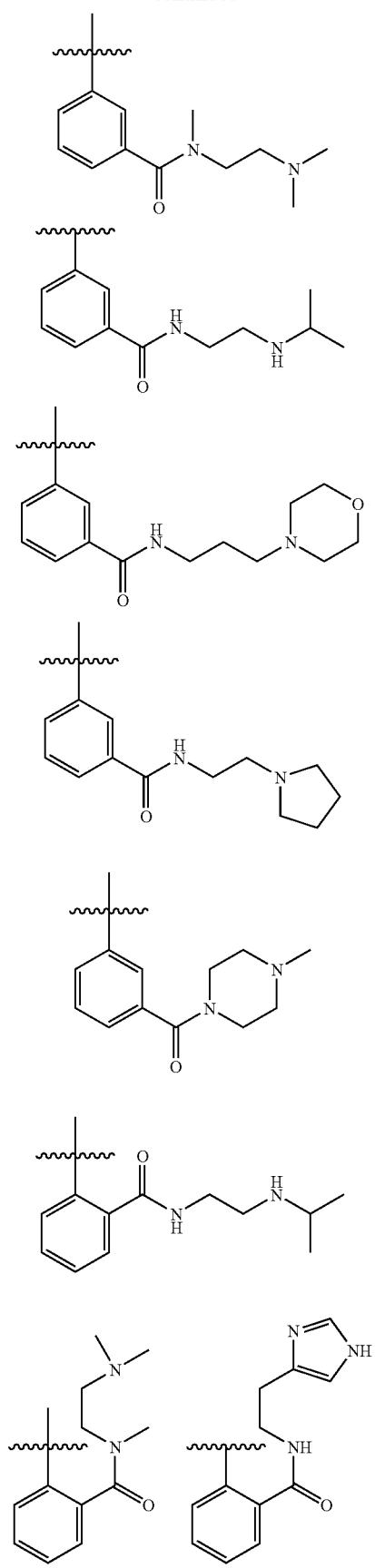
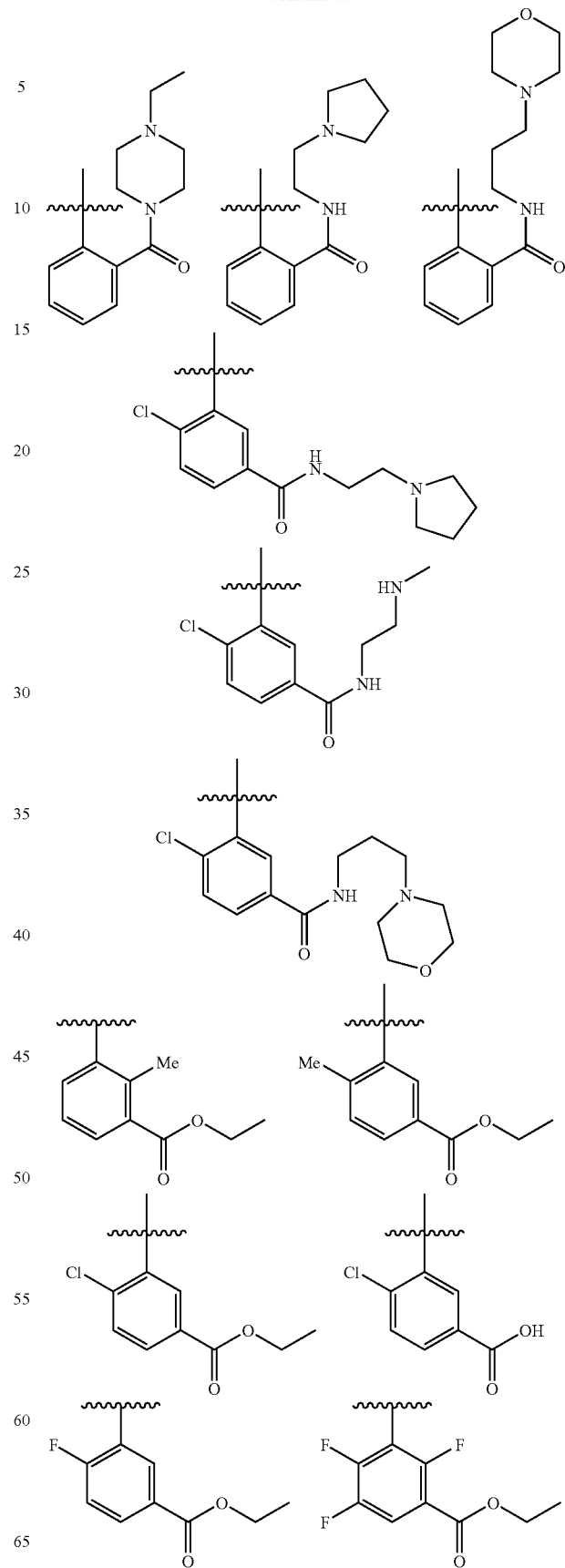

-continued

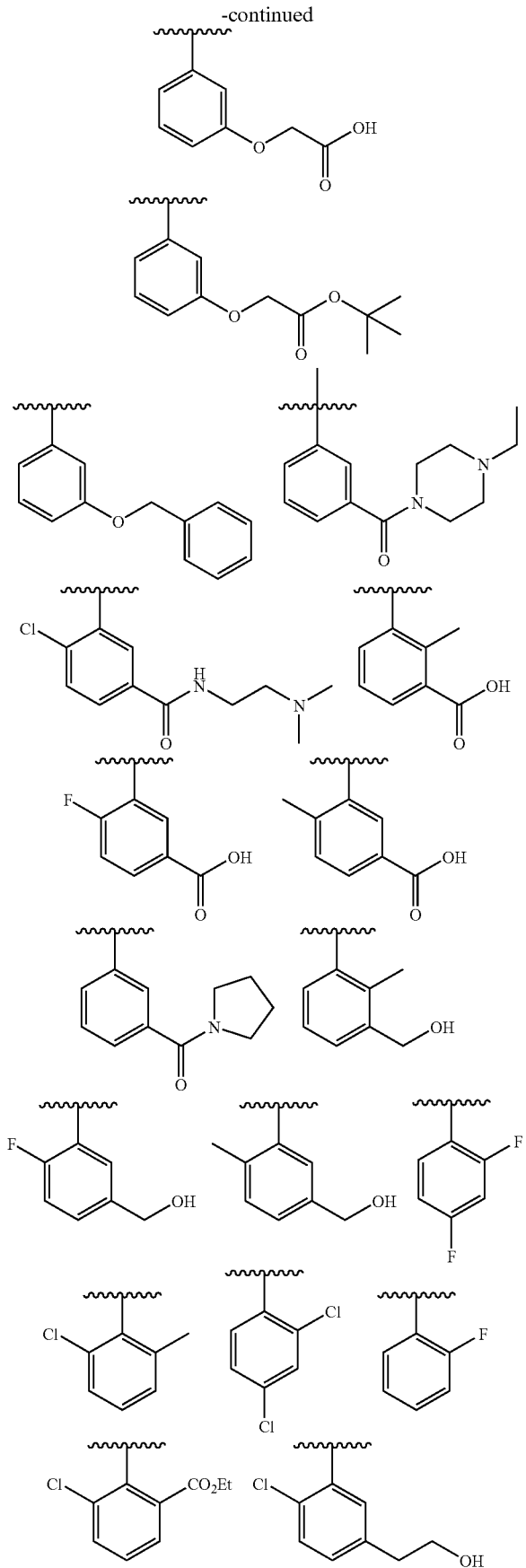
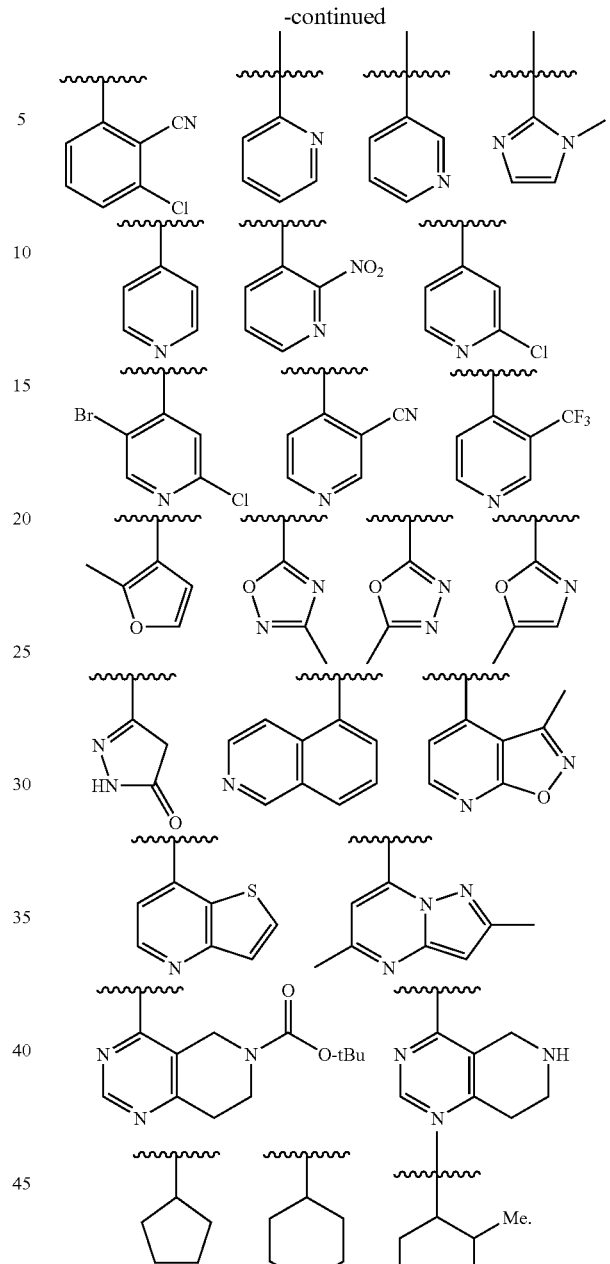

8. The compound of claim 1, wherein $R^3$ is H, Br, $OR^6$, $SR^6$, C(=O)$OR^6$, C(=O)$NR^6R^7$, C(=O)$R^6$, a 5-6 membered heteroaryl group having at least one ring nitrogen atom, or a $C_1$-$C_6$ alkyl group optionally substituted with $V_n$—C(=O)$OR^8$, $V_n$—$OR^8$, $V_n$—$NR^8R^9$ or $V_n$—aryl.

9. The compound of claim 8, wherein $R^3$ is
(i) H,
(ii) Br,
(iii) OH, OMe,
(iv) S-cyclohexyl,
(v) S-phenyl,
(vi) S-(2-pyridyl), S-(4-pyridyl), S-(2-pyrimidyl), S-(2-thiazolyl),
(vii) S-(thieno[3,2-b]pyrid-7-yl),
(viii) S—$CH_2CH_2$C(O)$OCH_3$,
(ix) S—$CH_2$-pyrid-2-yl, (x) SCH$_2$-(4-piperidyl), SCH$_2$—[N-(t-butylcarboxylate)piperid-4-yl), (xi) CO$_2$H, CO$_2$Et, (xii) C(O)NHCH$_2$CH$_2$N(CH$_3$)$_2$, C(O)(N-ethylpiperazin-4-yl), (xiii) C(O)H;

(xiv) 2-pyridyl, (xv) CH$_2$CH$_2$CO$_2$Me, CH=CHC(O)OCH$_3$, (xvi) CH$_2$OH, (xvii) CH=CHCH$_2$CH$_2$N(CH)$_3$, CH$_2$-(1-piperidyl), CH$_2$NMe$_2$, CH$_2$NH-cyclohexyl, CH$_2$NHCH$_2$CH$_2$NMe$_2$, or (xviii) benzyl.

10. A composition comprising a compound of claim 1 and a pharmaceutically acceptable diluent or carrier.

11. A method of treating a disease or condition in a mammal resulting from underactivity of glucokinase or which can be treated by activating glucokinase selected from the group consisting of insulin-dependent diabetes mellitus or non-insulin-dependent diabetes mellitus, comprising administering to said mammal an effective amount of a compound of claim 1.

12. A method of preparing a compound of claim 1, said method comprising:

(a) reacting a compound of the formula

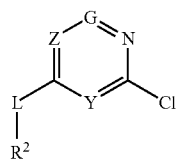

with a compound of the formula R$^1$NH$_2$ in the presence of a base catalyst or metal catalyst; or (b) reacting a compound of the formula

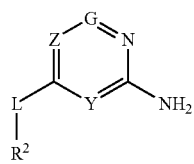

with a compound of the formula R$^1$—X, wherein X is Cl or Br, in the presence of a base catalyst or metal catalyst; or (c) reacting a compound of the formula

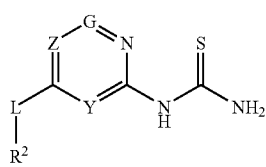

with a compound of the formula R$^{13}$COCHR$^{12}$X$^1$, wherein X$^1$ is a leaving group, in the presence of a base.

13. A compound of Formula Ib:

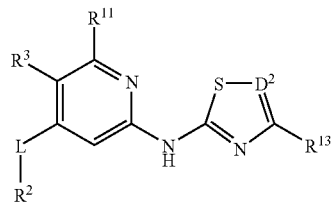

and salts thereof, wherein:

L is O, S, SO, SO$_2$, CHOH, C(O), or CH$_2$;

D$^2$ is CR$^{12}$ or N;

R$^2$ is aryl, heteroaryl, saturated or partially unsaturated cycloalkyl, or saturated or partially unsaturated heterocyclyl (optionally substituted with oxo), wherein said aryl, heteroaryl, cycloalkyl and heterocyclyl are monocyclic or bicyclic and are further optionally substituted with one or more groups independently selected from C$_1$-C$_6$ alkyl, F, Cl, Br, I, CF$_3$, CN, OR$^6$, C(=O)R$^6$, C(=O)OR$^6$, O(CH$_2$)$_n$C(=O)OR$^6$, C(=O)NR$^6$R$^7$ and NO$_2$;

R$^3$ is H, Br, OR$^6$, SR$^6$, C(O)OR$^6$, C(O)NR$^6$R$^7$, C(O)R$^6$, heteroaryl, or C$_1$-C$_6$ alkyl substituted with one or more groups independently selected from V$_n$aryl, V$_n$—OR$^8$, V$_n$—C(=O)OR$^8$ and V$_n$—NR$^8$R$^9$;

R$^6$ and R$^7$ are independently H, C$_1$-C$_6$ alkyl, saturated or partially unsaturated cycloalkyl, aryl, or heteroaryl, wherein said alkyl is optionally substituted with one or more groups independently selected from V$_n$-heterocyclyl [optionally substituted with C(O)O(C$_1$-C$_6$ alkyl)], V$_n$-heteroaryl, V$_n$—C(=O)OR$^8$, or R$^6$ and R$^7$ together with the atoms to which they are attached form a saturated or partially unsaturated heterocyclic ring, wherein said heterocyclic ring optionally comprises one or more additional ring nitrogen heteroatoms, wherein said heterocyclic ring is optionally substituted with one or more groups independently selected from C$_1$-C$_6$ alkyl;

R$^8$, R$^9$ and R$^{10}$ are independently H or alkyl;

R$^{11}$ is H or Cl;

R$^{12}$ is H, C$_1$-C$_6$ alkyl (optionally substituted with one or more groups independently selected from V$_n$—OR$^8$ or V$_n$—C(=O)OR$^8$), saturated or partially unsaturated cycloalkyl, saturated or partially unsaturated heterocyclyl, aryl, or heteroaryl (optionally substituted with C$_1$-C$_6$ alkyl);

R$^{13}$ is N-(1-6C alkanoyl)piperidin-4-yl;

each V is independently alkylene having from 1 to 4 carbons or alkenylene having from 2 to 4 carbons; and each n is independently 0 or 1.

14. A compound of claim 13, wherein R$^{13}$ is N-acetylpiperidin-4-yl.

15. A compound of claim 13 wherein:

L is O, S, SO, SO$_2$, CHOH, C(O), or CH$_2$;

D$^2$ is CR$^{12}$ or N;

R$^2$ is aryl, 3-pyridyl or 8-quinolinyl, wherein said aryl, pyridyl and quinolinyl are optionally substituted with one or more groups independently selected from 1-6C alkyl, Cl, CN, and C(=O)NR$^6$R$^7$;

R$^3$ is H, Br, S-aryl, O-aryl, CH$_2$-aryl, S-heteroaryl, O-heteroaryl or CH$_2$-heteroaryl, wherein said aryl and heteroaryl portions are optionally substituted with one or more groups independently selected from (1-3C) alkyl, F, Cl, Br, CN, $CF_3$, and O-(1-3C alkyl);

$R^6$ and $R^7$ are independently H, 1-6C alkyl, -(1-6C alkyl)$NH_2$, -(1-6C alkyl)NH(1-6C alkyl), -(1-6C alkyl)N(1-6C alkyl)$_2$, -(1-6C alkyl)-heteroaryl and -(1-6C alkyl)-heterocycle;

$R^8$ and $R^9$ are independently H or 1-6C alkyl;

$R^H$ is H or Cl; and $R^{12}$ is H or 1-6C alkyl.

16. A compound of claim 13, including salts thereof, selected from:

3-(2-(4-(1-Acetylpiperidin-4-yl)thiazol-2-ylamino)pyridin-4-yloxy)isonicotinonitrile;

1-(4-(2-(4-(2,6-dichlorophenylthio)pyridin-2-ylamino)thiazol-4-yl)piperidin-1-yl)ethanone;

1-(4-(2-(4-(2-chlorophenoxy)pyridin-2-ylamino)thiazol-4-yl)piperidin-1-yl)ethanone;

1-(4-(2-(4-(2,6-dimethylphenoxy)pyridin-2-ylamino)thiazol-4-yl)piperidin-1-yl)ethanone;

1-(4-(2-(4-(2-chloro-6-methylphenoxy)pyridin-2-ylamino)thiazol-4-yl)piperidin-1-yl)ethanone; and 3-(2-(3-(1-acetylpiperidin-4-yl)-1,2,4-thiadiazol-5-ylamino)-5-bromopyridin-4-yloxy)-4-chloro-N-(2-(dimethylamino)ethyl)benzamide.

\* \* \* \* \*

UNITED STATES PATENT AND TRADEMARK OFFICE
CERTIFICATE OF CORRECTION

PATENT NO. : 8,022,222 B2
APPLICATION NO. : 12/161366
DATED : September 20, 2011
INVENTOR(S) : Thomas D. Aicher et al.

It is certified that error appears in the above-identified patent and that said Letters Patent is hereby corrected as shown below:

Column 178, line 20, claim 1,
Please delete "$CO_7R^6$" and insert --$CO_2R^6$--.

Column 178, line 21, claim 1,
Please delete "$O(CH_2)C$" and insert --$O(CH_2)_nC$--.

Column 178, line 26, claim 1,
Please delete "CF)" and insert --$CF_3$)--.

Column 179, line 12, claim 1,
Please delete "$C_1$" and insert --Cl--.

Column 179, line 54, claim 1,
Please delete "$C_1$" and insert --Cl--.

Column 180, line 27, claim 2,
Please delete "$C_1$" and insert --Cl--.

Column 180, line 39, claim 2,
Please delete "$C_1$" and insert --Cl--.

Column 180, line 60, claim 3,
Please delete "$V_nOR^8$" and insert --$V_n$-$OR^8$--.

Column 180, line 61, claim 3,
Please delete "$V_nC($" and insert --$V_n$-C(--.

Column 181, line 21, claim 4,
Please delete "$C_rC_6$" and insert --$C_1$-C6--.

Signed and Sealed this
Thirteenth Day of December, 2011

David J. Kappos
*Director of the United States Patent and Trademark Office*

CERTIFICATE OF CORRECTION (continued)
U.S. Pat. No. 8,022,222 B2

Column 188, line 28, claim 13,
    Please delete "$V_n$aryl" and insert --$V_n$-aryl--.

Column 189, line 8, claim 15,
    Please delete "$R^{11}$" and insert --$R^{11}$--.